US012758611B2

(12) United States Patent
Kapiloff et al.

(10) Patent No.: US 12,758,611 B2
(45) Date of Patent: Oct. 13, 2026

(54) COMPOSITIONS FOR TREATING HEART DISEASE BY INHIBITING THE ACTION OF mAKAP-β

(71) Applicant: Anchored RSK3 Inhibitors, LLC, Los Altos, CA (US)

(72) Inventors: Michael S. Kapiloff, Los Altos, CA (US); Jinliang Li, Palo Alto, CA (US); Michael Kritzer, Cambridge, MA (US)

(73) Assignee: ANCHORED RSK3 INHIBITORS, LLC, Los Altos, CA (US)

( * ) Notice: Subject to any disclaimer, the term of this patent is extended or adjusted under 35 U.S.C. 154(b) by 17 days.

(21) Appl. No.: 18/432,983

(22) Filed: Feb. 5, 2024

(65) Prior Publication Data

US 2024/0216466 A1 Jul. 4, 2024

Related U.S. Application Data

(60) Continuation of application No. 17/580,692, filed on Jan. 21, 2022, now Pat. No. 11,931,402, which is a continuation of application No. 16/837,633, filed on Apr. 1, 2020, now Pat. No. 11,229,679, which is a continuation of application No. 15/946,238, filed on Apr. 5, 2018, now Pat. No. 10,617,737, which is a division of application No. 14/821,082, filed on Aug. 7, 2015, now Pat. No. 9,937,228, which is a continuation of application No. 14/213,583, filed on Mar. 14, 2014, now Pat. No. 9,132,174.

(60) Provisional application No. 61/798,268, filed on Mar. 15, 2013.

(51) Int. Cl.

| | |
|---|---|
| ***A61K 38/45*** | (2006.01) |
| ***A61K 31/519*** | (2006.01) |
| ***A61K 31/7048*** | (2006.01) |
| ***A61K 31/713*** | (2006.01) |
| ***A61K 38/00*** | (2006.01) |
| ***A61K 38/17*** | (2006.01) |
| ***A61K 48/00*** | (2006.01) |
| ***C12N 15/113*** | (2010.01) |

(52) U.S. Cl.

CPC ........ *A61K 38/1709* (2013.01); *A61K 31/519* (2013.01); *A61K 31/7048* (2013.01); *A61K 31/713* (2013.01); *A61K 38/005* (2013.01); *A61K 38/45* (2013.01); *A61K 48/00* (2013.01); *A61K 48/005* (2013.01); *C12N 15/1137* (2013.01); *C12Y 207/11001* (2013.01); *C12N 2310/14* (2013.01); *C12N 2750/14143* (2013.01)

(58) Field of Classification Search

CPC ............................ A61K 38/1709; A61K 38/45

See application file for complete search history.

(56) References Cited

U.S. PATENT DOCUMENTS

| | | | | |
|---|---|---|---|---|
| 7,691,997 | B2 | 4/2010 | Khvorova et al. | |
| 7,745,391 | B2 | 6/2010 | Mintz et al. | |
| 9,132,174 | B2 | 9/2015 | Kapiloff et al. | |
| 9,217,155 | B2 | 12/2015 | Gao et al. | |
| 9,937,228 | B2 | 4/2018 | Kapiloff et al. | |
| 10,029,386 | B2 | 7/2018 | Chung et al. | |
| 10,109,346 | B2 | 10/2018 | Cho et al. | |
| 10,617,737 | B2 | 4/2020 | Kapiloff et al. | |
| 2003/0134331 | A1 | 7/2003 | Marks et al. | |
| 2003/0194704 | A1* | 10/2003 | Penn | C12Q 1/6876 536/24.3 |
| 2005/0112128 | A1 | 5/2005 | Mckinsey et al. | |
| 2005/0255487 | A1 | 11/2005 | Khvorova | |
| 2007/0083334 | A1 | 4/2007 | Mintz et al. | |
| 2013/0136729 | A1 | 5/2013 | French et al. | |
| 2014/0286928 | A1 | 9/2014 | Kapiloff | |
| 2014/0296486 | A1 | 10/2014 | Gao et al. | |
| 2016/0038568 | A1 | 2/2016 | Kapiloff et al. | |
| 2019/0010493 | A1 | 1/2019 | Kapiloff | |

OTHER PUBLICATIONS

Huusko et al., 2012, AAV9-mediated VEGF-B Gene Transfer Improved Systolic Function in Progressive Left Ventricular Hypertrophy, Molecular Therapy, 20(12): 2212-2221.*

Li et al., 2010, The mAKAPbeta Scaffold Regulates Cardiac Myocyte Hypertrophy via Recruitment of Activated Calcineurin, J Mol Cell Cardiol, 48(2): 387 (18 pages).*

Dodge-Kafka et al., 2010, cAMP-stimulated Protein Phosphatase 2A Activity Associated with Muscle A Kinase-anchoring Protein (mAKAP) Signaling Complexes Inhibits the Phosphorylation and Activity of the CAMP-specific Phosphodiesterase PDE4D3, The Journal of Biological Chemistry, 285(15): 11078-11086.*

Kapiloff et al., 1999, mAKAP: an A-kinase anchoring protein targeted to the nuclear membrane of differentiated myocytes, Journal of Cell Science, 112: 2725-2736.*

Using siRNA for gene silencing is a rapidly evolving tool in molecular biology, ThermoFisher Scientific, retrieved Jun. 16, 2017 <https://http://www.thermofisher.com/us/en/home/references/ambion-tech-support/rnai-sirna/general-articles/-sirna-design-guidelines.html>.

Ahn JH, McAvoy T, Rakhilin SV, Nishi A, Greengard P, Nairn AC (2007) Protein kinase A activates protein phosphatase 2A by phosphorylation of the B56delta subunit. Proc Natl Acad Sci USA 104:2979-2984.

Ai X, Pogwizd SM (2005) Connexin 43 downregulation and dephosphorylation in nonischemic heart failure is associated with enhanced colocalized protein phosphatase type 2A. Circ Res 96:54-63.

(Continued)

*Primary Examiner* — Amber D Steele

(74) *Attorney, Agent, or Firm* — Haynes and Boone, LLP

(57) ABSTRACT

The present invention provides a method of protecting the heart from damage, by administering to a patient at risk of such damage, a pharmaceutically effective amount of a composition which inhibits the interaction of RSK3 and mAKAPβ, or the expression or activity of one or both of those molecules. This composition may be in the form of a peptide that specifically inhibits mAKAPβ binding to RSK3 or in the form of an siRNA construct which inhibits the expression of RSK3.

20 Claims, 53 Drawing Sheets
(20 of 53 Drawing Sheet(s) Filed in Color)

Specification includes a Sequence Listing.

(56) References Cited

OTHER PUBLICATIONS

Andino LM, Conlon TJ, Porvasnik SL, Boye SL, Hauswirth WW, Lewin AS (2007) Rapid, widespread transduction of the murine myocardium using self-complementary Adeno-associated virus. Genetic vaccines and therapy 5:13.
Backs J, Worst BC, Lehmann LH, Patrick DM, Jebessa Z, Kreusser MM, Sun Q, Chen L, Heft C, Katus HA, Olson EN (2011) Selective repression of MEF2 activity by PKA-dependent proteolysis of HDAC4. J Cell Biol 195:403-415.
Bauman AL, Scott JD (2002) Kinase- and phosphatase-anchoring proteins: harnessing the dynamic duo. Nat Cell Biol 4:E203-206.
Beavo JA, Bechtel PJ, Krebs EG (1974) Preparation of homogeneous cyclic AMP-dependent protein kinase(s) and its subunits from rabbit skeletal muscle. Methods Enzymol 38:299-308.
Benjamin EJ et al. (2017) Heart Disease and Stroke Statistics-2017 Update: A From the American Heart Association. Circulation 135:e146-e603.
Benjamin EJ et al. (2019) Heart Disease and Stroke Statistics-2019 Update: A Report From the American Heart Association. Circulation 139: e56-e528.
Bers DM (2006) Cardiac ryanodine• receptor phosphorylation: target sites and functional consequences. Biochem J 396:el-3.
Bione S, Maestrini E, Rivella S, Mancini M, Regis S, Romeo G, Toniolo D (1994) Identification of a novel X-linked gene responsible for Emery-Dreifuss muscular dystrophy. Nat Genet 8:323-327.
Black BL, Olson EN (1998) Transcriptional control of muscle development by myocyte enhancer factor-2 (MEF2) proteins. Annu Rev Cell Dev Biol 14:167-196.
Bonne G, Di Barletta MR, Vamous S, Becane HM, Hammouda EH, Merlini L, Muntoni F, Greenberg CR, Gary F, Urtizberea JA, Duboc D, Fardeau M, Toniolo D, Schwartz K (1999) Mutations in the gene encoding lamin NC cause autosomal dominant Emery-Dreifuss muscular dystrophy. Nat Genet 21:285-288.
Bourajjaj M, Armand AS, da Costa Martins PA, Weijts B, van der Nagel R, Heeneman S, Wehrens XH, De Windt LJ (2008) NFATc2 is a necessary mediator of calcineurin-dependent cardiac hypertrophy and heart failure. J Biol Chem 283:22295-22303.
Burns-Hamuro LL, Ma Y, Kammerer S, Reineke U, Self C, Cook C, Designing isoform-specific peptide disruptors of protein kinase A localization. Proc Natl Acad Sci U S A. Apr. 1, 2003;100(7):4072-7.
Brunton LL, Hayes JS, Mayer SE (1979) Hormonally specific phosphorylation of cardiac troponin I and activation of glycogen phosphorylase. Nature 280:78-80.
Bueno OF, Wilkins BJ, Tymitz KM, Glascock BJ, Kimball TF, Lorenz JN, Molkentin JD (2002) Impaired cardiac hypertrophic response in Calcineurin Abeta-deficient mice. Proc Natl Acad Sci U S A 99:4586-4591.
Bueno OF, Lips DJ, Kaiser RA Wilkins BJ, Dai YS, Glascock BJ, Klevitsky R, Hewett TE, Kimball TR, Aronow BJ, Doevendans PA, Molkentin JD (2004) Calcineurin Abeta gene targeting predisposes the myocardium to acute ischemia-induced apoptosis and dysfunction. Circ Res 94:91-99.
Burchfield JS, Xie M, Hill JA (2013) Pathological ventricular remodeling: mechanisms: part 1 of 2. Circulation 128:388-400.
Carlisle Michel JJ, Dodge KL, Wong W, Mayer NC, Langeberg LK, Scott JD (2004) PKA-phosphorylation of PDE4D3 facilitates recruitment of the mAKAP signalling complex. Biochem J 381:587-592.
Carnegie GK, Soughayer J, Smith FD, Pedroja BS, Zhang F, Diviani D, Bristow MR, Kunkel MT, Newton AC, Langeberg LK, Scott JD. AKAP-Lbc mobilizes a cardiac hypertrophy signaling pathway. Mol Cell 32: 169-179, 2008.
Chen L, Kurokawa J, Kass RS. Phosphorylation of the A-kinase-anchoring protein Yotiao contributes to protein kinase A regulation of a heart potassium channel. J Biol Chem 280: 31347-31352, 2005.
Clerk A, Cullingford TE, Fuller SJ, Giraldo A, Markou T, Pikkarainen S, Sugden PH (2007) Signaling pathways mediating cardiac myocyte gene expression in physiological and stress responses. J Cell Physiol 212:311-322.
Consensus (1987). "Effects of enalapril on mortality in severe congestive heart failure. Results of the Cooperative North Scandinavian Enalapril Survival Study (CONSENSUS)." N Engl J Med 316(23): 1429-1435.
De Arcangelis V, Soto D, Xiang Y (2008) Phosphodiesterase 4 and phosphatase 2A differentially regulate CAMP/protein kinase a signaling for cardiac myocyte contraction under stimulation ofbetal adrenergicreceptor. Mol Pharmacol 74:1453-1462.
Dobrev D, Wehrens XH (2014) Role of RyR2 phosphorylation in heart failure and arrhythmias: Controversies around ryanodine receptor phosphorylation in cardiac disease. Circ Res 114:1311-1319; discussion 1319.
Dodge-Kafka, K. L., M. Gildart, J. Li, H. Thakur, and M. S. Kapiloff. 2018. 'Bidirectional regulation of HDAC5 by mAKAPbeta signalosomes in cardiac myocytes', Journal of Molecular and Cellular Cardiology, 118: 13-25.
Diviani D, Soderling J, Scott JD. AKAP-Lbc anchors protein kinase A and nucleates Galpha 12-selective Rho-mediated stress fiber formation. J Biol Chem 276: 44247-44257, 2001.
Dodge KL, Khouangsathiene S, Kapiloff MS, Mouton R, Hill EV, Houslay MD, Langeberg LK, Scott JD. mAKAP assembles a protein kinase A/PDE4 phosphodiesterase CAMP signaling module. EMBO J 20: 1921-1930, 2001.
Dodge-Kafka KL, Kapiloff MS, "The mAKAP signaling complex: integration of CAMP, calcium, and MAP kinase signaling pathways," Eur J Cell Biol. Jul. 2006;85(7):593-602. Epub Feb. 7, 2006. Review.
Dodge-Kafka KL, Langeberg L, Scott JD (2006) Compartmentation of cyclic nucleotide signaling in the heart: the role of A-kinase anchoring proteins. Circ Res 98:993-1001.
DuBell WH, Lederer WJ, Rogers TB (1996) Dynamic modulation of excitation-contraction coupling by protein phosphatases in rat ventricular myocytes. J Physiol 493 (Pt 3):793-800.
DuBell WH, Gigena MS, Guatimosim S, Long X, Lederer WJ, Rogers TB (2002) Effects of PP1/PP2A inhibitor calyculin A on the E-C coupling cascade in murine ventricular myocytes. Am J Physiol Heart Circ Physiol 282:H38-48.
Dulhunty AF, Beard NA, Pouliquin P, Casarotto MG (2007) Agonists and antagonists of the cardiac ryanodine receptor: potential therapeutic agents? Pharmacol Ther 113:247-263.
Elbashir SM, Martinez J, Patkaniowska A, Lendeckel W, Tuschl T, Functional anatomy of SiRNAs for mediating efficient RNAi in *Drosophila melanogaster* embryo lysate, The EMBO Journal, vol. 20, No. 23, pp. 6877-6888, 2001.
Endo S, Zhou X, Connor J, Wang B, Shenolikar S (1996) Multiple structural elements define the specificity of recombinant human inhibitor-1 as a protein phosphatase-1 inhibitor. Biochemistry 35:5220-5228.
Fatkin D, MacRae C, Sasaki T, Wolff MR, Porcu M, Frenneaux M, Atherton J, Vidaillet HJ, Jr., Spudich S, De Girolami U, Seidman JG, Seidman C, Muntoni F, Muehle G, Johnson W, McDonough B (1999) Missense mutations in the rod domain of the lamin NC gene as causes of dilated cardiomyopathy and conduction-system disease. N Engl J Med 341:1715-1724.
Fischmeister R, Castro LR, Abi-Gerges A, Rochais F, Jurevicius J, Leroy J, Vandecasteele G (2006) Compartmentation of cyclic nucleotide signaling in the heart: the role of cyclic nucleotide phosphodiesterases. Circ Res 99:816-828.
Friday BB, Mitchell PO, Kegley KM, Pavlath GK (2003) Calcineurin initiates skeletal muscle differentiation by activating MEF2 and MyoD. Differentiation 71:217-227.
Gerber, Y., S. A. Weston, M. Enriquez-Sarano, C. Berardi, A. M. Chamberlain, S. M. Manemann, R. Jiang, S. M. Dunlay and V. L. Roger (2016). "Mortality Associated With Heart Failure After Myocardial Infarction: A Contemporary Community Perspective." Circ Heart Fail 9(1): e002460.
Gigena MS, Ito A, Nojima H, Rogers TB (2005) A B56 regulatory subunit of protein phosphatase 2A localizes to nuclear speckles in cardiomyocytes. Am J Physiol Heart Circ Physiol 289:H285-294.
Go AS et al. (2014) Heart disease and stroke statistics—2014 update: a report from the American Heart Association. Circulation 129:e28-e292.

(56) References Cited

OTHER PUBLICATIONS

Grossman W, Jones D, McLaurin LP (1975) Wall stress and patterns of hypertrophy in the human left ventricle. J Clin Invest 56:56-64.
Guo, H., B. Liu, L. Hou, E. The, G. Li, D. Wang, Q. Jie, W. Che and Y. Wei (2015). "The role of mAKAPbeta in the process of cardiomyocyte hypertrophy induced by angiotensin II." Int J Mol Med 35(5): 1159-1168.
Hanlon M, Sturgill TW, Sealy L (2001) ERK2- and p90(Rsk2)-dependent pathways regulate the CCAAT/enhancer-binding protein-beta interaction with serum response factor. J Biol Chem 276:38449-38456.
Hayes JS, Brunton LL, Mayer SE (1980) Selective activation of particulate cAMP-dependent protein kinase by isoproterenol and prostaglandin El. J Biol Chem 255:5113-5119.
Heidenreich, P. A., N. M. Albert, L. A. Allen, D. A. Bluemke, J. Butler, G. C. Fonarow, J. S. Ikonomidis, O. Khavjou, M. A. Konstam, T. M. Maddox, G. Nichol, M. Pham, I. L. Pina, J. G. Trogdon, C. American Heart Association Advocacy Coordinating, T. Council on Arteriosclerosis, B. Vascular, R. Council on Cardio-vascular, Intervention, C. Council on Clinical, E. Council on, Prevention and C. Stroke (2013). "Forecasting the impact of heart failure in the United States: a policy statement from the American Heart Association." Circ Heart Fail 6(3):606-619.
Heineke J, Molkentin JD (2006) Regulation of cardiac hypertrophy by intracellular signaling pathways. Nat Rev Mol Cell Biol 7:589-600.
Ho SN, Thomas DJ, Timmerman LA, Li X, Francke U, Crabtree GR (1995) NFATc3, a lymphoid-specific NFATc family member that is calcium-regulated and exhibits distinct DNA binding specificity. J Biol Chem 270:19898-19907.
Hoffmann R, Baillie GS, Mackenzie SJ, Yarwood SJ, Houslay MD (1999) The MAP kinase ERK2 inhibits the cyclic AMP-specific phosphodiesterase HSPDE4D3 by phosphorylating it at Ser579. EMBO J 18:893-903.
Houser SR (2014) Role ofRyR2 phosphorylation in heart failure and arrhythmias: protein kinase A-mediated hyperphosphorylation of the ryanodine receptor at serine 2808 does not alter cardiac contractility or cause heart failure and arrhythmias. Circ Res 114:1320-1327; discussion 1327.
Huang LJ, Durick K, Weiner JA, Chun J, Taylor SS. Identification of a novel protein kinase A anchoring protein that binds both type I and type II regulatory subunits. J Biol Chem. 1997;272:8057-8064.
Janknecht R, Hipskind RA, Houthaeve T, Nordheim A, Stunnenberg HG (1992) Identification of multiple SRF N-terminal phosphorylation sites affecting DNA binding properties. EMBO J 11:1045-1054.
Jugdutt BI (2003) Remodeling of the myocardium and potential targets in the collagen degradation and synthesis pathways. Curr Drug Targets Cardiovasc Haematol Disord 3:1-30.
Kato Y, Zhao M, Morikawa A, Sugiyama T, Chakravortty D, Koide N, Yoshida T, Tapping RI, Yang Y, Yokochi T, Lee JD (2000) Big mitogen-activated kinase regulates multiple members of the MEF2 protein family. J Biol Chem 275:18534-18540.
Keely SL (1977) Activation of cAMP-dependent protein kinase without a corresponding increase in phosphorylase activity. Res Commun Chem Pathol Pharmacol 18:283-290.
Keely SL (1979) Prostaglandin El activation of heart CAMP-dependent protein kinase: apparent dissociation of protein kinase activation from increases in phosphorylase activity and contractile force. Mol Pharmacol 15:235-245.
Kim Y, Phan D, van Rooij E, Wang DZ, McAnally J, Qi X, Richardson JA, Hill JA, Bassel-Duby R, Olson EN (2008) The MEF2D transcription factor mediates stress-dependent cardiac remodeling in mice. J Clin Invest 118:124-132.
Kumar, D., T. A. Hacker, J. Buck, L. F. Whitesell, E. H. Kaji, P. S. Douglas and T. J. Kamp (2005). "Distinct mouse coronary anatomy and myocardial infarction consequent to ligation." Coron Artery Dis 16(1): 41-44.
Lechward K, Awotunde OS, Swiatek W, Muszynska G (2001) Protein phosphatase 2A: variety of forms and diversity of functions. Acta Biochim Pol 48:921-933.
Lehnart, S. E., X. H. Wehrens, S. Reiken, S. Warrier, A. E. Belevych, R. D. Harvey, W. Richter, S. L. Jin, M. Conti and A. R. Marks (2005). "Phosphodiesterase 4D deficiency in the ryanodine-receptor complex promotes heart failure and arrhythmias." Cell 123(1): 25-35.
Li CL, Sathyamurthy A, Oldenborg A, Tank D, Ramanan N (2014) SRF phosphorylation by glycogen synthase kinase-3 promotes axon growth in hippocampal neurons. J Neurosci 34:4027-4042.
Li J, Negro A, Lopez J, Bauman AL, Henson E, Dodge-Kafka K, Kapiloff MS, "The mAKAPbeta scaffold regulates cardiac myocyte hypertrophy via recruitment of activated calcineurin," J Mol Cell Cardiol. Feb. 2010;48(2):387-94.
Li, J., S. Aponte Paris, H. Thakur, M. S. Kapiloff, and K. L. Dodge-Kafka. 2019. 'Muscle A-kinase-anchoring protein-beta-bound calcineurin toggles active and repressive transcriptional complexes of myocyte enhancer factor 2D', Journal of Biological Chemistry, 294: 2543-54.
Li M, Makkinje A, Damuni Z (1996) Molecular identification of I1PP2A, a novel potent heat-stable inhibitor protein of protein phosphatase 2A. Biochemistry 35:6998-7002.
Liu Q, Hofmann PA (2004) Protein phosphatase 2A-mediated cross-talk between p38 MAPK and ERK in apopfosis of cardiac myocytes. Am J Physiol Heart Circ Physiol 286:H2204-2212.
Mack CP (2011) Signaling mechanisms that regulate smooth muscle cell differentiation. Arterioscler Thromb Vase Biol 31:1495-1505.
Mackenzie KF, Topping EC, Bugaj-Gaweda B, Deng C, Cheung YF, Olsen AE, Stockard CR, High Mitchell L, Baillie GS, Grizzle WE, De Vivo M, Houslay MD, Wang D, Bolger GB (2008) Human PDE4A8, a novel brain-expressed PDE4 cAMP-specific phosphodiesterase that has undergone rapid evolutionary change. Biochem J 411:361-369.
MacKenzie SJ, Baillie GS, McPhee I, Bolger GB, Houslay MD (2000) ERK2 mitogen-activated protein kinase binding, phosphorylation, and regulation of the PDE4D cAMP-specific phosphodiesterases. The involvement of COOH-terminal docking sites and NH2-terminal UCR regions. J Biol Chem 275:16609-16617.
Martinez, E. C., C. L. Passariello, J. Li, C. J. Matheson, K. Dodge-Kafka, P. Reigan and M. S. Kapiloff (2015). "RSK3: A regulator of pathological cardiac remodeling." IUBMB Life 67(5): 331-337.
McCright B, Rivers AM, Audlin S, Virshup DM (1996) The B56 family of protein phosphatase 2A (PP2A) regulatory subunits encodes differentiation-induced phosphoproteins that target PP2A to both nucleus and cytoplasm. J Biol Chem 271:22081-22089.
Miano JM (2010) Role of serum response factor in the pathogenesis of disease. Lab Invest 90:1274-1284.
Monovich L, Vega RB, Meredith E, Miranda K, Rao C, Capparelli M, Lemon DD, Phan D, Koch KA, Chapo JA, Hood DB, McKinsey TA (2010) A novel kinase inhibitor establishes a predominant role for protein kinase D as a cardiac class lla histone deacetylase kinase. FEBS Lett 584:631-637.
Muchir A, Bonne G, van der Kooi AJ, van Meegen M, Baas F, Bolhuis PA, de Visser M, Schwartz K (2000) Identification of mutations in the gene encoding lamins A/C in autosomal dominant limb girdle muscular dystrophy with atrioventricular conduction disturbances (LGMDIB). Hum Mol Genet 9:1453-1459.
Naya FJ, Olson E (1999) MEF2: a transcriptional target for signaling pathways controlling skeletal muscle growth and differentiation. Curr Opin Cell Biol 11:683-688.
Naya FJ, Wu C, Richardson JA, Overbeek P, Olson EN (1999) Transcriptional activity of MEF2 during mouse embryogenesis monitored with a MEF2-dependent transgene. Development 126:2045-2052.
Newlon MG, Roy M, Morikis D, Hausken ZE, Coghlan V, Scott JD, Jennings PA (1999) The molecular basis for protein kinase A anchoring revealed by solution NMR. Nat Struct Biol 6:222-227.
Niggli E, Lederer WJ. Voltage-independent calcium release in heart muscle. Science 250: 565-568, 1990.
Ohh M, Park CW, Ivan M, Hoffman MA, Kim TY, Huang LE, Pavletich N, Chau V, Kaelin WG (2000) Ubiquitination of hypoxia-

(56) References Cited

OTHER PUBLICATIONS inducible factor requires direct binding to the beta-domain of the von Hippel-Lindau protein. Nat Cell Biol 2:423-427.
Okumura, S., G. Takagi, J. Kawabe, G. Yang, M. C. Lee, C. Hong, J. Liu, D. E. Vatner, J. Sadoshima, S. F. Vatner and Y. Ishikawa (2003). "Disruption of type 5 adenylyl cyclase gene preserves cardiac function against pressure overload." Proc Natl Acad Sci U S A 100(17): 9986-9990.
Passariello, C. L., J. Li, K. Dodge-Kafka and M. S. Kapiloff (2015). "mAKAP-a master scaffold for cardiac remodeling." J Cardiovasc Pharmacol 65(3): 218-225.
Passariello CL, Martinez EC, Thakur H, Cesareo M, Li J, Kapiloff MS (2016) RSK3 is required for concentric myocyte hypertrophy in an activated Rafl model for Noonan syndrome. J Mol Cell Cardiol 93:98-105.
Pawson T, Nash P (2003) Assembly of cell regulatory systems through protein interaction domains. Science 300:445-452.
Peter AK, Bjerke MA, Leinwand LA (2016) Biology of the cardiac myocyte in heart disease. Mol Biol Cell 27:2149-2160.
Ponikowski, P., A. A. Voors, S. D. Anker, H. Bueno, J. G. Cleland, A. J. Coats, V. Falk, J. R. Gonzalez-Juanatey, V. P. Harjola, E. A. Jankowska, M. Jessup, C. Linde, P. Nihoyannopoulos, J. T. Parissis, B. Pieske, J. P. Riley, G. M. Rosano, L. M. Ruilope, F. Ruschitzka, F. H. Rutten, P. van der Meer and M. Authors/Task Force (2016). "2016 ESC Guidelines for the diagnosis and treatment of acute and chronic heart failure: The Task Force for the diagnosis and treatment of acute and chronic heart failure of the European Society of Cardiology (ESC) Developed with the special contribution of the Heart Failure Association (HFA) of the ESC." Eur Heart J 37(27):2129-2200.
Potthoff MJ, Olson EN (2007) MEF2: a central regulator of diverse developmental programs. Development 134:4131-4140.
Prasad, K. M., Y. Xu, Z. Yang, S. T. Acton and B. A. French (2011). "Robust cardiomyocyte-specific gene expression following systemic injection of AAV: in vivo gene delivery follows a Poisson distribution." Gene Ther 18(1): 43-52.
Ranganathan A, Pearson GW, Chrestensen CA, Sturgill TW, Cobb MH (2006) The MAP kinase ERK5 binds to and phosphorylates p90 RSK. Arch Biochem Biophys 449:8-16.
Reiken S, Gaburjakova M, Gaburjakova J, He KI KL, Prieto A, Becker E, Yi Gh GH, Wang J, Burkhoff D, Marks AR (2001) beta-adrenergic receptor blockers restore cardiac calcium release channel (ryanodine receptor) structure and function in heart failure. Circulation 104:2843-2848.
Resjo S, Oknianska A, Zolnierowicz S, Manganiello V, Degerman E (1999) Phosphorylation and activation of phosphodiesterase type 38 (PDE3B) in adipocytes in response to serine/threonine phosphatase inhibitors: deactivation of PDE3B in vitro by protein phosphatase type 2A. Biochem J 341 (Pt 3):839-845.
Rivera VM, Miranti CK, Misr;i RP, Ginty DD, Chen RH, Blenis J, Greenberg ME (1993) A growth factor-induced kinase phosphorylates the serum response factor at a site that regulates its DNA-binding activity. Mol Cell Biol 13:6260-6273.
Schiattarella GG, Hill JA (2015) Inhibition of hypertrophy is a good therapeutic strategy in ventricular pressure overload. Circulation 131:1435-1447.
Scott JD, Dessauer CW, Tasken K (2013) Creating order from chaos: cellular regulation by kinase anchoring. Annu Rev Pharmacol Toxicol 53:187-210.
Scott, J. D. and T. Pawson (2009). "Cell signaling in space and time: where proteins come together and when they're apart." Science 326(5957): 1220-1224.
Sette C, Conti M (1996) Phosphorylation and activation of a CAMP-specific phosphodiesterase by the CAMP-dependent protein kinase. Involvement of serine 54 in the enzyme activation. J Biol Chern 271:16526-16534.
Sharma K, Kass DA (2014) Heart failure with preserved ejection fraction: mechanisms, clinical features, and therapies. Circ Res 115:79-96.
Silva, J. M., M. Z. Li, K. Chang, W. Ge, M. C. Golding, R. J. Rickles, D. Siolas, G. Hu, P. J. Paddison, M. R. Schlabach, N. Sheth, J. Bradshaw, J. Burchard, A. Kulkarni, G. Cavet, R. Sachidanandam, W. R. McCombie, M. A. Cleary, S. J. Elledge and G. J. Hannon (2005). "Second-generation shRNA libraries covering the mouse and human genomes." Nat Genet 37(11): 1281-1288.
Steinberg SF, Brunton LL (2001) Compartmentation of G protein-coupled signaling pathways in cardiac myocytes. Annu Rev Pharmacol Toxicol 41:751-773.
Treisman R (1985) Transient accumulation of c-fos RNA following serum stimulation requires a conserved 5' element and c-fos 3' sequences. Cell 42:889-902.
Valdivia HH, Kaplan JH, Ellis-Davies GC, Lederer WJ (1995) Rapid adaptation of cardiac ryanodine receptors: modulation by Mg2+ and phosphorylation. Science 267:1997-2000.
Virshup DM (2000) Protein phosphatase 2A: a panoply of enzymes. Curr Opin Cell Biol 12:180-185.
Wang X, Tang X, Li M, Marshall J, Mao Z (2005) Regulation of neuroprotective activity of myocyte-enhancer factor 2 by cAMP-protein kinase A signaling pathway in neuronal survival. J Biol Chem 280:16705-16713.
Wang, Y., E. G. Cameron, J. Li, T. L. Stiles, M. D. Kritzer, R. Lodhavia, J. Hertz, T. Nguyen, M. S. Kapiloff and J.L. Goldberg (2015). "Muscle A-Kinase Anchoring Protein-alpha is an Injury-Specific Signaling Scaffold Required for Neurotrophic- and Cyclic Adenosine Monophosphate-Mediated Survival." EBioMedicine 2(12): 1880-1887.
Wang, Z., H. I. Ma, J. Li, L. Sun, J. Zhang and X. Xiao (2003). "Rapid and highly efficient transduction by double-stranded adeno-associated virus vectors in vitro and in vivo." Gene Ther 10(26): 2105-2111.
Wera S, Hemmings BA (1995) Serine/threonine protein phosphatases. Biochem J 311 ( Pt 1):17-29.
Wilkins BJ, De Windt LJ, Bueno OF, Braz JC, Glascock BJ, Kimball TF, Molkentin JD (2002) Targeted disruption of NFATc3, but not NFATc4, reveals an intrinsic defect m calcineurin-mediated cardiac hypertrophic growth. Mol Cell Biol 22:7603-7613.
Wilkins BJ, Dai YS, Bueno OF, Parsons SA, Xu J, Plank DM, Jones F, Kimball TR, Molkentin JD (2004) Calcineurin/NFAT coupling participates in pathological, but not physiological, cardiac hypertrophy. Circ Res 94:110-118.
Wu X, Simpson J, Hong JH, Kim KH, Thavarajah NK, Backx PH, Neel BG, Araki T. MEK-ERK pathway modulation ameliorates disease phe-notypes in a mouse model of Noonan syndrome associated with the Raf1(L613V) mutation. J Clin Invest. 2011;121:1009-1025.
Writing Group, M., D. Mozaffarian, E. J. Benjamin, A. S. Go, D. K. Arnett, M. J. Blaha, M. Cushman, S. R. Das, S. de Ferranti, J. P. Despres, H. J. Fullerton, V. J. Howard, M. D. Huffman, C. R. Isasi, M. C. Jimenez, S. E. Judd, B. M. Kissela, J. H. Lichtman, L. D. Lisabeth, S. Liu, R. H. Mackey, D. J. Magid, D. K. McGuire, E. R. Mohler, 3rd, C. S. Moy, P. Muntner, M. E. Mussolino, K. Nasir, R. W. Neumar, G. Nichol, L. Palaniappan, D. K. Pandey, M. J. Reeves, C. J. Rodriguez, W. Rosamond, P. D. Sorlie, J. Stein, A. Towfighi, T. N. Turan, S. S. Virani, D. Woo, R. W. Yeh, M. B. Turner, C. American Heart Association Statistics and S. Stroke Statistics (2016). "Heart Disease and Stroke Statistics-2016 Update: A Report From the American Heart Association." Circulation 133(4): e38-360.
Wu H, Rothermel B, Kanatous S, Rosenberg P, Naya FJ, Shelton JM, Hutcheson KA, DiMaio JM, Olson EN, Bassel-Duby R, Williams RS (2001) Activation of MEF2 by muscle activity is mediated through a calcineurin-dependent pathway. EMBO J 20:6414-6423.
Xie M, Hill JA (2013) HDAC-dependent ventricular remodeling. Trends Cardiovasc Med 23:229-235.
Yang J, Drazba JA, Ferguson DG, Bond M (1998) A-kinase anchoring protein 100 (AKAPIOO) is localized in multiple subcellular compartments in the adult rat heart. J Cell Biol 142:511-522.
Zakhary DR, Fink MA, Ruehr ML, Bond M (2000) Selectivity and regulation of A-kinase anchoring proteins in the heart. The role of autophosphorylation of the type II regulatory subunit of cAMP-dependent protein kinase. J Biol Chem 275:41389-41395.

(56) References Cited

OTHER PUBLICATIONS

Zhang, L., S. Malik, J. Pang, H. Wang, K. M. Park, D. I. Yule, B. C. Blaxall and A. V. Smrcka (2013). "Phospholipase Cepsilon hydrolyzes perinuclear phosphatidylinositol 4-phosphate to regulate cardiac hypertrophy." Cell 153(1): 216-227.
Zhang Q, Bethmann C, Worth NF, Davies JD, Wasner C, Feuer A, Ragnauth CD, Yi Q, Mellad JA, Warren DT, Wheeler MA, Ellis JA, Skepper JN, Vorgerd M, Schlotter-Weigel B, Weissberg PL, Roberts RG, Wehnert M, Shanahan CM (2007) Nesprin-1 and -2 are involved in the pathogenesis of Emery Dreifuss muscular dystrophy and are critical for nuclear envelope integrity. Hum Mol Genet 16:2816-2833.
Marabotti, A., and Facchiano, A., "The misuse of terms in scientific literature," BioInformatics, vol. 26, No. 19, 2010, p. 2498.
McCartney, S., et al., "Cloning and characterization of A-kinase anchor protein 100 (AKAP100)," The Journal of Biological Chemistry, vol. 270, No. 16, Issue of Apr. 21, 1995, pp. 9327-9333.
Rababa'h, A., et al., "Protein kinase A and phosphodiesterase-4D3 binding to coding polymorphisms of cardiac muscle anchoring protein (mAKAP)," J Mol Biol., Sep. 2, 20133, 425(18), 23 pages.
Cell Biolabs Inc., Adenorviral Expression (https://www.cellbiolabs.com/adenoviral-expression, published online 2010).
International Search Report and Written Opinion in PCT/US2020/022721 dated Oct. 7, 2020, 12 pages.
Schulze et al., "Sodium/Calcium Exchanger (NCX1) Macromolecular Complex," J Biol Chem, vol. 278, No. 31, pp. 28849-28855 (2003).
Semenza, "Hypoxia-Inducible Factor 1 (HIF-1) Pathway," Science Signaling, vol. 407 cm8 (2007).
Semenza, "Regulation of Oxygen Homeostasis by Hypoxia-Inducible Factor 1," Physiology, vol. 24, pp. 97-106 (2009).
Sfichi-Duke et al., "Cardiomyopathy-causing deletion K210 in cardiac troponin T alters phosphorylation propensity of sarcomeric proteins," J Mol Cell Cardiol, vol. 48, pp. 934-942 (2010).
Shan et al., "Role of chronic ryanodine receptor phosphorylation in heart failure and β-adrenergic receptor blockade in mice," J Clin Invest, vol. 120, No. 12, pp. 4375-4387 (Dec. 2010).
Shan et al., "Phosphorylation of the ryanodine receptor mediates the cardiac fight or flight response in mice," J Clin Invest, vol. 120, No. 12, pp. 4388-4398 (Dec. 2010).
Shyu et al., "Intramyocardial injection of naked DNA encoding HIF-1α/VP16 hybrid to enhance angiogenesis in an acute myocardial infarction model in the rat," Cardiovasc Res, vol. 54, pp. 576-583 (2002).
Singh et al., "The Large Isoforms of A-Kinase Anchoring Protein 18 Mediate the Phosphorylation of Inhibitor-1 by Protein Kinase A and the Inhibition of Protein Phosphatase 1 Activity," Mol Pharmacol, vol. 79, No. 3, pp. 533-540 (2011).
Skroblin et al., "Mechanisms of Protein Kinase A Anchoring," Int Rev Cell Mol Biol, vol. 283, pp. 235-330 (2010).
Smith et al., "Identification of the First Specific Inhibitor of p90 Ribosomal S6 Kinase (RSK) Reveals an Unexpected Role for RSK in Cancer Cell Proliferation," Cancer Res, vol. 65, No. 3, pp. 1027-1034 (Feb. 1, 2005).
Smith et al., "AKAP-Lbc enhances cyclic AMP control of the ERK1/2 cascade," Nat Cell Biol, vol. 12, No. 12, pp. 1242-1249, (Dec. 2010).
Spinale et al., "Membrane-Associated Matrix Proteolysis and Heart Failure," Circ. Res., vol. 112, pp. 195-208 (Jan. 4, 2013).
Stelzer et al., "Differential Roles of Cardiac Myosin-Binding Protein C and Cardiac Troponin I in the Myofibrillar Force Responses to Protein Kinase A Phosphorylation," Circ Res, vol. 101, pp. 503-511 (Aug. 31, 2007).
Stiles et al., "The role of soluble adenylyl cyclase in neurite outgrowth," Biochimica et Biophysica Acta, vol. 1842, pp. 2561-2568 (2014).
Sumandea et al., "Cardiac Troponin T, a Sarcomeric AKAP, Tethers Protein Kinase A at the Myofilaments," J Biol Chem, vol. 286, No. 1, pp. 530-541 (Jan. 7, 2011).
Takeishi et al., "Activation of mitogen-activated protein kinases and p90 ribosomal S6 kinase in failing human hearts with dilated cardiomyopathy," Cardiovascular Research, vol. 53, pp. 131-137 (2002).
Terrenoire et al., "The Cardiac IKs Potassium Channel Macromolecular Complex Includes the Phosphodiesterase PDE4D3," J Biol Chem, vol. 284, No. 14, pp. 9140-9146 (Apr. 3, 2009).
Thomas et al., "Ribosomal S6 kinase 2 interacts with and phosphorylates PDZ domain-containing proteins and regulates AMPA receptor transmission," Proc Natl Acad Sci USA, vol. 102, No. 42, pp. 15006-15011 (Oct. 18, 2005).
Tingley et al., "Gene-trapped mouse embryonic stem cell-derived cardiac myocytes and human genetics implicate AKAP10 in heart rhythm regulation," Proc Natl Acad Sci USA, vol. 104, No. 20, pp. 8461-8466 (May 15, 2007).
Uys et al., "Myomegalin is a novel A-kinase anchoring protein involved in the phosphorylation of cardiac myosin binding protein C," BMC Cell Biol, vol. 12, No. 18 (2011).
Vargas et al., "Myocyte enhancer factor 2 (MEF2) tethering to muscle selective A-kinase anchoring protein (mAKAP) is necessary for myogenic differentiation," Cellular Signalling, vol. 24, pp. 1496-1503 (2012).
Welch et al., "Networking with AKAPs: Context-dependent Regulation of Anchored Enzymes," Mol Interv, vol. 10, Issue 2, pp. 86-97 (Apr. 2010).
Wollert et al., "Cardiotrophin-1 Activates a Distinct Form of Cardiac Muscle Cell Hypertrophy. Assembly of sarcomeric units in series VIA gp130/leukemia inhibitory factor receptor-dependent pathways," J Biol Chem, vol. 271, No. 16, pp. 9535-9545 (1996).
Wong et al., "mAKAP Compartmentalizes Oxygen-Dependent Control of HIF-1α," Sci Signal, vol. 1, Issue 51, pp. 1-9(Dec. 23, 2008).
Wu et al., "MEK-ERK pathway modulation ameliorates disease phenotypes in a mouse model of Noonan syndrome associated with the Raf1(L613V) mutation," J Clin Invest\, vol. 121, pp. 1009-1025 (Mar. 2011).
Xu et al., "Cardiomyocyte-Specific Loss of Neurofibromin Promotes Cardiac Hypertrophy and Dysfunction," Circ Res, vol. 105, pp. 304-311 (Jul. 31, 2009).
Yang et al., "Enhanced cardiac PI3Kα signalling mitigates arrhythmogenic electrical remodelling in pathological hypertrophy and heart failure," Cardiovasc Res, vol. 93, pp. 252-262 (2012).
Zhang et al., "Phospholipase Cϵ Scaffolds to Muscle-specific A Kinase Anchoring Protein (mAKAPβ) and Integrates Multiple Hypertrophic Stimuli in Cardiac Myocytes," Journal of Biological Chemistry, vol. 286, No. 26, pp. 23012-23021 (Jul. 1, 2011).
Zhao et al., "Regulation and Interaction of pp90(rsk) Isoforms with Mitogen-activated Protein Kinases," J Biol Chem, vol. 271, No. 47, pp. 29773-29779 (1996).
Lin et al., "Molecular cloning of a brain-specific calcium/calmodulin-dependent protein kinase," Proc. Natl. Acad. Sci. USA, vol. 84, pp. 5962-5966 (Aug. 1987).
Graeme K Carnegie et al., "AKAP-Lbc mobilizes a cardiac hypertrophy signaling pathway," Mol Cell. 32(2): pp. 169-179 (Oct. 24, 2008).
Yi Zhao et al., "RSK3 Encodes a Novel pp90rsk Isoform with a Unique N-Terminal Sequence: Growth Factor-Stimulated Kinase Function and Nuclear Translocation," Molecular and Cellular Biology, vol. 15, No. 8, pp. 4353-4363 (Aug. 1995).
"Genome sequence of the Brown Norway rat yields insight into mammalian evolution," Nature, vol. 428, pp. 493-521 (Apr. 2004).
Lundby, A., et al., "Quantitative maps of protein phosphorylation sites across 14 different rat organs and tissues," Nature Communications, 3:876, 10 pages, Jun. 6, 2012.
Daya et al., 2008, Gene Therapy Using Adeno-Associated Virus Vectors, Clinical Microbiology Reviews, 21(4):583-593.
Abrenica et al., "The A-kinase anchor protein AKAP121 is a negative regulator of cardiomyocyte hypertrophy," J Mol Cell Cardiol, vol. 46, pp. 674-681 (2009).
Anjum et al., "The RSK family of kinases: emerging roles in cellular signalling," Nat Rev Mol Cell Biol, vol. 9, pp. 747-758 (Oct. 2008).
Amirak et al., "p90 Ribosomal S6 kinases play a significant role in early gene regulation in the cardiomyocyte response to Gq-protein-

(56) References Cited

OTHER PUBLICATIONS coupled receptor stimuli, endothelin-1 and α1-adrenergic receptor agonists," Biochemical Journal, vol. 456, pp. 351-363 (2013).
Appert-Collin et al., "The A-kinase anchoring protein (AKAP)-Lbc-signaling complex mediates α1 adrenergic receptor-induced cardiomyocyte hypertrophy," Proc Natl Acad Sci USA, vol. 104, pp. 10140-10145 (Jun. 12, 2007).
Avkiran et al., "Targeting Na+/H+ exchanger regulation for cardiac protection: a RSKy approach?" Curr Opin Pharmacol, vol. 8, pp. 133-140 (2008).
Bain et al., "The selectivity of protein kinase inhibitors: a further update," Biochem J, vol. 408, pp. 297-315 (2007).
Bauman et al., "The mAKAP Signalosome and Cardiac Myocyte Hypertrophy," IUBMB Life, vol. 59, No. 3, pp. 163-169, (Mar. 2007).
Beene et al., "A-kinase anchoring proteins take shape," Curr Opin Cell Biol, vol. 19, pp. 192-198 (2007).
Bers, "Calcium Cycling and Signaling in Cardiac Myocytes," Annu Rev Physiol, vol. 70, pp. 23-49 (2008).
Brown et al., "The Rac and Rho Hall of Fame: A Decade of Hypertrophic Signaling Hits," Circ Res, vol. 98, pp. 730-742 (2006).
Buck et al., "C/EBPβ-Thr217 Phosphorylation Signaling Contributes to the Development of Lung Injury and Fibrosis in Mice," PLoS One, vol. 6, Issue 10, e25497 (Oct. 2011).
Burns-Hamuro et al., "Designing isoform-specific peptide disruptors of protein kinase A localization," Proceedings of the National Academy of Sciences, vol. 100, No. 7, pp. 4072-4077 (Apr. 1, 2003).
Cappola, "Molecular Remodeling in Human Heart Failure," J Am Coll Cardiol, vol. 51, No. 2, pp. 137-138 (2008).
Cariolato et al., "A-Kinase Anchoring Protein (AKAP)-Lbc Anchors a PKN-based Signaling Complex Involved in α1-Adrenergic Receptor-induced p38 Activation," J Biol Chem, vol. 286, No. 10, pp. 7925-7937 (Mar. 11, 2011).
Carlucci et al., "Control of mitochondria dynamics and oxidative metabolism by CAMP, AKAPs and the proteasome," Trends in Cell Biol, vol. 18, No. 12, pp. 604-613 (Oct. 24, 2008).
Carnegie et al., "AKAP-Lbc Nucleates a Protein Kinase D Activation Scaffold," Mol Cell, vol. 15, pp. 889-899 (Sep. 24, 2004).
Chaturvedi et al., "Subcellular Localization and Biological Actions of Activated RSK1 Are Determined by Its Interactions with Subunits of Cyclic AMP-Dependent Protein Kinase," Mol Cell Biol, vol. 26, No. 12, pp. 4586-4600 (Jun. 2006).
Chen et al., "Phosphorylation of the A-kinase anchoring Protein Yotiao Contributes to Protein Kinase A Regulation of a Heart Potassium Channel," J. Biol. Chem., vol. 280, pp. 31347-31352 (2005).
Chen et al., "Mutation of an A-kinase-anchoring protein causes long-QT syndrome," Proc Natl Acad Sci USA, vol. 104, No. 52, pp. 20990-20995 (Dec. 26, 2007).
Chen et al., "Protein kinase A-induced myofilament desensitization to Ca2+ as a result of phosphorylation of cardiac myosin-binding protein C," J. Gen. Physiol., vol. 136, No. 6, pp. 615-627 (Nov. 29, 2010).
Christian et al., "Small Molecule AKAP-Protein Kinase A (PKA) Interaction Disruptors That Activate PKA Interfere with Compartmentalized cAMP Signaling in Cardiac Myocytes," J Biol Chem, No. 286, pp. 9079-9096 (Mar. 18, 2011).
Cuello et al., "Evidence for Direct Regulation of Myocardial Na+/H+ Exchanger Isoform 1 Phosphorylation and Activity by 90-kDa Ribosomal S6 Kinase (RSK): Effects of the Novel and Specific RSK Inhibitor fmk on Responses to α1-Adrenergic Stimulation," Molecular Pharmacology, vol. 71, No. 3, pp. 799-806 (2007).
Diviani et al., "Anchoring of both PKA and 14-3-3 inhibits the Rho-GEF activity of the AKAP-Lbc signaling complex," EMBO J, vol. 23, No. 14, pp. 2811-2820 (2004).
Diviani et al., "A-kinase anchoring proteins: scaffolding proteins in the heart," Am J Physiol Heart Circ Physiol, vol. 301, pp. H1742-53 (2011).
Diviani et al., "AKAP-Lbc Anchors Protein Kinase A and Nucleates G α12-selective Rho-mediated Stress Fiber Formation," J Biol Chem, vol. 276, pp. 44247-44257 (2001).
Dodge et al., "mAKAP assembles a protein kinase A/PDE4 phosphodiesterase cAMP signaling module," EMBO J, vol. 20, No. 8, pp. 1921-1930 (2001).
Dodge-Kafka et al., "A-Kinase Anchoring Proteins as the Basis for cAMP Signaling," Handb Exp Pharmacol, vol. 186, pp. 3-14 (2008).
Dodge-Kafka et al., "CAMP-stimulated Protein Phosphatase 2A Activity Associated with Muscle A kinase-anchoring Protein (mAKAP) Signaling Complexes Inhibits the Phosphorylation and Activity of the cAMP-specific Phosphodiesterase PDE4D3," J Biol Chem, vol. 285, No. 15, pp. 11078-11086 (Apr. 9, 2010).
Dodge-Kafka et al., "The mAKAP signaling complex: Integration of CAMP, calcium, and MAP kinase signaling pathways," Eur J Cell Biol, vol. 85, pp. 593-602 (2006).
Dodge-Kafka et al., "The protein kinase A anchoring protein mAKAP coordinates two integrated cAMP effector pathways," Nature, vol. 437, pp. 574-578 (Sep. 22, 2005).
Dummler et al., "Functional Characterization of Human RSK4, a New 90-kDa Ribosomal S6 Kinase, Reveals Constitutive Activation in Most Cell Types," J Biol Chem, vol. 280, No. 14, pp. 13304-13314 (2005).
Edgley et al., "Targeting Fibrosis for the Treatment of Heart Failure: A Role for Transforming Growth Factor-β," Cardiovasc Ther, vol. 30, pp. e30-e40 (2012).
Eide et al., "Molecular Cloning, Chromosomal Localization, and Cell Cycle-Dependent Subcellular Distribution of the A-Kinase Anchoring Protein, AKAP95," Exp Cell Res, vol. 238, pp. 305-316 (1998).
Escobar et al., "Structural evidence for perinuclear calcium microdomains in cardiac myocytes," J Mol Cell Cardiol, vol. 50, pp. 451-459 (2011).
Fabiato, "Calcium-induced release of calcium from the cardiac sarcoplasmic reticulum," American Physiological Society, pp. C1-C14 (1983).
Farah et al., "The troponin complex and regulation of muscle contraction," FASEB J, vol. 9, pp. 755-767 (Jun. 1995).
Faul et al., "Protein Kinase A, Ca2+/Calmodulin-Dependent Kinase II, and Calcineurin egulate the Intracellular Trafficking of Myopodin between the Z-Disc and the Nucleus of Cardiac Myocytes," Mol Cell Biol, vol. 27, No. 23, pp. 8215-8227 (Dec. 2007).
Fink et al., "AKAP-Mediated Targeting of Protein Kinase A Regulates Contractility in Cardiac Myocytes," Circ Res, pp. 291-297 (Feb. 16, 2001).
Fisher et al., "Evidence for Two Catalytically Active Kinase Domains in pp90rsk," Molecular and Cellular Biology, vol. 16, No. 3, pp. 1212-1219 (Mar. 1996).
Fodstad et al., "Four potassium channel mutations account for 73% of the genetic spectrum underlying long-QT syndrome (LQTS) and provide evidence for a strong founder effect in Finland," Ann Med, vol. 36 (Suppl 1), pp. 53-63, (2004).
Francis et al., "Structure and function of cyclic nucleotide-dependent protein kinases," Annu. Rev. Physiol., vol. 56, pp. 237-272 (1994).
Fraser et al., "A novel lipid-anchored A-kinase Anchoring Protein facilitates cAMP-responsive membrane events," EMBO J, vol. 17, No. 8, pp. 2261-2272 (1998).
Frey et al., "Hypertrophy of the Heart: A New Therapeutic Target?" Circulation, vol. 109, pp. 1580-1589 (2004).
Fuller et al., "Molecular Mechanism of Calcium Channel Regulation in the Fight-or-Flight Response," Sci Signal, vol. 3, Issue 141 ra70 (Sep. 28, 2010).
Gaffin et al., "Long-term rescue of a familial hypertrophic cardiomyopathy caused by a mutation in the thin filament protein, tropomyosin, via modulation of a calcium cycling protein," J. Mol. Cell. Cardiol., vol. 51, pp. 812-820 (2011).
Gao et al., "CAMP-Dependent Regulation of Cardiac L-type Ca2+ Channels Requires Membrane Targeting of PKA and Phosphorylation of Channel Subunits," Neuron, vol. 19, pp. 185-196 (Jul. 1997).

(56) References Cited

OTHER PUBLICATIONS

Gao et al., "Rational design and characterization of a Rac GTPase-specific small molecule inhibitor," Proc Natl Acad Sci USA, vol. 101, No. 20, pp. 7618-7623 (May 18, 2004).
Gelb et al., "RAS signaling pathway mutations and hypertrophic cardiomyopathy: getting into and out of the thick of it," J Clin Invest, vol. 121, No. 3, pp. 844-847 (Mar. 2011).
Gentilucci et al., "Peptides and Peptidomimetics in Medicine, Surgery and Biotechnology," Curr Med Chem, vol. 13, pp. 2449-2466 (2006).
Gold et al., "Molecular Basis of AKAP Specificity for PKA Regulatory Subunits," Mol Cell, vol. 24. pp. 383-395 (Nov. 3, 2006).
International Preliminary Report issued in PCT/US2018/040913 dated Nov. 15, 2019, 23 pages.
Lee, S. et al., "AKAP6 inhibition impairs myoblast differentiation and muscle regeneration: Positive loop between AKAP6 and myogenin," Scientific Reports 5, doi: 10.1038/srep16523, Nov. 13, 2015, pp. 1-14.
Kapiloff, M. S. et al., "Disruption of RSK3 binding to muscle A-kinase anchoring protein in vivo via adeno-associated virus expression of a competing peptide attenuates pressure overload-induced cardiac hypertrophy," J Clin Exp Cardiolog, vol. 6, Issue 4, 2015, 8 pages.
International Search Report and Written Opinion, PCT/US2018/040913, dated Nov. 6, 2018, 19 pages.
Kapiloff, M. S., "mAKAP: A Scaffold that Coordinates Stress-Related Cardiac Signal Transduction," American Heart Association Council on Basic Cardiovascular Sciences, 2011 Scientific Sessions, New Orleans, Louisiana, 21 pages.
Goldschmidt-Clermont et al., "Inflammation, stem cells and atherosclerosis genetics," Curr Opin Mol Ther, vol. 12, No. 6, pp. 712-723 (2010).
Good et al., "Scaffold Proteins: Hubs for Controlling the Flow of Cellular Information," Science, vol. 332, pp. 680-686 (May 6, 2011).
Gould et al., "cDNA cloning and sequencing of the protein-tyrosine kinase substrate, ezrin, reveals homology to band 4.1.," EMBO J, vol. 8, No. 13, pp. 4133-4142 (1989).
Gray et al., "Regulation of ion channels by cAMP-dependent protein kinase and A-kinase anchoring proteins," Curr Opin Neurobiol, vol. 8, pp. 330-334 (1998).
Guo et al., "Kinetics of FKBP12.6 Binding to Ryanodine Receptors in Permeabilized Cardiac Myocytes and Effects on Ca Sparks," Circ Res, vol. 106, pp. 1743-1752 (Jun. 11, 2010).
Hagemann et al., "Dual Site Phospholamban Phosphorylation and Its Physiological Relevance in the Heart," Trends Cardiovasc Med, vol. 12, No. 2, pp. 51-56 (2002).
Hanks et al., "The Protein Kinase Family: Conserved Features and Deduced Phylogeny of the Catalytic Comains," Science, vol. 241, pp. 42-52 (Jul. 1, 1988).
Harada et al., "Phosphorylation and Inactivation of BAD by Mitochondria-Anchored Protein Kinase A," Mol Cell, vol. 3, pp. 413-422 (Apr. 1999).
Hell, "β-Adrenergic Regulation of the L-Type Ca2+ Channel CaV1.2 by PKA Rekindles Excitement," Sci Signal, vol. 3, Issue 141 pe33, pp. 1-4 (Sep. 28, 2010).
Henn et al., "Identification of a Novel A-kinase Anchoring Protein 18 Isoform and Evidence for Its Role in the Vasopressin-induced Aquaporin-2 Shuttle in Renal Principal Cells," J Biol Chem, vol. 279, No. 25, pp. 26654-26665, (2004).
Hill et al., "Cardiac Plasticity," N Engl J Med, vol. 358, No. 13, pp. 1370-1380 (Mar. 27, 2008).
Huang et al., "D-AKAP2, a novel protein kinase A anchoring protein with a putative RGS domain," Proc Natl Acad Sci USA, vol. 94, pp. 11184-11189 (Oct. 1997).
Huang et al., "Identification of a Novel Protein Kinase A Anchoring Protein That Binds Both Type I and Type II Regulatory Subunits," J. Biol. Chem., vol. 272, pp. 8057-8064 (1997).
Hulme et al., "A Novel Leucine Zipper Targets AKAP15 and Cyclic AMP-dependent Protein Kinase to the C Terminus of the Skeletal Muscle Ca2+ Channel and Modulates Its Function," J Biol Chem, vol. 277, No. 6, pp. 4079-4087 (2002).
Hulme et al., "β-Adrenergic regulation requires direct anchoring of PKA to cardiac CaV1.2 channels via a leucine zipper interaction with A kinase-anchoring protein 15," Proc Natl Acad Sci USA, vol. 100, No. 22, pp. 13093- 13098 (Oct. 28, 2003).
Hulme et al., "Phosphorylation of serine 1928 in the distal C-terminal domain of cardiac CaV1.2 channels during β1-adrenergic regulation," Proc Natl Acad Sci USA, vol. 103, No. 44, pp. 16574-16579 (Oct. 31, 2006).
Hundsrucker et al., "Direct AKAP-Mediated Protein-Protein Interactions as Potential Drug Targets," Hand Exp Pharmacol, vol. 186, pp. 483-503 (2008).
Hundsrucker et al., "High-affinity AKAP7σ-protein kinase A interaction yields novel protein kinase A-anchoring disruptor peptides," Biochem. J., vol. 396, pp. 297-306 (2006).
Itho et al., "Role of p90 Ribosomal S6 Kinase-Mediated Prorenin-Converting Enzyme in Ischemic and Diabetic Myocardium," Circulation, vol. 113, pp. 1787-1798 (Apr. 11, 2006).
Jaakkola et al., "Targeting of HIF-α to the von Hippel-Lindau Ubiquitylation Complex by O2-Regulated Prolyl Hydroxylation," Science, vol. 292, pp. 468-472 (Apr. 20, 2001).
Kamisago et al., "Mutations in sarcomere protein genes as a cause of dilated cardiomyopathy," N Engl J Med, vol. 343, No. 23, pp. 1688-1696 (Dec. 7, 2000).
Kammerer et al., "Amino acid variant in the kinase binding domain of dual-specific A kinase-anchoring protein 2: A disease susceptibility polymorphism," Proc Natl Acad Sci USA, vol. 100, No. 7, pp. 4066-4071 (Apr. 1, 2003).
Kapiloff et al., "mAKAP and the ryanodine receptor are part of a multi-component signaling complex on the cardiomyocyte nuclear envelope," J Cell Sci, vol. 114, No. 17, pp. 3167-3176 (2001).
Kapiloff et al., "A-kinase Anchoring Proteins: Temporal and Spatial Regulation of Intracellular Signal Transduction in the Cardiovascular System," Journal Cardiovasc Pharmacol, vol. 58, No. 4, pp. 337-338 (Oct. 2011).
Kapiloff et al., "mAKAP: an A-kinase anchoring protein targeted to the nuclear membrane of differentiated myocytes," J Cell Sci, vol. 112, pp. 2725-2736 (1999).
Kapiloff et al., "An Adenylyl Cyclase-mAKAPβ Signaling Complex Regulates CAMP Levels in Cardiac Myocytes," J Biol Chem, vol. 284, No. 35, pp. 23540-23546 (Aug. 28, 2009).
Kapiloff et al., "Calcium/calmodulin-dependent protein kinase mediates a pathway for transcriptional regulation," Proc. Natl. Acad. Sci. USA, vol. 88, pp. 3710-3714 (May 1991).
Kapiloff et al., "Variable Effects of Phosphorylation of Pit-1 Dictated by the DNA Response Elements," Science, vol. 253, pp. 786-789 (Aug. 16, 1991).
Kapiloff, "Contributions of Protein Kinase A Anchoring Proteins to Compartmentation of CAMP Signaling in the Heart," Molecular Pharmacology, vol. 62, No. 2, pp. 193-199 (2002).
Kehat et al., "Molecular Pathways Underlying Cardiac Remodeling During Pathophysiological Stimulation," Circulation, vol. 122, pp. 2727-2735 (2010).
Kehat et al., "Extracellular Signal-Regulated Kinases 1 and 2 Regulate the Balance Between Eccentric and Concentric Cardiac Growth," Circ Res, vol. 108, pp. 176-183 (2011).
Kentish et al., "Phosphorylation of Troponin I by Protein Kinase A Accelerates Relaxation and Crossbridge Cycle Kinetics in Mouse Ventricular Muscle," Circ Res, vol. 88, pp. 1059-1065 (May 25, 2001).
Kido et al., "Hypoxia-Inducible Factor 1-Alpha Reduces Infarction and Attenuates Progression of Cardiac Dysfunction After Myocardial Infarction in the Mouse," J Am Coll Cardiol, vol. 46, No. 11, pp. 2116-2124 (Dec. 6, 2005).
Kimura et al., "Targeted Deletion of the Extracellular Signal-Regulated Protein Kinase 5 Attenuates Hypertrophic Response and Promotes Pressure Overload-Induced Apoptosis in the Heart," Circ Res, vol. 106, pp. 961-970 (Mar. 19, 2010).
Kinderman et al., "A Novel and Dynamic Mechanism for AKAP Binding to RII Isoforms of CAMP-dependent Protein Kinase," Mol Cell., vol. 24, No. 3, pp. 397-408 (Nov. 3, 2006).

(56) References Cited

OTHER PUBLICATIONS

Klussmann et al., "Ht31: the first protein kinase A anchoring protein to integrate protein kinase A and Rho signaling," FEBS Lett, vol. 507, pp. 264-268 (2001).
Kodama et al., "Significance of ERK cascade compared with JAK/STAT and PI3-K pathway in gp130-mediated cardiac hypertrophy," Am J Physiol Heart Circ Physiol, vol. 279, pp. H1635-H1644 (2000).
Kontaridis et al., "Deletion of Ptpn11 (Shp2) in Cardiomyocytes Causes Dilated Cardiomyopathy via Effects on the Extracellular Signal-Regulated Kinase/Mitogen-Activated Protein Kinase and RhoA Signaling Pathways," Circulation, vol. 117, pp. 1423-1435 (2008).
Kritzer et al., "AKAPs: The architectural underpinnings of local cAMP signaling," J Mol Cell Cardiol, vol. 52, pp. 351-358 (2012).
Kritzer et al., "The Scaffold Protein Muscle A-Kinase Anchoring Protein β Orchestrates Cardiac Myocyte Hypertrophic Signaling Required for the Development of Heart Failure," Circulation Heart Failure, vol. 7, pp. 663-672 (Jul. 2014).
Lacana et al., "Cloning and Characterization of a Protein Kinase A Anchoring Protein (AKAP)-related Protein That Interacts with and Regulates Sphingosine Kinase 1 Activity," J Biol Chem, vol. 277, No. 36, pp. 32947-32953 (2002).
Layland et al., "Regulation of cardiac contractile function by troponin I phosphorylation," Cardiovasc Res, vol. 66, pp. 12-21 (2005).
Lester et al., "Anchoring of protein kinase A facilitates hormone-mediated insulin secretion," Proc Natl Acad Sci USA, vol. 94, pp. 14942-14947 (Dec. 1997).
Li et al., "Protein kinase A-anchoring (AKAP) domains in brefeldin A-inhibited guanine nucleotide-exchange protein 2 (BIG2)," Proc Natl Acad Sci USA, vol. 100, No. 4, pp. 1627-1632 (Feb. 18, 2003).
Li et al., "The mAKAPβ scaffold regulates cardiac myocyte hypertrophy via recruitment of activated calcineurin," Journal of Molecular and Cellular Cardiology, vol. 48, pp. 387-394 (2010).
Li et al., "Regulation of MEF2 transcriptional activity by calcineurin/mAKAP complexes," Exp Cell Res, vol. 319, pp. 447-454 (2013).
Li et al., "Anchored p90 Ribosomal S6 Kinase 3 Is Required for Cardiac Myocyte Hypertrophy," Cellular Research, vol. 112, pp. 128-139 (Jan. 4, 2013).
Lohse et al., "What Is the Role of β-Adrenergic Signaling in Heart Failure?" Circ Res, vol. 93, pp. 896-906 (Nov. 14, 2003).
Lu et al., "Recent progress in congenital long QT syndrome," Curr Opin Cardiol., vol. 25, No. 3, pp. 216-221 (May 2010).
Lygren et al., "AKAP-complex regulates the Ca2+ re-uptake into heart sarcoplasmic reticulum," EMBO Rep, vol. 8, No. 11, pp. 1061-1067 (2007).
Lygren B et al., "The potential use of AKAP18σ as a drug target in heart failure patients," Expert Opin. Biol. Ther., vol. 8, pp. 1099-1108 (2008).
Maekawa et al., "Inhibiting p90 Ribosomal S6 Kinase Prevents Na+-H+ Exchanger-Mediated Cardiac Ischemia-Reperfusion Injury," Circulation, vol. 113, pp. 2516-2523 (2006).
Maloney et al., "Synthesis of a Potent and Selective Inhibitor of p90 Rsk," Org. Lett., vol. 7, No. 6, pp. 1097-1099 (2005).
Maron et al., "Hypertrophic cardiomyopathy," Lancet, vol. 381, pp. 242-255 (Jan. 19, 2013).
Maruyama et al., "Gα12/13 Mediates α1-Adrenergic Receptor-Induced Cardiac Hypertrophy," Circ Res, vol. 91, pp. 961-969 (Nov. 15, 2002).
Marx et al., "PKA Phosphorylation Dissociates FKBP12.6 from the Calcium Release Channel (Ryanodine Receptor): Defective Regulation in Failing Hearts," Cell, vol. 101, pp. 365-376 (May 12, 2000).
Marx et al., "Phosphorylation-dependent Regulation of Ryanodine Receptors: A Novel Role for Leucine/Isoleucine Zippers," J Cell Biol, vol. 153, pp. 699-708 (May 7, 2001).
Marx et al., "Requirement of a Macromolecular Signaling Complex for β Adrenergic Receptor Modulation of the KCNQ1-KCNE1 Potassium Channel," Science, vol. 295, pp. 496-499 (Jan. 18, 2002).
Maxwell et al., "The tumour suppressor protein VHL targets hypoxia-inducible factors for oxygen-dependent proteolysis," Nature, vol. 399, pp. 271-275 (May 20, 1999).
Mayers et al., "The Rho Guanine Nucleotide Exchange Factor AKAP13 (BRX) Is Essential for Cardiac Development in Mice," J Biol Chem, vol. 285, No. 16, pp. 12344-12354 (Apr. 16, 2010).
McConnell et al., "Disruption of Protein Kinase A Interaction with A-kinase-anchoring Proteins in the Heart in vivo: effects on cardiac contractility, protein kinase A phosphorylation, and troponin I proteolysis," J Biol Chem, vol. 284, No. 3, pp. 1583-1592 (Jan. 16, 2009).
McKinsey et al., "Small-molecule therapies for cardiac hypertrophy: moving beneath the cell surface," Nat Rev Drug Discov, vol. 6, pp. 617-635 (Aug. 2007).
Michel et al., "Spatial Restriction of PDK1 Activation Cascades by Anchoring to mAKAPα," Molecular Cell, vol. 20, pp. 661-672 (Dec. 9, 2005).
Michele et al., "Cardiac Dysfunction in Hypertrophic Cardiomyopathy Mutant Tropomyosin Mice is Transgene-Dependent, Hypertrophy-Independent, and Improved by β-blockade," Circ. Res, vol. 91, pp. 255-262 (Aug. 9, 2002).
Morissette et al., "The Rho effector, PKN, regulates ANF gene transcription in cardiomyocytes through a serum response element," Am J Physiol Heart Circ Physiol, vol. 278, pp. H1769-H1774 (2000).
Naga Prasad et al., "Agonist-dependent Recruitment of Phosphoinositide 3-Kinase to the Membrane by β-Adrenergic Receptor Kinase 1: A role in receptor sequestration," J Biol Chem, vol. 276, No. 22, pp. 18953-18959 (2001).
Naga Prasad et al., "Phosphoinositide 3-kinase regulates β2-adrenergic receptor endocytosis by AP-2 recruitment to the receptor/β-arrestin complex," J Cell Biol, vol. 158, No. 3, pp. 563-575 (Nov. 3, 2002).
Nakagami et al., "Gene Polymorphism of Myospryn (Cardiomyopathy-Associated 5) Is Associated with Left Ventricular Wall Thickness in Patients with Hypertension," Hypertens Res, vol. 30, No. 12, pp. 1239-1246 (2007).
Nakamura et al., "LV systolic performance improves with development of hypertrophy after transverse aortic constriction in mice," Am J Physiol Heart Circ Physiol, vol. 281, pp. H1104-H1112 (Sep. 2001).
Nakayama et al., "Siah2 Regulates Stability of Prolyl-Hydroxylases, Controls HIF1α Abundance, and Modulates Physiological Responses to Hypoxia," Cell, vol. 117, pp. 941-952 (Jun. 25, 2004).
Nauert et al., "Gravin, an autoantigen recognized by serum from myasthenia gravis patients, is a kinase scaffold protein," Curr Biol, vol. 7, No. 1, pp. 52-62 (1996).
Nerbonne et al., "Molecular Physiology of Cardiac Repolarization," Physiol Rev, vol. 85, pp. 1205-1253 (Oct. 2005).
Negro et al., "Signalosomes as therapeutic targets," Prog Pediatr Cardiol, vol. 25, pp. 51-56 (2008).
Nichols et al., "Sympathetic Stimulation of Adult Cardiomyocytes Requires Association of AKAP5 With a Subpopulation of L-Type Calcium Channels," Circ Res, vol. 107, pp. 747-756 (Sep. 17, 2010).
Nicol et al., "Activated MEK5 induces serial assembly of sarcomeres and eccentric cardiac hypertrophy," EMBO J., vol. 20, No. 11, pp. 2757-2767 (2001).
Niggli et al., "Voltage-Independent Calcium Release in Heart Muscle," Science, vol. 250, No. 4980, pp. 565-568 (Oct. 26, 1990).
Oka et al., "Genetic Nanipulation of Periostin Expression Reveals a Role in Cardiac Hypertrophy and Ventricular Remodeling," Circ. Res, vol. 101, pp. 313-321 (Aug. 3, 2007).
Papa et al., "The NADH: Ubiquinone Oxidoreductase (Complex I) of the Mammalian Respiratory Chain and the CAMP Cascade," Journal of Bioenergetics and Biomembranes, vol. 34, No. 1, pp. 1-10 (Feb. 2002).
Pare et al., "Nesprin-1α contributes to the targeting of mAKAP to the cardiac myocyte nuclear envelope," Exp Cell Res, vol. 303, pp. 388-399 (2005).
Pare et al., "The mAKAP complex participates in the induction of cardiac myocyte hypertrophy by adrenergic receptor signaling," Journal of Cell Science, vol. 118, pp. 5637-5646 (2005).

(56) References Cited

OTHER PUBLICATIONS

Passariello et al., "p90 ribosomal S6 kinase 3 contributes to cardiac insufficiency in a-tropomyosin Glu180Gly transgenic mice," Am J Physiol Heart Circ Physiol, vol. 305, pp. H1010-H1019 (2013).
Passariello et al., "Disruption of RSK3 binding to muscle A-kinase anchoring protein in vivo via adeno-associated virus expression of a competing peptide attenuates pressure overload-inducted cardiac hypertrophy," Journal of Molecular and Cellular Cardiology, Abstracts from the 2014 ISHR-NAS Annual Meeting, Miami, Florida, USA, vol. 74, p. S5 (2014).
Patel et al., "Disruption of Protein Kinase A Localization Using a Trans-activator of Transcription (TAT)-conjugated A-kinase-anchoring Peptide Reduces Cardiac Function," J Biol Chem, vol. 285, No. 36, pp. 27632-27640 (Sep. 3, 2010).
Pawson et al., "Signal integration through blending, bolstering and bifurcating of intracellular information," Nat Struct Mol Biol, vol. 17, No., 6, pp. 653-658 (Jun. 6, 2010).
Perino et al., "Integrating Cardiac PIP3 and cAMP Signaling through a PKA Anchoring Function of p110γ," Mol Cell., vol. 42, No. 1, pp. 84-95 (Apr. 8, 2011).
Perrino et al., "Intermittent pressure overload triggers hypertrophy-independent cardiac dysfunction and vascular rarefaction," J Clin Invest, vol. 116, No. 6, pp. 1547-1560 (Jun. 2006).
Perrino et al., "AKAP121 downregulation impairs protective cAMP signals, promotes mitochon-drial dysfunction, and increases oxidative stress," Cardiovasc Res, vol. 88, pp. 101-110 (2010).
Prabhakar et al., "A Familial Hypertrophic Cardiomyopathy α-Tropomyosin Mutation Causes Severe Cardiac Hypertrophy and Death in Mice," J Mol Cell Cardiol, vol. 33 pp. 1815-1828 (2001).
Reynolds et al., "Identification and mapping of protein kinase A binding sites in the costameric protein myospryn," Biochim Biophys Acta, vol. 1773, No. 6, pp. 891-902 (Jun. 2007).
Richards et al., "Characterization of Regulatory Events Associated with Membrane Targeting of p90 Ribosomal S6 Kinase 1," Mol Cell Biol, vol. 21, No. 21, pp. 7470-7480 (2001).
Rockman et al., "Segregation of atrial-specific and inducible expression of an atrial natriuretic factor transgene in an in vivo murine model of cardiac hypertrophy," Proc Natl Acad Sci USA, vol. 88, pp. 8277-8281 (Sep. 1991).
Rockman et al., "Seven-transmembrane-spanning receptors and heart function," Nature, vol. 415, pp. 206-212 (Jan. 10, 2002).
Roger et al., "Heart Disease and Stroke Statistics—2011 Update: A Report From the American Heart Association," Circulation, vol. 123, pp. e18-e209 (Feb. 1, 2011).
Rose et al., "Mitogen-Activated Protein Kinase Signaling in the Heart: Angels Versus Demons in a Heart-Breaking Tale," Physiol Rev., vol. 90, No. 4, pp. 1507-1546 (Oct. 2010).
Rusconi et al., "CIP4 is required for the hypertrophic growth of neonatal cardiac myocytes," Journal of Biomedical Science, vol. 20, No. 56, pp. 1-7 (2013).
Russell et al., "The intermediate filament protein, synemin, is an AKAP in the heart," Arch Biochem Biophys, vol. 456, pp. 204-215 (2006).
Sadoshima et al., "Angiotensin II and Other Hypertrophic Stimuli Mediated by G Protein-Coupled Receptors Activate Tyrosine Kinase, Mitogen-Activated Protein Kinase, and 90-KD S6 Kinase in Cardiac Myocytes. The Critical Role of Ca(2+)-Dependent Signaling," Circ. Res, vol. 76, pp. 1-15 (1995).
Sapkota et al., "BI-D1870 is a specific inhibitor of the p90 RSK (ribosomal S6 kinase) isoforms in vitro and in vivo," Biochem J., vol. 401, pp. 29-38 (2007).
Scholten et al., "Analysis of the cGMP/cAMP Interactome Using a Chemical Proteomics Approach in Mammalian Heart Tissue Validates Sphingosine Kinase Type 1-interacting Protein as a Genuine and Highly Abundant AKAP," J Proteome Res, vol. 5, pp. 1435-1447 (2006).
Scholten et al., "Diversity of CAMP-Dependent Protein Kinase Isoforms and Their Anchoring Proteins in Mouse Ventricular Tissue," J Proteome Res, vol. 6, pp. 1705-1717 (2007).

* cited by examiner

FIGURE 2

>h-RSK3 1-42 in yellow
MDLSMKKFAVRRFFSVYLRRKSRSKSSSLSRLEEEGVVKEIDISHHVKEGFEKADPSQFELLKVLGQGSY
GKVFLVRKVKGSDAGQLYAMKVLKKATLKVRDRVRSKMERDILAEVNHPFIVKLHYAFQTEGKLYLILDF
LRGGDLFTRLSKEVMFTEEDVKFYLAELALALDHLHSLGIIYRDLKPENILLDEEGHIKITDFGLSKEAI
DHDKRAYSFCGTIEYMAPEVVNRRGHTQSADWWSFGVLMFEMLTGSLPFQGKDRKETMALILKAKLGMPQ
FLSGEAQSLLRALFKRNPCNRLGAGIDGVEEIKRHPFFVTIDWNTLYRKEIKPPFKPAVGRPEDTFHFDP
EFTARTPTDSPGVPPSANAHHLFRGFSFVASSLIQEPSQQDLHKVPVHPIVQQLHGNNIHFTDGYEIKED
IGVGSYSVCKRCVHKATDTEYAVKIIDKSKRDPSEEIEILLRYGQHPNIITLKDVYDDGKFVYLVMELMR
GGELLDRILRQRYFSEREASDVLCTITKTMDYLHSQGVVHRDLKPSNILYRDESGSPESIRVCDFGFAKQ
LRAGNGLLMTPCYTANFVAPEVLKRQGYDAACDIWSLGILLYTMLAGFTPFANGPDDTPEEILARIGSGK
YALSGGNWDSISDAAKDVVSKMLHVDPHQRLTAMQVLKHPWVVNREYLSPNQLSRQDVHLVKGAMAATYF
ALNRTPQAPRLEPVLSSNLAQRRGMKRLTSTRL

FIGURE 3

LOCUS r-mAKAP\(rattus) 2314 aa 30-DEC-
1999
ORIGIN
1 mltmsvtlsp lrsqgpdpma tdaspmainm tptveqeege geeavkaida eqqygkpppl
61 htaadwkivl hlpeietwlr mtservrdlt ysvqqdadsk hvdvhlvqlk dicedisdhv
121 eqihailete fslkllsysv nvivdihavq llwhqlrvsv lvlrerilqg lqdangnytr
181 qtdilqafse ettegrldsl tevddsgqlt ikcsqdylsl dcgitafels dyspsedllg
241 glgdmttsqa ktksfdswsy semekefpel irsvglltva tepvpsscge anedssqasl
301 sddhkgehge dgapvpgqql dstvgmssld gtlanaaehp setakqdsts spqlgakktq
361 pgpceittpk rsirdcfnyn edsptqptlp krglflketq knerkgsdrk gqvvdlkpel
421 srstpslvdp pdrsklclvl qssypsspsa asqsyeclhk vglgnleniv rshikeisss
481 lgrltdchke klrlkkphkt laevslcrip kqgggsgkrs estgssagps mvspgapkat
541 mrpetdsast asgglchqrn rsgqlpvqsk assppcshs sesslgsdsi kspvpllskn
601 ksqkssppap chatqngqvv eawygsdeyl alpshlkqte vlalkleslt kllpqkprge
661 tiqdiddwel semnsdseiy ptyhikkkht rlgtvspsss sdiasslges iesgplsdil
721 sdedlclpls svkkftdeks erpsssekne shsatrsali qklmhdiqhq enyeaiweri
781 egfvnkldef iqwineamet tenwtppkae tdslrlylet hlsfklnvds hcalkeavee
841 eghqllelvv shkaglkdtl rmiasqwkel qrqikrqhsw ilraldtika eilatdvsve
901 deegtgspka evqlchletq rdaveqmslk lyseqytsgs krkeefanms kahaegsngl
961 ldfdseyqel wdwlidmesl vmdshdlmms eeqqqhlykr ysvemsirhl kksellskve
1021 alkkgglslp ddilekvdsi nekwellgkt lrekiqdtia ghsgsgprdl lspesgslvr
1081 qlevrikelk rwlrdtelfi fnsclrqeke gtsaekqlqy fkslcreikq rrrgvasilr
1141 lcqhlıddrd tcnlnadhqp mqliivnler rweaivmqav qwqtrlqkkm gkesetlnvi
1201 dpglmdlngm sedalewdet disnklisvh eesndldqdp epmlpavkle ethhkdsgye
1261 eeagdcggsp ytsnitapss phiyqvyslh nvelhedsht pflkssPkft gttqptvltk
1321 slskdssfss tkslpdllgg sglvrpysch sgdlsqnsgs esgivsegdn emptnsdmsl
1381 fsmvdgspsn petehpdpqm gdaanvleqk fkdngesikl ssvsrasvsp vgcvngkagd
1441 lnsvtkhtad clgeelqgkh dvftfydysy lqgsklklpm imkqpqseka hvedpllggf
1501 yfdkksckak hqasesqpda ppherilasa phemgrsayk ssdiektftg iqsarqlsll
1561 srsssvesls pggdlfglgi fkngsdslqr stsleswlts yksnedlfsc hssgdisvss
1621 gsvgelskrt ldllnrleni qspseqkikr svsdmtlqss sqkmpfagqm sldvassine
1681 dspasltels ssdelslcse divlhknkip esnasfrkrl nrsvadesdv nvsmivnvsc
1741 tsactddedd sdllssstlt lteeelclkd edddssiatd deiyeesnlm sgldyiknel
1801 qtwirpklsl trekkrsgvt deikvnkdgg gnekanpsdt ldieallngs irclsenngn
1861 gktpprthgs gtkgenkkst ydvskdphva dmengniest pererekpqg lpevsenlas
1921 nvktisesel seyeavmdgs edssvarkef cppndrhppq mgpklqhpen qsgdckpvqn
1981 pcpgllseag vgsrqdsngl kslpndapsg arkpagccll eqneteesas issnasccnc
2041 kpdvfhqkdd edcsvhdfvk eiidmastal ksksqpesev aaptsltqik ekvlehshrp
2101 ihlrkgdfys ylslsshdsd cqevtnyide ksstplppda vdsglddked mdcffeacve
2161 depvneeagl pgalpnesai edgaeqkseq ktasspvlsd ktdlvplsgl spqkgaddak
2221 egddvshtsq gcaesteptt psgkanaegr srmqgvsatp eenaasakpk iqafslnakq
2281 pkgkvamryp spqtltckek lvnfhedrhs nmhr
//
1694-1833 in yellow is RSK-binding domain

FIGURE 10

Table 1. Echocardiographic Data for RSK3$^{-/-}$ Mice After Transverse Aortic Constriction

| | Sham | | TAC | |
|---|---|---|---|---|
| RSK3 | +/+ | −/− | +/+ | −/− |
| n | 11 | 11 | 13 | 12 |
| LVPW;d, mm | 0.69±0.03 | 0.62±0.02 | 0.94±0.05$^{\dagger\dagger\dagger}$ | 0.72±0.03$^{**}$ |
| LVPW;s, mm | 1.07±0.04 | 0.88±0.02$^{**}$ | 1.19±0.06 | 1.01±0.06$^{*}$ |
| LVAW;d, mm | 0.73±0.02 | 0.64±0.02$^{*}$ | 0.97±0.03$^{\dagger\dagger\dagger}$ | 0.81±0.03$^{\dagger**}$ |
| LVAW;s, mm | 1.00±0.05 | 0.93±0.04 | 1.36±0.05$^{\dagger\dagger}$ | 1.13±0.05$^{\dagger**}$ |
| LVID;d, mm | 4.19±0.13 | 4.24±0.07 | 4.27±0.14 | 4.26±0.09 |
| LVID;s, mm | 3.08±0.14 | 3.20±0.11 | 3.26±0.17 | 3.22±0.10 |
| % FS, % | 26.8±1.7 | 24.5±1.8 | 24.1±1.9 | 24.5±1.9 |
| Endocardial area;d, mm$^2$ | 25.4±0.8 | 25.1±0.5 | 25.8±0.7 | 27.0±0.9 |
| Endocardial area;s, mm$^2$ | 18.8±0.6 | 19.1±0.4 | 20.5±0.9 | 20.9±1.0 |
| Endocardial %FAC, % | 25.5±1.5 | 23.8±1.3 | 20.9±2.0 | 22.9±1.7 |
| Heart rate, bpm | 473±9 | 470±8 | 478±11 | 471±8 |
| Pressure gradient, mm Hg | | | 45±3 | 42±5 |

d indicates diastole; FS, fractional shortening; LVAW, left ventricular anterior wall thickness; LVID, left ventricular internal diameter; LVPW, left ventricular posterior wall thickness; RSK3, p90 ribosomal S6 kinase type 3; s, systole; and TAC, transverse aortic constriction.

M-mode measurements: LVPW, LVAW, and LVID. % FS = (LVID;d − LVID;s)/(LVID;d). B-mode measurements: %FAC = (endocardial area;d − endocardial area;s)/(endocardial area;d). *P comparing −/− vs. +/+; †Ps comparing transverse aortic constriction vs sham-operated for the same genotype. All data are mean ± SEM.

FIGURE 11

Gene Expression for $RSK3^{-/-}$ Mice After Transverse Aortic Constriction

| Gene | Protein | Sham | | TAC | |
|---|---|---|---|---|---|
| | | $RSK3^{+/+}$ | $RSK3^{-/-}$ | $RSK3^{+/+}$ | $RSK3^{-/-}$ |
| Nppa | Atrial natriuretic factor | 1.00±0.05 | 1.42±0.25 | 22.42±6.40$^{\dagger}$ | 5.70±1.34$^{*\dagger}$ |
| Myh7 | β-myosin heavy chain | 1.00±0.10 | 1.07±0.23 | 15.23±6.35 | 2.65±0.43$^{\dagger}$ |
| Acta1 | α-skeletal actin | 1.00±0.19 | 1.19±0.18 | 12.27±3.67$^{\dagger}$ | 8.08±1.54$^{*\dagger}$ |
| Nppb | Brain natriuretic peptide | 1.00±0.12 | 0.94±0.22 | 4.06±0.68$^{*\dagger}$ | 3.24±0.88$^{\dagger}$ |
| Tgfb2 | Transforming growth factor β2 | 1.00±0.09 | 0.97±0.17 | 2.77±0.42$^{*\dagger}$ | 1.37±0.07$^{*}$ |
| Fhl1 | Four and one-half LIM domains 1 | 1.00±0.12 | 1.01±0.08 | 2.05±0.40$^{\dagger}$ | 1.22±0.17 |
| Rcan1 | Regulator of calcineurin 1 | 1.00±0.09 | 0.85±0.06 | 1.91±0.39$^{\dagger}$ | 1.22±0.18 |
| Col6a1 | Collagen VI α1 | 1.00±0.08 | 0.90±0.08 | 1.56±0.09$^{*\dagger}$ | 1.28±0.08$^{*\dagger}$ |
| Hif1a | Hypoxia-inducible factor 1α | 1.00±0.06 | 1.09±0.12 | 1.43±0.10$^{\dagger}$ | 1.34±0.07 |
| Slc8a1 | Sodium/calcium exchanger 1 | 1.00±0.13 | 0.98±0.08 | 1.07±0.07 | 0.93±0.08 |
| Mapk3 | ERK1 | 1.00±0.06 | 0.96±0.07 | 1.06±0.04 | 1.09±0.04 |
| Dmd | Dystrophin | 1.00±0.09 | 1.09±0.08 | 1.05±0.08 | 1.06±0.08 |
| Tnnc1 | Cardiac troponin C | 1.00±0.06 | 1.10±0.05 | 1.00±0.10 | 1.16±0.06 |
| Rps6ka3 | RSK2 | 1.00±0.04 | 0.91±0.05 | 0.94±0.07 | 1.05±0.05 |
| Srf | Serum response factor | 1.00±0.05 | 0.97±0.05 | 0.90±0.06 | 1.07±0.06 |
| Vcl | Vinculin | 1.00±0.05 | 0.96±0.06 | 0.89±0.04 | 0.97±0.05 |
| Actc1 | α-cardiac actin | 1.00±0.05 | 0.92±0.02 | 0.86±0.08 | 0.95±0.05 |
| Akap6 | mAKAP | 1.00±0.10 | 0.93±0.06 | 0.88±0.05 | 0.95±0.09 |
| Itgb1bp2 | Melusin | 1.00±0.07 | 1.00±0.03 | 0.74±0.09$^{\dagger}$ | 0.89±0.03$^{\dagger}$ |
| Tnnt2 | Cardiac troponin T | 1.00±0.06 | 1.08±0.05 | 0.73±0.05$^{\dagger}$ | 0.85±0.05$^{\dagger}$ |
| Ryr2 | Ryanodine receptor | 1.00±0.10 | 0.93±0.09 | 0.73±0.10 | 0.85±0.08 |
| Mapk1 | ERK2 | 1.00±0.03 | 1.03±0.06 | 0.73±0.06$^{*\dagger}$ | 0.96±0.03$^{*}$ |
| Max | myc-associated factor X | 1.00±0.04 | 0.97±0.10 | 0.70±0.05$^{*\dagger}$ | 0.88±0.06$^{*}$ |
| Ckm | Creatine kinase | 1.00±0.04 | 0.94±0.05 | 0.69±0.08$^{\dagger}$ | 0.93±0.05$^{*}$ |
| Myh6 | α-myosin heavy chain | 1.00±0.12 | 0.91±0.08 | 0.62±0.09$^{\dagger}$ | 0.77±0.09 |
| Adra1a | $\alpha_{1A}$-adrenergic receptor | 1.00±0.13 | 1.14±0.22 | 0.60±0.10$^{\dagger}$ | 1.03±0.11$^{*}$ |
| Pln | Phospholamban | 1.00±0.07 | 1.19±0.09 | 0.60±0.09$^{\dagger}$ | 0.88±0.06$^{*\dagger}$ |
| Mapk7 | ERK5 | 1.00±0.05 | 0.91±0.03 | 0.58±0.06$^{*\dagger}$ | 0.72±0.07$^{\dagger}$ |
| Atp2a2 | SERCA2 | 1.00±0.10 | 0.94±0.05 | 0.54±0.07$^{\dagger}$ | 0.77±0.06$^{*\dagger}$ |
| Tnni3 | Cardiac troponin I | 1.00±0.09 | 1.08±0.06 | 0.52±0.09$^{*\dagger}$ | 0.78±0.07$^{*\dagger}$ |

ERK, extracellular signal-regulated kinase; mAKAP, muscle A-kinase anchoring protein; SERCA2, sarco/endoplasmic reticulum Ca2+-ATPase 2; and TAC, transverse aortic constriction.

Total mouse heart RNA was assayed by NanoString technology for the indicated mRNAs and normalized by he data for GAPDH All data (mean ± SEM) are fold-expression comparedwith the sham +/+ cohort. n = 5 for all cohorts. *$P$ values comparing −/− vs +/+; $^{\dagger}P$ values comparing TAC and sham-operated for the same genotype. Analysis of the complete dataset showed that gene expression for the sham and the TAC $RSK3^{-/-}$ cohorts were highly correlated (Pearson r≥89%); in contrast, he TAC $RSK3^{+/+}$ dataset diverged from the other 3 cohorts (r<83%). ANOVA (2-factor with replication) comparing the TAC datasets: $P$=0.05 for −/− vs. +/+; $P$=3.3 ×$10^{-14}$ for interaction between genes and cohorts.

FIGURE 12

Breeding of $RSK3^{-/-}$ Mice

| Genotype | +/+ | +/- | -/- |
|---|---|---|---|
| *n* | 72 | 128 | 63 |

| Sex | M | F |
|---|---|---|
| *n* | 117 | 146 |

Genotype data were obtained at 4 weeks of age for the offspring of 38 +/- X +/- matings.

FIGURE 13

Echocardiographic data for RSK3$^{-/-}$ mice when unstressed

| *RSK3* | | +/+ | -/- | |
|---|---|---|---|---|
| *n* | | *15* | *18* | |
| **LVPW;d** | mm | 0.66 ± 0.03 | 0.62 ± 0.03 | |
| **LVPW;s** | mm | 0.99 ± 0.04 | 0.93 ± 0.03 | |
| **LVAW;d** | mm | 0.71 ± 0.02 | 0.70 ± 0.02 | |
| **LVAW;s** | mm | 1.06 ± 0.03 | 1.08 ± 0.03 | |
| **LVID;d** | mm | 3.94 ± 0.09 | 4.22 ± 0.08 | * |
| **LVID;s** | mm | 2.66 ± 0.09 | 2.92 ± 0.08 | * |
| **FS** | % | 32.6 ± 1.2 | 30.8 ± 1.0 | |
| **Endocardial Area;d** | $mm^2$ | 21.1 ± 0.8 | 23.8 ± 0.8 | * |
| **Endocardial Area;s** | $mm^2$ | 13.2 ± 0.6 | 14.9 ± 0.6 | |
| **Endocardial FAC** | % | 37.2 ± 1.4 | 37.1 ± 1.8 | |
| **Heart Rate** | bpm | 477 ± 8 | 485 ± 5 | |

FIGURE 14

Gravimetric Data for RSK3$^{-/-}$ Mice Following TAC

| | | Sham | | TAC | | | | |
|---|---|---|---|---|---|---|---|---|
| ***RSK3*** | | +/+ | -/- | +/+ | | -/- | | |
| *n* | | *14* | *14* | *11* | | *12* | | |
| **Biventricular Weight** | mg | 94 ± 3 | 88 ± 2 | 140 ± 7 | †††† | 110 ± 5 | ††† | ** |
| **Body Weight** | g | 22.1 ± 0.7 | 20.5 ± 0.6 | 21.4 ± 0.8 | | 19.9 ± 0.8 | | |
| **Tibial Length** | mm | 16.5 ± 0.2 | 16.4 ± 0.1 | 16.6 ± 0.2 | | 16.5 ± 0.2 | | |
| **BiVW/Body Weight** | mg/g | 4.3 ± 0.1 | 4.3 ± 0.1 | 6.6 ± 0.4 | ††††† | 5.6 ± 0.2 | †††† | * |
| **BiVW/Tibial Length** | mg/mm | 5.7 ± 0.1 | 5.4 ± 0.1 | 8.4 ± 0.4 | ††††† | 6.7 ± 0.2 | †††† | ** |

BiVW, Biventricular Weight. * *p*-values comparing -/- vs. +/+; † *p*-values comparing TAC vs. Sham-operated for the same genotype. All data are mean ± sem.

FIGURE 15

Echocardiographic data for RSK3$^{-/-}$ mice - Isoproterenol Infusion

| | | Saline Pump | | Isoproterenol Pump | |
|---|---|---|---|---|---|
| **RSK3** | | +/+ | -/- | +/+ | -/- |
| *n* | | *10* | *10* | *14* | *20* |
| **LVPW;d** | mm | 0.70 ± 0.04 | 0.65 ± 0.03 | 0.78 ± 0.03 | 0.78 ± 0.02 †† |
| **LVPW;s** | mm | 0.97 ± 0.06 | 0.89 ± 0.04 | 1.16 ± 0.05 † | 1.09 ± 0.04 † |
| **LVAW;d** | mm | 0.72 ± 0.02 | 0.64 ± 0.05 | 0.81 ± 0.02 † | 0.79 ± 0.02 †† |
| **LVAW;s** | mm | 1.06 ± 0.05 | 0.92 ± 0.06 | 1.30 ± 0.04 ††† | 1.28 ± 0.04 †††† |
| **LVID;d** | mm | 3.96 ± 0.10 | 4.42 ± 0.10 ** | 4.37 ± 0.09 † | 4.50 ± 0.10 |
| **LVID;s** | mm | 2.84 ± 0.11 | 3.43 ± 0.11 ** | 3.02 ± 0.11 | 3.18 ± 0.13 |
| **FS** | % | 28.3 ± 1.3 † | 22.5 ± 1.7 * | 31.1 ± 1.3 | 29.7 ± 1.8 † |
| **Endocardial Area;d** | $mm^2$ | 22.6 ± 1.0 | 25.7 ± 1.0 * | 26.6 ± 0.9 † | 26.8 ± 0.8 |
| **Endocardial Area;s** | $mm^2$ | 14.6 ± 1.0 | 19.1 ± 0.6 *** | 17.2 ± 0.8 | 17.8 ± 0.7 |
| **Endocardial FAC** | % | 35.8 ± 2.1 | 25.4 ± 1.3 *** | 35.3 ± 2.2 | 33.1 ± 2.3 † |
| **Heart Rate** | bpm | 491 ± 9 | 481 ± 7 | 584 ± 10 †††† | 589 ± 8 †††† |

M-mode measurements: LVPW, Left ventricular posterior wall thickness; LVAW, Left ventricular anterior wall thickness; LVID, Left ventricular internal diameter; d, diastole; s, systole; FS, fractional shortening = (LVID;d − LVID;s)/(LVID;d). B-mode measurements: FAC = (Endocardial Area;d − Endocardial Area;s)/(Endocardial Area;d). * *p*-values comparing -/- vs. +/+; † *p*-values comparing isoproterenol vs. saline infusion for the same genotype. All data are mean ± s.e.m.

FIGURE 16

Gravimetric Data for $RSK3^{-/-}$ mice - Isoproterenol infusion

| | | Saline Pump | | Isoproterenol Pump | |
|---|---|---|---|---|---|
| *RSK3* | | +/+ | -/- | +/+ | -/- |
| *n* | | 5 | 7 | 12 | 12 |
| **Biventricular Weight** | mg | 96 ± 4 | 102 ± 6 | 128 ± 5 †† | 124 ± 5 † |
| **Body Weight** | g | 22.2 ± 1.0 | 22.0 ± 1.7 | 24.3 ± 0.6 | 22.1 ± 0.8 * |
| **Tibial Length** | mm | 17.0 ± 0.2 | 16.6 ± 0.2 | 16.8 ± 0.1 | 16.6 ± 0.2 |
| **BiVW/Body Weight** | mg/g | 4.4 ± 0.1 | 4.7 ± 0.2 | 5.3 ± 0.1 †† | 5.6 ± 0.2 †† |
| **BiVW/Tibial Length** | mg/mm | 5.7 ± 0.2 | 6.1 ± 0.3 | 7.6 ± 0.2 †† | 7.5 ± 0.2 †† |

* BiVW, Biventricular Weight. * *p*-values comparing -/- vs. +/+; † *p*-values comparing isoproterenol vs. saline infusion for the same genotype. All data are mean ± sem.

FIGURE 17

Echocardiographic data for RSK3$^{-/-}$ mice - Chronic Exercise (Swimming)

| | | Rested | | Swam | |
|---|---|---|---|---|---|
| ***RSK3*** | | +/+ | -/- | +/+ | -/- |
| *n* | | 6 | 6 | 9 | 8 |
| **LVPW;d** | mm | 0.61 ± 0.02 | 0.56 ± 0.03 | 0.62 ± 0.02 | 0.58 ± 0.01 |
| **LVPW;s** | mm | 0.91 ± 0.03 | 0.90 ± 0.04 | 0.96 ± 0.04 | 0.88 ± 0.04 |
| **LVAW;d** | mm | 0.67 ± 0.02 | 0.65 ± 0.04 | 0.66 ± 0.02 | 0.63 ± 0.01 |
| **LVAW;s** | mm | 0.94 ± 0.03 | 0.89 ± 0.07 | 0.93 ± 0.04 | 0.94 ± 0.04 |
| **LVID;d** | mm | 4.09 ± 0.10 | 4.30 ± 0.07 | 4.39 ± 0.07 † | 4.17 ± 0.10 |
| **LVID;s** | mm | 3.06 ± 0.08 | 3.33 ± 0.08 * | 3.25 ± 0.07 | 3.04 ± 0.11 |
| **FS** | % | 25.2 ± 0.6 | 22.7 ± 1.5 | 26.1 ± 1.1 | 27.2 ± 1.5 |
| **Endocardial Area;d** | $mm^2$ | 25.7 ± 1.3 | 27.7 ± 0.9 | 30.0 ± 0.8 † | 27.7 ± 1.1 |
| **Endocardial Area;s** | $mm^2$ | 19.7 ± 1.1 | 20.9 ± 1.0 | 22.2 ± 0.6 † | 21.3 ± 1.1 |
| **Endocardial FAC** | % | 23.2 ± 1.1 | 24.7 ± 1.7 | 26.0 ± 1.0 | 23.4 ± 1.6 |
| **Heart Rate** | bpm | 479 ± 11 | 476 ± 14 | 437 ± 13 † | 434 ± 7 † |

M-mode measurements: LVPW, Left ventricular posterior wall thickness; LVAW, Left ventricular anterior wall thickness; LVID, Left ventricular internal diameter; d, diastole; s, systole; FS, fractional shortening = (LVID;d − LVID;s)/(LVID;d). B-mode measurements: FAC = (Endocardial Area;d − Endocardial Area;s)/(Endocardial Area;d). * *p*-values comparing -/- vs. +/+; † *p*-values comparing Swam vs. Rested for the same genotype. All data are mean ± s.e.m.

FIGURE 18

Gravimetric Data for RSK3$^{-/-}$ mice - Chronic Exercise (Swimming)

| | | Rested | | Swam | | |
|---|---|---|---|---|---|---|
| *RSK3* | | +/+ | -/- | +/+ | -/- | |
| *n* | | *9* | *10* | *9* | *10* | |
| **Biventricular Weight** | mg | 95 ± 4 | 90 ± 5 | 103 ± 4 | 87 ± 3 | * |
| **Body Weight** | g | 22.9 ± 0.8 | 21.7 ± 0.8 | 23.1 ± 0.8 | 19.9 ± 0.9 | * |
| **Tibial Length** | mm | 16.9 ± 0.3 | 16.6 ± 0.2 | 17.0 ± 0.2 | 16.4 ± 0.3 | |
| **BiVW/Body Weight** | mg/g | 4.2 ± 0.1 | 4.1 ± 0.1 | 4.5 ± 0.1 † | 4.4 ± 0.1 † | |
| **BiVW/Tibial Length** | mg/mm | 5.6 ± 0.1 | 5.4 ± 0.2 | 6.0 ± 0.2 | 5.3 ± 0.1 | ** |

' BiVW, Biventricular Weight. * *p*-values comparing -/- vs. +/+; † *p*-values comparing Swam vs. Rested for the same genotype. *All data are mean ± sem.*

FIGURE 19

Commercial antibodies used in this project.

| *Antigen* | *Species* | *Company* |
|---|---|---|
| α-actinin | mouse monoclonal EA-53 | Sigma-Aldrich |
| Rat ANF | Rabbit | US Biological |
| HA tag | Mouse HA-7 monoclonal | Sigma-Aldrich |
| ERK1/2 | Rabbit | Cell Signaling Technology |
| p44/p42 ERK $T^{202}/Y^{204}$ | Rabbit | Cell Signaling Technology |
| GSK-3β | Rabbit monoclonal 27C10 | Cell Signaling Technology |
| phospho-GSK-3β $S^{9}$ | Rabbit monoclonal 5B3 | Cell Signaling Technology |
| Myc tag | Mouse 4A6 monoclonal | Millipore |
| phospho-myosin binding protein C $S^{282}$ | Rabbit | Enzo |
| RSK3 | Goat C-20 | Santa Cruz Biotechnology |
| RSK3 | Goat N-16 | Santa Cruz Biotechnology |
| RSK3 | Mouse 1F6 monoclonal H00006196-M01 | Abnova |
| RSK3 | Rabbit #9343 | Cell Signaling Technology |
| phospho-RSK3 $S^{218}$ | Rabbit AF893 | R&D Systems |
| phospho-RSK3 $S^{369}$ | Rabbit | Millipore |
| phospho-troponin I $S^{23/24}$ | Rabbit | Cell Signaling Technology |
| phospho-eEF2K $S^{366}$ | Rabbit | Cell Signaling Technology |

FIGURE 20

Oligonucleotides siRNA oligonucleotides from Dharmacon

| | | |
|---|---|---|
| Rat RSK3 | On-Targetplus J-080945-10 siRNA | CGCAAGAAGUCGCGCUCCA (SEQ ID NO: 3) |
| Rat RSK3 | On-Targetplus J-080945-11 siRNA | UUGAGAUCCUCCUGCGGUA (SEQ ID NO: 4) |
| Control siRNA | On-Targetplus Non-targeting siRNA #1 | Not provided by manufacturer |

Oligonucleotides for RT-PCR

| | | |
|---|---|---|
| Rat RSK3 | rRSK3+0.2 | GAACATGAAGAAGTTCACGGTGCG (SEQ ID NO: 5) |
| | rRSK3-0.5 | TCTCTCTCCATCTTAGACCGGACCC (SEQ ID NO: 6) |

Oligonucleotides for Genotyping

| | | |
|---|---|---|
| Mouse RSK3 | RSK3Ex2+5' | CCCCAGAGCAAACAACTTTCTCAGATTG (SEQ ID NO: 7) |
| | RSK3Ex2-3' | CGATTCTGACAATCACAGGCTCAACTAATGT (SEQ ID NO: 8) |

FIGURE 31

Table: Echocardiographic Data at 16 Weeks of Age

| | | WT | RSK3 | | TM180 | | TM180; RSK3 | | |
|---|---|---|---|---|---|---|---|---|---|
| *n* | | 17 | 16 | | 16 | | 17 | | |
| Parameter | Units | | | | | | | | |
| LVID;d | mm | 4.18 ± 0.06 | 4.18 ± 0.08 | | 3.82 ± 0.03 | *** | 3.92 ± 0.03 | *** | † |
| LVID;s | mm | 2.89 ± 0.06 | 3.09 ± 0.08 | * | 2.39 ± 0.04 | *** | 2.57 ± 0.02 | *** | ††† |
| % FS | % | 30.9 ± 1.0 | 26.3 ± 0.9 | ** | 37.7 ± 0.7 | *** | 34.3 ± 0.6 | * | †† |
| LVPW;d | mm | 0.62 ± 0.02 | 0.60 ± 0.03 | | 0.64 ± 0.03 | | 0.61 ± 0.02 | | |
| Endocardial Area;d | $mm^2$ | 23.6 ± 0.7 | 22.2 ± 0.7 | | 19.3 ± 0.4 | *** | 19.2 ± 0.4 | *** | |
| Endocardial Area;s | $mm^2$ | 15.3 ± 0.8 | 14.5 ± 0.6 | | 10.3 ± 0.3 | *** | 11.5 ± 0.1 | *** | |
| Endocardial %FAC | % | 35.1 ± 1.4 | 34.9 ± 1.3 | | 44.4 ± 1.3 | *** | 39.7 ± 1.1 | * | † |
| Heart Rate | BPM | 492 ± 32 | 493 ± 10 | | 493 ± 9 | | 512 ± 12 | | |

M-mode measurements: LVID, Left ventricular internal diameter; LVPW, Left ventricular posterior wall thickness; d, diastole; s, systole; % FS, fractional shortening = (LVID;d − LVID;s)/(LVID;d). B-mode measurements: %FAC = (Endocardial Area;d − Endocardial Area;s)/(Endocardial Area;d). * *p*-values when compared to WT; † *p*-values when compared to TM180. All data are mean ± sem.

FIGURE 34

| | | WT | $RSK3^{-/-}$ | TM180 | | TM180; $RSK3^{-/-}$ | |
|---|---|---|---|---|---|---|---|
| *n* | | 24 | 18 | 14 | | 21 | |
| Body Weight | g | 27.8 ± 0.8 | 28.1 ± 1.4 | 26.7 ± 1.1 | | 26.6 ± 1.0 | |
| Tibial Length | mm | 17.7 ± 0.1 | 17.6 ± 0.2 | 17.6 ± 0.1 | | 17.5 ± 0.1 | |
| Biventricular Weight | mg | 108 ± 3 | 111 ± 6 | 85 ± 3 | *** | 86 ± 4 | *** |
| Biatrial Weight | mg | 7.75 ± 0.45 | 8.11 ± 0.59 | 10.71 ± 0.68 | ** | 11.33 ± 0.73 | *** |
| Wet Lung Weight | mg | 145 ± 3 | 138 ± 6 | 162 ± 5 | * | 143 ± 4 | †† |
| Biventricular Weight /TL | mg/mm | 6.11 ± 0.18 | 6.31 ± 0.30 | 4.85 ± 0.18 | *** | 4.90 ± 0.20 | *** |
| Biatrial Weight/TL | mg/mm | 0.44 ± 0.03 | 0.46 ± 0.03 | 0.61 ± 0.04 | *** | 0.65 ± 0.04 | *** |
| Wet Lung Weight/TL | mg/mm | 8.21 ± 0.16 | 7.81 ± 0.29 | 9.19 ± 0.27 | ** | 8.18 ± 0.20 | †† |

TL – tibial length. * *p*-values when compared to WT; † *p*-values when compared to TM180. All data are mean ± sem.

FIGURE 35

| Gene | Protein | WT | *RSK3*$^{-/-}$ | TM180 | TM180; *RSK3*$^{-/-}$ |
|---|---|---|---|---|---|
| **Related to Interstitial Fibrosis** | | | | | |
| Col1a1 | collagen type I α1 | 1.00 ± 0.04 | 0.96 ± 0.09 | 1.21 ± 0.04 * | 0.76 ± 0.09 † |
| Col1a2 | collagen type I α2 | 1.00 ± 0.02 | 1.11 ± 0.04 * | 1.38 ± 0.03 ** | 1.06 ± 0.18 * |
| Col3a1 | collagen type III α1 | 1.00 ± 0.03 | 0.94 ± 0.13 | 1.21 ± 0.16 | 0.79 ± 0.05 |
| Col5a1 | collagen type V α1 | 1.00 ± 0.10 | 1.09 ± 0.05 | 0.94 ± 0.13 | 0.85 ± 0.10 |
| Col6a1 | collagen type VI α1 | 1.00 ± 0.07 | 1.02 ± 0.04 | 1.28 ± 0.14 | 0.76 ± 0.14 |
| Col8a1 | collagen type VIII α1 | 1.00 ± 0.11 | 0.86 ± 0.08 | 2.85 ± 0.04 ** | 1.42 ± 0.11 *† |
| Tgfb1 | transforming growth factor β1 | 1.00 ± 0.10 | 1.16 ± 0.07 | 1.23 ± 0.23 | 0.88 ± 0.13 |
| Tgfb2 | transforming growth factor β2 | 1.00 ± 0.13 | 0.96 ± 0.10 | 2.13 ± 0.79 | 1.45 ± 0.23 |
| Postn | periostin | 1.00 ± 0.15 | 0.79 ± 0.10 | 2.16 ± 0.19 * | 1.23 ± 0.09 † |
| Fbn1 | fibrillin-1 | 1.00 ± 0.18 | 0.76 ± 0.07 | 1.94 ± 0.11 | 0.65 ± 0.07 † |
| Fgl2 | fibrinogen-like protein 2 | 1.00 ± 0.11 | 1.01 ± 0.04 | 1.70 ± 0.18 * | 1.10 ± 0.11 † |
| Fn1 | fibronectin 1 | 1.00 ± 0.06 | 0.94 ± 0.06 | 1.26 ± 0.15 | 0.69 ± 0.18 |
| Mfap5 | microfibrillar associated protein 5 | 1.00 ± 0.11 | 1.01 ± 0.09 | 1.78 ± 0.15 * | 1.29 ± 0.18 |
| Mmp2 | matrix metallopeptidase 2 | 1.00 ± 0.13 | 1.16 ± 0.08 | 1.77 ± 0.12 * | 1.14 ± 0.19 |
| Pcolce | procollagen C-endopeptidase enhancer | 1.00 ± 0.04 | 1.10 ± 0.06 | 1.23 ± 0.14 | 0.80 ± 0.05 *† |
| Rtn4 | reticulon 4 (a.k.a Nogo) | 1.00 ± 0.05 | 1.07 ± 0.13 | 1.40 ± 0.14 | 0.92 ± 0.13 |
| Srf | serum response facto | 1.00 ± 0.13 | 1.15 ± 0.27 | 1.23 ± 0.11 | 0.67 ± 0.08 † |
| **Sarcomeric Proteins** | | | | | |
| Acta1 | skeletal muscle α-actin | 1.00 ± 0.23 | 0.65 ± 0.28 | 1.87 ± 0.79 | 0.93 ± 0.28 |
| Actc1 | cardiac muscle α-actin | 1.00 ± 0.05 | 0.91 ± 0.17 | 0.88 ± 0.03 | 0.42 ± 0.07 **†† |
| Myh6 | cardiac muscle α-myosin heavy chain | 1.00 ± 0.05 | 1.09 ± 0.20 | 3.41 ± 0.38 ** | 1.78 ± 0.58 |
| Myh7 | cardiac muscle β-myosin heavy chain | 1.00 ± 0.17 | 0.56 ± 0.19 | 1.61 ± 0.55 | 1.43 ± 0.32 |
| Tnni3 | cardiac muscle troponin I | 1.00 ± 0.02 | 1.10 ± 0.06 | 1.00 ± 0.10 | 0.54 ± 0.12 *† |
| Tnnt2 | cardiac muscle troponin T | 1.00 ± 0.02 | 1.05 ± 0.13 | 0.88 ± 0.13 | 0.54 ± 0.10 * |
| Capg | gelsolin-like capping protein | 1.00 ± 0.05 | 0.92 ± 0.04 | 1.26 ± 0.09 | 0.91 ± 0.06 † |
| **Related to Calcium Cycling** | | | | | |
| Atp2a2 | sarco/endoplasmic reticulum $Ca^{2+}$-ATPase 2 | 1.00 ± 0.03 | 0.97 ± 0.16 | 0.83 ± 0.05 * | 0.36 ± 0.12 *† |
| Cacna1c | L-type channel channel subunit α1c | 1.00 ± 0.12 | 1.01 ± 0.27 | 0.91 ± 0.09 | 0.39 ± 0.11 *† |
| Pln | phospholamban | 1.00 ± 0.02 | 1.04 ± 0.09 | 0.96 ± 0.16 | 0.67 ± 0.14 |
| **Signal Transduction** | | | | | |
| Adra1a | α1-adrenergic receptor | 1.00 ± 0.13 | 1.28 ± 0.40 | 1.30 ± 0.07 | 0.46 ± 0.11 *†† |
| Adrb1 | β1-adrenergic receptor | 1.00 ± 0.06 | 1.11 ± 0.20 | 0.77 ± 0.20 | 0.46 ± 0.07 ** |
| Adrb2 | β2-adrenergic receptor | 1.00 ± 0.03 | 1.93 ± 0.40 | 1.65 ± 0.38 | 1.52 ± 0.21 |
| Akap6 | mAKAP | 1.00 ± 0.07 | 0.93 ± 0.19 | 1.16 ± 0.06 | 0.56 ± 0.11 *† |
| Dusp4 | dual specificity protein phosphatase 4 | 1.00 ± 0.12 | 1.09 ± 0.16 | 1.47 ± 0.39 | 0.87 ± 0.23 |
| Mapk1 | extracellular signal-regulated kinase 2 | 1.00 ± 0.01 | 1.03 ± 0.10 | 1.11 ± 0.13 | 0.64 ± 0.14 |
| Mapk3 | extracellular signal-regulated kinase 1 | 1.00 ± 0.05 | 1.39 ± 0.06 * | 1.18 ± 0.17 | 0.75 ± 0.11 |
| Mapk7 | extracellular signal-regulated kinase 5 | 1.00 ± 0.11 | 1.81 ± 0.25 | 2.40 ± 0.18 ** | 1.33 ± 0.26 † |
| Rps6ka1 | ribosomal S6 kinase 1 | 1.00 ± 0.10 | 1.33 ± 0.11 | 1.85 ± 0.20 | 0.87 ± 0.20 |
| Rps6ka3 | ribosomal S6 kinase 2 | 1.00 ± 0.04 | 1.02 ± 0.09 | 1.15 ± 0.11 | 0.83 ± 0.11 |
| Fhl1 | four and a half LIM domains protein 1 | 1.00 ± 0.02 | 0.99 ± 0.10 | 1.14 ± 0.12 | 0.61 ± 0.05 **† |
| Rcan1 | regulator of calcineurin 1 | 1.00 ± 0.21 | 0.79 ± 0.04 | 0.91 ± 0.13 | 0.77 ± 0.06 |

Total mouse heart RNA was assayed by NanoString technology for the indicated mRNAs. All data (mean ± s.e.m.) are fold-expression compared to the WT cohort. $n = 3$ for all cohorts. * p-values when compared to WT; † p-values when compared to TM180. p(ANOVA - two factor with replication) comparing the TM180 and the TM180; *RSK3*$^{-/-}$ cohorts = 1.6 x10$^{-8}$.

FIGURE 44

```
LOCUS       hRSK3        5817 bp    DNA     linear   PRI 22-JAN-2009
DEFINITION  Homo sapiens ribosomal protein S6 kinase, 90kDa, polypeptide 2
(RPS6KA2), transcript variant 1, mRNA.
BASE COUNT     1285 a      1585 c      1591 g      1356 t
ORIGIN
        1 gcggagaagg aggcggaggg agcgattgtg gccccggccg cggtggccgg cgcggcctgc
       61 cctttgtgac cgcagctcgc gccccacgcc ccgcgcccat ggccgccgtg ccgggctccc
      121 tggccacgcg tgcccgcccg cggacctgag ccccgcgcct gggatgccgg ggatgcgcgt
      181 cccccggccc tgcggctgct ccgggctggg cgcggggcga tggacctgag catgaagaag
      241 ttcgccgtgc gcaggttctt ctctgtgtac ctgcgcagga agtcgcgctc caagagctcc
      301 agcctgagcc ggctcgagga agaaggcgtc gtgaaggaga tagacatcag ccatcatgtg
      361 aaggagggct ttgagaaggc agatccttcc cagtttgagc tgctgaaggt tttaggacaa
      421 ggatcctatg gaaaggtgtt cctggtgagg aaggtgaagg ggtccgacgc tgggcagctc
      481 tacgccatga aggtccttaa gaaagccacc ctaaaagttc gggaccgagt gagatcgaag
      541 atggagagag acatcttggc agaagtgaat caccccttca ttgtgaagct tcattatgcc
      601 tttcagacgg aaggaaagct ctacctgatc ctggacttcc tgcggggagg ggacctcttc
      661 acccggctct ccaaagaggt catgttcacg gaggaggatg tcaagttcta cctggctgag
      721 ctggccttgg ctttagacca tctccacagc ctggggatca tctacagaga tctgaagcct
      781 gagaacatcc tcctggatga agaggggcac attaagatca cagatttcgg cctgagtaag
      841 gaggccattg accacgacaa gagagcgtac tccttctgcg ggacgatcga gtacatggcg
      901 cccgaggtgg tgaaccggcg aggacacacg cagagtgccg actggtggtc cttcggcgtg
      961 ctcatgtttg agatgctcac ggggtccctg ccgttccagg ggaaggacag gaaggagacc
     1021 atggctctca tcctcaaagc caagctgggg atgccgcagt tcctcagtgg ggaggcacag
     1081 agtttgctgc gagctctctt caaacggaac ccctgcaacc ggctgggtgc tggcattgac
     1141 ggagtggagg aaattaagcg ccatcccttc tttgtgacca tagactggaa cacgctgtac
     1201 cggaaggaga tcaagccacc gttcaaacca gcagtgggca ggcctgagga caccttccac
     1261 tttgaccccg agttcacagc gcggacgccc acagactctc ctggcgtccc cccgagtgca
     1321 aacgctcatc acctgtttag aggattcagc tttgtggcct caagcctgat ccaggagccc
     1381 tcacagcaag atctgcacaa agtcccagtt cacccaatcg tgcagcagtt acacgggaac
     1441 aacatccact tcaccgatgg ctacgagatc aaggaggaca tcggggtggg ctcctactca
     1501 gtgtgcaagc gatgtgtgca taaagccaca gacaccgagt atgccgtgaa gatcattgat
     1561 aagagcaaga gagacccctc ggaagagatt gagatcctcc tgcggtacgg ccagcacccg
     1621 aacatcatca ccctcaagga tgtctatgat gatggcaagt ttgtgtacct ggtaatggag
     1681 ctgatgcgtg gtggggagct cctggaccgc atcctccggc agagatactt ctcggagcgc
     1741 gaagccagtg acgtcctgtg caccatcacc aagaccatgg actacctcca ttcccagggg
     1801 gttgttcatc gagacctgaa gccgagtaac atcctgtaca gggatgagtc ggggagccca
     1861 gaatccatcc gagtctgcga cttcggcttt gccaagcagc tgcgcgcggg gaacgggctg
     1921 ctcatgacac cctgctacac ggccaatttc gtggccccgg aggtcctgaa gcgtcaaggc
     1981 tatgatgcgg cgtgtgacat ctggagtttg ggcatcctgt tgtacaccat gctggcagga
     2041 tttacccctt ttgcaaatgg gccagacgat acccctgagg agattctggc gcggatcggc
     2101 agtgggaagt atgccctttc tgggggaaac tgggactcga tatctgacgc agctaaagac
     2161 gtcgtgtcca agatgctcca cgtggacccc catcagcgcc tgacggcgat gcaagtgctc
     2221 aaacacccgt gggtggtcaa cagagagtac ctgtccccaa accagctcag ccgacaggac
     2281 gtgcacctgg tgaagggcgc gatggccgcc acctactttg ctctaaacag aacacctcag
     2341 gccccgcggc tggagcccgt gctgtcatcc aacctggctc agcgcagagg catgaagaga
     2401 ctcacgtcca cgcggctgta gcgggtggga ccctggcccc agcgtcccct gccagcatcc
     2461 tcgtgggctc acagaccccg gcctcggagc ccgtctggca cccagagtga ccacaagtcc
     2521 agcagggagg cggcgcccgc cctcgccgtg tccgtgtttt ctttttcagc cccggagagg
     2581 gtcctgacct gggggcttct ccaagcctca ctgcgccagc ctccccgccc gctctctttt
     2641 ctcccaagcg aaaccaaatg cgccccttca cctcgcgtgc ccgtgcgagg ccggggggctt
     2701 ctttcagagc ccgcgggtcc tctcatacat ggcttctgtt tctgccgaga gatctgtttt
     2761 ccaattatga agccggtcgg tttggtcaga ctcccgacac ccacgtccca ggtacccggt
```

FIGURE 44 (continued)

2821 gggaaagtgg cagtgcgagg gcgcagccat tggtggttgc agggccccag agggctgggg
2881 tgacctggca tcccggggct ccccacgggc tggatgacgg ggttggcact gtggcgtcca
2941 ggaggagatg cctggttctg cccaaaataa tccaaagagc cgtttcctcc tcgcccttca
3001 gtttttgcct gaggtgctgg gtagcccatc ctttcctctg tcccagattc aaatgaggag
3061 taagagccca gacgagagga aggcaggctg gatctttgcc ttgagagctc cgtgtcacca
3121 ggatggaagg gggtgcctct cggaggagcc tgtgtccacc tccagtctcg gctttccccg
3181 gggggccaag cgcactgggc tgccgtctgt ccccagctcc cgtggccaca cagctatctg
3241 gaggctttgc agggagtcgt gggttctcgc acctgctcag ccctgtgtcg gcttcctgtg
3301 tgctcaccta aagctgtggt tttgctgtgt tcacttcgat ttttctggtc tgtggagaaa
3361 ctgtgaattg gagaaatgga gctctgtggc ttcccaccca aaccttctca gtccagctgg
3421 aggctggagg gagacacagg ccccacccag cagactgagg ggcagaggca caggtgggag
3481 ggcagcggag atcagcgtgg acaggagcga tgcactttgt agatgctgtg gctttgtgtt
3541 gcgttttgtg tctctgttgc acagatctgt tttttcacac tgatccgtat tcccctgggt
3601 gtgcacacag ggcgggtgtg gggcatttag gccatgctgt gctctacttc attgagtaaa
3661 atcgagtgag aggttccggg cagcaggatc gacgcccagt ccagccggca gagggaacac
3721 acgggtcctt cattgtcctg taagggtgtt gaagatgctc cctggcggcc cccaagcaga
3781 ctagatggga ggaggcgccg ctcagcccct caccctgcat cactgaagag cggcgcctct
3841 gcagcaagca gggcttcagg aggtgcccgc tggccacagc caggttttcc ctaagaagat
3901 gttattttgt tgggttttgt tccccctcca tctcgattct cgtacccaac taaaaaaaaa
3961 aaaataaaga aaaaatgtgc tgcgttctga aaaataactc cttagcttgg tctgattgtt
4021 ttcagacctt aaaatataaa cttgtttcac aagctttaat ccatgtggat tttttttttc
4081 ttagagaacc acaaaacata aaaggagcaa gtcggactga atacctgttt ccatagtgcc
4141 cacagggtat tcctcacatt ttctccatag aagatgcttt ttcccaaggc tagaacgact
4201 tccaccatga tgaatttgct ttttaggtct taattatttc acttcttttt agaaacttag
4261 gaagaagtgg ataatcctga ggtcacacaa tctgtcctcc cagaaatgaa caaaagtcat
4321 caccttttct gcttgctaca caggcaacga ttcccccatc agctgcccgg accctttggc
4381 ctggcttggt gtgcaggcct gtctgtttgc ttaaagtcag tgggttctgg tgcagggagt
4441 gagaagtggg ggaagtgaaa gggaaagcat ccgtgagaaa gcggccacgg ttttccctcc
4501 ttgtgtgccc atggggcacc agctcatggt ctttttcagt catcccagtt tgtacagact
4561 tagcttctga actctaagaa tgccaaaggg accgacgaga ctccccatca cagcgagctc
4621 tgtccttaca tgtatttgat gtgcatcagc ggaggagaac actggcttgg ccctgctccg
4681 ctgagtgtct gtgaaatacc tctactttcc ctcccatatc cagaacaaaa tgatacttga
4741 catccttcca caaaagtcag cctaaagaag ttatggtatc atatgttaaa ctaagctttc
4801 aaaaacctta gtgaaatagc aagtgactgc tttcaagcag cagtcgacat gtaaatgaag
4861 gtgttcttag aattcgcatt ttgccagctc agcgcacctc cacaacgaat gaaatgctcc
4921 gtatgatttg cacaaatgac atagacctcc ccaaaagtta actggctctc cttcctcaca
4981 cagttcatca taacccaacc ccccaccccc gggtcatgaa aatcacagaa cttataaaca
5041 cattgaaccc tagatctcag gcttcctgac ctaccgccag tggccccttg ctggccaccc
5101 tatagggtcc tccttccctg gcagcccccc atgtgggaga aatacctgat tctcccaatc
5161 tgcagtggga gagctttgct gaattccatc ccaaagtcaa acatgggcaa gaggtgagga
5221 tttcactttt accctcaagt ccgatttgtc tgtgatttta aactaactgt gtatgtattg
5281 atgtttggaa gattgtttga attttaaagt gataatagta cttaatgtta tccagtattg
5341 ttcattaaat ggtgttatcc taaagctgca cttgggattt ttacctaacg ctttactgat
5401 tctctcaagc acatggcaaa gtttgatttg cactccgttc atttctgaca cgttttgctg
5461 cctcctacct ttctaagcgt catgcaaatt cgagaatgga gaaggacgct gccggtccct
5521 gagcggtgtg gagagggcgg aaggtggact ccagcgcagc ttgaggggct gaggacggag
5581 gctgcagcat ctgtgtcgtt ctactgagca cgcttctctg cctcgctcct gactcagcac
5641 tttgttcact ggctcagcag ttatgtttac acatcatttt tatgttcctg ctttgtaatt
5701 catgtttgag atgggtggcc actgtacaga tatttattac gctttccaga ctttctgaat
5761 agattttttt gaataaacat ggttttatga agtgtaatct tttctagcc taacaat

//

FIGURE 45

```
LOCUS       r-mAKAP         8841 bp    DNA     linear       12-AUG-2005
SOURCE
  ORGANISM
COMMENT     This file is created by Vector NTI
            http://www.invitrogen.com/
COMMENT     VNTDATE|175006528|
COMMENT     VNTDBDATE|382622673|
COMMENT     LSOWNER|
COMMENT     VNTNAME|r-mAKAP|
COMMENT     VNTAUTHORNAME|Michael Kapiloff|
COMMENT     VNTAUTHORTEL|305-243-7863|
COMMENT     VNTAUTHOREML|mkapiloff@med.miami.edu|
FEATURES             Location/Qualifiers
     CDS             128..7069
                     /vntifkey="4"
                     /label=128(d2)
                     /note="mAKAP protein"
     misc_feature    7210..7228
                     /vntifkey="21"
                     /label=7210\siRNA\target
BASE COUNT     2565 a      2078 c      2143 g      2055 t
ORIGIN
        1 gcatcatgca gcaggtcaaa caaggcatct cctagtattg catcctccag atgtgctgta
       61 aacatcaaaa ggagacgctg ggagcaggag atgctgtttt ggaaagaagt aaggcttaga
      121 tttctccatg ttaaccatga gcgtgacact ttccccactg aggtcacagg gcccagatcc
      181 catggcgacg gatgcttcac ccatggccat caacatgaca cccactgtgg agcaggagga
      241 aggagaggga gaggaagccg tgaaggccat agacgctgag cagcagtatg gaaagccacc
      301 tccgctccac acagcagccg actggaagat tgtcctgcac ttacctgaga ttgagacctg
      361 gctccggatg acctcagaga gggtccgtga cctgacctac tcagtccagc aggatgcaga
      421 cagcaagcat gtggatgtgc atctagttca gctgaaggac atttgtgagg atatttctga
      481 ccatgtggag cagatccatg ccctccttga gacggagttt tccctaaagc tgctgtccta
      541 ctcggtcaac gtcatcgtag acatccacgc agtacagctg ctctggcacc agctccgcgt
      601 atccgtgctg gtcctccggg agcgcatcct acaaggtctg caggacgcca atggcaacta
      661 caccaggcag actgacattc tgcaagcgtt ctctgaagaa acaacggagg gccggcttga
      721 ttcccttaca gaagtggacg actcagggca gttaactatc aaatgttcac aggattactt
      781 gtctctggat tgtggcatta ccgcatttga actctccgac tacagtccaa gtgaggatct
      841 gcttggtggc ctgggcgaca tgaccaccag ccaggccaaa actaaatctt ttgactcttg
      901 gagctacagt gagatggaga aagagttccc tgagcttatc cgaagcgttg ggctgcttac
      961 agtggccacc gagcctgtcc cttccagctg tggagaagcc aatgaggatt catctcaagc
     1021 gtccctttca gatgatcaca aaggtgaaca cggggaagac ggtgctcccg tacctggaca
     1081 gcagctggac tcaacggtgg gaatgtcttc cttagacggc acgctggcaa atgctgccga
     1141 acacccttcg gagacagcaa aacaagactc tacttcctcc ccacagcttg gtgcgaagaa
     1201 aacccagcct ggtccttgtg aaattacgac tcccaagaga tccatccgcg attgctttaa
     1261 ttataacgag gactccccca cacagcccac attacccaaa agagggcttt ttctaaaaga
     1321 aactcaaaag aatgagcgca aaggcagtga caggaagggg caggtggttg atttaaagcc
     1381 tgaactgagc agaagcaccc cttccctggt ggaccccct gacagatcga agctctgcct
     1441 agtgttgcag tcctcctacc ccagcagccc ttctgctgcc agccagtcct atgaatgttt
     1501 gcacaaggtg gggctcggca atcttgaaaa catagtcaga agtcacatta aagaaatttc
     1561 ttccagtctg ggaaggctta ctgactgcca taaagagaaa ttgcgactga aaaagccaca
     1621 caagaccttg gccgaagtgt ctctgtgcag aatccctaaa cagggaggcg gttcaggaaa
     1681 gcgatctgag agcaccggga gctcagcagg gcccagcatg gtatcacctg gagctcccaa
     1741 agccacgatg agaccagaaa cagattctgc gtctacagcc tcaggtggcc tgtgccacca
```

FIGURE 45 (continued)

```
1801 gagaaatcgc agtggacaat tgccagtgca gtcgaaggcc tccagttcac cccctttgcag
1861 tcacagcagt gaatcttctc ttggctcaga tagcatcaaa tccccggttc ctcttctttc
1921 aaaaaacaaa agccaaaaaa gctccccacc tgctccatgt cacgccacac agaacggtca
1981 ggtggtggag gcctggtacg gctctgatga gtacctagcg ctgccctctc acctgaagca
2041 gacggaggtg ttagctctca agctggagag cctaaccaag ctcctacccc agaaacccag
2101 aggagagacc atccaggata ttgatgactg ggaactgtct gaaatgaatt cagattccga
2161 aatctatcca acataccaca tcaagaaaaa acacacgaga ctgggcacag tgtctccaag
2221 ctcatccagc gacatagcct catctctcgg ggagagcatt gaatccgggc ccctgagtga
2281 cattctttct gacgaggact tatgtctgcc cctctccagc gtgaaaaagt tcactgacga
2341 gaaatcagag agaccttcat cctccgagaa gaacgagagc cattctgcaa caagatcagc
2401 tttgattcag aaactaatgc acgatattca gcaccaagag aactatgaag ccatctggga
2461 aagaattgag ggtttgtga acaagctgga tgaattcatt cagtggctaa acgaagccat
2521 ggagaccacc gagaactgga ctcctcctaa agccgagacc gacagcctcc ggctgtacct
2581 ggagacacac ttgagtttta agttgaacgt agacagccac tgtgccctca aggaagccgt
2641 ggaggaagaa ggacaccaac ttcttgagct cgttgtatct cacaaagcag gactgaagga
2701 cacgctgagg atgattgcga gtcaatggaa ggagctgcag aggcaaatca aacggcaaca
2761 cagctggatt ctcagagccc tggacaccat caaagccgag atactggcta ctgatgtgtc
2821 tgtggaggac gaggagggga cgggaagccc caaggccgag gttcagctct gccacctgga
2881 aacacagaga gacgccgtgg aacagatgtc cctgaagctg tacagcgagc agtacaccag
2941 cgggagcaag aggaaggaag agtttgccaa catgtcgaaa gcgcacgcgg agggaagcaa
3001 tgggcttctg gactttgatt cagaatatca ggagctctgg gattggctga ttgacatgga
3061 gtccctcgtg atggacagcc acgacctgat gatgtcagag gagcagcagc agcatcttta
3121 caagaggtac agtgtggaaa tgtccatcag gcatctgaaa aagtcagagc tactcagcaa
3181 ggttgaagct ttgaagaaag gtggcctttc actaccagac gatatcctgg aaaaagtgga
3241 ttcaattaat gaaaaatggg agctgcttgg gaaaacccta agagagaaga tacaggacac
3301 aatagcgggg cacagtgggt cgggcccacg tgacctgcta tctcctgaaa gcggaagcct
3361 ggtaaggcag ctggaggtca ggatcaaaga gctgaaaagg tggctaagag atacagagct
3421 tttcatcttc aattcctgtc tgagacaaga gaaggaagga acaagcgccg agaaacagct
3481 ccaatacttt aagtcgctct gtcgtgagat caagcagcgg cgtcgaggag tggcctccat
3541 tctgaggttg tgccagcacc ttctggatga ccgggacacg tgcaacctga acgcagatca
3601 ccagcccatg cagctgatca ttgtaaacct cgagaggcgg tgggaggcca tcgtcatgca
3661 agctgtccag tggcaaacac ggttacaaaa gaagatgggg aaggaatccg agactttgaa
3721 tgtgattgat cctggcttga tggacctgaa tggaatgagt gaggatgccc tggaatggga
3781 tgaaacagac ataagtaaca aactcattag tgtgcatgaa gaatcaaacg accttgatca
3841 agacccagag cctatgctac ccgcagtgaa gcttgaagag acacaccaca aggactctgg
3901 ttatgaagag gaggcaggtg actgtggagg gtctccgtat acctcaaata tcactgcacc
3961 ttccagccca cacatttacc aagtgtacag tcttcacaat gtggagctcc acgaggacag
4021 ccacactcca tttctgaaaa gcagccctaa gttcacaggc acaacacagc ctactgtttt
4081 aactaagagc ctcagcaagg actcttcctt ttcatctaca aaatcgttac cagaccttct
4141 agggggttcc ggtttggtga ggccttactc gtgtcacagt ggagacttga gccagaattc
4201 aggcagtgag agtggaattg tcagcgaagg agacaacgag atgccgacca actctgacat
4261 gagcttgttc agtatggtag acgggtcccc aagtaaccct gaaacggagc atccggaccc
4321 acaaatggga gatgcagcca atgtgctaga gcaaaagttt aaagacaacg ggaaagcat
4381 taagctttca agtgtctctc gggcatccgt ctcaccagtg ggttgtgtaa atggaaaagc
4441 aggggattta aacagtgtta ccaaacacac tgctgattgt ttgggagaag aactacaagg
4501 aaaacatgac gtgtttacat tttatgatta ctcgtacctc caaggctcaa aactcaaatt
4561 accaatgata atgaaacagc cacagagtga aaaggcacac gtggaggatc cccttcttgg
4621 tggtttttat tttgataaaa agtcctgcaa agctaaacat caggcttcag agtcacaacc
4681 agatgcgcct ccccacgaaa ggattctggc aagcgcgccc cacgagatgg gacgcagcgc
4741 atacaaaagt agcgacatag agaagacatt cacgggcatt cagagtgcca gacagctctc
4801 ccttctatct cgtagctcat ctgtagagtc cctttctcca gggggtgatt tgtttggatt
4861 gggaatcttt aaaaatggca gtgacagcct ccagcggagc acttctttag aaagttggtt
```

FIGURE 45 (continued)

```
4921 gacatcctat aagagcaatg aggatctctt tagctgtcac agctctgggg acataagtgt
4981 gagcagtggc tcagttggtg agctgagtaa gaggacgtta gaccttctga atcgcctgga
5041 gaatatacag agcccctcgg agcaaaagat caagcggagt gtttctgaca tgactctaca
5101 aagcagttcc caaaagatgc ccttcgctgg ccagatgtca ctggatgtcg catcctccat
5161 caatgaagac tctccggcat ctcttacaga actgagtagt agcgatgagc tctctctttg
5221 ctcggaggac attgtgttac acaaaaacaa gatcccagaa tccaacgcat cattcaggaa
5281 gcgcctgaat cgctcagtgg ctgatgagag cgacgtcaat gttagcatga ttgtcaatgt
5341 gtcctgcacc tctgcttgca ctgatgatga agatgacagc gacctcctct ccagctccac
5401 tctcacctta actgaagaag agctgtgcct caaagatgag gatgacgact ccagtattgc
5461 aacagatgat gaaatttatg aagagagcaa cctgatgtct gggctggact acataaagaa
5521 tgaactgcag acttggataa gaccaaaact ttccttgacg agagaaaaga aacggtccgg
5581 tgtcactgat gaaataaagg tcaataaaga tgggggaggc aatgagaagg ccaatccctc
5641 ggacaccctg gacatcgagg cccttctcaa tggctccata agatgtcttt ccgaaaacaa
5701 cgggaatggt aagactccgc ccagaactca tggctcagga accaaaggtg aaaataagaa
5761 aagtacgtat gacgttagta aggatccgca cgtggctgac atggaaaatg gcaatattga
5821 aagtacccca gaaagagaaa gggagaagcc acaagggctt ccagaggtgt cagagaacct
5881 tgcttcaaat gtgaaaacga tttctgaatc tgagctcagc gagtatgaag cagtaatgga
5941 tggttctgag gattcaagtg ttgccagaaa ggaattttgt cccccaaatg acagacatcc
6001 tccacagatg ggtcccaaac tccagcatcc cgaaaatcaa agtggcgact gcaagccagt
6061 ccagaaccct tgcccggggc tactgtcgga agctggcgtt ggaagcaggc aagacagcaa
6121 tggactaaaa tctttgccta acgatgcacc aagtggggct agaaaacctg ccggttgctg
6181 cctgctggag cagaatgaga cagaggaaag tgcttctatc agcagcaacg cttcctgttg
6241 caactgcaag ccagatgttt tccatcaaaa agatgatgaa gattgttcag tacatgactt
6301 tgttaaggaa atcattgaca tggcatcaac agccctaaaa agtaagtcac agcctgaaag
6361 tgaggtggcc gcacccacat cactaaccca aattaaggag aaggtgttag agcattcgca
6421 ccggcccata cacctgagaa agggggactt ttactcctac ttatcacttt cgtcccacga
6481 cagtgactgt ggggaggtca ccaattacat agatgagaag agcagtactc cattgccacc
6541 ggacgctgtg gactctggct tagatgacaa ggaagacatg gactgcttct ttgaagcttg
6601 tgttgaggat gagcctgtca atgaggaagc tggtctcccc ggtgcccttc ccaatgaatc
6661 agccatcgag gatggagcag agcaaaagtc agaacaaaag acagccagct ctcctgtgct
6721 cagtgacaag acagacctgg tgcctctttc aggactttcc cctcagaagg gagctgatga
6781 tgcaaaggaa ggagatgatg tgtctcacac ttcccagggc tgtgcagaga gcacagagcc
6841 taccaccccc tcaggaaagg ccaatgcaga ggggaggtca agaatgcaag gtgtatcagc
6901 aacgccagaa gaaaacgctg cttcggccaa accgaaaatt caagctttct ctttgaatgc
6961 aaaacagcca aaaggcaagg ttgccatgag gtatcccagc ccccaaactc taacctgtaa
7021 agagaagctc gtaaactttc atgaagatcg acacagtaac atgcataggt agagtgtaat
7081 gcccccacgc atggaaatca tctcattgaa agatagcctg gctgaagctc agggctagcc
7141 caatccaccc tgggccggtc ttgggctcca tcctgttatc actgccgcct gtcacattga
7201 ctttctgaag acgaaccttc cttccgaatg cagtctgtcc acgtgggcct ctcgacctgg
7261 atgtgtgcat tgcttctctt aggtgatcat cctagttcca caaagctgct tgttctcccg
7321 tggattcctg tcccaagcta cctctggcaa ccctgtctct ccagcaagac ttcggttttc
7381 cctcccccctc ctccccccccc ttaaagttcc gcggctcacc aaattgatgg tccatcaaac
7441 ccactgtctg gaatgatacc cctcccatca gtacttgacc aatgttatgt tttgctctga
7501 aaactttcgc tgtattagac caatgtttat tgaaagagat ttacctaaaa agcccgccct
7561 tgatttggtt gcagtataga ggagacacat tgatccttct aacaaaatta agtgatgtct
7621 gaaagcgcca ttttaattat ttctttttaa ataatgatct atgcagcact tcaagaaaca
7681 actataacag tgttgtatct tataaactgg tacattctac tattaagttt gtttttggtt
7741 tctatgcttc ttgaggtggt gatgagaaaa atggtttttt ttttaaaacg gtgtgccttg
7801 ctgtattact tatagcattt attaaaaagc tgctttcatg gtaagattac actggtttga
7861 aaggaggaaa tagcaaggtt aagatgcgtg cataatttct gtatatatgt ataagctagt
7921 gcaaacactg atgtatgaca gtataaaatg ctttcatgtt tgtgatgtcc agtggtgtgg
7981 aatataagcc ttaaacccgt tcgattgcat ggtaattaaa attggcataa taaaaatagc
```

FIGURE 45 (continued)

```
8041 ttattggggg aaaggaaaat taatgatctc ttctacctgt gtttaccaat ttctttcatg
8101 tggttctggg aaagaaaaag aaacaaaccc catatattag cttccaaaat atccatattg
8161 cacagaaggc ttaagttgct tagactacag actgggcctg aagacttcat gattttccaa
8221 atttttctgt ttcactataa acatccgaaa tagcaaagat ttctttcccc tccatcaaca
8281 gcattttatt ctgaatgttt ttatttctac ttgttaatgg tttaaagttg tatttggaga
8341 tctcttacat gccctaattt attttaaata tttgaatggg tttggtggat ggtatagaaa
8401 atttaattat tattttattt aaactacaga tttcaggtgt atttattttg ttaaatattc
8461 catttggtct tttggtcttt ttatgacttg aaagtttcag cttttaattt atatcataac
8521 tcctactaaa gtgcctgaca cacagtaggt atttcataga gtttcctgaa ttagagtatt
8581 gggtggttta tatatatata tatatatatg agattcctgc attaaaacta gaaaaagatg
8641 tgcaaagtga accagacaca gcatattatc agatttcaaa aaggaaagag aacatagcca
8701 cagaaatgac aatcattcat tcagtagatt agcatctttt gcctgcaagt caccattcta
8761 gattcaggga gagcagctat gaccgatgca ctgcctttgg aggcttctgt gttagagaca
8821 gagtgacctc gtgccgaatt c
//
```

COMPOSITIONS FOR TREATING HEART DISEASE BY INHIBITING THE ACTION OF mAKAP-β

CROSS-REFERENCE TO RELATED APPLICATION

The present application is a CON of Ser. No. 17/580,692, filed Jan. 21, 2022 (now U.S. Pat. No., 11,931,402), which is a CON of Ser. No. 16/837,633, filed Apr. 1, 2020 (now U.S. Pat. No. 11,229,679), which is a CON of Ser. No. 15/946,238 filed Apr. 5, 2018 (now U.S. Pat. No. 10,617,737) which is a DIV of Ser. No. 14/821,082 filed Aug. 7, 2015 (now U.S. Pat. No. 9,937,228) which is a CON of Ser. No. 14/213,583 filed Mar. 14, 2014 (now U.S. Pat. No. 9,132,174) which claims the benefit of 61/798,268 filed Mar. 15, 2013.

STATEMENT OF GOVERNMENTAL SUPPORT

This invention was made with Government support under contract RO1 HL 075398 awarded by the National Institutes of Health. The Government has certain rights in this invention.

REFERENCE TO SEQUENCE LISTING, COMPUTER PROGRAM, OR COMPACT DISK

The instant application contains a Sequence Listing which has been submitted electronically in XML file format and is hereby incorporated by reference in its entirety. Said XML copy, created on Jan. 30, 2024, is named 65274_6US06_SL.xml and is 49,857 bytes in size.

BACKGROUND OF THE INVENTION

The heart is capable of undergoing hypertrophic growth in response to a variety of stimuli.

Hypertrophic growth may occur as the result of physical training such as running or swimming. However, it also occurs as the result of injury or in many forms of heart disease. Hypertrophy is the primary mechanism by which the heart reduces stress on the ventricular wall. When the growth is not accompanied by a concomitant increase in chamber size, this is called concentric hypertrophy. Hypertrophy occurs as the result of an increase in protein synthesis and in the size and organization of sarcomeres within individual myocytes. For a more thorough review of cardiac remodeling and hypertrophy, see Kehat (2010) and Hill (2008), each herein incorporated by reference in their entirety. The prevailing view is that cardiac hypertrophy plays a major role in heart failure. Traditional routes of treating heart failure include afterload reduction, blockage of beta-adrenergic receptors (β-ARs) and use of mechanical support devices in afflicted patients. However, the art is in need of additional mechanisms of preventing or treating cardiac hypertrophy.

AKAPs and Cardiac Hypertrophy

Ventricular myocyte hypertrophy is the primary compensatory mechanism whereby the myocardium reduces ventricular wall tension when submitted to stress because of myocardial infarction, hypertension, and congenital heart disease or neurohumoral activation. It is associated with a nonmitotic growth of cardiomyocytes, increased myofibrillar organization, and upregulation of specific subsets of "fetal" genes that are normally expressed during embryonic life (Frey 2004, Hill 2008). The concomitant aberrant cardiac contractility, $Ca^{2+}$ handling, and myocardial energetics are associated with maladaptive changes that include interstitial fibrosis and cardiomyocyte death and increase the risk of developing heart failure and malignant arrhythmia (Cappola 2008, Hill 2008). Increased in prevalence by risk factors such as smoking and obesity, heart failure is a syndrome that affects about six million Americans and has an annual incidence of 1% of senior citizens (Roger 2011). Since the five-year survival rate after diagnosis is still very poor (lower than 50%), many efforts have been made during the last years to define the molecular mechanisms involved in this pathological process.

Cardiac hypertrophy can be induced by a variety of neuro-humoral, paracrine, and autocrine stimuli, which activate several receptor families including G protein-coupled receptors, cytokine receptors, and growth factor tyrosine kinase receptors (Brown 2006, Frey 2004). In this context, it is becoming increasingly clear that AKAPs can assemble multiprotein complexes that integrate hypertrophic pathways emanating from these receptors. In particular, recent studies have now identified anchoring proteins including mAKAP and AKAP-Lbc and D-AKAP1 that play a central role in organizing and modulating hypertrophic pathways activated by stress signals.

mAKAP. In cardiomyocytes, mAKAPβ is localized to the nuclear envelope through an interaction with nesprin-1α (Pare 2007). mAKAPβ assembles a large signaling complex that integrates hypertrophic signals initiated by α1-adrenergic receptors (α1-ARs) and β-ARs, endothelin-1 receptors, and gp130/leukemia inhibitor factor receptors (FIG. 46A) (Dodge-Kafka 2005, Pare 2005). Over the last few years, the molecular mechanisms as well as the signaling pathways whereby mAKAPβ mediates cardiomyocyte hypertrophy have been extensively investigated. It is now demonstrated that mAKAPβ can recruit the phosphatase calcineurin Aβ (CaNAβ) as well as the hypertrophic transcription factor nuclear factor of activated T cells c3 (NFATc3) (Li 2010). In response to adrenergic receptor activation, anchored CaNAβ dephosphorylates and activates NFATc3, which promotes the transcription of hypertrophic genes (FIG. 46A) (Li 2010). The molecular mechanisms controlling the activation of the pool of CaNAβ bound to the mAKAPβ complex are currently not completely understood but seem to require mobilization of local $Ca^{2+}$ stores. In this context, it has been shown that mAKAP favors PKA-induced phosphorylation of RyR2 (Kapiloff 2001), which, through the modulation of perinuclear $Ca^{2+}$ release, could activate CaNAβ (FIG. 46A). In line with this hypothesis, the deletion of the PKA anchoring domain from mAKAPβ has been shown to suppress the mAKAP-mediated hypertrophic response (Pare 2005). On the other hand, recent findings indicate that mAKAPβ also binds phospholipase Cε(PLCε) and that disruption of endogenous mAKAPβ-PLCεcomplexes in rat neonatal ventricular myocytes inhibits endothelin 1-induced hypertrophy (Zhang 2011). This suggests that the anchoring of PLCε to the nuclear envelope by mAKAPβ controls hypertrophic remodeling. Therefore, it is also plausible that at the nuclear envelope, PLCε might promote the generation of inositol 1,4,5-trisphosphate, which through the mobilization of local $Ca^{2+}$ stores, might promote the activation of CaNAβ and NFATc3 bound to mAKAPβ (FIG. 46A).

In cardiomyocytes, the dynamics of PKA activation within the mAKAP complex are tightly regulated by AC5 (Kapiloff 2009) and the PDE4D3 (Dodge-Kafka 2005, Dodge 2001) that are directly bound to the anchoring protein. The mAKAP-bound AC5 and upstream β-AR may be localized within transverse tubules adjacent to the nuclear envelope (Escobar 2011). In response to elevated cAMP levels, mAKAP-bound PKA phosphorylates both AC5 and PDE4D3 (Dodge-Kafka 2005, Dodge 2001, Kapiloff 2009). This induces AC5 deactivation and PDE4D3 activation, which locally decreases cAMP concentration and induces deactivation of anchored PKA (FIG. 46A). Dephosphorylation of PDE4D3 is mediated by the phosphatase PP2A that is also associated with mAKAPβ (FIG. 46A) (Dodge-Kafka 2010). Collectively, these findings suggest that the mAKAP complex generates cyclic pulses of PKA activity, a hypothesis that was supported experimentally by live cell imaging studies (Dodge-Kafka 2005).

AKAPs and Hypoxia

Myocardial oxygen levels need to be maintained within narrow levels to sustain cardiac function. During ischemic insult, in response to conditions of reduced oxygen supply (termed hypoxia), cardiomyocytes mobilize hypoxia-inducible factor 1α (HIF-1α), a transcription factor that promotes a wide range of cellular responses necessary to adapt to reduced oxygen (Semenza 2007). Transcriptional responses activated by HIF-1α control cell survival, oxygen transport, energy metabolism, and angiogenesis (Semenza 2007). Under normoxic conditions, HIF-1α is hydroxylated on two specific proline residues by the prolyl hydroxylase domain proteins (PHDs) and subsequently recognized and ubiquitinated by the von Hippel-Lindau protein (Jaakkola 2001, Maxwell 1999). Ubiquitinated HIF-1α is targeted to the proteasome for degradation. On the other hand, when oxygen concentration falls, the enzymatic activity of PHD proteins is inhibited. Moreover, PHD proteins are ubiquitinated by an E3 ligase named "seven in absentia homolog 2 (Siah2)" and targeted for proteasomal degradation (Nakayama 2004). This inhibits HIF-1α degradation and allows the protein to accumulate in the nucleus where it promotes gene transcription required for the adaptive re-sponse to hypoxia. In line with this finding, the delivery of exogenous HIF-1α improves heart function after myocardial infarction (Shyu 2002), whereas cardiac overexpression of HIF-1α reduces infarct size and favors the formation of capillaries (Kido 2005).

Recent findings indicate that mAKAP assembles a signaling complex containing HIF-1α, PHD, von Hippel-Lindau protein, and Siah2 (Wong 2008). This positions HIF-1α in proximity of its upstream regulators as well as to its site of action inside the nucleus. In this configuration, under normoxic conditions, negative regulators associated with the mAKAP complex favor HIF-1α degradation (Wong 2008). On the other hand, during hypoxia, the activation of Siah2 within the mAKAP complex promotes HIF-1α stabilization, allowing the transcription factor to induce transcription (Wong 2008). Therefore, mAKAP assembles a macromolecular complex that can favor degradation or stabilization of HIF-1α in cardiomyocytes in response to variations of oxygen concentrations. In this context, mAKAP could play an important role in cardiomyocyte protection during cardiac ischemia, when coronary blood flow is reduced or interrupted. By coordinating the molecular pathways that control HIF-1α stabilization in cardiomyocytes, mAKAP might favor HIF-1α-mediated transcriptional responses, controlling the induction of glycolysis (which maximizes ATP production under hypoxic conditions), the efficiency of mitochondrial respiration, and cell survival during ischemia (Semenza 2009).

Myofibrillar assembly driving nonmitotic growth of the cardiac myocyte is the major response of the heart to increased workload (Kehat 2010). Although myocyte hypertrophy per se may be compensatory, in diseases such as hypertension and myocardial infarction, activation of the hypertrophic signaling network also results in altered gene expression ("fetal") and increased cellular apoptosis and interstitial fibrosis, such that left ventricular hypertrophy is a major risk factor for heart failure. Current therapy for pathologic hypertrophy is generally limited to the broad downregulation of signaling pathways through the inhibition of upstream cell membrane receptors and ion channels (McKinsey 2007). Novel drug targets may be revealed through the identification of signaling enzymes that regulate distinct pathways within the hypertrophic signaling network because of isoform specificity or association with unique multimolecular signaling complexes.

p90 ribosomal S6 kinases (RSK) are pleiotropic extracellular signal-regulated kinase (ERK) effectors with activity that is increased in myocytes by most hypertrophic stimuli (Anjum 2008, Sadoshima 2005, Kodama 2000). In addition, increased RSK activity has been detected in explanted hearts from patients with end-stage dilated cardiomyopathy (Takeishi 2002). There are 4 mammalian RSK family members that are ubiquitously expressed and that overlap in substrate specificity (Anjum 2008). RSKs are unusual in that they contain 2 catalytic domains, N-terminal kinase domain and C-terminal kinase domain (FIG. 4A, Anjum 2008). The N-terminal kinase domain phosphorylates RSK substrates and is activated by sequential phosphorylation of the C-terminal kinase domain and N-terminal kinase domain by ERK (ERK1, ERK2, or ERK5) and 3'-phosphoinositide-dependent kinase 1 (PDK1), respectively (Anjum 2008).

By binding scaffold proteins, RSKs may be differentially localized within subcellular compartments, conferring isoform-specific signaling bound to the scaffold protein muscle A-kinase anchoring protein (mAKAP) (Michael 2005). PDK1 activation of RSK was enhanced by co-expression with the mAKAP scaffold in a recombinant system. In cardiac myocytes, mAKAPβ (the alternatively spliced form expressed in muscle cells) organizes signalosomes that transduce cAMP, mitogen-activated protein kinase, $Ca^{2+}$, and hypoxic signaling by binding a diverse set of enzymes, ion channels, and transcription factors (Kritzer 2012).

SUMMARY OF THE INVENTION

The following brief summary is not intended to include all features and aspects of the present invention, nor does it imply that the invention must include all features and aspects discussed in this summary.

The present inventors have discovered methods of treating cardiac pathological processes by inhibiting the signaling properties of individual mAKAP signaling complexes using drugs that target unique protein-protein interactions. Such a therapeutic strategy offers an advantage over classical therapeutic approaches because it allows the selective inhibition of defined cellular responses.

In particular, the present inventors have found that disrupting mAKAP-mediated protein-protein interactions can be used to inhibit the ability of mAKAP to coordinate the activation of enzymes that play a central role in activating key transcription factors that initiate the remodeling process leading to cardiac hypertrophy.

Specifically, the inventors have discovered that inhibiting the binding interaction between type 3 ribosomal S6 kinase (RSK3) and mAKAPβ can protect the heart from damage caused by various physical stresses, for example pressure overload and prolonged exposure to high levels of catecholamines.

Thus, the present invention comprises, in certain aspects a method for protecting the heart from damage, by administering to a patient at risk of such damage, a pharmaceutically effective amount of a composition which inhibits the interaction of RSK3 and mAKAPβ.

The invention also relates to a method of treating heart disease, by administering to a patient a pharmaceutically effective amount of a composition which inhibits the interaction of RSK3 and mAKAPβ.

The invention also relates to compositions which inhibit the interaction of RSK3 and mAKAPβ.

In still other embodiments, the inhibitors include any molecule that inhibits the expression or activity of RSK3 and mAKAPβ.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2. Shows the amino acid sequence of RSK3 (SEQ ID NO:1).

FIG. 3. Shows the amino acid sequence of mAKAP (SEQ ID NO: 2).

FIG. 10 shows echocardiographic data for $RSK^{-/-}$ mice after transverse aortic constriction.

FIG. 11 shows gene expression for $RSK^{-/-}$ mice after transverse aortic constriction.

FIG. 12 shows breeding of $RSK^{-/-}$ mice.

FIG. 13 shows echocardiographic data for $RSK^{-/-}$ mice when unstressed.

FIG. 14 shows gravimetric data for $RSK^{-/-}$ mice following TAC.

FIG. 15 shows echocardiographic data for $RSK^{-/-}$ mice after isoproterenol infusion.

FIG. 16 shows gravimetric data for $RSK^{-/-}$ mice after isoproterenol infusion.

FIG. 17 shows echocardiographic data for $RSK^{-/-}$ mice after chronic exercise.

FIG. 18 shows gravimetric data for $RSK^{-/-}$ mice after chronic exercise.

FIG. 19 shows sources of commercial antibodies used.

FIG. 20 shows sequences of oligonucleotides (SEQ ID Nos:3-8).

FIGS. 22 and 5A). Note that the relatively increased detection of RSK4 with this antibody is consistent with RSK4 being constitutive active in cells.[2] Similarly, the relatively high signals for phospho-RSK3 are more likely attributable to an enhanced baseline ERK phosphorylation of RSK3 in cells than an increased specificity of this antibody for the RSK3 isoform.[8] RSK3 is a minority of the total RSK protein in myocytes (see FIG. 24C). As a result, signal derived from endogenous proteins in whole cell lysates using these phospho-specific antibodies cannot be attributed solely to RSK3.

FIGS. 22A-22D. RSK Activation in Neonatal Cardiac Myocytes. Neonatal rat ventricular myocytes were treated for 1 hour with 10 μmol/L PE, 10% FBS, or 1000 U/mL LIF in the absence or presence of the MAPK inhibitors as indicated. Total RSK was detected using the non-specific monoclonal RSK3 antibody 1F6 and the phospho-$S^{218}$ antibody. *p<0.05 relative to same condition without inhibitor; †\p<0.005 relative to control; n=2-7. FIG. 22A is a Western Blot showing total RSK detected from neonatal rat ventricular myocytes treated for 1 hour with 10 μmol/L PE, 10% FBS, or 1000 U/mL LIF in the absence or presence of 10 μM BIX02189 or 20 μM PD98059. Total RSK was detected using the non-specific monoclonal RSK3 antibody 1F6 and the phospho-$S^{218}$ antibody. FIG. 22B is a Western Blot showing total RSK detected from neonatal rat ventricular myocytes treated for 1 hour with 10 μmol/L PE, 10% FBS, or 1000 U/mL LIF in the absence or presence of 10 μM PE, 10 μM BIX02189, 10 μM PD98059, 0.1 μM or 10 μM PD0325901, 10 μM SP600125 or 10 μMSB103580. Total RSK was detected using the non-specific monoclonal RSK3 antibody 1F6 and the phospho-$S^{218}$ antibody. FIG. 22C is a graph representing a compilation of the experiment presented in FIG. 22A. FIG. 22D is a graph representing a compilation of the experiment presented in FIG. 22B. The PE bars are the same in both graphs. PD0325901 is selective for MEKI/2 at 0.1 μmol/L, but also inhibits MEK5 at 10 μmol/L. BIX02189 is specific for MEK5. SP600125 and SB103580 are selective for JNK and p38, respectively.

FIG. 31 shows echocardiographic data for mice treated as in Example 2 at 16 weeks of age.

FIG. 34 for panels B and D.

FIG. 35. *p-values compared to WT cohort; †p-values compared to TM180 cohort.

FIG. 34 shows gravimetric data for mice treated as in Example 2.

FIG. 35 shows gene expression data from the method of Example 2.

FIG. 43A shows the complete nucleotide (SEQ ID NO:21) and deduced amino acid (SEQ ID NO:22) sequence of human RSK3. (Zhao et al. (1995) Mol. Cell. Biol. 15(8): 4353.) The sequence was derived from a full-length cDNA clone. The deduced RSK3 protein sequence is indicated in the one-letter amino acid code beginning at the first methionine residue preceding the 733-codon open reading frame and terminating at the asterisk. Highly conserved amino acid residues among the known protein kinases are shown in boldface type. The unique N-terminal region of RSK3 (which bears no homology to RSK1 or RSK2) is underlined; the putative bipartite nuclear targeting motif is indicated by parentheses. An in-frame stop codon upstream of the first methionine is indicated (ooo). This nucleotide sequence was submitted to the EMBL-GenBank data library and assigned accession number X85106. FIG. 43B shows in vitro translation of RSK3. In vitro transcripts were generated with T7 polymerase from the vector alone (lane 1) or from the vector with an RSK3 insert by using T7 polymerase (lane 2, sense oriented) or Sp6 polymerase (lane 3, antisense oriented). Subsequent in vitro translation was performed with rabbit reticulocyte lysate in the presence of $^{35}$Smethionine. Proteins were then resolved by SDSPAGE (10% polyacrylamide) followed by autoradiography. FIG. 43C shows immunoblotting with RSK3-specific antiserum. Antiserum N-67 was raised against a peptide (KFA VRRFFSVYLRR) derived from the unique N-terminal region of RSK3 (residues 7 to 20 of SEQ ID NO:1). In this example, proteins derived from human skin fibroblasts were separated by SDS-PAGE followed by Western immunoblotting. Blots were probed with preimmune serum or N-67. A band of 83 kDa was detected when N-67 was used.

FIG. 44. Shows the nucleotide sequence of RSK3 (SEQ ID NO: 23).

FIG. 45. Shows the amino acid sequence of mAKAP (SEQ ID NO: 24).

DETAILED DESCRIPTION OF THE INVENTION

As discussed above, AKAP-based signaling complexes play a central role in regulating physiological and pathological cardiac events. As such, the present inventors have examined inhibiting the signaling properties of individual AKAP signaling complexes using drugs that target unique protein-protein interactions as an approach for limiting cardiac pathological processes. Such a therapeutic strategy offers an advantage over classical therapeutic approaches since it allows the selective inhibition of defined cellular responses.

Anchoring proteins including mAKAP are therapeutic targets for the treatment of cardiac hypertrophy and heart failure. In particular, the present inventors have found that disrupting AKAP-mediated protein-protein interactions can be used to inhibit the ability of mAKAP to coordinate the activation of enzymes that play a central role in activating key transcription factors that initiate the remodeling process leading to cardiac hypertrophy.

Figure 41:
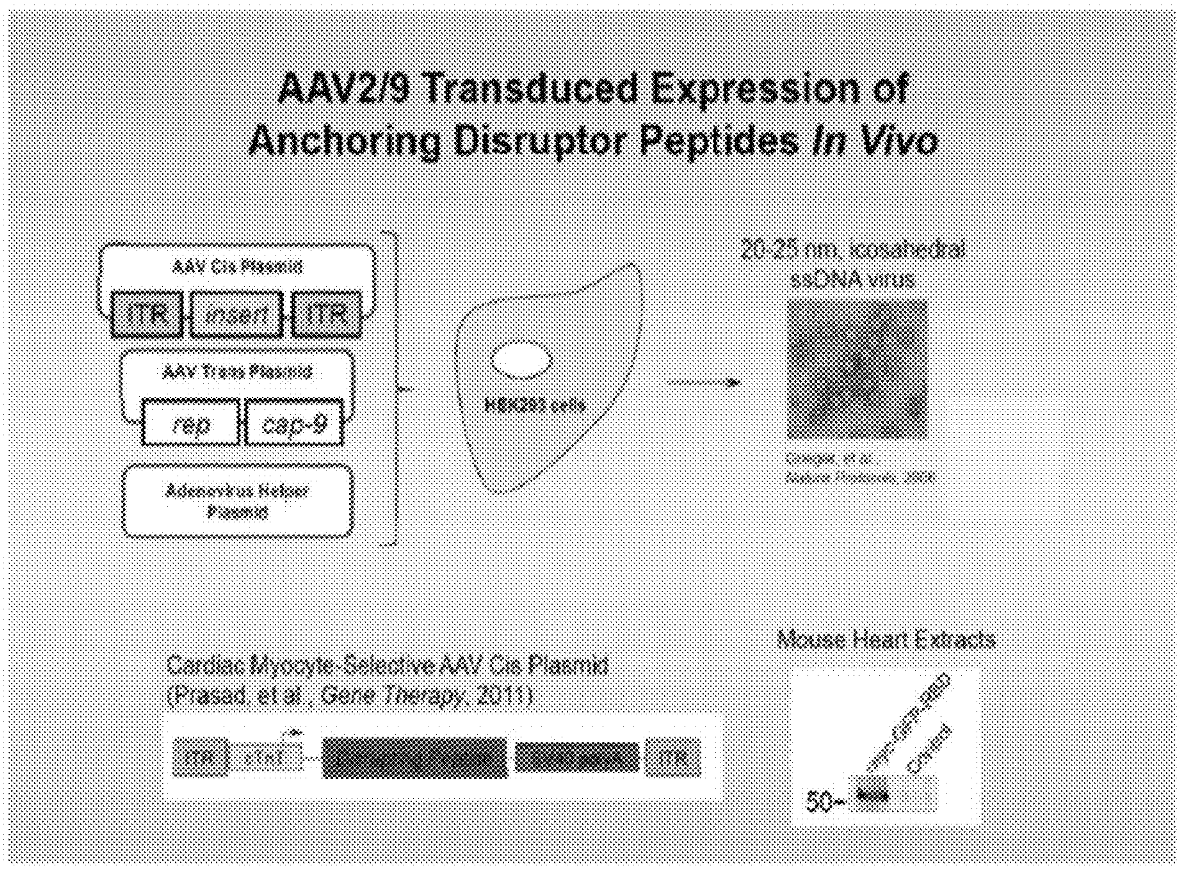
FIG. 41 shows AAV2/9 transduced expression of anchoring disruptor peptides in vivo.

In particular, the inventors have found that type 3 ribosomal S6 kinase (RSK3) binds mAKAPβ directly via the unique N-terminal domain of RSK3, defining a novel enzyme-scaffold interaction. The inventors have found that anchored RSK3 regulates concentric cardiac myocyte growth, revealing an isoform-specific target for therapeutic intervention in pathologic cardiac hypertrophy. Delivery of such peptides that might inhibit RSK3-mAKAPβ interaction can be enhanced by the use of cell-penetrating sequences such as the transactivator of transcription peptide and polyarginine tails, or conjugation with lipid-derived groups such as stearate. Stability may also be enhanced by the use of peptidomimetics [i.e., peptides with structural modifications in the original sequence giving protection against exo- and endoproteases without affecting the structural and functional properties of the peptide. Alternatively, as shown in FIG. 41, peptides can be delivered by intracellular expression via viral-based gene therapy vectors.

The inventors have also found that small molecule disruptors can be used to target specific interaction within AKAP-based complexes. Small molecule disruptors can be identified by combining rational design and screening approaches. Such compounds can be designed to target-specific binding surfaces on AKAPs, to disrupt the interaction between AKAPs and PKA in cardiomyocytes and to enhance the contractility of intact hearts for the treatment of chronic heart failure.

The present invention relates to methods of treating any cardiac condition, which is initiated through the interaction of RSK3 and mAKAPβ. Such cardiac dysfunction can result in signs and symptoms such as shortness of breath and fatigue, and can have various causes, including, but not limited to hypertension, coronary artery disease, myocardial infarction, valvular disease, primary cardiomyopathy, congenital heart disease, arrhythmia, pulmonary disease, diabetes, anemia, hyperthyroidism and other systemic diseases.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (4th Ed., 2012); "Current Protocols in Molecular Biology" Volumes I-III [Ausubel, R. M., ed. (1994)]; "Cell Biology: A Laboratory Handbook" Volumes I-III [J. E. Celis, 3rd ed. (2005))]; "Current Protocols in Immunology" Volumes I-III [Coligan, J. E., ed. (2005)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984); C. Machida, "Viral Vectors for Gene Therapy: Methods and Protocols" (2010); J. Reidhaar-Olson and C. Rondinone, "Therapeutic Applications of RNAi: Methods and Protocols" (2009).

The following definitions and acronyms are used herein:

ANF atrial natriuretic factor

CTKD C-terminal kinase domain

ERK extracellular signal-regulated kinase

FBS fetal bovine serum

GFP green fluorescent protein

Iso isoproterenol

LIF leukemia inhibitory factor mAKAP muscle A-kinase anchoring protein

NTKD N-terminal kinase domain

PDK1 3'phosphoinositide-dependent kinase 1

PE phenylephrine

RBD RSK binding domain

RSK p90 ribosomal S6 kinase siRNA small interfering RNA oligonucleotide

TAC transverse aortic constriction

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

The present invention recognizes that the interaction of RSK3 and mAKAPβ mediates various intracellular signals and pathways which lead to cardiac myocyte hypertrophy and/or dysfunction. As such, the present inventors have discovered various methods of inhibiting that interaction in order to prevent and/or treat cardiac myocyte hypertrophy and/or dysfunction.

Thus, the present invention includes a method for protecting the heart from damage, by administering to a patient at risk of such damage, a pharmaceutically effective amount of a composition, which inhibits the interaction of RSK3 and mAKAPβ. It should be appreciated that "a pharmaceutically effective amount" can be empirically determined based upon the method of delivery, and will vary according to the method of delivery.

The invention also relates to a method of treating heart disease, by administering to a patient a pharmaceutically effective amount of a composition, which inhibits the interaction of RSK3 and mAKAPβ.

The invention also relates to compositions which inhibit the interaction of RSK3 and mAKAPβ. In particular embodiments, these inhibiting compositions or "inhibitors" include peptide inhibitors, which can be administered by any known method, including by gene therapy delivery. In other embodiments, the inhibitors can be small molecule inhibitors.

Specifically, the present invention is directed to methods and compositions for treating or protecting the heart from damage, by administering to a patient at risk of such damage, a pharmaceutically effective amount of a composition which (1) inhibits the interaction of RSK3 and mAKAPβ; (2) inhibits the activity of RSK3 and mAKAPβ; or (3) inhibits the expression of RSK3 and mAKAPβ.

The invention also relates to methods of treating or protecting the heart from damage, by administering to a patient at risk of such damage, a pharmaceutically effective amount of a composition which inhibits a cellular process mediated by the anchoring of RSK3 through its N-terminal domain.

In one embodiment, the composition includes an RSK3 peptide. In a preferred embodiment, the RSK3 peptide is obtained from the amino terminus of the RSK3 amino acid sequence. In a particularly preferred embodiment, the RSK3 peptide is amino acids 1-42 of the RSK3 amino acid sequence.

In another embodiment, the composition includes a small interfering RNA siRNA that inhibits the expression of either or both of RSK3 and mAKAPβ.

The composition of the invention can be administered directly or can be administered using a viral vector. In a preferred embodiment, the vector is adeno-associated virus (AAV).

In another embodiment, the composition includes a small molecule inhibitor. In preferred embodiments, the small molecule is SL0101 or BI-D1870.

In another embodiment, the composition includes a molecule that inhibits the binding, expression or activity of mAKAPβ. In a preferred embodiment, the molecule is a mAKAPβ peptide. The molecule may be expressed using a viral vector, including adeno-associated virus (AAV).

In yet another embodiment, the composition includes a molecule that interferes with RSK3-mediated cellular processes. In preferred embodiments, the molecule interferes with the anchoring of RSK3 through its N-terminal domain.

The invention also relates to diagnostic assays for determining a propensity for heart disease, wherein the binding interaction of RSK3 and mAKAPβ is measured, either directly, or by measuring a downstream effect of the binding of RSK3 and mAKAPβ. The invention also provides a test kit for such an assay.

In still other embodiments, the inhibitors include any molecule that inhibits the expression of RSK3 and mAKAPβ, including antisense RNA, ribozymes and small interfering RNA (siRNA).

The invention also includes an assay system for screening of potential drugs effective to inhibit the expression and/or binding of RSK3 and mAKAPβ. In one instance, the test drug could be administered to a cellular sample with the RSK3 and mAKAPβ, or an extract containing the RSK3 and mAKAPβ, to determine its effect upon the binding activity of the RSK3 and mAKAPβ, by comparison with a control. The invention also provides a test kit for such an assay.

In preparing the peptide compositions of the invention, all or part of the RSK3 (FIG. 2) or mAKAPβ (FIG. 3) amino acid sequence may be used. In one embodiment, the amino-terminal region of the RSK3 protein is used as an inhibitor. Preferably, at least 10 amino acids of the RSK3 amino terminus are used. More preferably, about 18 amino acids of the RSK3 amino terminus are used. Most preferably, amino acids from about 1-42 of the RSK3 amino terminus are used.

In other embodiments, at least 10 amino acids of the mAKAPβ sequence are used. More preferably, at least 25 amino acids of the mAKAPβ sequence are used. Most preferably, peptide segments from amino acids 1694-1833 of the mAKAP sequence are used.

It should be appreciated that various amino acid substitutions, deletions or insertions may also enhance the ability of the inhibiting peptide to inhibit the interaction of RSK3 and mAKAPβ. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes, which do not significantly alter the activity, or binding characteristics of the resulting protein.

The following is one example of various groupings of amino acids:

- Amino acids with nonpolar R groups: Alanine, Valine, Leucine, Isoleucine, Proline, Phenylalanine, Tryptophan, Methionine.
- Amino acids with uncharged polar R groups: Glycine, Serine, Threonine, Cysteine, Tyrosine, Asparagine, Glutamine.
- Amino acids with charged polar R groups (negatively charged at pH 6.0): Aspartic acid, Glutamic acid.
- Basic amino acids (positively charged at pH 6.0): Lysine, Arginine, Histidine (at pH 6.0).
- Another grouping may be those amino acids with phenyl groups: Phenylalanine, Tryptophan, Tyrosine.
- Another grouping may be according to molecular weight (i.e., size of R groups): Glycine (75), Alanine (89), Serine (105), Proline (115), Valine (117), Threonine (119), Cysteine (121), Leucine (131), Isoleucine (131), Asparagine (132), Aspartic acid (133), Glutamine (146), Lysine (146), Glutamic acid (147), Methionine (149), Histidine (at pH 6.0) (155), Phenylalanine (165), Arginine (174), Tyrosine (181), Tryptophan (204).
- Particularly preferred substitutions are:
- Lys for Arg and vice versa such that a positive charge may be maintained;
- Glu for Asp and vice versa such that a negative charge may be maintained;
- Ser for Thr such that a free —OH can be maintained; and
- Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces—turns in the protein's structure. Two amino acid sequences are "substantially homologous" when at least about 70% of the amino acid residues (preferably at least about 80%, and most preferably at least about 90 or 95%) are identical, or represent conservative substitutions.

Likewise, nucleotide sequences utilized in accordance with the invention can also be subjected to substitution, deletion or insertion. Where codons encoding a particular amino acid are degenerate, any codon which codes for a particular amino acid may be used. In addition, where it is desired to substitute one amino acid for another, one can modify the nucleotide sequence according to the known genetic code.

Two nucleotide sequences are "substantially homologous" when at least about 70% of the nucleotides (preferably at least about 80%, and most preferably at least about 90 or 95%) are identical.

The term "standard hybridization conditions" refers to salt and temperature conditions substantially equivalent to 5×SSC and 65 C for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20 C below the predicted or determined $T_m$ with washes of higher stringency, if desired.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in a cardiac myocyte feature.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment, as well as a small molecule inhibitor, can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic compositions of the invention are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition of RSK3-mAKAPβ binding desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Because of the necessity for the inhibitor to reach the cytosol, a peptide in accordance with the invention may need to be modified in order to allow its transfer across cell membranes, or may need to be expressed by a vector which encodes the peptide inhibitor. Likewise, a nucleic acid inhibitor (including siRNAs and antisense RNAs) can be expressed by a vector. Any vector capable of entering the cells to be targeted may be used in accordance with the invention. In particular, viral vectors are able to "infect" the cell and express the desired RNA or peptide. Any viral vector capable of "infecting" the cell may be used. A particularly preferred viral vector is adeno-associated virus (AAV).

With respect to small molecule inhibitors, any small molecule that inhibits the interaction of RSK3 and mAKAPβ may be used. In addition, any small molecules that inhibit the activity of RSK3 and/or mAKAPβ may be used. Particularly preferred small molecules include BI-D1870, available from Enzo Life Sciences

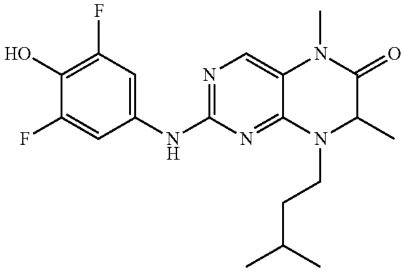 [SMILES: CC(C)CCN1c2nc(Nc3cc(F)c(O)c(F)c3)ncc2N(C)C(=O)C1C]

and SL0101, available from Millipore:

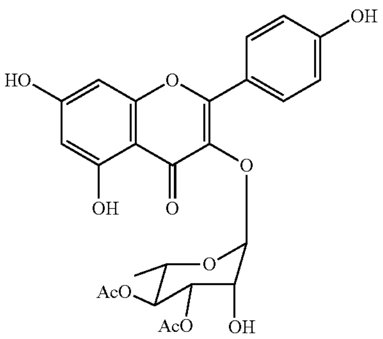 [SMILES: CC(=O)OC1C(C)OC(Oc2c(-c3ccc(O)cc3)oc3cc(O)cc(O)c3c2=O)C(O)C1OC(C)=O]

Small molecules with similar structures and functionalities can likewise be determined by rational and screening approaches.

Likewise, any small molecules that inhibit the expression of RSK3 and/or mAKAPβ may be used.

In yet more detail, the present invention is described by the following items which represent preferred embodiments thereof:

1. A method of protecting the heart from damage, by administering to a patient at risk of such damage, a pharmaceutically effective amount of a composition which inhibits the interaction of RSK3 and mAKAPβ.
2. The method of item 1, wherein the composition is a RSK3 peptide.
3. The method of item 2, wherein the RSK3 peptide is obtained from the amino terminus of the RSK3 amino acid sequence.
4. The method of item 3, wherein the RSK3 peptide is amino acids 1-42 of the RSK3 amino acid sequence.
5. The method of item 2, wherein the polypeptide is administered directly.
6. The method of item 2, wherein the polypeptide is administered using a viral vector.
7. The method of item 6, wherein the vector is adeno-associated virus (AAV).
8. The method of item 1, wherein the composition is a small interfering RNA (siRNA) that inhibits the expression of RSK3.
9. A method of treating heart disease, by administering to a patient a pharmaceutically effective amount of a composition which inhibits the interaction of RSK3 and mAKAPβ.
10. The method of item 9, wherein the composition is a RSK3 peptide.
11. The method of item 10, wherein the RSK3 peptide is obtained from the amino terminus of the RSK3 amino acid sequence.
12. The method of item 11, wherein the RSK3 peptide is amino acids 1-42 of the RSK3 amino acid sequence.
13. The method of item 9, wherein the polypeptide is administered directly.
14. The method of item 9, wherein the polypeptide is administered using a viral vector.
15. The method of item 14, wherein the vector is adeno-associated virus (AAV).
16. The method of item 19, wherein the composition is a small interfering RNA (siRNA) that inhibits the expression of RSK3.
17. A composition comprising a molecule which inhibits the interaction ofRSK3 and mAKAPβ.
18. The composition of item 17, wherein the molecule is a peptide.
19. The composition of item 18, wherein the molecule is a RSK3 peptide.
20. The composition of item 19, wherein the RSK3 peptide is obtained from the amino terminus of the RSK3 amino acid sequence.
21. The composition of item 20, wherein the RSK3 peptide is amino acids 1-42 of the RSK3 amino acid sequence.
22. The composition of item 17, wherein the molecule is expressed using a viral vector.
23. The composition of item 22, wherein the vector is adeno-associated virus (AAV).
24. The composition of Item 17, wherein the molecule is a small molecule.
25. A method of treating or preventing heart disease, by administering to a patient a pharmaceutically effective amount of a composition which inhibits the activity of RSK3.

26. The composition of item 25, wherein the small molecule is SL0101 or BI-01870.
27. A method of treating or preventing heart disease, by administering to a patient a pharmaceutically effective amount of a composition which inhibits the activity of mAKAPβ.
28. The method of item 27, wherein the composition is a mAKAPβ peptide.
29. The composition of item 28, wherein the mAKAPβ peptide is amino acids 1694-1833 of the mAKAP amino acid sequence.
30. The composition of item 28, wherein the mAKAPβ peptide is amino acids 1735-1833 of the mAKAP amino acid sequence.
31. The composition of item 27, wherein the molecule is expressed using a viral vector.
32. The composition of item 31, wherein the vector is adeno-associated virus (AAV).

The following examples are provided to aid the understanding of the present invention, the true scope of which is set forth in the appended claims. It is understood that modifications can be made in the procedures set forth without departing from the spirit of the invention.

EXAMPLES

The compositions and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the processes, formulations and/or methods of the invention may be made without departing from the spirit of the invention and the scope of the appended claims.

Example 1

Methods

Reagents

Figure 21:
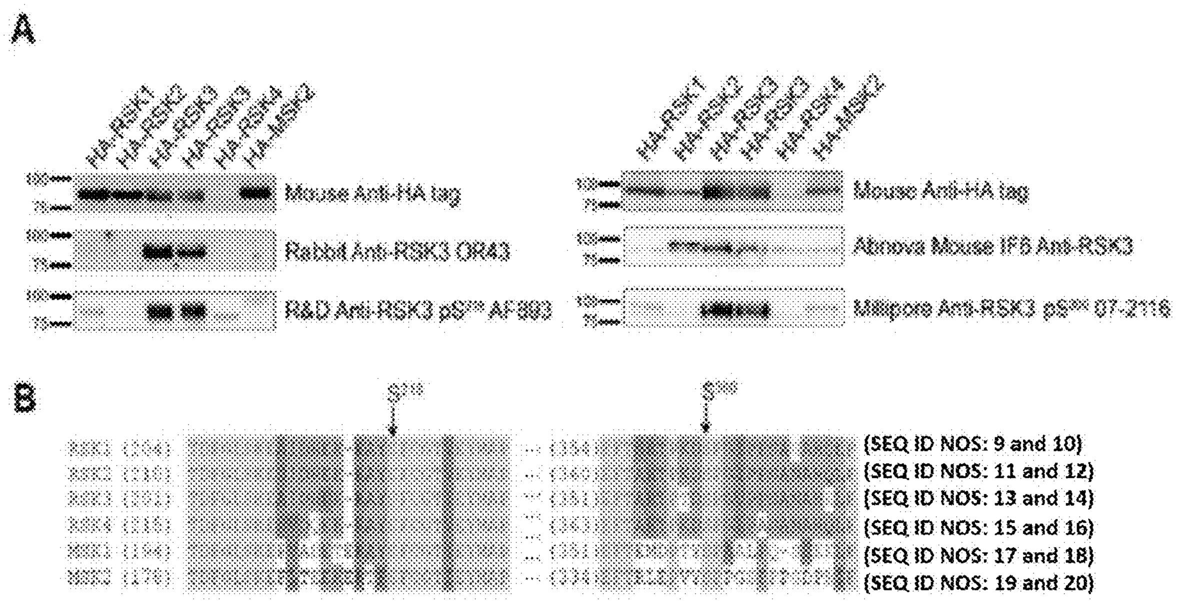
FIG. 21 Specificity of RSK3 Antibodies. A. HA-tagged RSK1, RSK2, RSK3 (in duplicate at different concentrations), RSK4, and MSK2 were expressed in COS-7 cells, and whole cell lysates were used for western blots with the indicated antibodies. B. Alignment of RSK and MSK family members (RSK1: SEQ ID NOs: 9 and 10; RSK2: SEQ ID NOs: 11 and 12; RSK3: SEQ ID NOs: 13 and 14; RSK4: SEQ ID NOs: 15 and 16; MSK1: SEQ ID NOs: 17 and 18; MSK1: SEQ ID NOs: 19 and 20). MSK1 and MSK2 are the only two other mammalian protein kinases that like RSK have a NTKD and a CTKD. When affinity purified, the OR43 antibody is highly selective for RSK3. The inventors did not test the Cell Signaling rabbit anti-RSK3 antibody #9343, since it is apparently RSK3-specific as shown by data provided by the manufacturer. The inventors also did not test the Santa Cruz goat anti-RSK3 antibody C-20 (sc-1431) used for immunoprecipitation of RSK3, since according to the manufacturer C-20 detects both RSK3 and to a lesser extent RSK2. The Santa Cruz goat anti-RSK3 antibody N-16 (sc-13378), also used for immunoprecipitation, is specific for RSK3 since the antigen was a peptide within the unique RSK3 N-terminus according to the manufacturer and as evident from our experiments. However, the monoclonal mouse anti-RSK3 antibody 1F6 (also sold as M01) sold by a variety of companies also readily detects RSK2. As might be expected from the conservation of the antigen sequence, the "RSK3" phospho-specific antibodies readily detected other RSK and MSK family members. Phosphorylation of $S^{218}$ was associated with a decreased mobility of most of the enzymes in SDS-PAGE, consistent with the multiple phosphorylation events that would be expected prior to PDK1 phosphorylation of that residue (Cf.

Commercial antibodies and oligonucleotides are listed in FIG. 19 and FIG. 20. The commercially available RSK3 antibodies were of varying specificity (FIG. 21). Additional reagents and detailed methods are provided.

$RSK^{-/-}$ Mouse

All experiments involving animals were approved by the Institutional Animal Care and Use Committee at the University of Miami. Constitutive RSK3 knockout mice were backcrossed to C57BL/6 mice over 10 generations. All experiments were performed with littermate controls and mice that were 8 to 10 weeks of age at the beginning of the study. Transverse aortic constriction was performed as previously described (Rockman 1991), and isoproterenol infusion was via Alzet 2002 osmotic pumps (Durect). Echocardiography was performed under isoflurane anesthesia on a Vevo 770 High-Resolution Imaging System (VisualSonics).

RNA Assays mRNA species were assayed using NanoString technology, a direct and multiplexed measurement of gene expression without amplification, using fluorescent molecular bar codes and single-molecule imaging to identify and count multiple transcripts in a single reaction; 100 ng of RNA was hybridized in solution to a target-specific code set overnight at 65° C., and individual mRNAs were counted using a NanoString Digital Analyzer.

Statistics

For all experiments, n refers to the number of individual mice or individual myocyte preparations. All data are expressed as mean±SEM. P values were calculated using Student t tests and are not corrected for multiple comparisons. Repeated symbols represent P values of different orders of magnitude (i.e., $P<0.05$, $P<0.005$, and others). All datasets involving multiple comparisons for which P values are provided also were significant by ANOVA ($\alpha=0.05$).

Results mAKAPβ: A Scaffold for RSK

Figure 1:
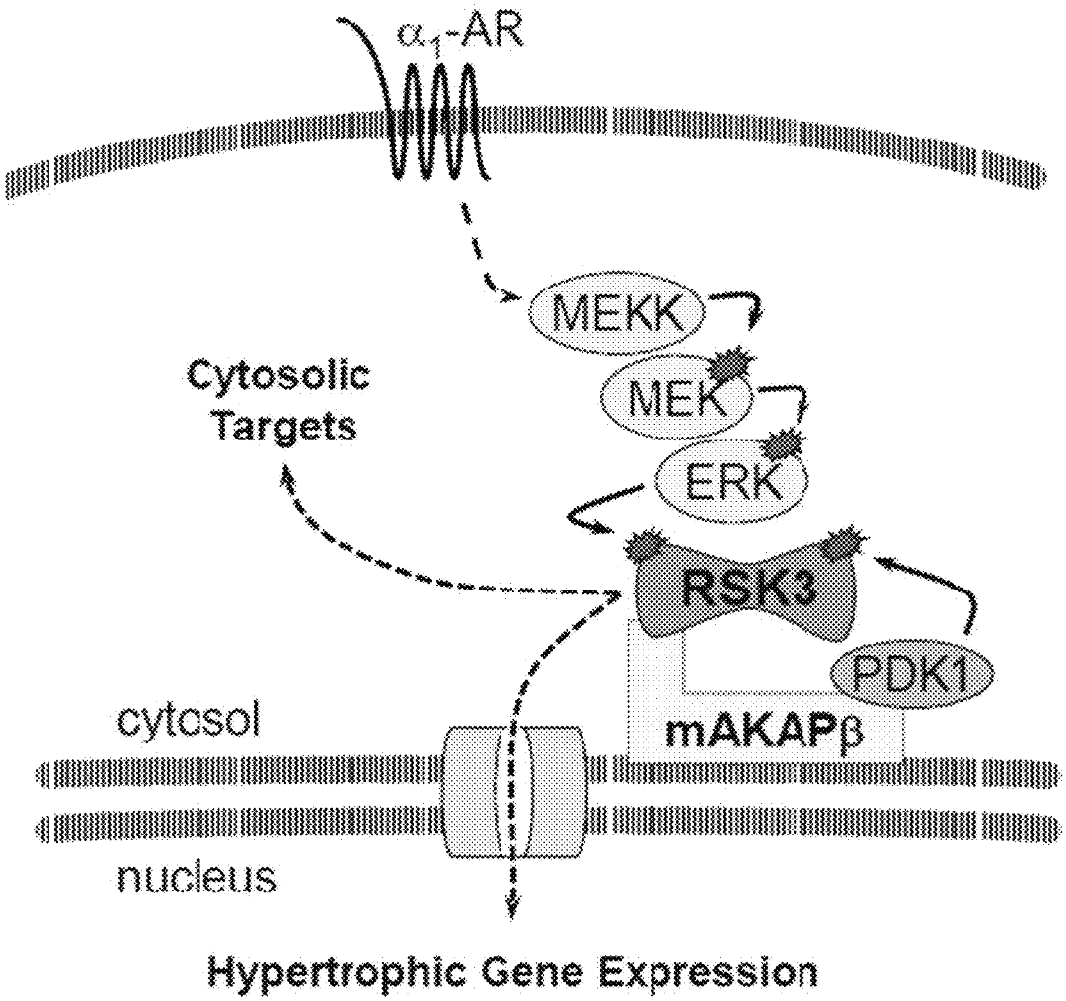
FIG. 1. Model for RSK3 signaling. MAP-Kinase signaling induced by al-adrenergic receptor (α1-AR) stimulation and potentially other upstream signals activates anchored RSK3 in conjunction with PDK1 at anchored sites, including at perinuclear mAKAPβ signalosomes. Targets for RSK3 may include cytosolic and nuclear proteins, especially those involved in the regulation of hypertrophic gene expression.
Figure 4:
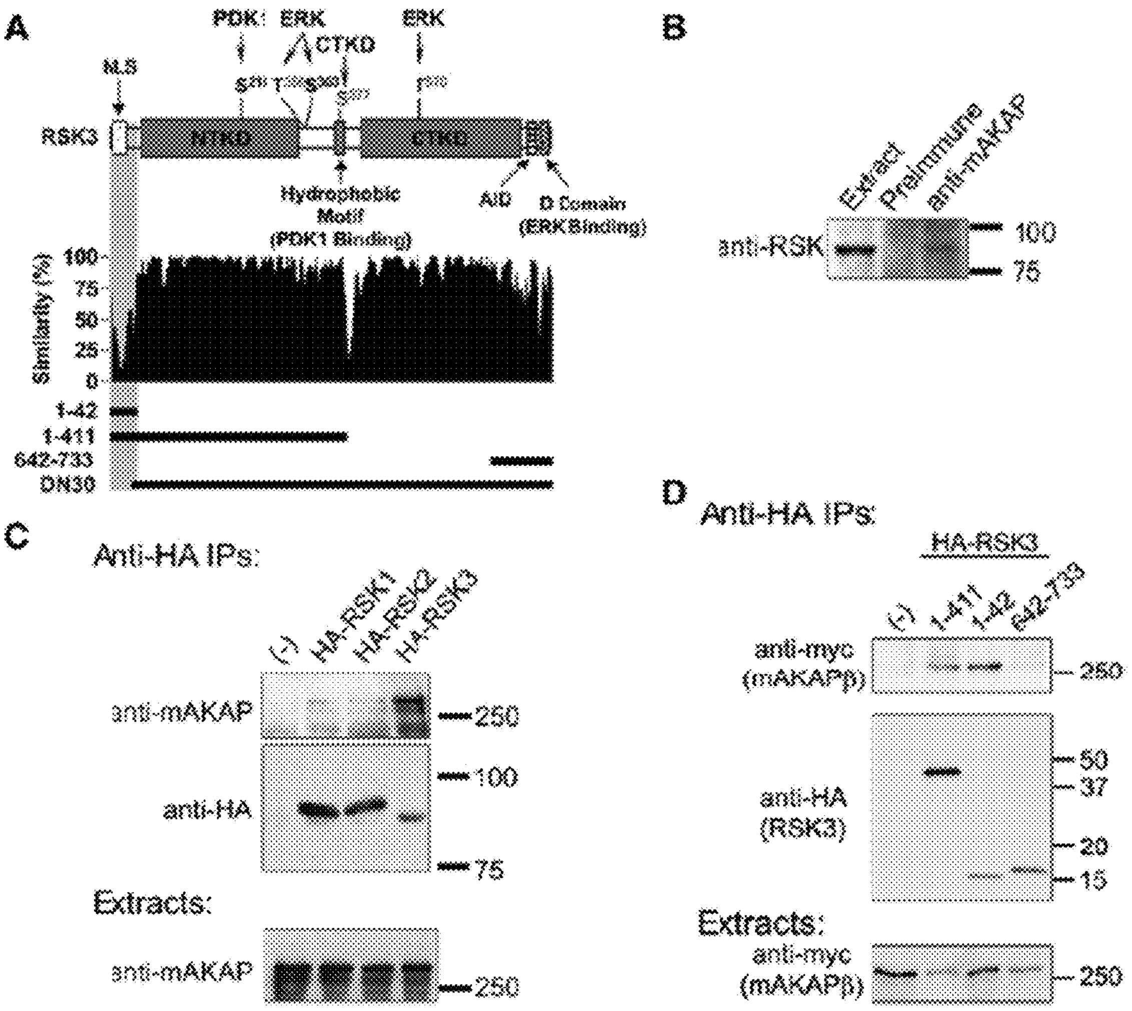
FIG. 4. The unique p90 ribosomal S6 kinase type 3 (RSK3) N-terminal domain binds muscle A-kinase anchoring protein (mAKAP). A, p90 ribosomal S6 kinases (RSKs) contain 2 catalytic domains, N-terminal kinase domain (NTKD) and C-terminal kinase domain (CTKD).[3] Only RSK3 has an N-terminal nuclear localization signal (NLS). This NLS is within the same unique region of RSK3 that binds mAKAPβ. In inactive RSK3, the CTKD binds the autoinhibitory domain (AID) α-helix. Prebound to the D-domain, when activated, extracellular signal-regulated kinase (ERK) phosphorylates RSK3 residues including the CTKD activation loop ($T^{570}$). The CTKD then autophosphorylates $S^{377}$, permitting phosphoinositide-dependent kinase 1 (PDK1) binding and phosphorylation of the NTKD activation loop ($S^{218}$). The NTKD phosphorylates RSK substrates. RSKs 1 to 4 were aligned and sequence similarity was calculated using Vector NTI AlignX (Invitrogen). RSK3 fragments used for mapping are indicated. B, Rat neonatal myocyte extract (lane 1, 0.2% total extract) was immunoprecipitated with preimmune (lane 2) or anti-VO56 mAKAP (lane 3) sera and detected using a pan-RSK antibody (C-20; see FIG. 21 legend). C, HA-tagged kinases and myc-tagged mAKAPα were expressed by cotransfection of HEK293 cells and coimmunoprecipitated with anti-HA antibody. D, HA-tagged RSK3 fragments and myc-tagged mAKAPβ were expressed by cotransfection of COS-7 cells and coimmunoprecipitated with anti-HA antibody. n2:3 for each panel.

The inventors have previously published that RSK proteins and activity are associated with mAKAPα complexes in the brain (Michel 2005). The inventors now show that RSK also is associated with mAKAPβ in cardiac myocytes (FIG. 4B). To determine whether mAKAP preferentially binds a specific RSK isoform, hemagglutinin (HA)-tagged RSK family members were co-expressed with mAKAP in HEK293 cells. In contrast to RSK1 and RSK2, RSK3 robustly mediated the coimmunoprecipitation of both mAKAPα and mAKAPβ (FIG. 4C). RSK family members are similar in primary sequence with the exception of the extreme N-terminal and C-terminal domains and a small region after the hydrophobic motif (FIG. 4A). Consistent with the selective binding of RSK3 to the scaffold, the N-terminal domain of RSK3 bound mAKAPβ (FIG. 4D).

RSK3 Function in Neonatal Cardiac Myocytes

Figure 22:
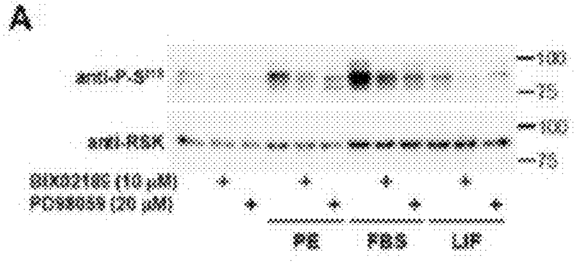
Figure 22:
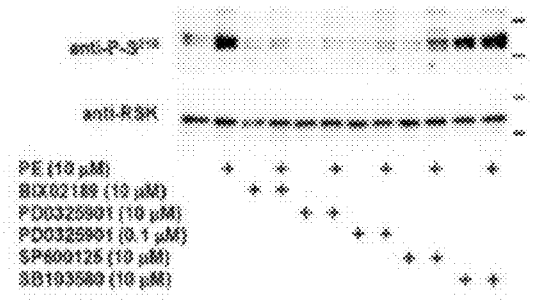
Figure 22:
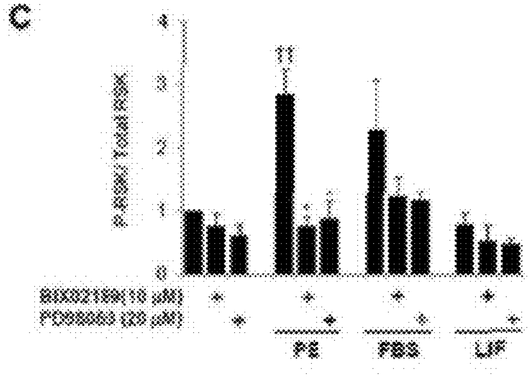
Figure 22:
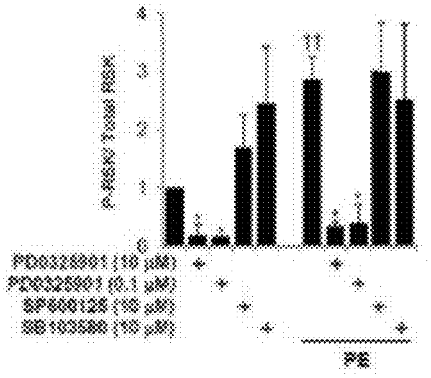
Figure 23:
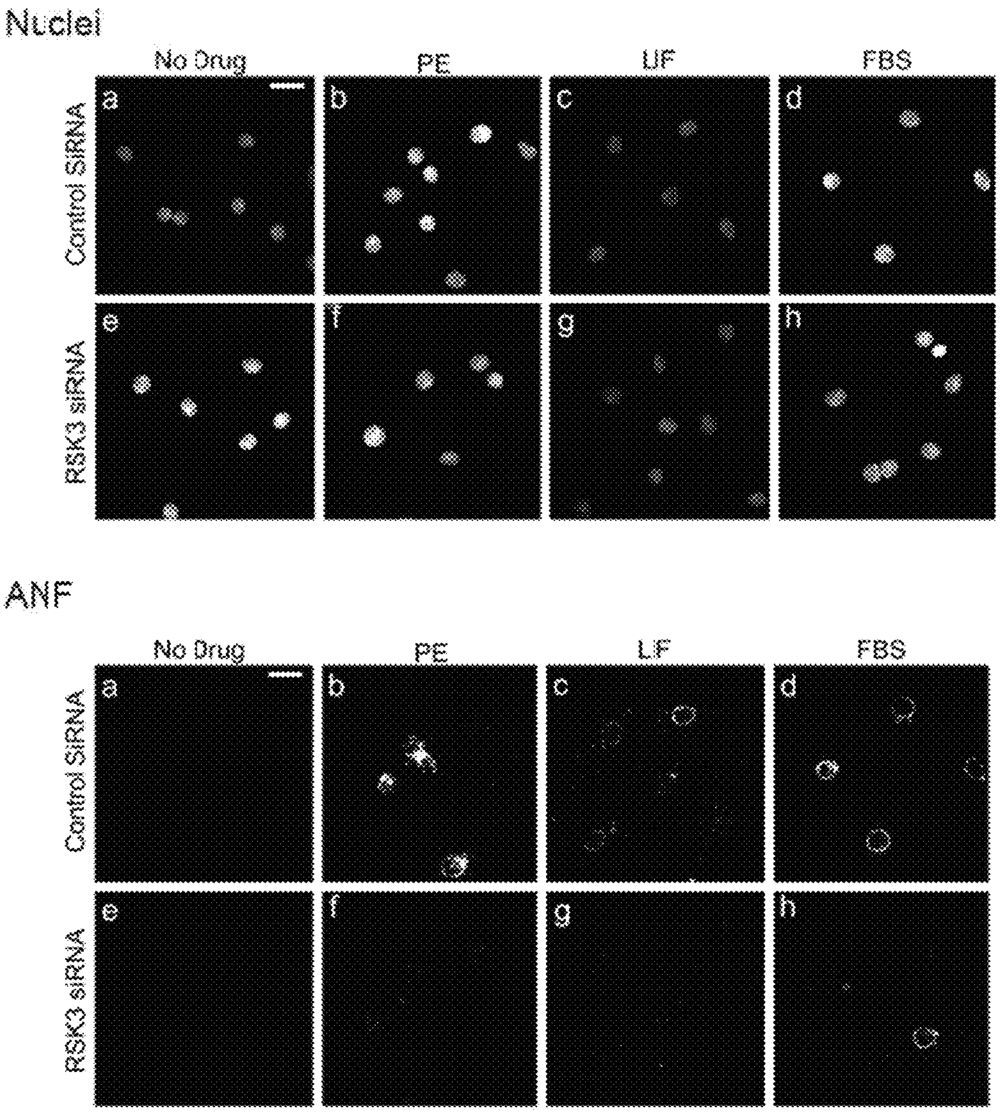
FIG. 23 shows grayscale images of FIG. 5D.

RSK family members can be activated in most cell types by ERK, but not c-Jun N-terminal kinases or p38 (Anjum 2008). ERK phosphorylation is permissive for PDK1 phosphorylation of the RSK N-terminal kinase domain, such that PDK1 phosphorylation of RSK $S^{218}$ is indicative of full activation of the enzyme (FIG. 4A). To show that ERK activates RSK in cardiac myocytes, the inventors treated neonatal rat ventricular myocytes with different hypertrophic agonists and mitogen-activated protein kinase pathway inhibitors and detected RSK activation using a pan-RSK $S^{218}$ phosphor-specific antibody (FIGS. 21 and 22). The α-adrenergic stimulation with phenylephrine (PE) induced RSK phosphorylation 3-fold by both MEK1/2-dependent (that activates ERK1/2) and MEK5-dependent (that activates ERK5) mechanisms (FIG. 22). Moreover, MEK1/2 inhibition reduced RSK baseline phosphorylation. c-Jun N-terminal kinase and p38 inhibition did not affect PE activation and, in fact, variably increased baseline RSK phosphorylation. Fetal bovine serum and leukemia inhibitory factor also increased the level of activated RSK, but that occurred more so because of an increase in total RSK protein expression than because of ERK phosphorylation.

Similar results were found for HA-tagged RSK3 (FIG. 5A). Acute PE treatment induced the phosphorylation of HA-RSK3 ERK ($S^{360}$) and PDK1 ($S^{218}$) sites through both MEK1/2-dependent and MEK5-dependent signaling. Together, these results confirmed that in cardiac myocytes ERK is responsible for RSK activation.

The inventors have previously demonstrated that mAKAPβ complexes are required for the hypertrophy of cultured myocytes (Li 2010, Pare 2005, Dodge-Kafka 2005). Therefore, the inventors proposed the hypothesis that RSK3 signaling is a major determinant of cardiac myocyte growth. Neonatal myocytes were transfected with small interfering RNA oligonucleotides (siRNA) that diminished RSK3 mRNA and protein levels by >75% (FIG. 5B). RSK3 siRNA did not induce the apoptosis of myocytes cultured either in the absence or in the presence of serum (FIG. 5C). Importantly, in the presence of α-adrenergic stimulation, RSK3 siRNA inhibited morphologic hypertrophy by 34% and atrial natriuretic factor expression completely (FIG. 5D-5F and FIG. 23). In addition, RSK3 siRNA had smaller, but detectable, effects on leukemia inhibitory factor and fetal bovine serum-stimulated hypertrophy. The results obtained by RSK3 RNA interference were confirmed with a second distinct RSK3 siRNA.

Figure 24:
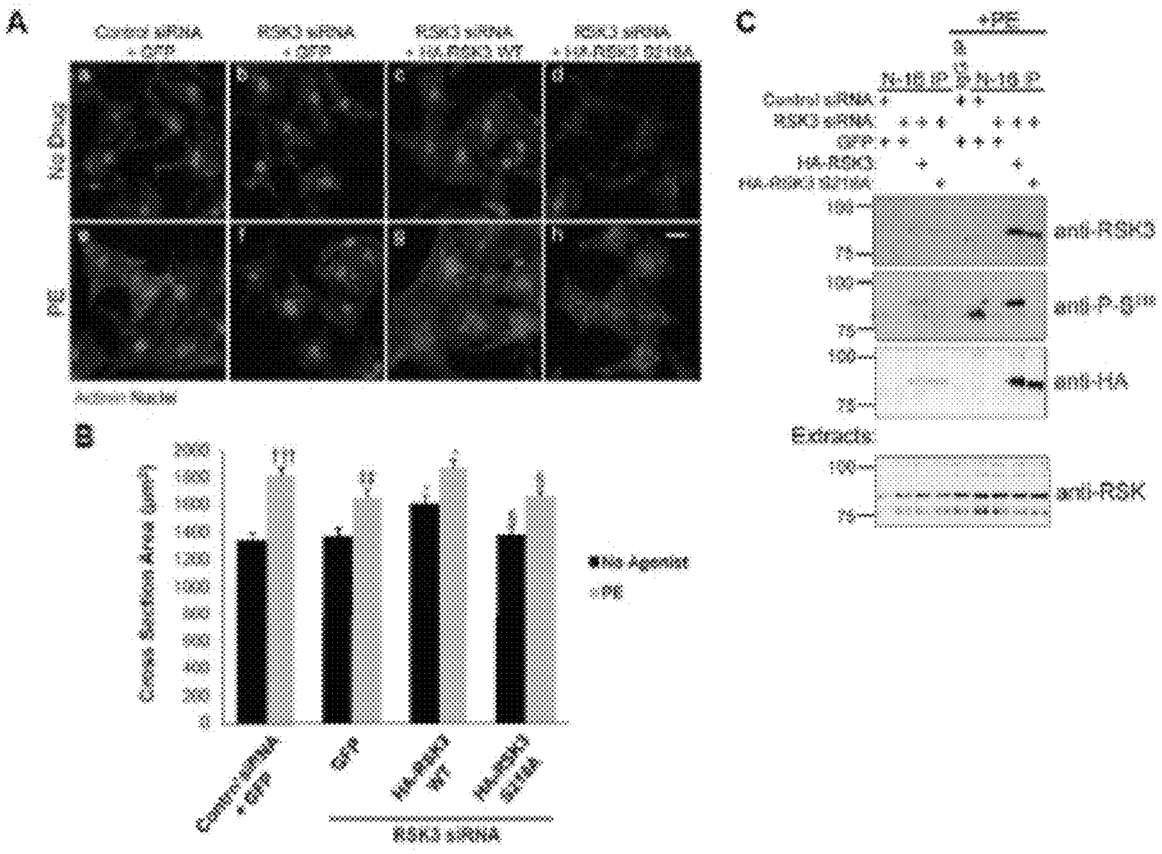
FIG. 24. Active RSK3 induces neonatal rat ventricular myocyte hypertrophy. Myocytes transfected with control or RSK3 siRNA oligonucleotides and infected with adenovirus to express GFP, HA-RSK3 or HA-RSK3 $S^{218}$A were cultured for 2 days±10 μmol/L PE. A. Immunocytochemistry for α-actinin (red) and Hoechst (blue); bar=20 μm. B. Cross-section area of myocytes. n=4-5. p<0.05: † compared to no agonist control; ‡, compared to control siRNA+GFP+PE; * compared to similarly treated GFP+RSK3 siRNA samples; § compared to similarly treated HA-RSK3 WT+RSK3 siRNA samples. C. Whole extracts and RSK3 immunoprecipitated with N-16 antibody were assayed by western blot. RSK3 in the immunoprecipitates and RSK in whole cell extracts were detected with purified OR43 and mouse 1F6 antibodies, respectively. Red asterisks indicate detectable endogenous and HA-tagged RSK3 proteins. Note that the signal obtained with both the phospho-$S^{218}$ and OR43 RSK3 antibodies were attenuated by the RSK3 siRNA and enhanced by HA-RSK3 expression. No signal was obtained for the HA-RSK3 S218A mutant with the phospho-$S^{218}$ antibody. The level of expression of HA-RSK3 in non-treated cells was similar to the level of expression of endogenous RSK3 in PE-treated cells. Importantly, neither expression of HA-tagged proteins, nor the use of the siRNA, affected the signal obtained using the pan-RSK antibody for whole cell extracts.
Figure 25:
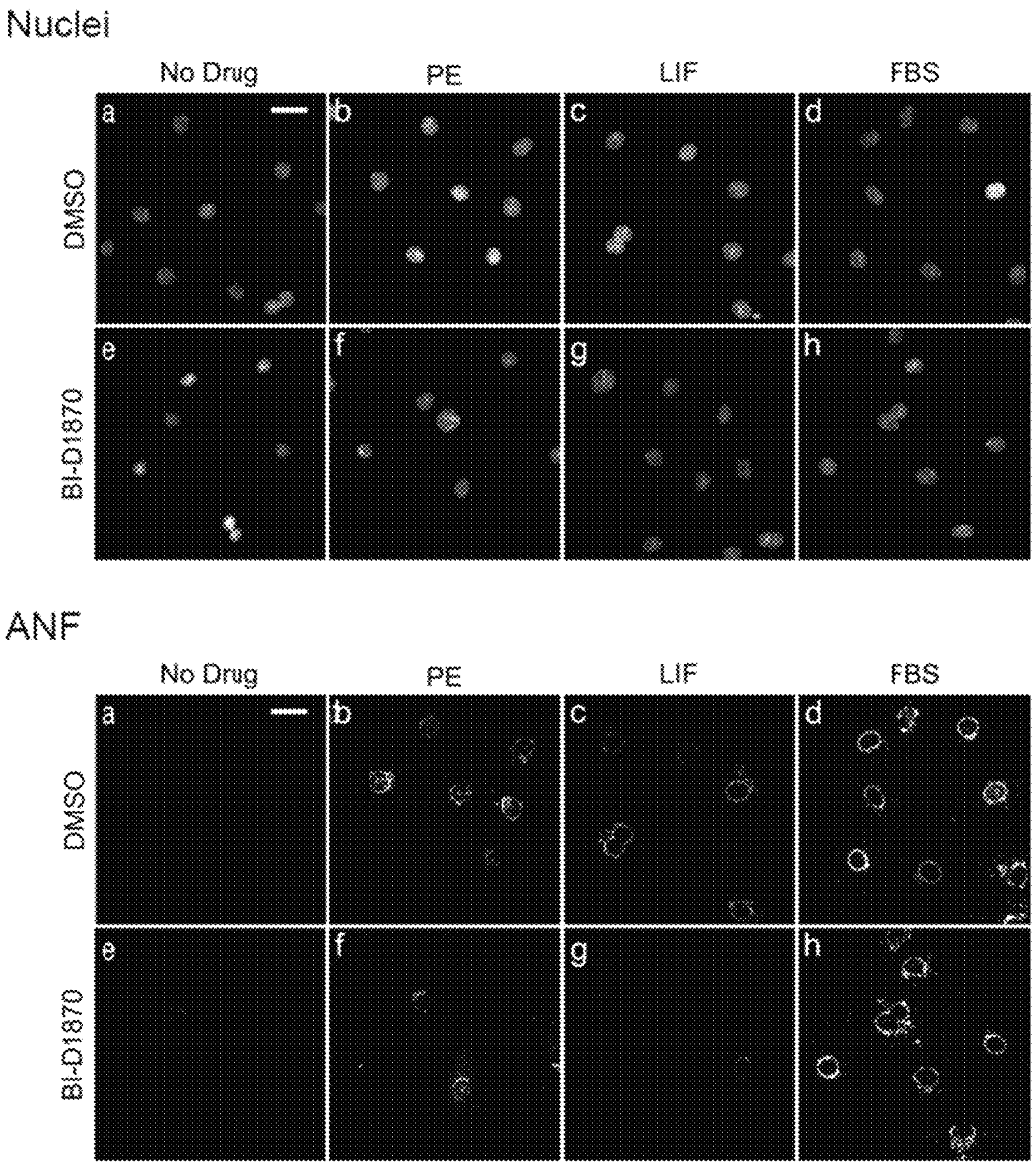
FIG. 25 shows grayscale images of FIG. 6A.
Figure 26:
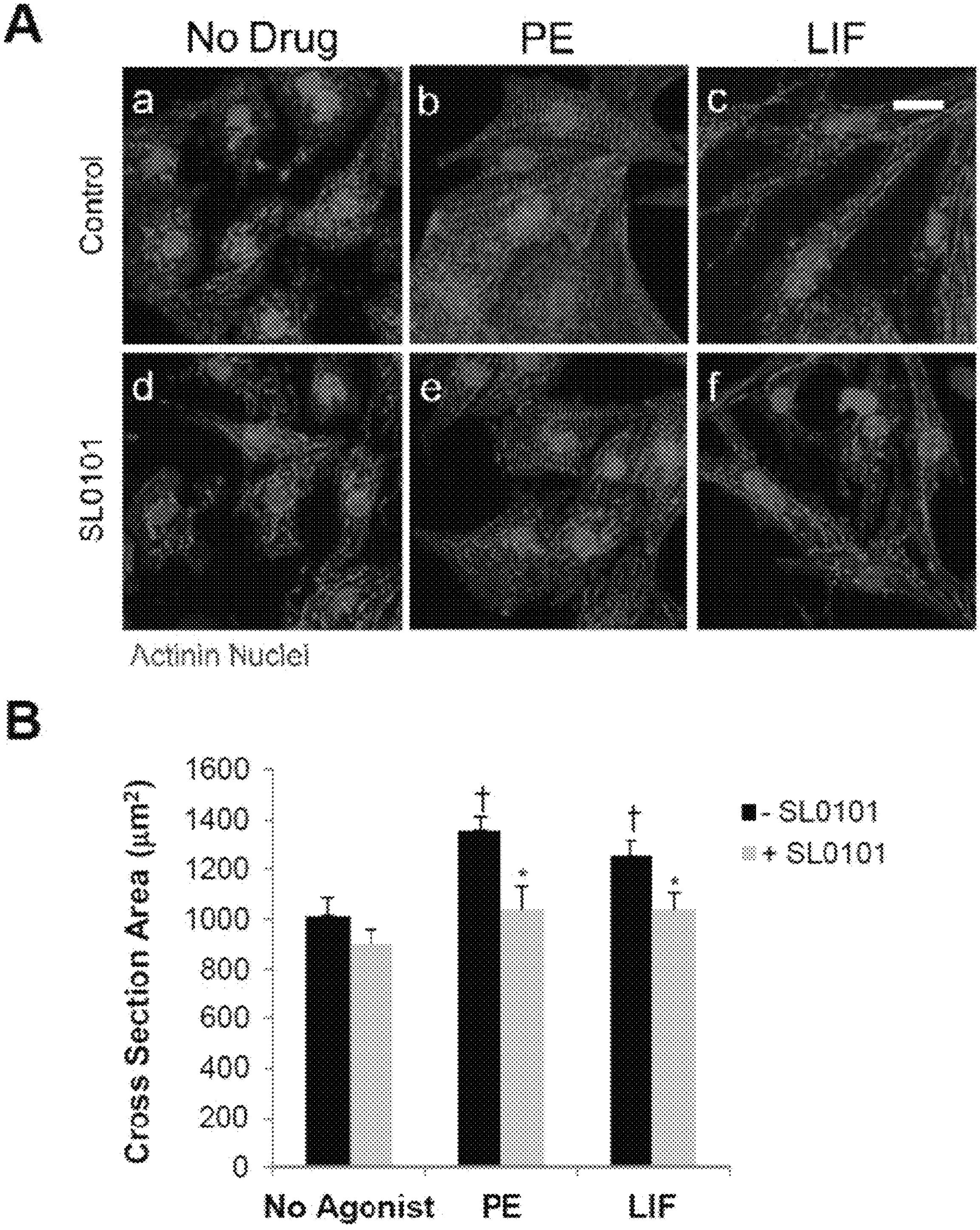
FIG. 26 shows Inhibition of neonatal rat ventricular myocyte hypertrophy with the RSK active site inhibitor SL0101. Myocytes were cultured for 2 days±10 μmol/L PE, 1000 U/mL LIF and/or 50 μmol/L SL0101 or 0.1% DMSO carrier. A. Immunocytochemistry for α-actinin (red) and Hoechst (blue); bar=20 μm. B. Cross-section area of myocytes. n=5. † compared to no agonist control; * compared to no SL0101.

Endogenous RSK3 proteins are expressed at a relatively low level in cardiac myocytes compared with the other RSK family members and are induced in expression by long-term PE treatment (FIG. 24C). As a result, RSK3 RNA interference did not affect the level of total RSK in the myocyte, only diminishing the RSK3 detected after immunoprecipitation with a specific RSK3 antibody (FIG. 5B and FIG. 24C). In control experiments, the inhibition of PE-induced hypertrophy by the RSK3 siRNA was rescued by the expression of recombinant HA-tagged human RSK3, but not by an inactive HA-RSK3 $S^{218}A$ mutant (FIGS. 24A and 24B). Remarkably, in these experiments, the cross-section area of unstimulated myocytes was increased by adenoviral-based expression of wild-type HA-RSK3 enzyme at a level comparable with that of endogenous RSK3 in PE-treated cells without affecting total RSK levels. Finally, to confirm that RSK activity was important for neonatal myocyte hypertrophy, the inventors used the pan-RSK inhibitors BI-D1870 (FIG. 6 and FIG. 25) and SL0101 (FIG. 26) (Smith 2005, Sapkota 2007, Malone 2005), finding that, like RSK3 siRNA, these compounds inhibited agonist-induced myocyte hypertrophy.

High-Affinity RSK3 Binding Domain in mAKAP

Figure 7:
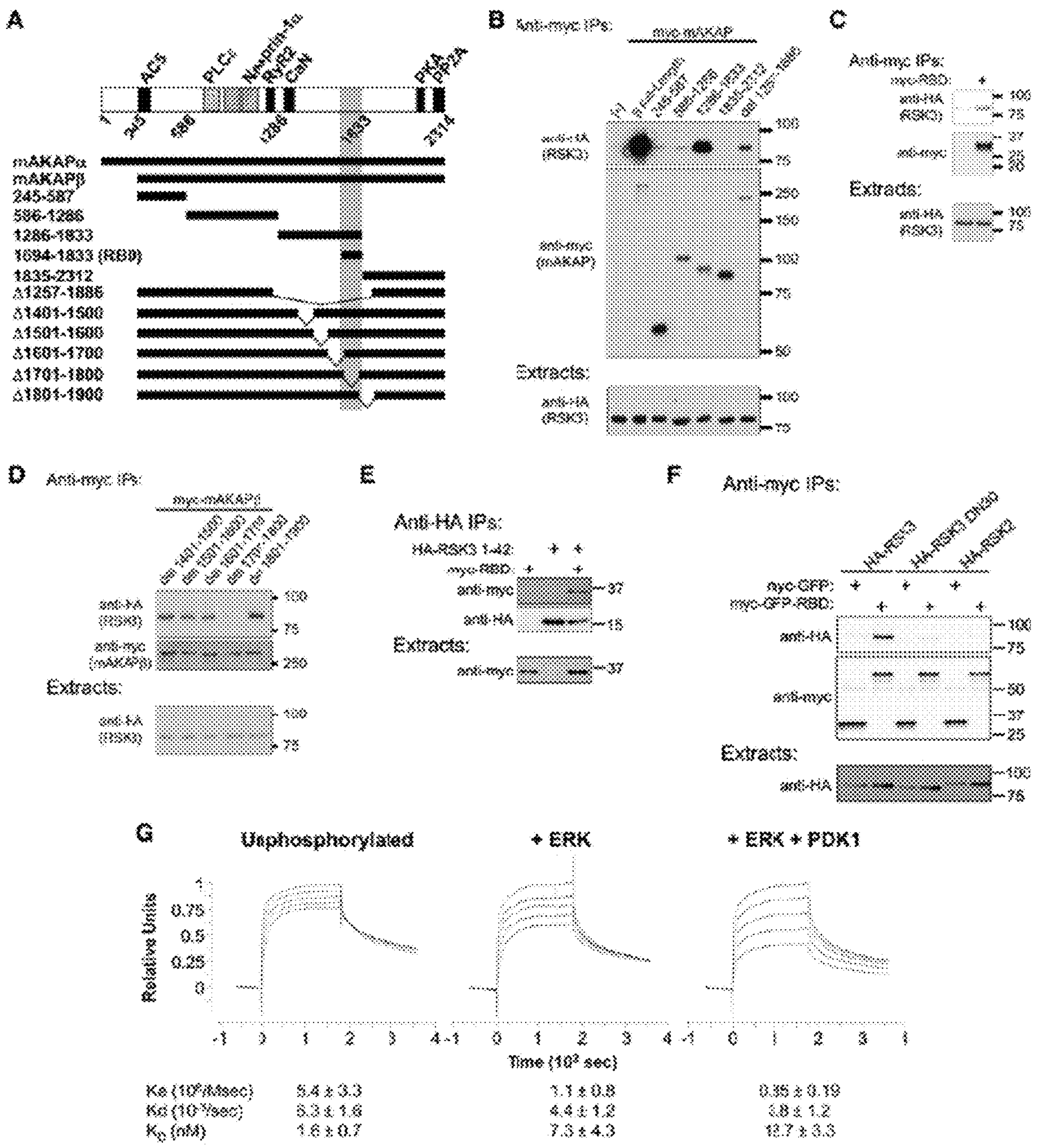
FIG. 7. The p90 ribosomal S6 kinase type 3 (RSK3) binding site within muscle A-kinase anchoring protein (mAKAP). A, mAKAP domain structure. Direct binding partners whose sites have been finely mapped in mAKAPβ are shown (Li 2010, Pare 2005, Zhang 2011, Dodge-kafka 2010, Kapiloff 2009, Kapiloff 1999, Marx 2001). mAKAPβ starts at residue 245 of mAKAPα. All fragments are numbered per mAKAPα. The grey bar indicates the RSK3 binding site. B-F, Specific tag antibodies were used to immunoprecipitate myc-tagged mAKAPβ and HA-tagged p90 ribosomal S6 kinase (RSK) proteins (see FIG. 4A) co-expressed in either HEK293 (B) or COS-7 (C-F) cells (n=3) for all panels. G, Surface plasmon resonance using purified bacterially expressed proteins. Unphosphorylated (left), extracellular-regulated signaling kinase (ERK)-phosphorylated (middle), and ERK and phosphoinositide-dependent kinase 1 (PDK1)-phosphorylated (right) His-RSK3 (12.5-200 nmol/L in perfusate) were bound to His-mAKAP 1286 to 1833 (solid state). Each curve was repeated 3 times using different protein preparations.

The inventors considered that the requirement for RSK3 in myocyte hypertrophy was attributable to the association of RSK3 with specific signaling complexes. To address this hypothesis, the inventors defined the mAKAP domains responsible for RSK3 binding. HA-tagged RSK3 was coexpressed in heterologous cells with myc-tagged mAKAPβ fragments and coimmunoprecipitated using a myc-tag antibody (FIGS. 7A and 7B). RSK3 preferentially associated with mAKAP amino acid residues 1286 to 1833, although it also weakly associated with mAKAP 245 to 587 and 525 to 1286. Consistent with this result, RSK3 binding to a full-length mAKAPβ protein with an internal deletion of residues 1257 to 1886 was reduced by >85%. Further mapping showed that the main RSK3 binding domain (RBD) of mAKAP mapped to a fragment encompassing residues 1694 to 1833 (FIG. 7C). Accordingly, RSK3 bound poorly to a full-length mAKAPβ protein with an internal deletion of residues 1701 to 1800 (FIG. 7D). As shown, the unique N-terminal domain of RSK3 bound full-length mAKAPβ (FIG. 4D). The mAKAP RBD also bound HA-RSK3 1 to 42 (FIG. 7E), but not to the N-terminally truncated RSK3 mutant (HA-RSK3 DN30) or the HA-tagged full-length RSK2 (FIG. 7F). These results imply that the mAKAP RBD is responsible for the selective binding of RSK3 to mAKAP.

The inventors next tested whether mAKAP-RSK3 binding is direct (FIG. 7G). The binding of bacterially expressed His-tagged mAKAP 1286 to 1833 and full-length RSK3 was analyzed by surface plasmon resonance. The binding was direct and of high affinity (nanomolar $K_D$). The inventors previously reported that once activated, RSK3 binds mAKAPα less well in cells (Michele 2005). Interestingly, previous RSK3 phosphorylation by either ERK or both ERK and PDK1 decreased the RSK3 binding affinity for mAKAP 5-fold and 8-fold, respectively, through a decrease in the association rate constant.

Figure 5:
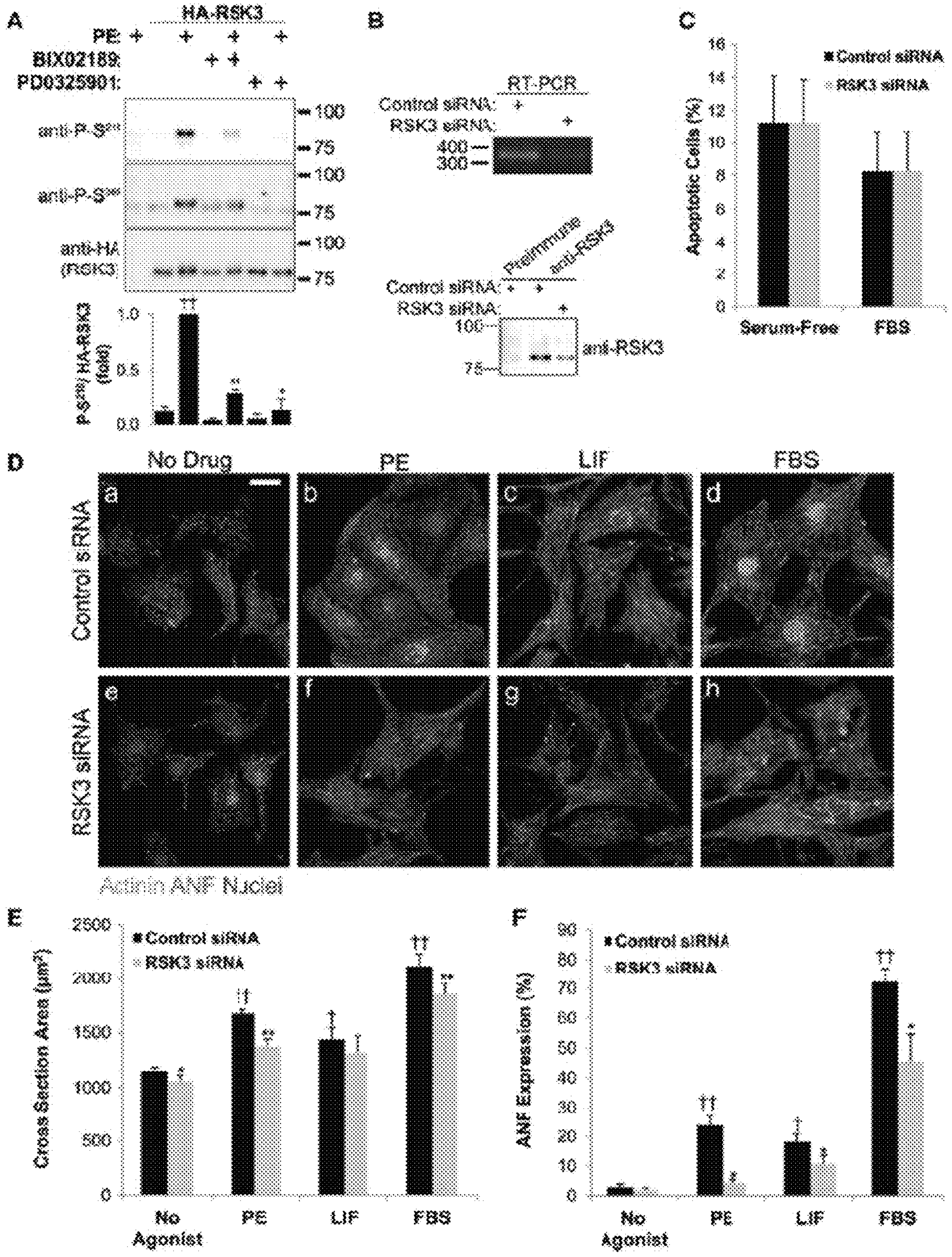
FIG. 5. p90 ribosomal S6 kinase type 3 (RSK3) signaling is important for neonatal rat ventricular myocyte hypertrophy. A, Neonatal myocytes were infected with Adeno-HA-RSK3 for 1 day in maintenance media before being serum-starved for 2 days and then treated for 1 hour with 10 μmol/L phenylephrine (PE), 10 μmol/L BIX02189, or 0.1 μmol/L PD0325901. Whole cell extracts were used for immunoblotting (n=3). B-F, Myocytes were transfected with control or RSK3 siRNA oligonucleotides and cultured for 2 days±10% fetal bovine serum (FBS), 10 μmol/L PE, or 1000 U/mL leukemia inhibitory factor (LIF). B, RSK3 reverse-transcriptase polymerase chain reaction (RT-PCR; top) and Western blot for RSK3 immunoprecipitated with N-16 antibody (bottom) using PE-treated myocytes. C, Results obtained by TUNEL staining (n=3). D, Immunocytochemistry for α-actinin (green), atrial natriuretic factor (ANF; red), and Hoechst (blue); bar=20 μm. Separate ANF and Hoechst channels are provided in FIG. 23. E, Cross-section area of myocytes (n=4-8). F, Fraction of myocytes expressing ANF (n=4-5). *P values comparing samples treated with the same hypertrophic agonist. †P values compared with no hypertrophic agonist control.

Disruption of RSK3 Anchoring Inhibits Neonatal Myocyte Hypertrophy The identification of the high-affinity mAKAP RBD provided the opportunity to test whether anchoring of RSK3 is important for its function. When expressed in neonatal myocytes, a green fluorescent protein-mAKAP RBD fusion protein competed the association of endogenous RSK3 and mAKAPβ (FIG. 8A). Expression of green fluorescent protein-mAKAP RBD fusion protein markedly inhibited PE-induced hypertrophy (FIG. 8B-5D), similar to RSK3 siRNA (FIG. 5). Together, these results imply that RSK3 anchored to scaffolds through its unique N-terminal domain is required for the hypertrophy of cultured myocytes.

Role of RSK3 in Cardiac Hypertrophy In Vivo

Figure 27:
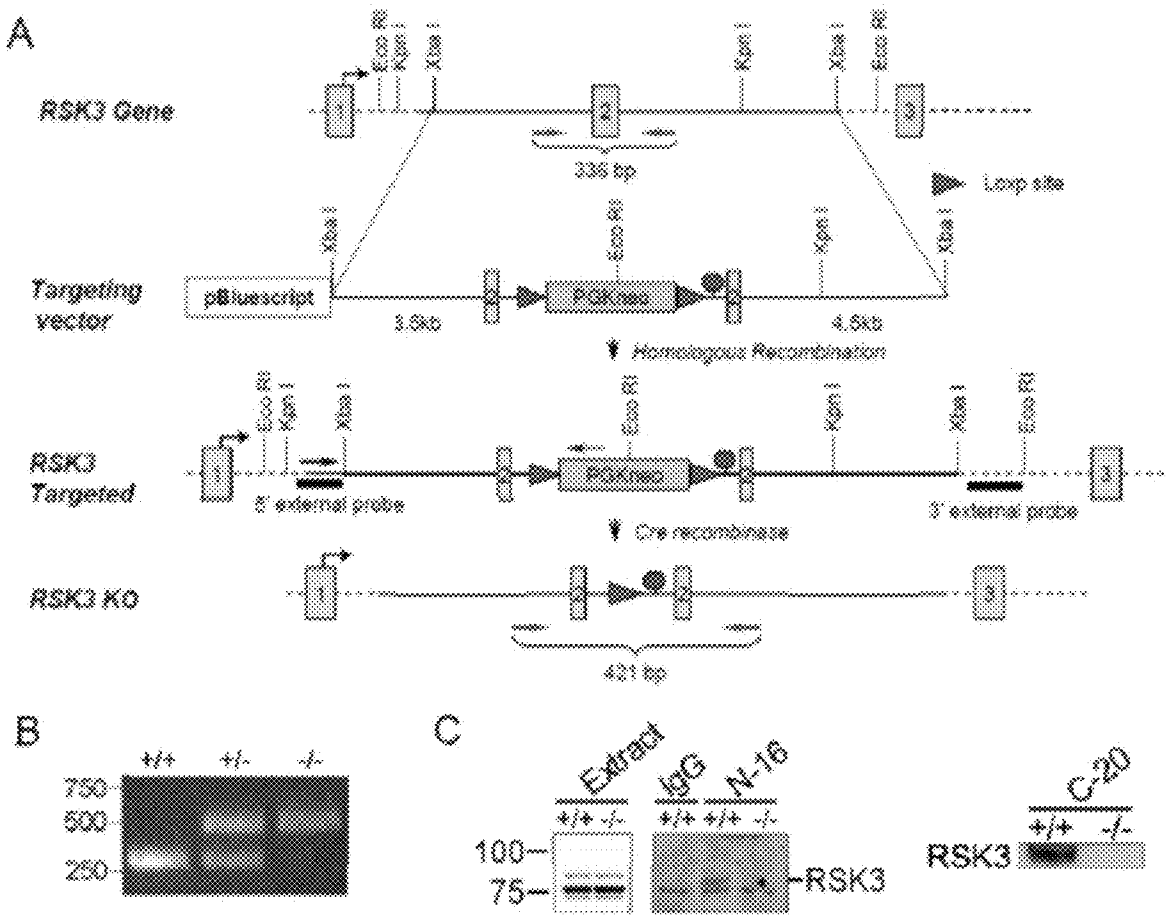
FIG. 27. Design of RSK3 Knock-out Mouse. A. A PGK-neo cassette was inserted into Exon 2 interrupting translation at amino acid residue 67 within the ATP-binding cassette of the RSK3 NTKD. Fidelity of homologous recombination was confirmed using external probes for southern blotting and by PCR using the primers shown in black (sequence not shown). Prior to any experimentation, the PGKneo cassette was removed by mating targeted mice to a global cre trangenic mouse. PCR primers (red) used for genotyping were RSK3Ex2+5' and RSK3Ex2-3' that produce 336 and 421 bp fragments for wildtype and knock-out alleles, respectively. B. Example of mouse tail genotyping. C. Western blot of RSK3 proteins detected using OR43 RSK3 antibody following immunoprecipitation by N-16 or C-20 antibodies. No RSK3 protein was detected in the knock-out mouse hearts. Western blot of whole heart extracts with the mouse 1F6 antibody (left panel) showed that despite the loss of RSK3 protein, total RSK detected in the knock-out hearts was the same as in wildtype.
Figure 28:
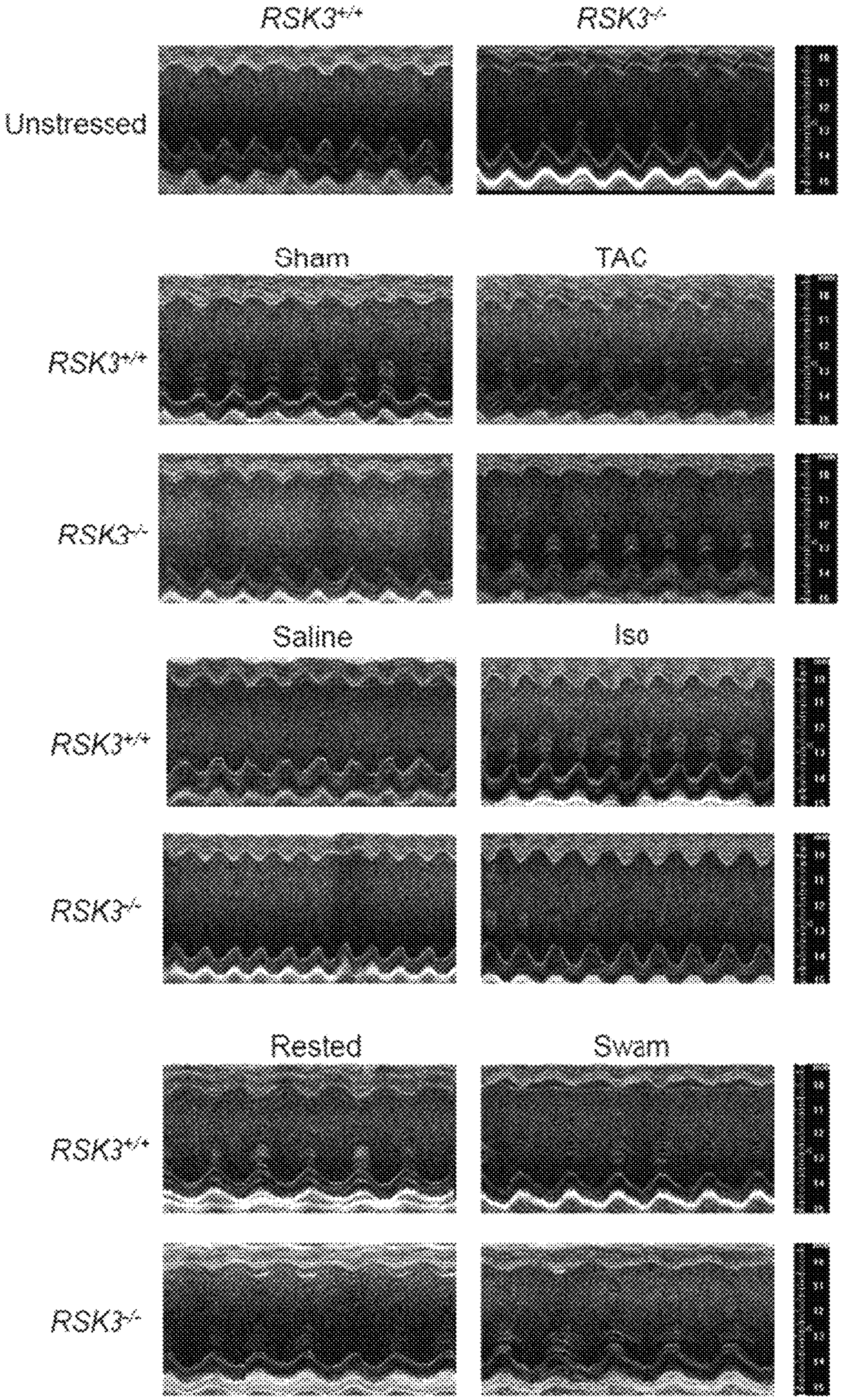
FIG. 28. Echocardiography. Representative M-mode tracings for unstressed, sham-operated and TAC, saline and isoproterenol infused, and rested and swam mice. See FIGS. 10, 13, 15 and 17 for results.

The results obtained in vitro suggested that active RSK3 contributes to the development of pathologic myocyte hypertrophy. Further evidence supporting this hypothesis was obtained using a new RSK3 knockout mouse. By homologous recombination, stop codons were inserted into the second exon of the RSK3 (Rps6ka2) gene encoding the ATP-binding motif of the N-terminal kinase domain (Hanks 1988), resulting in the constitutive absence of RSK3 protein in homozygous null mice (FIG. 27). In general, $RSK^{-/-}$ mice appeared normal in morphology, were bred according to Mendelian genetics (FIG. 12), and exhibited no excess mortality up to 6 months of age. Before any stress, the $RSK3^{-/-}$ mice had generally normal cardiac function, with the only measureable difference from wild-type littermates being a slight increase in left ventricular internal dimensions detected by echocardiography (FIGS. 13 and 28).

The inventors tested whether RSK3 is required for compensated cardiac hypertrophy by subjecting the $RSK3^{-/-}$ mice to pressure overload for 2 weeks (FIG. 9A). By echocardiography, transverse aortic constriction (TAC) induced a 36% increase in posterior wall thickness in wild-type mice, but only a 16% increase in $RSK3^{-/-}$ mice (FIGS. 10 and 28). The decreased hypertrophy was not accompanied by a change in contractility (fractional shortening). Postmortem gravimetric analysis showed that the corresponding increase in biventricular weight after TAC was similarly diminished in the knockout mice (48% for $RSK3^{+/+}$ vs. 26% for $RSK3^{-/-}$ mice; FIG. 14). TAC primarily induces concentric growth of cardiac myocytes.

Inspection of wheat germ agglutinin-stained heart sections revealed that consistent with these results, RSK3 knockout attenuated the TAC-induced increase in myocyte transverse cross-section area by ~46% (FIGS. 9B and 9C). Proportional results were obtained by morphometric analysis of adult cardiac myocytes isolated from the TAC mice (FIG. 9D-9G).

To characterize the $RSK3^{-/-}$ cardiac phenotype at a molecular level, the inventors surveyed for differences in the cardiac expression of 30 genes encoding proteins involved either in cardiac remodeling or in hypertrophic signaling (FIG. 11). Approximately two-thirds of the genes in our panel were significantly increased or decreased in expression by TAC. In general, the changes in expression were attenuated by RSK3 knockout. For example, TAC-induced atrial natriuretic factor expression was dramatically inhibited in $RSK3^{-/-}$ mice, consistent with the results obtained for PE-treated neonatal myocytes. Although after 2 weeks of pressure overload the small increases in cellular apoptosis and interstitial fibrosis detectable by histology for wild-type mice did not reach significance when compared with sham-operated controls, these signs of remodeling tended to be less in the knockout mice ($8.2\pm2.0$ vs. $4.2\pm1.0\times10^{-4}$ TUNEL-positive nuclei and 0.49%±0.18% vs. 0.29%±0.11% collagen staining for wild-type and $RSK3^{-/-}$ TAC hearts, respectively). Interestingly, 2 genetic markers of fibrosis that were significantly induced in TAC wild-type mice, transforming growth factor β2 and collagen VI α1 (Yang 2012), were attenuated in expression by RSK3 knockout (FIG. 11).

Figure 29:
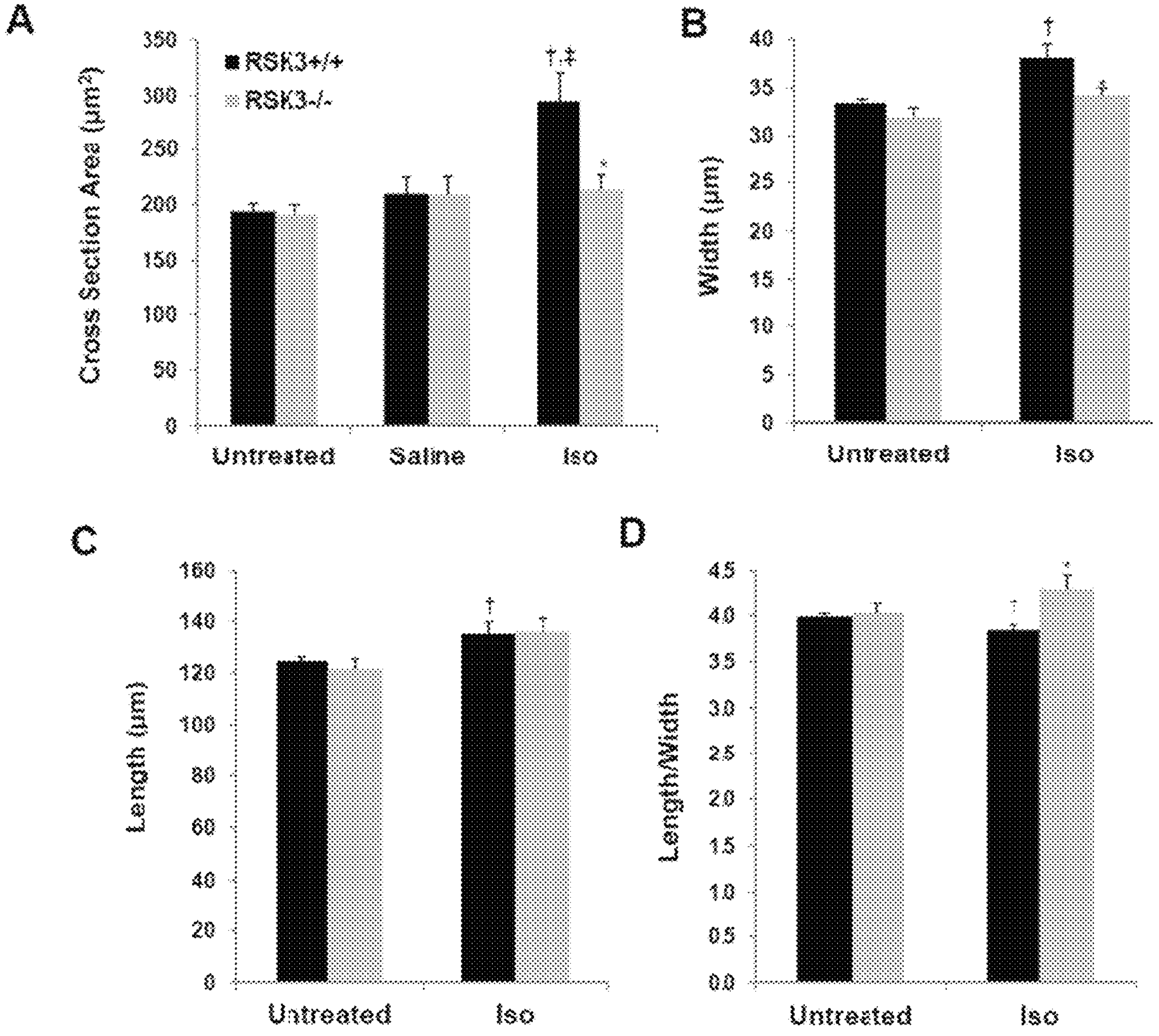
FIG. 29. RSK3 is required for Isoproterenol-induced myocyte growth in width in vivo. A. Cross-section area of myocytes in tissue sections. n=3-5. Width (B), Length (C) and Length/Width Ratio (D) of acutely dissociated adult cardiac myocytes. n=5-6. † p-values comparing to untreated $RSK3^{+/+}$ mice; ‡ p-values comparing to saline-infused $RSK3^{+/+}$ mice; * p-values comparing to Iso-infused $RSK3^{+/+}$ mice.

To further explore the role of RSK3 in cardiac hypertrophy, the inventors used a second in vivo pathological stressor, chronic isoproterenol (Iso) infusion via subcutaneous osmotic pumps, and a physiological stressor, chronic exercise via swimming. Although Iso infusion resulted in a minor increase in ventricular wall thickness by echocardiography (FIG. 15), at the cellular level Iso significantly induced myocyte growth in width in a RSK3-dependent manner as measured by histology and after myocyte isolation (FIG. 29). Unlike TAC, Iso infusion also induced eccentric growth, as evidenced by increased myocyte length and ventricular dilation by echocardiography (FIGS. 15 and 16). This eccentric growth was not inhibited by RSK3 knockout. Together with the TAC data, these results demonstrate that RSK3 contributes to the induction of concentric myocyte hypertrophy in pathologic conditions.

Finally, $RSK3^{-/-}$ mice were exercised by swimming. As expected (Perrino 2006), after swimming, wild-type mice exhibited a decreased resting heart rate (consistent with improved physical conditioning) and increased left ventricular internal dimensions (FIGS. 17 and 28). After exercise, there were no significant differences between RSK3 knockout and wild-type mice detectable by echocardiography, and the cohorts exhibited a similar increase in biventricular weight indexed by body weight (6% and 7%, respectively; FIG. 18).

Detailed Methods

Reagents: Commercial antibodies are listed in FIG. 19. Secondary antibodies included horseradish peroxidase (HRP)-conjugated donkey secondary antibodies (Jackson ImmunoResearch) and Alexa dye-conjugated donkey secondary antibodies (Invitrogen). Monoclonal 211, polyclonal VO54, VO56 and OR010 mAKAP antibodies were as previously described and are available through Covance Research Products (Kehat 2010). OR42 and OR43 rabbit anti-RSK3 antisera were generated using bacterially-expressed His-tagged RSK3 (full-length) and affinity purified using antigen-coupled Affigel resin (Biorad). FL099 and FL100 rabbit anti-mAKAP antisera were generated using bacterially-expressed GST-tagged mAKAP 245-340. Oligonucleotides are listed in FIG. 20. Other reagents included: BIX02189—Boehringer Ingelheim Pharmaceuticals; PD0325901, SB103580, SL0101, and SP600125—EMD Chemicals Inc.

All adenovirus were constructed using the pTRE shuttle vector and the Adeno-X Tet-off System (Clontech) and purified after amplification using Vivapure AdenoPACK kits (Sartorius Stedim). These adenoviruses conditionally express recombinant protein when co-infected with tetracycline transactivator-expressing virus (adeno-tTA for "tet-off" or reverse tTA for "tet-on"). HA-tagged RSK and MSK2 expression plasmids acquired from Dario Alessi and John Blenis (McKinsey 2007, Anjum 2008, Sadoshima 1995) and myc-tagged mAKAP mammalian expression vectors (pCDNA3.1 (−) myc-his) and adenovirus were as previously described (Kodama 2000, Takeishi 2002). GFP-RBD was expressed using a pEGFP-based plasmid. Bacterial expression vectors for mAKAP and RSK3 were constructed using pET30 and pGEX-4T parent vectors, and proteins were purified using His-bind (Novagen) and Glutathione Uniflow Resins (Clontech).

Neonatal rat myocytes isolation and culture: 1-3 day old Sprague-Dawley rats were decapitated and the excised hearts placed in 1×ADS Buffer (116 mmol/L NaCl, 20 mmol/L HEPES, 1 mmol/L $NaH_2PO_4$, 5.5 mmol/L glucose, 5.4 mmol/L KCl, 0.8 mmol/L $MgSO_4$, pH 7.35). The atria were carefully removed and the blood washed away. The ventricles were minced and incubated with 15 mL 1×ADS Buffer containing 3.3 mg type II collagenase (Worthington, 230 U/mg) and 9 mg Pancreatin (Sigma) at 37° C. while shaking at 80 RPM. After 15 minutes, the dissociated cardiac myocytes were separated by centrifugation at 50×g for 1 minute, resuspended in 4 mL horse serum and incubated 37° C. with occasional agitation. The steps for enzymatic digestion and isolation of myocytes were repeated 10-12 times to maximize yield. The myocytes were pooled and spun down again at 50×g for 2 minutes and resuspended in Maintenance Medium (DMEM:M199, 4:1) supplemented with 10% horse serum and 5% fetal bovine serum. To remove any contaminating fibroblasts, the cells were preplated for 1 hour before plating on gelatin-coated tissue culture plasticware. This procedure yields >90% pure cardiac myocytes. After 1 day in culture, the media was changed to maintenance medium containing 0.1 mmol/L bromodeoxyuridine to suppress fibroblast growth.

Experiments were initiated 1 day after myocyte isolation. Adenoviral infection was performed by addition of adenovirus (multiplicity of infection=5-50) to the media. Plasmids and siRNA oligonucleotides were transfected using Transfast (Promega) and Dharmafect (Thermofisher), respectively, as recommended by the manufacturers using cells cultured in maintenance medium supplemented with 4% horse serum. Starting the day after gene transduction, the cells were treated for as long as 2 days, as indicated for each experiment.

Immunoprecipitations: HEK293 and COS-7 cells were transfected with Lipofectamine 2000 (Invitrogen) or Polyethylenimine "Max" (Polysciences). Cells (including myocytes) were lysed in buffer (20 mmol/L HEPES, pH 7.4, 150 mmol/L NaCl, 5 mmol/L EDTA, 0.5% Triton, 50 mmol/L NaF, 1 mmol/L sodium orthovanadate, 1 mmol/L DTT, and protease inhibitors). After centrifugation at 10,000×g for 10 minutes at 4° C., the clarified extracts were used for immunoprecipitation using appropriate antibodies (10 μg purified antibody or 1-5 μL whole serum) and 20 μL protein G sepharose (Millipore, Fastflow) for 3 hours to overnight at 4° C. The beads were washed 3-5 times with lysis buffer, and the immunoprecipitated proteins were eluted with 1× Laemmli buffer for western blotting. Western blots were developed using horseradish peroxidase-conjugated donkey secondary antibodies, Supersignal West Chemiluminescent Substrates (Thermo Scientific) and X-ray film or a Fujifilm LAS-3000 imaging system.

Immunocytochemistry: Cultured neonatal cardiomyocytes on plastic coverslips were fixed in 3.7% formaldehyde in PBS, permeabilized with 0.3% Triton X-100 in PBS, and blocked with PBS containing 0.2% BSA and 1% horse serum for 1 hour. The slides were then sequentially incubated for 1 hour with primary and Alexa fluorescent dye-conjugated specific-secondary antibodies (Invitrogen, 1:1000) diluted in blocking buffer. The slips were washed three times with blocking buffer. 1 μg/mL Hoechst 33258 was included in the last wash stop to label nuclei. Slides were sealed in SlowFade Gold antifade buffer (Invitrogen) for fluorescent microscopy. Wide-field images were acquired using a Leica DMI 6000 Microscope.

Surface Plasmon Resonance: SPR analysis was performed using a BIAcore T100. 200 resonance units His-tagged mAKAP 1286-1833 were covalently immobilized using NHS (N-hydroxysuccinamide) and EDC [1-ethyl-3-(3-(dimethylamino)propyl)carbodiimide] (Biacore amine coupling kit) to the surface of a sensor chip (BIAcore type CM5). His-RSK3 analytes (6.25-200 nmol/L) in HBS buffer (10 mmol/L Hepes, pH 7.4, 150 mmol/L NaCl, and 0.005% Surfactant P20) were injected at a flow rate of 30 μL/min for 5 minutes, followed by buffer alone for another 5 minutes. Sensorgrams were processed by BIAcore T100 evaluation software.

For phosphorylated His-RSK3, 20 μg His-RSK3 was phosphorylated with 2 μg ERK2 (Millipore, 14-550) and/or PDK1 (Sigma, P7498) for 5 hours in kinase buffer (20 mmol/L MOPS, pH 7.2, 25 mmol/L β-glycerol phosphate, 5 mmol/L EGTA, 1 mmol/L sodium orthovanadate, 1 mmol/L DTT) with 0.5 mmol/L MgATP. Phospho-His-RSK3 was purified using His-binding beads and concentrated before use.

Generation of $RSK3^{-/-}$ mouse: All experiments involving animals were approved by the Institutional Animal Care and Use Committee at the University of Miami. Constitutive knock-out mice were generated using a targeting vector that inserted into Exon 2 a neomycin resistance gene (PGKneo) flanked by loxp sites (FIG. 27). Targeted 129SvJ ES cells were injected into C57BL/6J blastocysts. PGKneo was removed by crossing mutant mice with B6.C-Tg(CMV-cre) 1Cgn/J (The Jackson Laboratory). $RSK^{+/-}$ Mice were selected for loss of the cre transgene and backcrossed to C57BL/6 mice over 10 generations. All experiments were performed with littermate controls and mice that were 8-12 weeks of age. The numbers of mice in each cohort are listed in the various tables and figures.

Isoproterenol infusion: Alzet 2002 osmotic pumps (Durect) were sterilely loaded with 200 μL saline or saline and isoproterenol to deliver 60 mg/kg/day for 14 days. 8 week old mice were anaesthetized, and the pump was inserted sterilely subcutaneously into the shaved back through a transverse incision made intra-scapulae. The wound was closed with surgical staples and covered with betadine solution. Mice were housed separately after surgery.

Transverse Aortic Constriction: All tools were sterilized with a Germinator 500 Dry Sterilizer and Betadine Solution (10% povidone-iodine topical solution). Anesthesia was induced with 5% isoflurane and maintained with 2% isoflurane and 100% oxygen at a flow rate of 1.5 L/min using a SurgiVet flow regulator via nose cone. Loss of consciousness was verified by toe pinch. Mouse fur over the left chest and sternum was removed with a calcium hydroxide lotion (e.g. Nair), and the surgical site was sterilized with betadine. The skin was incised exposing the pectoralis muscle and the second left intercostal space. The pectoralis muscle and the second rib were blunt dissected and retracted revealing the thymus within the mediastinum. The lobes of the thymus were retracted to reveal the transverse aortic arch as well as the right innominate and left common carotid arteries. Blunt dissection though the connective tissue between these two arteries and under the aorta allowed for the passage of a 6-0 silk using a modified ligation aid (Fine Science Tools 18062-12). A 27 gauge needle was placed on top of the aorta and the 6-0 silk was tied around the needle. The needle was removed, leaving a constricted aorta. The chest was closed in two layers with 5-0 Polysorb Suture. Isoflurane administration was terminated, and the mice were maintained on 100% oxygen by nose cone until conscious. Immediately post-operatively, buprenorphrine (0.05-0.1 mg/kg s.c.) was administered and then q12 h prn. The mice were allowed to recover under a heat lamp until alert and active. Sham-operated mice that experience all but the placement of the aortic ligature served as controls.

Swimming: 8-10 week old mice were forced to swim in water tanks every day for 4 weeks. The swimming tank measured >225 $cm^{2'}$ with a depth of 15 cm and a water temperature of 30-32° C. Mice were continuously observed to avoid any drowning. The first day of training consisted of two 10-min sessions separated by at least 4 h. Sessions were increased by 10 min each day until 90-min sessions were reached. Additional cohorts were housed normally without exercise to serve as a "sham swim" control group. Food and water were provided ad libitum throughout the month period for all mice.

Echocardiography: Mice minimally anesthetized with 1-2% isoflurane were studied using a Vevo 770@, High-Resolution Imaging System (VisualSonics). The pressure gradient following TAC was calculated from the pulse wave Doppler velocity at the point of ligation as follows: $P=4v^2$; P=the induced pressure gradient (in mmHg) and v=the velocity across the constriction (in m/s).[7]

Adult mouse myocytes isolation by Langendorff perfusion: Mice were anesthetized using Ketamine (80-100 mg/kg) and Xylazine (5-10 mg/kg) IP followed by 200 U heparin IP and cardiac excision. The heart was placed immediately in perfusion buffer (NaCl 120 mmol/L, KCl 5.4 mmol/L, $Na_2HPO_4 \cdot 7H_2O$ 1.2 mmol/L, $NaHCO_3$20.0 mmol/L, $MgCl_2 \cdot 6H_2O$ 1.6 mmol/L, Taurine 5 mmol/L, Glucose 5.6 mmol/L) equilibrated with 95% $O_2$ and 5% $CO_2$. The heart was attached via the aorta to the condenser outlet of a Harvard Langendorff apparatus. $Ca^{2+}$-free perfusion lasted for 5 minutes with a constant rate at 2.2 mL/min at 37° C. The heart was digested by continuous perfusion with 25 mL buffer containing 25 mg type II collagenase (Worthington, 315 U/mg) and 1.3 mg protease (Sigma type XIV). After removal of the atria, the ventricles were then immersed in 5 mL of the same enzyme solution for dissociation by cutting into small pieces and by passing through a large bore pipette. The cell slurry was filtered through a 150-200 μm nylon mesh and the myocytes relaxed by incubation for 10 minutes in perfusion buffer containing 10 mmol/L KCl. The cells were fixed in suspension in perfusion buffer containing 3.7% formaldehyde, before morphometric analysis by light microscopy.

Histochemistry: Heart tissue was fixed in 3.7% formaldehyde. De-paraffinized 5 μm tissue sections were stained using the Picrosirius Red Stain Kit (Polysciences) and Alexa Fluor 555 Wheat Germ Agglutinin conjugate (Invitrogen) as recommended by the manufacturers. The cross-section area of >150 myocytes in >3 distinct regions of the left ventricle were measured per heart using the wheat germ agglutinin sections. Collagen content was assayed using the Picrosirius Red stained sections and polarized light microscopy for >3 5× objective fields per heart. TUNEL staining for both fixed cells and tissue sections was performed using the In Situ Cell Death Detection Kit, TMR red (Roche). Morphometrics and collagen content were measured using IPLab microscope software (BD Biosciences).

Morphometry: Morphometric data was acquired using IPLab Software. For neonatal myocytes, at least 6 separate images, each containing >100 cells, were assayed for cross-section area and perinuclear prepro-ANF staining per condition for each repetition of the experiment. For adult mouse cardiac myocytes, the maximum lengths perpendicular (width) or parallel (length) to the myofibrils were measured for >100 freshly dissociated myocytes per heart.

RNA Assays: Total RNA was quantified with a Nanodrop 8000 Spectrophotometer (Thermo Scientific) and quality controlled using with a Bioanalyzer 2100 and the RNA 6000 Nano kit (Agilent). qRT-PCR was performed using SYBR green.

The NanoString assay is based on direct, multiplexed measurement of gene expression without amplification, utilizing fluorescent molecular barcodes and single molecule imaging to identify and count multiple transcripts in a single reaction. For Nanostring assay, 100 ng total RNA were hybridized in solution to a target-specific codeset overnight at 65° C. The codeset contained dual, adjacently placed 50 bp oligonucleotide probes against a panel of 30 genes, one set of probes fluorescently bar-coded and the other biotinylated. The hybridization reactions were loaded onto the NanoString Prep station which removes excess oligonucleotides and binds the hybridized mRNA to the Streptavidin-coated cartridge surface. The cartridges were loaded onto the NanoString Digital Analyzer, and 1155 fields of view were fluorescently scanned to count only those individual mRNAs bound to both a biotinylated and fluorescently bar-coded probe. Datasets for each RNA sample were background-subtracted and normalized using Gapdh. In validation assays, NanoString counts were directly proportional over 3 orders of magnitude to the mRNA levels obtained by qRT-PCR and had a similar minimum level of detection.

Statistics: For all experiments, n refers to the number of individual mice or individual myocyte preparations. All data are expressed as mean±s.e.m. p-values were calculated using two-tailed Student's t-tests, paired or un-paired as appropriate, and are not corrected for multiple comparisons. Repeated symbols represent p-values of different orders of magnitude, for example: *p<0.05, p<0.005, *** p<0.0005, etc. All datasets involving multiple comparisons for which p-values are provided were also significant by ANOVA, a0.05.

Discussion

RSK activity is associated with the function of the nervous system, immunity, muscle, and cancer (Anjum 2008). Human RSK2 mutations cause X-linked Coffin-Lowry syndrome, which includes mental and growth retardation and skeletal and facial anomalies, but rare cardiac abnormality. In the heart, RSK1 and RSK2 can activate the $Na^+/H^+$ exchanger NHE1, and α-adrenergic-induced NHE1 phosphorylation is blocked by fmk, which inhibits all RSKs except RSK3 (Cuello 2007). The inventors now reveal a role for RSK3 in the cardiovascular system, regulation of pathological myocyte hypertrophy.

Figure 6:
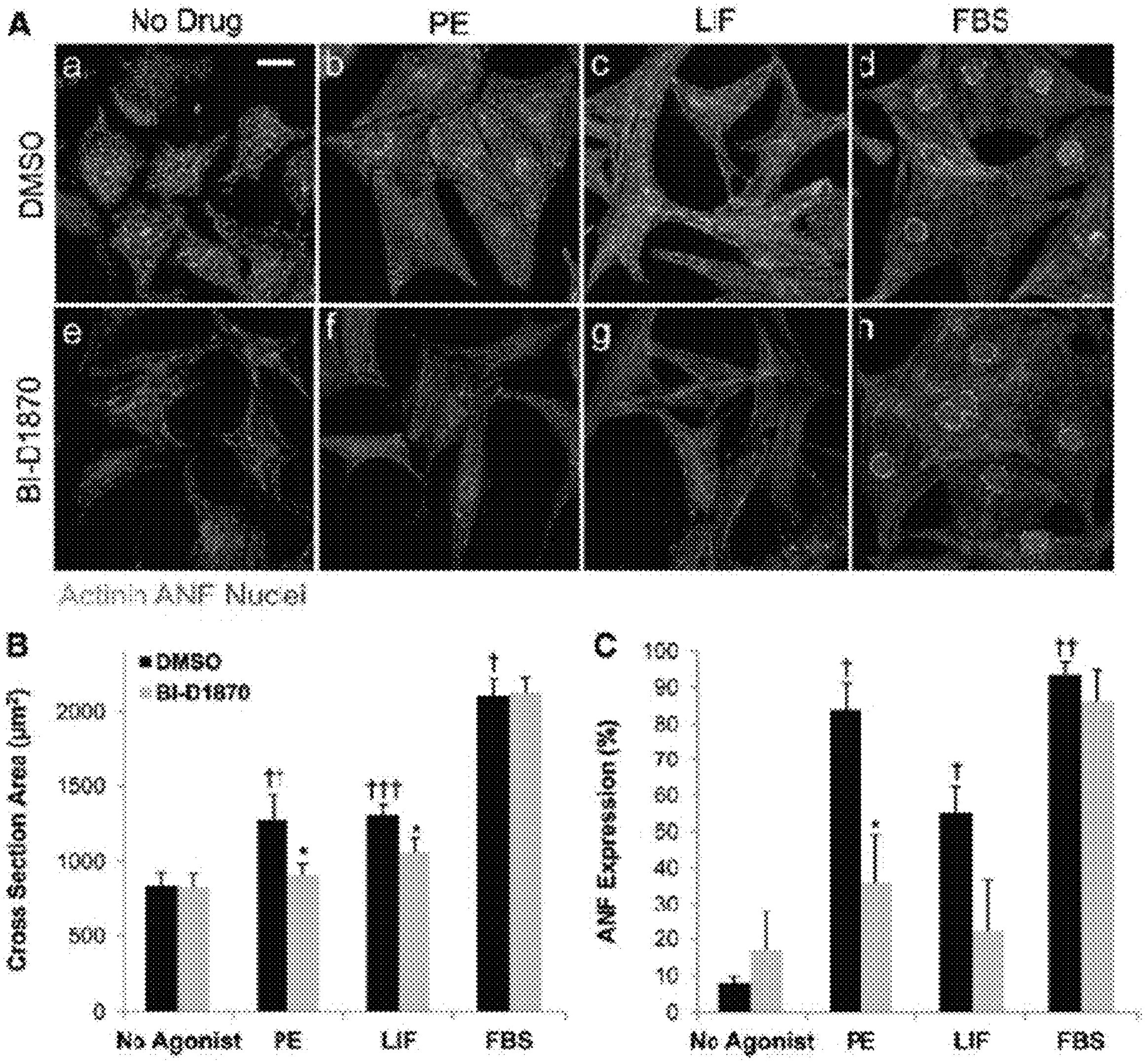
FIG. 6. Inhibition of neonatal rat ventricular myocyte hypertrophy with p90 ribosomal S6 kinase (RSK) inhibitor. Myocytes were cultured for 2 days±10 μmol/L phenylephrine (PE), 1000 U/mL leukemia inhibitory factor (LIF), 10% fetal bovine serum (FBS), or 10 μmol/L BI-D1870 or 1% DMSO carrier. A, Immunocytochemistry for α-actinin (green), atrial natriuretic factor (ANF; red), and Hoechst (blue); bar=20 μm. Separate ANF and Hoechst channels are provided in FIG. 25. B, Cross-section area of myocytes (n=3-7). C, Fraction of myocytes expressing ANF (n=3). *P values compared with DMSO. †P values compared with no agonist control.

Cardiac myocytes can grow in both width and length, termed concentric and eccentric hypertrophy, respectively (Kehat 2010). Concentric myocyte hypertrophy involves the parallel assembly of contractile units (sarcomeres), increasing potential myocyte tension and wall thickness. In contrast, eccentric myocyte hypertrophy involves the serial assembly of sarcomeres along the axis of contraction, mainly contributing to increased ventricular wall area. The inventors found that RSK3 was required for TAC-induced concentric hypertrophy, as well as for Iso-induced myocyte growth in width in vivo. These differences can be modeled in vitro. Interleukin-6 cytokines such as leukemia inhibitory factor and cardiotrophin-1 induce an elongated and eccentric phenotype for cultured neonatal myocytes, in contrast to the symmetric growth stimulated by PE (Wollert 1996). Interestingly, the growth of the cultured myocytes tended to depend on RSK3 more when induced by α-adrenergic stimulation than by leukemia inhibitory factor (FIGS. 5 and 6). The greater inhibition of PE-induced morphologic hypertrophy was consistent with the more robust activation of RSK by PE than leukemia inhibitory factor (FIG. 22), as well as the results obtained in vivo.

RSK3 was activated in myocytes by ERK1, ERK2, and ERK5 (FIG. 5A). Whereas RSK3 has been absent from the cardiac literature, ERK signaling has been well-studied both in human disease and in animal models. The autosomal-dominant human syndromes Noonan, Costello, cardiofaciocutaneous, and LEOPARD result from mutations in PTPN11, HRAS, RAF1, BRAF, MEK1, and MEK2 that activate ERK1/2 signaling (Wu 2011). These Rasopathies feature developmental delay, dysmorphic features, and defects in multiple organ systems, often including a hypertrophic phenotype Gelb 2011). In mice, left ventricular hypertrophy has been induced by cardiac myocyte-specific expression of constitutively active H-Ras and MEK1, as well as cardiac-specific deletion of the Ras GTPase-activating protein neurofibromin that inhibits Ras signaling (Rose 2010, Xu 2009). Conversely, transgenic expression of dominant-negative Raf1 inhibited the hypertrophy due to pressure overload.

Recently, investigators have shown that cardiac myocyte-specific knockout of all 4 ERK1/2 alleles resulted in a severe, fatal dilated cardiomyopathy without increased myocyte death (Kehat 2011). ERK1/2-null myocytes were longer and narrower than those from control animals. PTPN11 (Shp2) knockout that decreased ERK1/2 activation also resulted in an elongated myocyte morphology and dilated cardiomyopathy (Kontaridis 2008).

Conversely, myocytes from constitutively active MEK1 transgenic mice were shorter and wider (Kehat 2011). In contrast to the ERK1/2 and Shp2 knockout mice, the inventors found that deletion of the down-stream effector RSK3 resulted in a milder phenotype, with the defect in concentric growth significant only after TAC and Iso infusion. Together, these observations are consistent with the hypothesis that ERK1/2 signaling through RSK3 promotes stress-induced concentric growth of cardiac myocytes independently of other signaling pathways that regulate eccentric hypertrophy.

The inventors found that RSK3 was activated in myocytes by not only ERK1/2 but also ERK5. There is evidence that MEK5-ERK5 signaling primarily induces eccentric myocyte hypertrophy (Nicol 2001), although ERK5 also may contribute to concentric growth (Kimura 2010).

Figure 9:
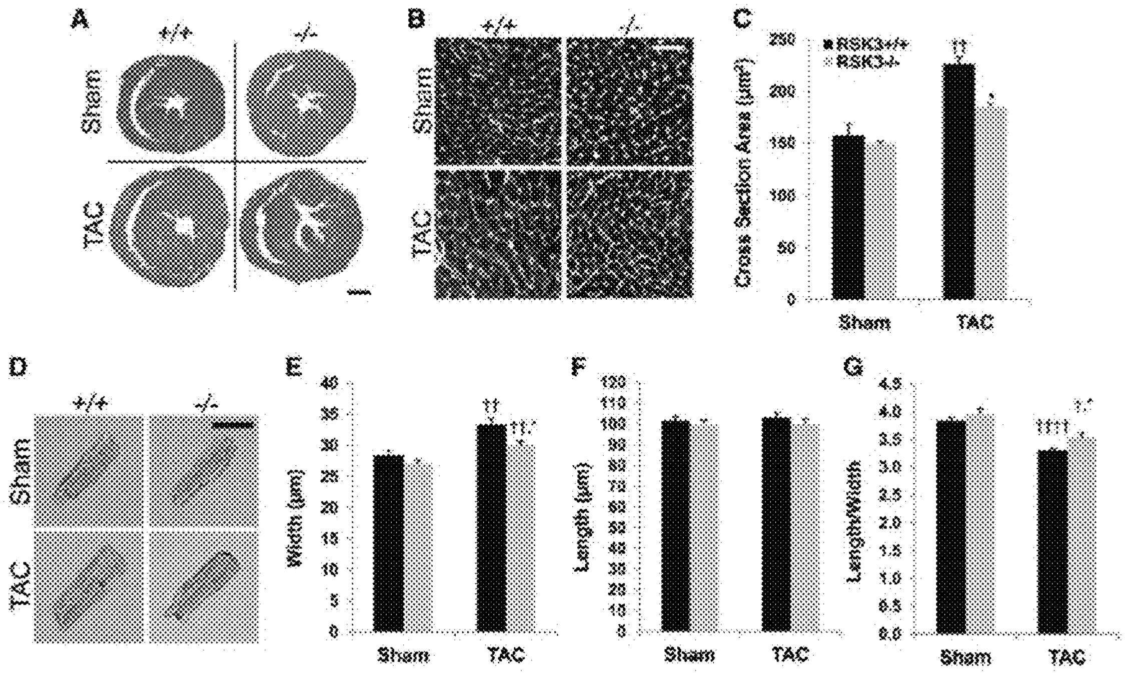
FIG. 9. p90 ribosomal S6 kinase type 3 (RSK3) knockout attenuates the effects of pressure overload in vivo. A, Hematoxylin and eosin-stained transverse sections. Bar=1 mm. B, Wheat-germ agglutinin-stained sections. Bar=50 μm. C, Cross-section area of myocytes in tissue sections (n=4-9). D, Bright field images of acutely dissociated adult cardiac myocytes. Bar=50 μm. Width (E), length (F), and length/width ratio (G) of isolated myocytes (n=5-6). †P values compared with sham-operated mice of the same genotype; *P values compared with $RSK3^{+/+}$ transverse aortic constriction (TAC) mice.

The data obtained using the RSK knockout mouse establish a function for RSK3 in pathological remodeling. Without being bound by any particular theory, it is also possible that RSK3 has a role in physiologic hypertrophy. For example, the myocytes isolated from unstressed $RSK3^{-/-}$ mice tended to be smaller in both width and length (FIGS. 9 and 29). In addition, after swimming, $RSK3^{-/-}$ biventricular weight was less than that of wild-type mice, albeit not significantly after normalization by body weight (FIG. 18).

Figure 30:
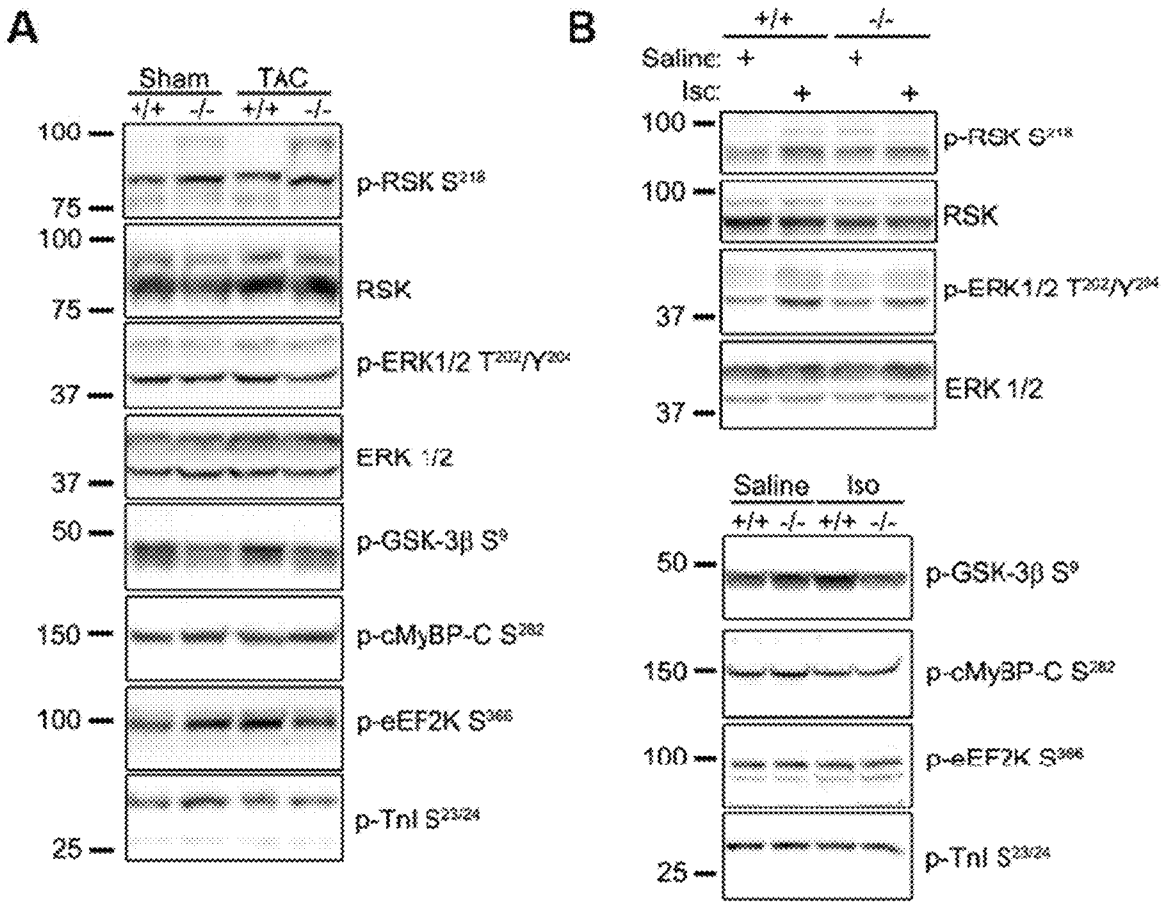
FIG. 30. Phosphorylation of RSK3, ERK1/2, and known RSK substrates in mice hearts. 150 μg total heart extracts were analyzed by western blot for the indicated proteins for 2 weeks TAC (A) and isoproterenol infusion (B) cohorts. GSK-3β$S^{9}$, myosin binding protein C (cMyBP-C) $S^{282}$, eukaryotic elongation factor-2 kinase (eEF2K) $S^{366}$, and cardiac troponin I (TnI) $S^{23/24}$ are known RSK substrates. Mouse IF6 RSK antibody was used to assay total RSK protein. No consistent changes in levels of total protein or phosphorylated proteins were detected.

It is remarkable that even though RSK3 constitutes a minority of the total RSK in the myocyte (FIGS. 24 and 30), RSK3 activity is, nevertheless, required for myocyte growth. The differential anchoring of RSK3 by scaffold proteins provides a mechanism by which RSK3 may specifically function in vivo. Scaffolds are likely to be most important for enzymes such as RSK3 that are low in abundance and that have broad intrinsic substrate specificity. RSK protein kinases catalyze the phosphorylation of RxRxx(S/T) sites and overlap in specificity with other AGC kinases (Anjum 2008). By co-localizing enzymes, their upstream activators, and substrate effectors, scaffolds can accelerate the kinetics of signaling, amplify responses, increase specificity in enzyme catalysis, and direct signaling to specific subcellular compartments (Good 2011). The prior art provides limited guidance with respect to RSK compartmentation in cells or participation in multi-molecular signaling complexes. On mitogen stimulation, cytosolic RSK1 (and potentially other RSK isoenzymes) can transiently translocate to the plasma membrane, whereas activated RSK tends to be enriched in the nucleus (Anjum 2008). In neurons, RSKs bind PDZ domain-containing proteins via their conserved C-terminal STxL peptides, directing the kinases to substrates involved in synaptic transmission (Thomas 2005). By another mechanism, RSK1 binds type 1 protein kinase A and D-AKAP-1, a mitochondrion-localized scaffold (Chaturvedi 2006, Huang 1997). Consistent with the fact that the inventors can only detect RSK3 in myocytes after immunoprecipitation, the inventors have not been able to detect endogenous RSK3 protein by immunocytochemistry. When overexpressed at a low level, HA-RSK3 was enriched at the nuclear envelope, the predominant location for mAKAPβ in the cardiac myocyte (Pare 2005). By characterizing in detail the protein-protein interaction between the unique RSK3 N terminus and mAKAPβ, the inventors have identified a new mechanism by which RSK3 can be specifically anchored by ≥1 scaffolds that may be targeted to different signaling compartments.

The inventors demonstrated the functional significance of this RSK3 anchoring using a competing binding peptide (mAKAP RBD) that inhibited myocyte hypertrophy.

The regulation of NHE1 by RSK1/2 has spurred recent interest in using RSK inhibitors to treat heart disease (Avkiram 2008). The inventors show that RSK3 knockout reduced TAC-induced hypertrophy without diminishing cardiac function and while inhibiting the expression of genetic markers for pathological remodeling. RSK inhibition may have multiple applications, including its use in acquired diseases such as hypertension (pressure overload) and for the treatment of the aforementioned Rasopathies. Recently, a Noonan syndrome mouse model (Raf1 $L^{613}V$ knock-in) mouse was treated with PD0325901, resulting in the attenuated progression of cardiac hypertrophy cardiomyopathy and other Noonan characteristics (Wu 2011). Targeting of RSK3 offers an alternative approach to avoid some of the harmful side effects of global ERK pathway inhibition. The use of RSK3 inhibitors that either competitively bind the active site or disrupt anchoring are offered as novel cardiac therapies.

Example 2

Remodeling of the extracellular matrix and the induction of myocardial interstitial fibrosis is an important factor contributing to the development of heart failure in cardiac disease (Spinale 2013, Edgley 2012). Increased deposition of fibrillar collagen and disruption of the normal cellular architecture of the myocardium can result in decreased compliance and both diastolic and systolic dysfunction, as well as arrhythmia due to interference with the electrical conduction system. p90 ribosomal S6 kinases (RSK) are pleiotropic protein kinases that are activated in myocytes in response to many stress-related stimuli (Anjum 2008, Sadoshima 2005, Kodama 2000). The inventors have shown that type 3 RSK (RSK3) is required for the induction of concentric myocyte hypertrophy in mice subjected to pressure overload (Li 2013). Activated by sequential phosphorylation by extracellular signal-regulated kinases (ERKs) and 3'-phosphoinositide-dependent kinase 1, RSK3 is one of four RSK family members expressed in the heart (Anjum 2008). Remarkably, even though RSK3 comprises a minority of RSK enzyme in cardiac myocytes, RSK3 is required for hypertrophy (Li 2013). Due to its role in pathological hypertrophy, the inventors have suggested that RSK3 targeting might be beneficial in the prevention of heart failure. To our knowledge, however, the prior art is deficient in showing whether RSK family members also regulate cardiac fibrosis. In this study, the inventors now show a role for RSK3 in interstitial fibrosis that is independent of its function in hypertrophic signal transduction.

Hypertrophic cardiomyopathy (HCM) is the most commonly inherited heart defect (1 in 500 individuals) and the leading cause of sudden death in children, accounting for 36% of sudden deaths in young athletes (Maron 2013). HCM is caused by dominant mutations in sarcomeric proteins that typically induce myocyte hypertrophy and disarray and interstitial fibrosis. However, the phenotype and clinical course resulting from HCM mutations can vary such that genotype-positive patients without left ventricular hypertrophy can display myocardial fibrosis, diastolic dysfunction, and ECG abnormalities (Maron 2013). Studies using transgenic mice also indicate that the phenotype of HCM mutations depends upon genetic background (Prabhakar 2001, Michele 2002). As described below, expression of the HCM mutation Glu180Gly amino acid substitution of the thin filament protein α-tropomyosin (TM180) in mice of a mixed C57BL/6; FVB/N background results in a small left ventricle with interstitial fibrosis. The inventors show that RSK3 is required in this non-hypertrophic HCM model for the development of interstitial fibrosis and the signs of left-sided heart failure.

Methods

Supplemental Material

Reagents: Primary antibodies included mouse 1F6 monoclonal anti-RSK3 (Abnova, cat #H00006196-M01) that detects all RSK family members (Spinale 2013), OR43 rabbit anti RSK3, and N-16 goat anti-RSK3 (Santa Cruz Biotechnology). Secondary antibodies included horseradish peroxidase (HRP)-conjugated donkey secondary antibodies (Jackson ImmunoResearch). RSK3 immunoprecipitation was performed as previously described (Spinale 2013).

Mice: All experiments involving animals were approved by the Institutional Animal Care and Use Committee at the University of Miami. The $RSK3^{-/-}$ C57BL/6 mouse was mated to the TM180 transgenic FVB/N mouse (Spinale 2013, Edgley 2012). All mice studied were littermates from $RSK3^{-/+}$ X TM180; $RSK3^{-/+}$ breedings, such that the background strain was 50:50 C57BL/6; FVB/N. All four genotypes were present in typical Mendelian proportion. Unless otherwise specifies, all experiments were performed with mice that were 16 weeks of age. Genotyping was performed at weaning by PCR using tail biopsy samples as previously described (Spinale 2013, Edgley 2012).

Echocardiography: A Vevo 770TM High-Resolution In Vivo Imaging System (VisualSonics) with a RMVTM 707B "High Frame" Scan-head was used for imaging. Mice were anesthetized with 1.5% isoflurane for both B-mode and M-mode imaging.

Histochemistry: Heart tissue was fixed in 3.7% formaldehyde. De-paraffinized 5 μm tissue sections were stained using the Picrosirius Red Stain Kit (Polysciences) and Alexa Fluor 555 Wheat Germ Agglutinin conjugate (Invitrogen) as recommended by the manufacturers. The cross-section area of >150 myocytes in >3 distinct regions of the left ventricle were measured per heart using the wheat germ agglutinin sections. Collagen content was assayed using the Picrosirius Red stained sections and linearly polarized light microscopy for >3 4× objective fields per heart. Note that while linearly polarized light microscopy is a highly specific assay for fibrillar collagen, the values obtained are an underestimate of total collagen content. TUNEL staining for both fixed cells and tissue sections was performed using the In Situ Cell Death Detection Kit, TMR red (Roche). Morphometrics and collagen content were measured using IPLab microscope software (BD Biosciences). All analyses were performed by a blinded investigator.

RNA Assay: Total RNA was quantified with a Nanodrop 8000 Spectrophotometer (ThermoScientific) and quality controlled using with a Bioanalyzer 2100 and the RNA 6000 Nano kit(Agilent). The NanoString assay is based on direct, multiplexed measurement of gene expression without amplification, utilizing fluorescent molecular barcodes and single molecule imaging to identify and count multiple transcripts in a single reaction. Briefly, 100 ng total RNA were hybridized in solution to a target-specific codeset overnight at 65° C. The codeset contained dual, adjacently placed 50 bp oligonucleotide probes against the entire panel of genes, one set of probes fluorescently bar-coded and the other biotinylated. The hybridization reactions were loaded onto the NanoString Prep station which removes excess oligonucleotides and binds the hybridized mRNA to the Streptavidin-coated cartridge surface. The cartridges were loaded onto the NanoString Digital Analyzer, and 1150 fields of view were fluorescently scanned to count only those individual mRNAs bound to both a biotinylated and fluorescently bar-coded probe. Datasets for each RNA sample were normalized to internal positive controls and background-subtracted. Probe sequences are available upon request.

Statistics: For all experiments, n refers to the number of individual mice. All data are expressed as mean±s.e.m. p-values were calculated using two-tailed Student's t-tests, paired or un-paired as appropriate, and are not corrected for multiple comparisons. Repeated symbols represent p-values of different orders of magnitude: * $p<0.05$,  $p<0.005$, * $p<0.0005$.

Results

Figure 32:
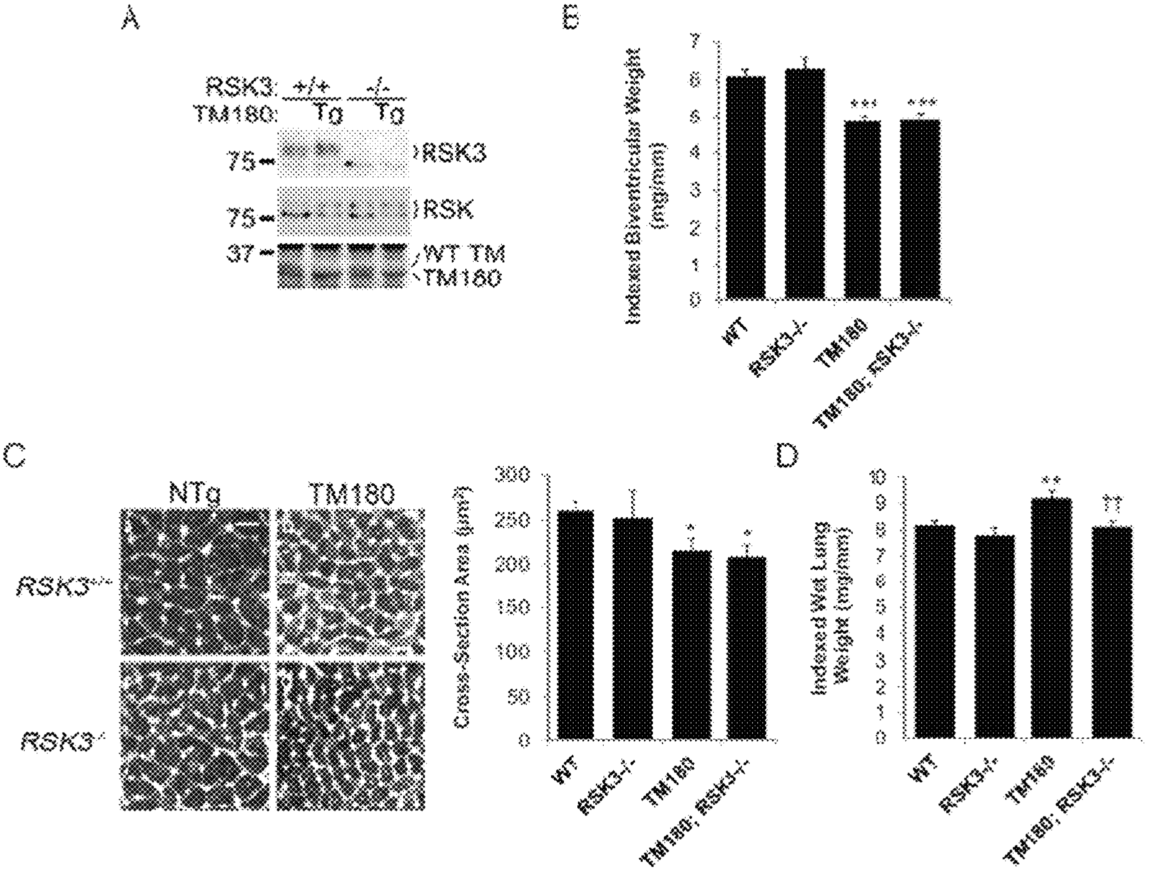
FIG. 32. TM180 C57BL/6; FVB/N mice have a small heart phenotype. A. Top panel: RSK3 protein was immunoprecipitated using N-16 antibody and detected using OR43 antibody. Middle panel: Total RSK protein in heart extracts was detected using mouse anti-RSK antibody. Bottom panel: Ponceau staining for total heart protein shows that the major α-TM wildtype band is replaced by a lower TM180 band in transgenic hearts (Prabhakar 2001). n=3 B. Biventricular weight indexed to tibial length. C. Wheat germ agglutinin-strained heart sections. Bar=50 μm. n=6 for each cohort. D. Wet lung weight indexed to tibial length. *p-values compared to WT cohort; †p-values compared to TM180 cohort. Cf.
Figure 36:
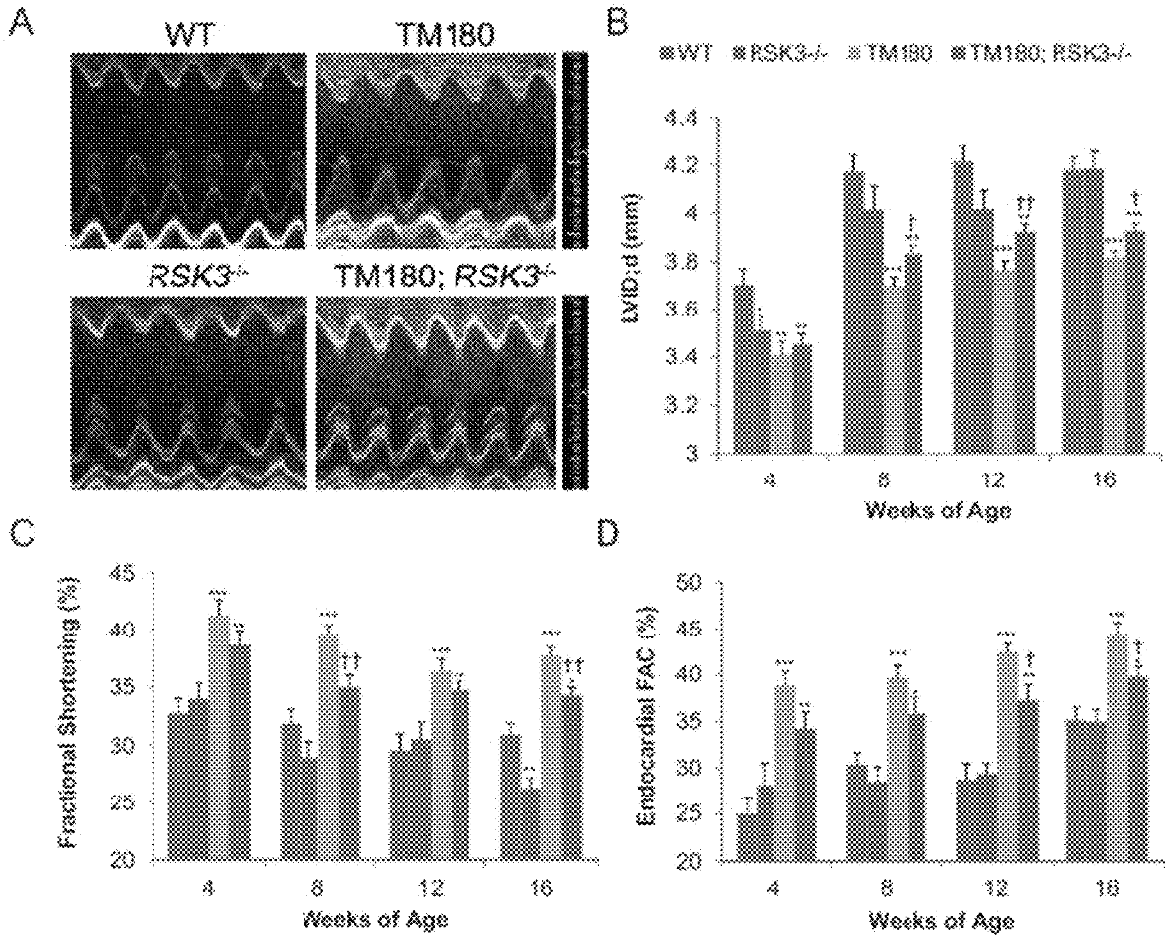
FIG. 36 shows electrocardiography from the mice treated as in Example 2. A. Representative M-mode images for 16 week old mice. See FIG. 31 for values. B. Left ventricular internal diameter in diastole (LVID; d) for mice at the indicated ages by Mmode. C. Fractional shortening (%) by M-Mode for mice at the indicated ages. D. Endocardial Percent Fractional Area Change (Endocardial FAC) by B-Mode for mice at the indicated ages. * p-values when compared to WT; †p-values when compared to TM180. n=15-19 for each cohort. At all ages, the TM180 mice had significantly smaller internal LVID; d and significantly higher fractional shortening and Endocardial FAC than wildtype mice. At all ages, the TM180; RSK3−/− mice had mean values for these parameters that were closer to wildtype than those for the TM180 mice, albeit significance ($p<0.05$) between the TM180 and TM180; RSK3−/− mice cohorts was not reached for all of the age groups for each parameter.
Figure 37:
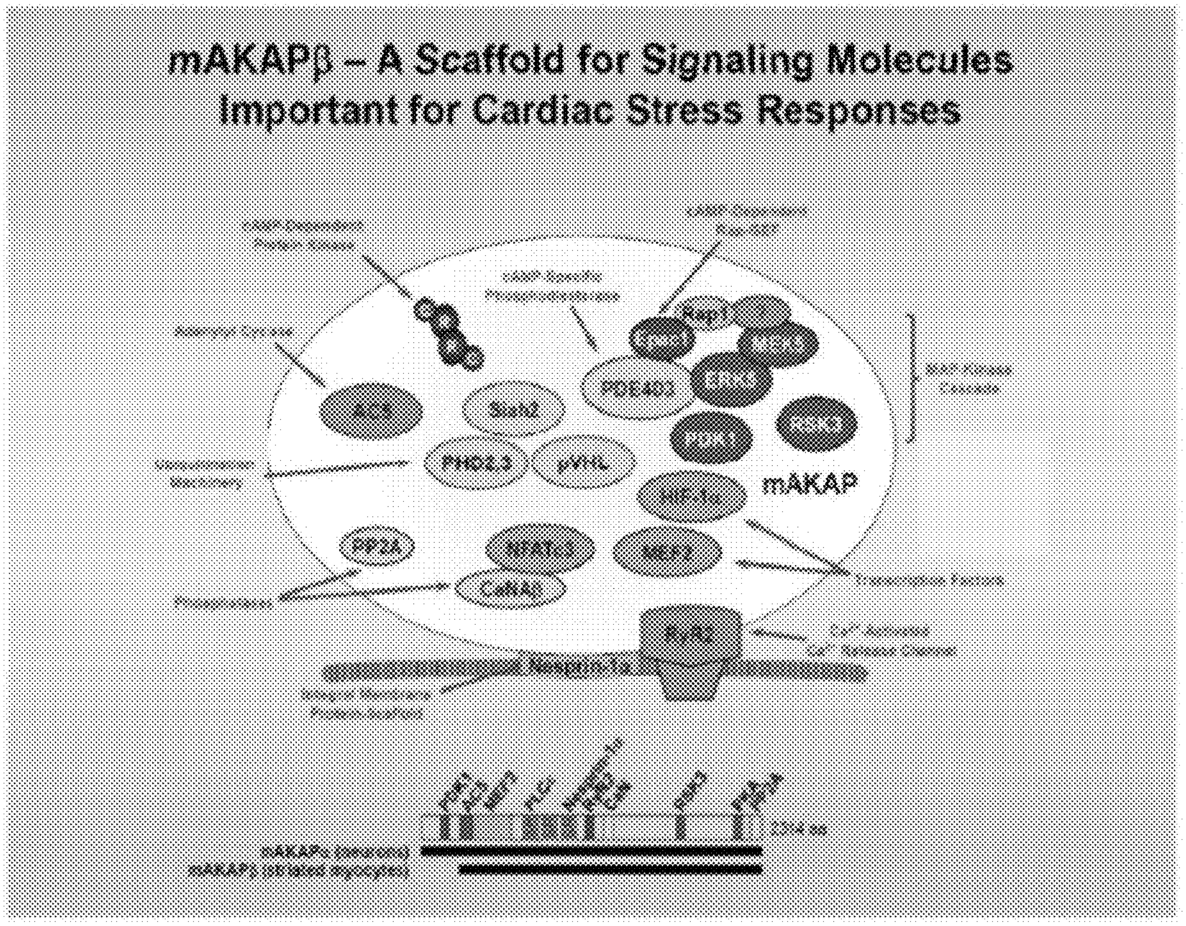
FIG. 37 shows mAKAPβ as a scaffold for signaling molecules important for cardiac stress responses.
Figure 38:
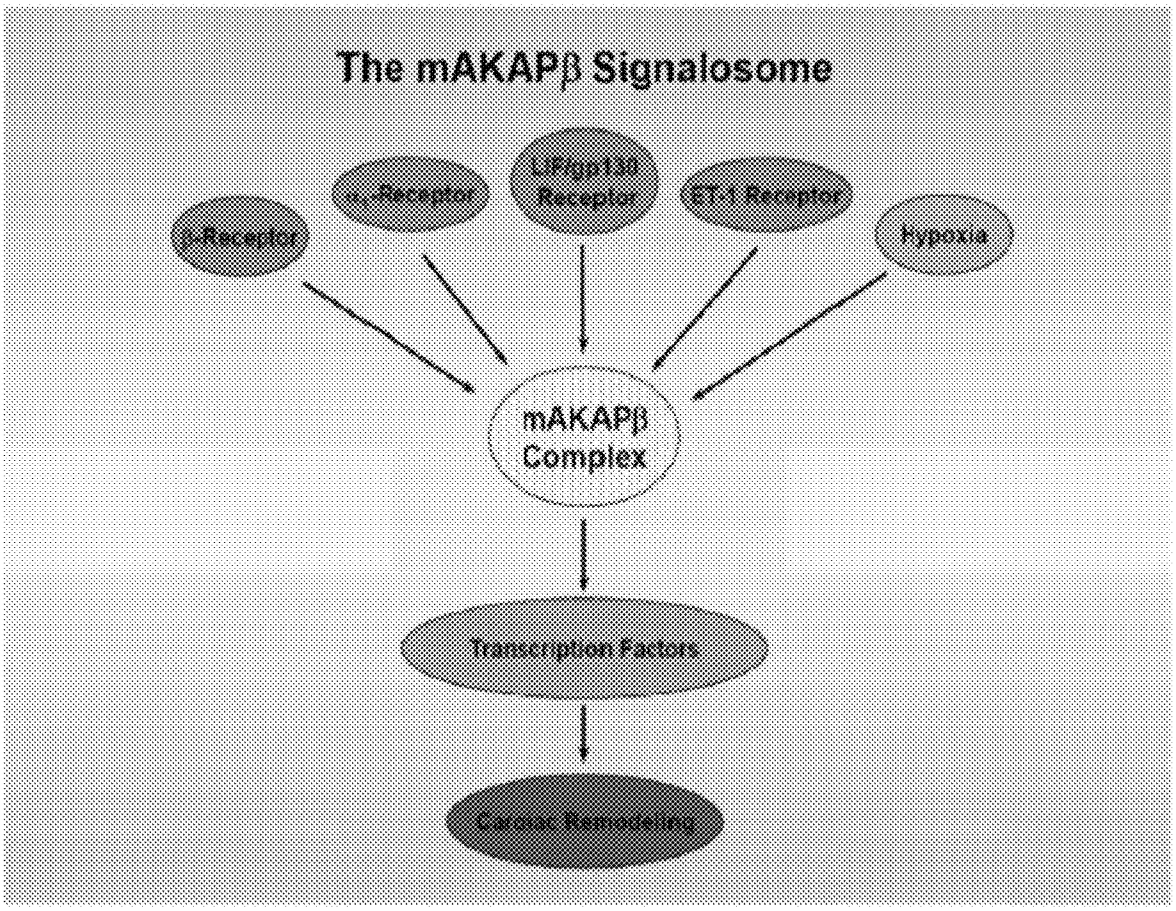
FIG. 38 shows the mAKAPβ signalosome.

FVB/N TM180 transgenic mice were crossed with C57BL/6 RSK3 knock-out mice such that all mice were of a mixed 50:50 background. RSK3 expression was slightly higher (~25%, p=0.12) in the TM180 mice, while absent in $RSK3^{-/-}$ mice, with no evidence of compensatory changes in the expression of other RSK family members (FIG. 32). Expression of the TM180 transgene was evident by the expected change in α-tropomyosin bands detected by total protein stain (Prabhakar 2001). In these mice of mixed lineage, the TM180 transgene induced a small heart phenotype that included a reduced biventricular weight (21%) and left ventricular myocytes with a proportionally smaller cross-section area (FIGS. 32 and 34). By echocardiography, the TM180 mice had reduced left ventricular internal dimensions, but increased contractility, i.e., both increased fractional shortening on M-mode and increased endocardial fractional area shortening on B-mode (FIGS. 31 and 36). That the changes in the TM180 left ventricle were pathologically important were implied by both an increased atrial weight and a significant, albeit small (12%) increase in wet lung weight, consistent with the presence of mild pulmonary edema and left-sided heart failure (FIGS. 32D and 34).

RSK3 knock-out had little effect on the heart in the absence of the TM180 transgene. While RSK3 knock-out did not reverse the small heart phenotype of the TM180 mouse nor prevent the atrial enlargement (FIGS. 32B,C and FIG. 34), the cardiac function of TM180; $RSK3^{-/-}$ mice was more like wildtype mice, including a 29% lesser decrease in short axis dimension by echocardiography (FIGS. 31 and 36). Notably, the increase in fractional shortening and endocardial fractional area shortening due to the TM180 transgene were both attenuated by ~50% by RSK knock-out. That the more "normal" cardiac function of the TM180; $RSK3^{-/-}$ mice was physiologically important was implied by the observation that wet lung weight was no longer increased following RSK3 knock-out (FIG. 32D and FIG. 34).

Figure 33:
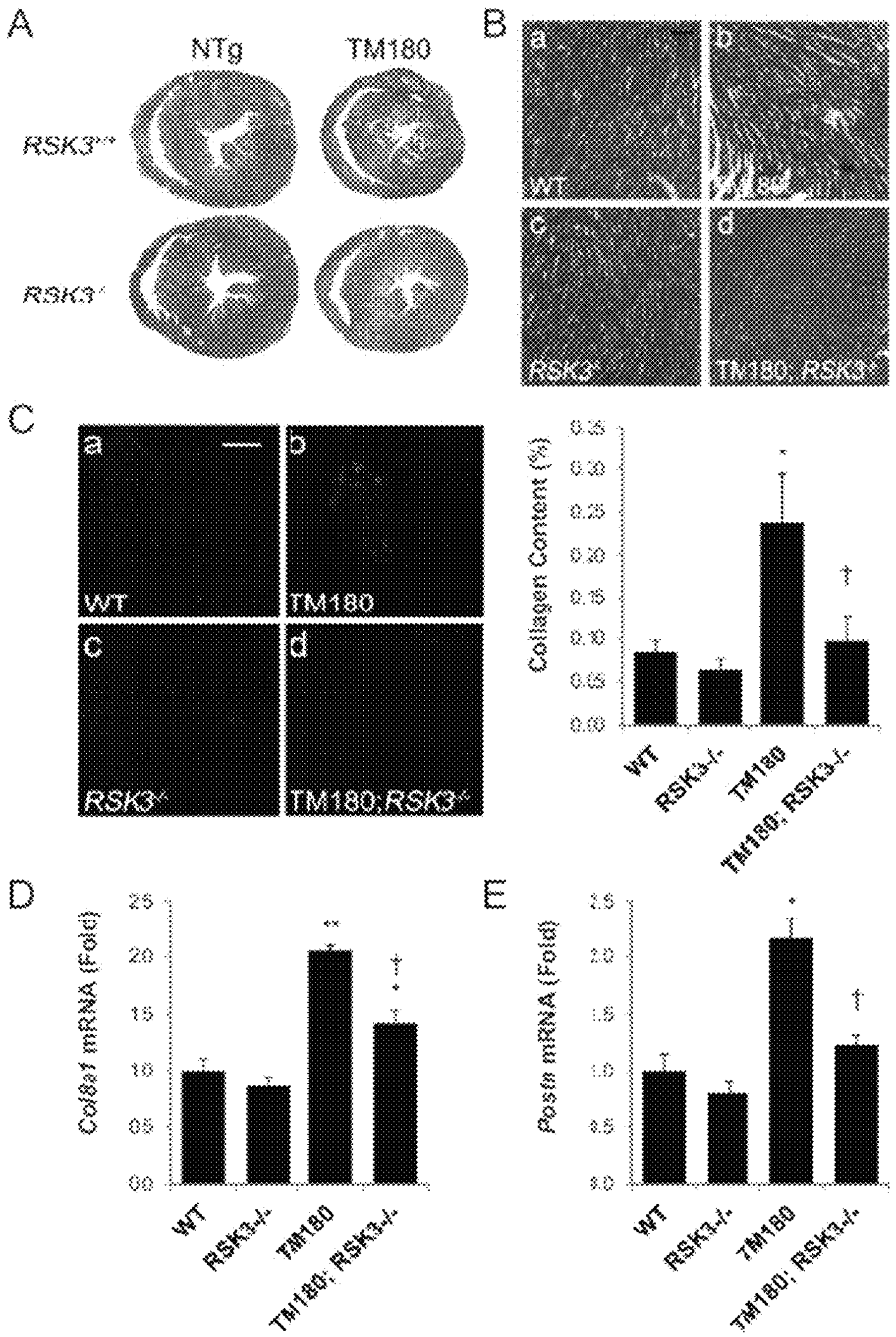
FIG. 33. RSK3 is required for TM180 induced interstitial fibrosis. A. Trichrome staining of transverse sections. B. Higher magnification of trichrome stained section. Bar=100 μm. C. Picrosirius red staining of left ventricular sections and fibrillar collagen content quantified by linearly polarized light microscopy. Bar=200 μm. n=10-13; p(ANOVA) =0.002. D and E. Col8A1 (periostin) mRNA levels. n=3. Cf.

There was no increase in cellular death associated with the TM180 transgene at 16 weeks of age (~$10^{-4}$ TUNEL-positive nuclei for all cohorts, data not shown). However, trichrome staining of the TM180 hearts revealed a patchy interstitial fibrosis in the myocardium not present in wild-type mice that was greatly reduced in the absence of RSK3 (FIG. 33A,B). Likewise, picrosirius red staining showed that fibrillar collagen content was increased by the TM180 transgene only in the presence of RSK3 (FIG. 33C). These results were corroborated by assay of the expression of genes involved in cardiac function and remodeling (FIG. 35). Notably, genes involved in cardiac fibrosis, including Col8a1 and Postn, (Oka 2007) encoding collagen type al and periostin, respectively, were induced by the TM180 transgene in a RSK3-dependent manner (FIG. 33D,E).

Discussion

When expressed in FVB/N mice, the HCM TM180 mutation results in concentric left ventricular hypertrophy, extensive fibrosis, atrial enlargement, and death within 5 months (Prabhakar 2001). In contrast, expression of the TM180 mutation in C57BL/6 mice resulted in no ventricular hypertrophy or fibrosis and a lower heart weight (Michele 2002). The inventors found that in a mixed C57BL/6; FVB/N background, the TM180 transgene induced an intermediate phenotype, including decreased ventricular and increased atrial weights, smaller ventricular myocytes, interstitial fibrosis, and increased contractility by echocardiography. The TM180 mutation is thought to induce cardiomyopathy as a result of the increased $Ca^{2+}$ sensitivity and increased maximum tension generation of TM180 filaments (Prabhakar 2001). Hence, increasing $Ca^{2+}$ reuptake through manipulation of phospholamban and the sarco/endoplasmic reticulum $Ca^{2+}$-ATPase 2A (SERCA2A) can ameliorate the TM180 FVB/N phenotype (Gaffin 2011). The inventors have utilized the TM180 transgenic mouse to investigate the role of RSK3 in cardiac fibrosis. While the inventors and others have found that total heart ERK1/2 is activated in TM180 FVB/N mice (Gaffin 2011), in the mixed background mice, total ERK1/2 and RSK phosphorylation was not increased. Instead, the inventors only noted a slight increase in RSK3 protein levels (FIG. 32A). Importantly, RSK3 knock-out blocked the TM180 associated induction of fibrotic gene expression and interstitial fibrosis, as well as improving cardiac function both in terms of echocardiographic findings and wet lung weight. These findings complement our previous observation that RSK3 is specifically required for pathological cardiac hypertrophy. Without being bound by a particular theory, the inventors suggest that due to RSK3 anchoring through its unique N-terminal domain to scaffold proteins such as mAKAP (muscle A-kinase anchoring protein), RSK3 serves a unique function in the heart, despite the higher level of expression of other RSK isoenzymes (Li 2013). There are reports that RSK phosphorylation of CEBP/β is involved in pathological fibrosis of the liver and lung, but there is no published data relating to RSK family members in the heart. The inventors suggest that specific RSK3 inhibition should now be considered more broadly as a therapeutic target both in hypertrophic and fibrotic heart diseases.

Figure 39:
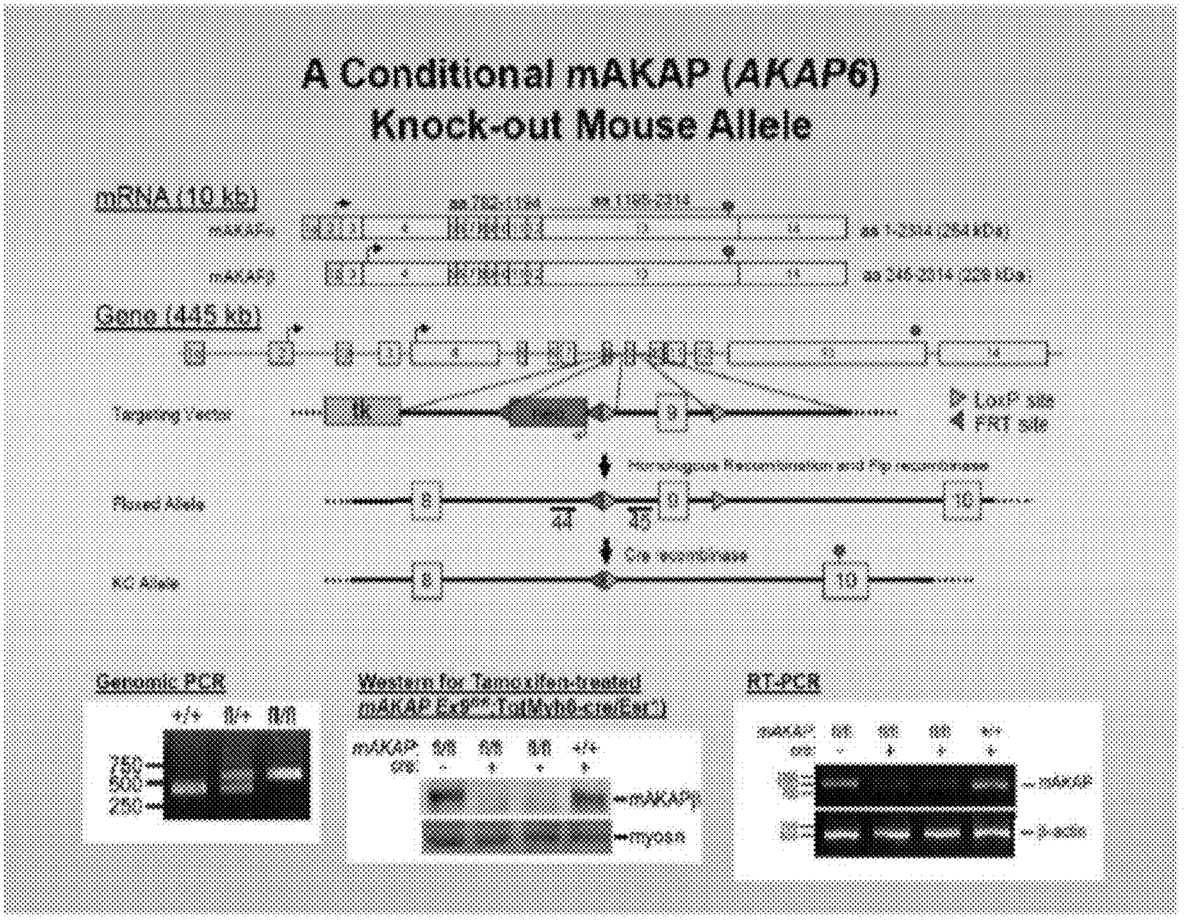
FIG. 39 shows a conditional mAKAP (AKAP6) knockout mouse allele.

Example 3 mAKAP gene structure and the strategy for a conditional mAKAP allele. The mAKAP gene contains 12 common (light blue) and 3 alternatively-spliced exons (beige and yellow). FIG. 39. A targeting vector containing negative (tk) and positive (neo) selectable markers was designed to conditionally delete the common Exon 9. The inventors obtained 6 targeted ES cell clones as shown by Southern blots. After breeding of targeted mice, the neo cassette was deleted by mating to a FLP recombinase transgenic. Mating to a mouse expressing cre recombinase will result in the deletion of Exon 9 (KO allele), producing a frame shift and introduction of a stop codon (red) in Exon 10. Mouse genotyping is being performed by PCR of genomic DNA with primers 44 and 45. (FIG. 39). For the western blot: mAKAP $Ex9^{fl/fl}$; Tg(Myh6-cre/Esr1) mice (lanes 2 and 3) and mAKAP $Ex9^{fl/fl}$ (lane 1) and Tg(Myh6-cre/Esr1) (lane 4) control mice were fed 500 mg tamoxifen/kg dry food for one week before the hearts were collected to prepare total RNA and protein extracts. RT-PCR was performed using primers located within mAKAP exons 4 and 11 which yield a 1022 bp for wildtype (and floxed) mRNA and a 901 bp product for a mAKAP mRNA species lacking exon 9. While control β-actin mRNA was similarly detected for all samples (bottom panel), >90% less PCR product was obtained for CKO mouse hearts (top panel, lanes 2 and 3) compared to that observed with the control hearts (lanes 1 and 4). Western blots were performed using VO54 mAKAP-specific antibody. No mAKAP protein was detectable for heart extracts prepared from CKO mice (lanes 2 and 3, top panel). Equal loading was determined by Ponceau total protein stain (bottom panel).

mAKAP $Ex9^{fl/fl}$; Tg(Myh6-cre/Esr1) mice (fl/fl; MCMTg) and Tg(Myh6-cre/Esr1) (MCM Tg) at 8 weeks of age were fed tamoxifen-containing chow for one week, rested for one week and then subjected for to 2 weeks of Transverse Aortic Constriction before analysis.

Transverse Aortic Constriction: All tools were sterilized with a Germinator 500 Dry Sterilizer and Betadine Solution (10% povidone-iodine topical solution). Anesthesia was induced with 5% isoflurane and maintained with 2% isoflurane and 100% oxygen at a flow rate of 1.5 L/min using a SurgiVet flow regulator via nose cone. Loss of consciousness was verified by toe pinch. Mouse fur over the left chest and sternum was removed with a calcium hydroxide lotion (e.g. Nair), and the surgical site was sterilized with betadine. The skin was incised exposing the pectoralis muscle and the second left intercostal space. The pectoralis muscle and the second rib were blunt dissected and retracted revealing the thymus within the mediastinum. The lobes of the thymus were retracted to reveal the transverse aortic arch as well as the right innominate and left common carotid arteries. Blunt dissection though the connective tissue between these two arteries and under the aorta allowed for the passage of a 6-0 silk using a modified ligation aid (Fine Science Tools 18062-12). A 27 gauge needle was placed on top of the aorta and the 6-0 silk was tied around the needle. The needle was removed, leaving a constricted aorta. The chest was closed in two layers with 5-0 Polysorb Suture. Isoflurane administration was terminated, and the mice were maintained on 100% oxygen by nose cone until conscious. Immediately post-operatively, buprenorphine (0.05-0.1 mg/kg s.c.) was administered and then q12 h prn. The mice were allowed to recover under a heat lamp until alert and active. Sham-operated mice that experience all but the placement of the aortic ligature served as controls.

Figure 40:
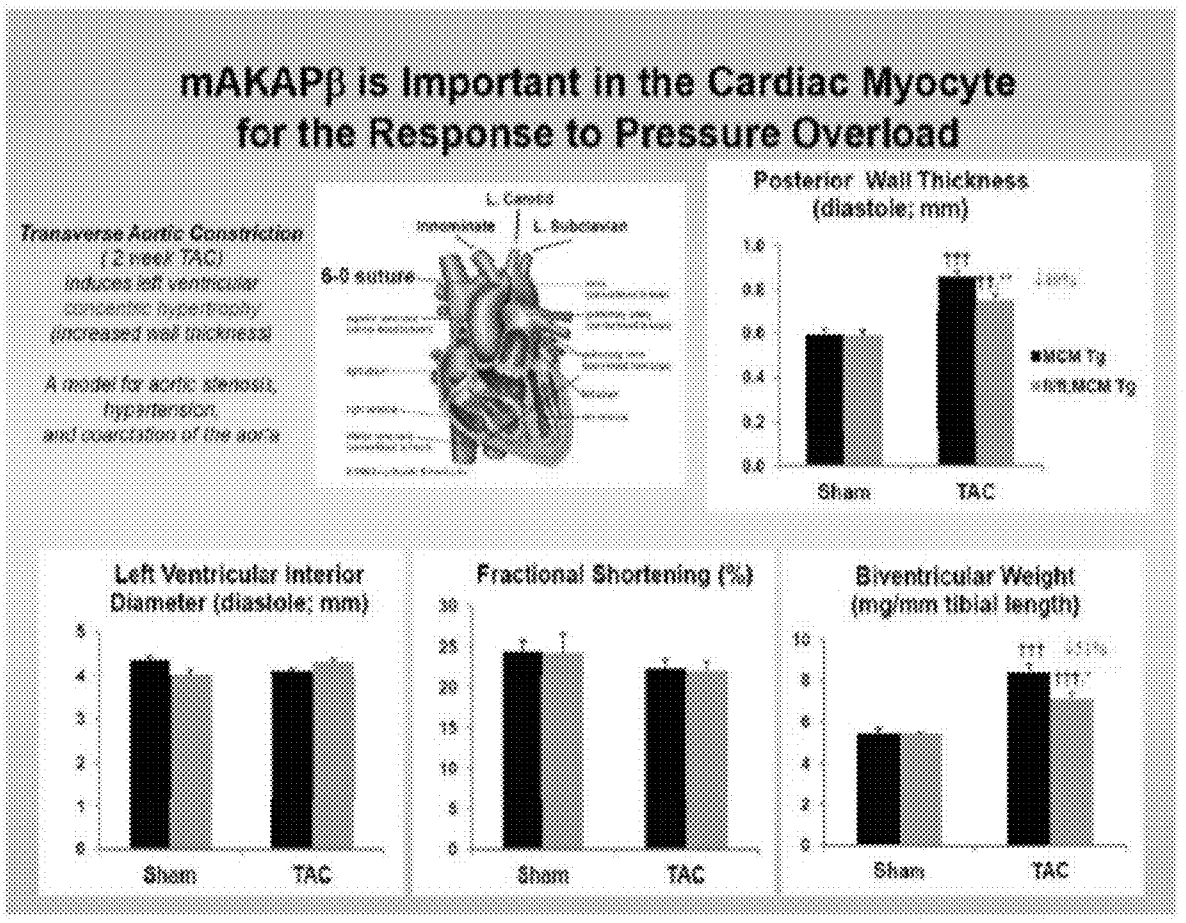
FIG. 40 shows that mAKAPβ is important in the cardiac myocyte for the response to pressure overload.

Echocardiography: Mice minimally anesthetized with 1-2% isoflurane were studied using a Vevo 770@, High-Resolution Imaging System (VisualSonics). The pressure gradient following TAC was calculated from the pulse wave Doppler velocity at the point of ligation as follows: $P=4v^2$; P=the induced pressure gradient (in mmHg) and v=the velocity across the constriction (in m/s). (FIG. 40).

Example 4

Figure 8:
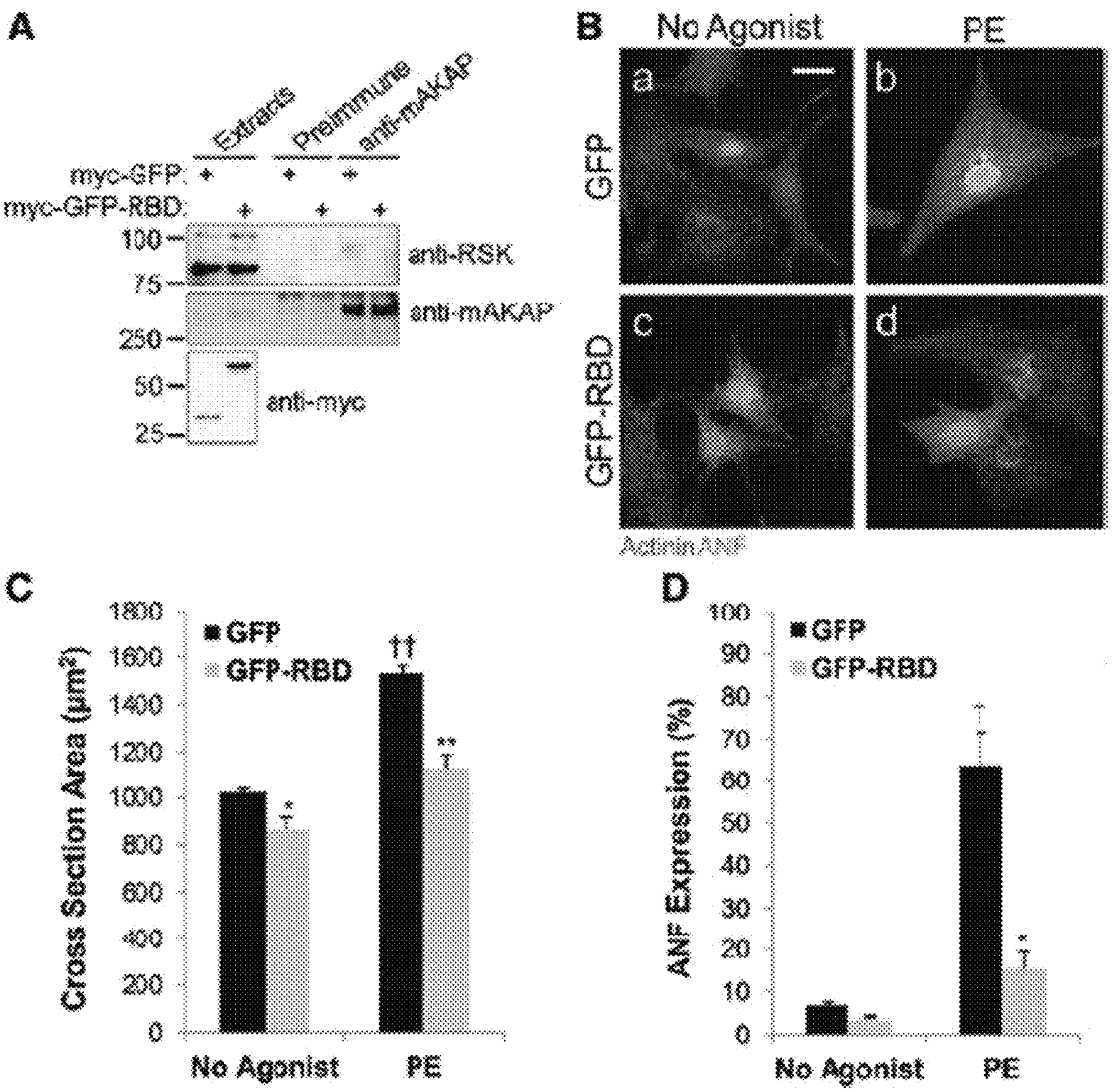
FIG. 8. p90 ribosomal S6 kinase type 3 (RSK3) anchoring is important for neonatal rat ventricular myocyte hypertrophy. A, Muscle A-kinase anchoring protein beta (mAKAPβ) complexes were immunoprecipitated using FL100 mAKAP antiserum from phenylephrine (PE)-treated, adenovirus-infected myocytes expressing myc-green fluorescent protein (GFP) or myc-GFP-mAKAP RSK binding domain (RBD) fusion protein (GFP-RBD; mAKAP 1694-1833) and detected with the pan-RSK 1F6 and mAKAP 211 antibodies. B, Transfected myocytes expressing GFP or GFP-RBD (green) were stained with α-actinin (blue) and atrial natriuretic factor (ANF; red) antibodies. Bar=20 μm. C, Cross-section area of myocytes (n=5). D, Fraction of myocytes expressing ANF (n=3). *P values comparing to GFP-expressing samples. †P values compared with no agonist control.

RSK3 anchoring is important for neonatal rat ventricular myocyte hypertrophy. FIG. 8.A. mAKAPβ complexes were immunoprecipitated using FL100 mAKAP antiserum from PE-treated, adenovirus-infected myocytes expressing myc-GFP or myc-GFP-RBD (mAKAP 1694-1833) and detected with the pan-RSK 1F6 and mAKAP 211 antibodies. B. Transfected myocytes expressing GFP or GFP-RBD (green) were stained with α-actinin (blue) and ANF (red) antibodies. Bar=20 μm. C. Cross-section area of myocytes. n=5. D. Fraction of myocytes expressing ANF. n=3. * p-values comparing to GFP-expressing samples. †p-values comparing to no agonist control.

Neonatal rat myocytes isolation and culture: 1-3 day old Sprague-Dawley rats were decapitated and the excised hearts placed in 1×ADS Buffer (116 mmol/L NaCl, 20 mmol/L HEPES, 1 mmol/L $NaH_2PO_4$, 5.5 mmol/L glucose, 5.4 mmol/L KCl, 0.8 mmol/L $MgSO_4$, pH 7.35). The atria were carefully removed and the blood washed away. The ventricles were minced and incubated with 15 mL 1×ADS Buffer containing 3.3 mg type II collagenase (Worthington, 230 U/mg) and 9 mg Pancreatin (Sigma) at 37° C. while shaking at 80 RPM. After 15 minutes, the dissociated cardiac myocytes were separated by centrifugation at 50×g for 1 minute, resuspended in 4 mL horse serum and incubated 37° C. with occasional agitation. The steps for enzymatic digestion and isolation of myocytes were repeated 10-12 times to maximize yield. The myocytes were pooled and spun down again at 50×g for 2 minutes and resuspended in Maintenance Medium (DMEM:M199, 4:1) supplemented with 10% horse serum and 5% fetal bovine serum. To remove any contaminating fibroblasts, the cells were preplated for 1 hour before plating on gelatin-coated tissue culture plasticware. This procedure yields >90% pure cardiac myocytes. After 1 day in culture, the media was changed to maintenance medium containing 0.1 mmol/L bromodeoxyuridine to suppress fibroblast growth.

Experiments were initiated 1 day after myocyte isolation. Adenoviral infection was performed by addition of adenovirus (multiplicity of infection=5-50) to the media. Plasmids and siRNA oligonucleotides were transfected using Transfast (Promega) and Dharmafect (Thermofisher), respectively, as recommended by the manufacturers using cells cultured in maintenance medium supplemented with 4% horse serum. Starting the day after gene transduction, the cells were treated for as long as 2 days, as indicated for each experiment.

Immunocytochemistry: Cultured neonatal cardiomyocytes on plastic coverslips were fixed in 3.7% formaldehyde in PBS, permeabilized with 0.3% Triton X-100 in PBS, and blocked with PBS containing 0.2% BSA and 1% horse serum for 1 hour. The slides were then sequentially incubated for 1 hour with primary and Alexa fluorescent dye-conjugated specific-secondary antibodies (Invitrogen, 1:1000) diluted in blocking buffer. The slips were washed three times with blocking buffer. 1 μg/mL Hoechst 33258 was included in the last wash stop to label nuclei. Slides were sealed in SlowFade Gold antifade buffer (Invitrogen)

for fluorescent microscopy. Wide-field images were acquired using a Leica DMI 6000 Microscope.

Figure 42:
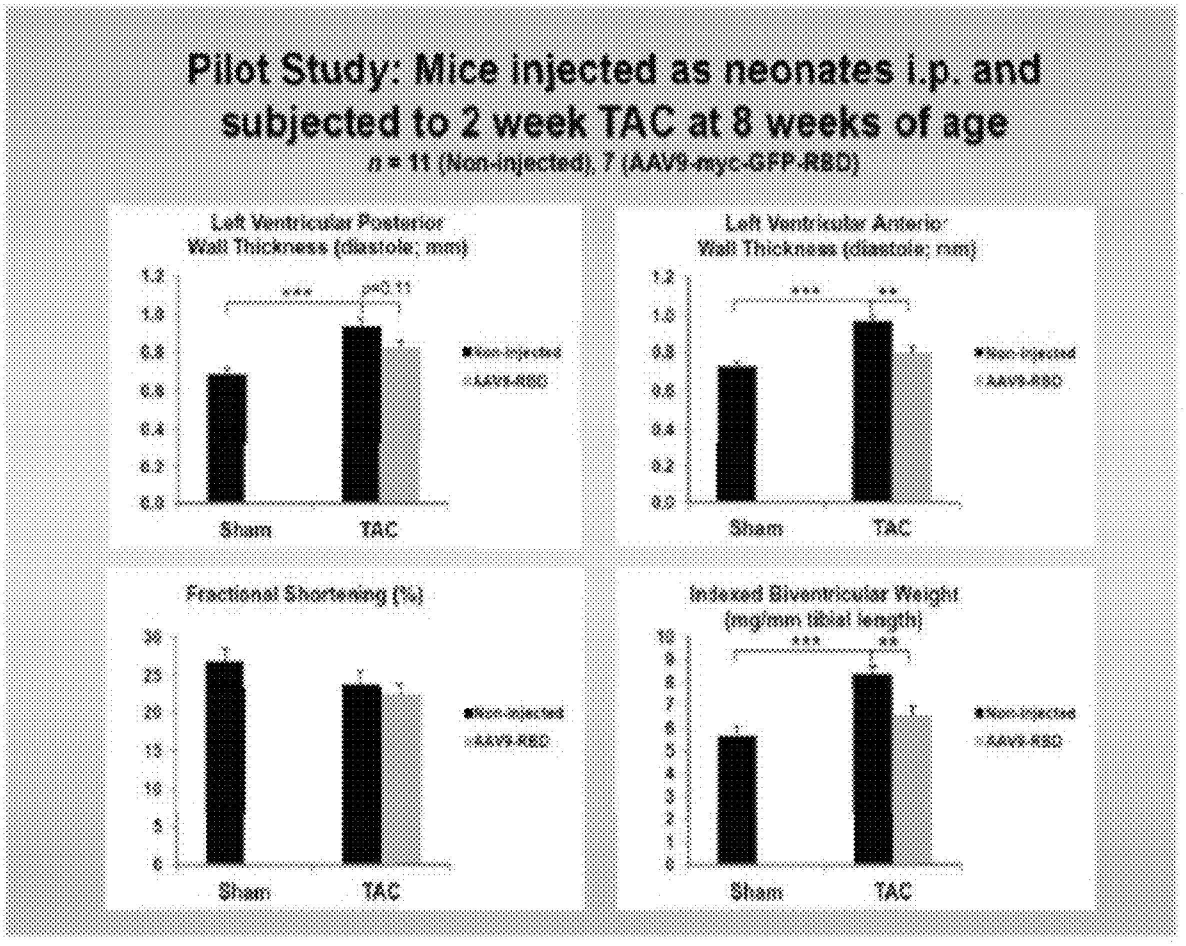
FIG. 42 shows results from a pilot study where mice were injected intraperitoneally as neonates and subjected to 2 week transverse aortic constriction (TAC) at 8 weeks of age.
Figure 43:
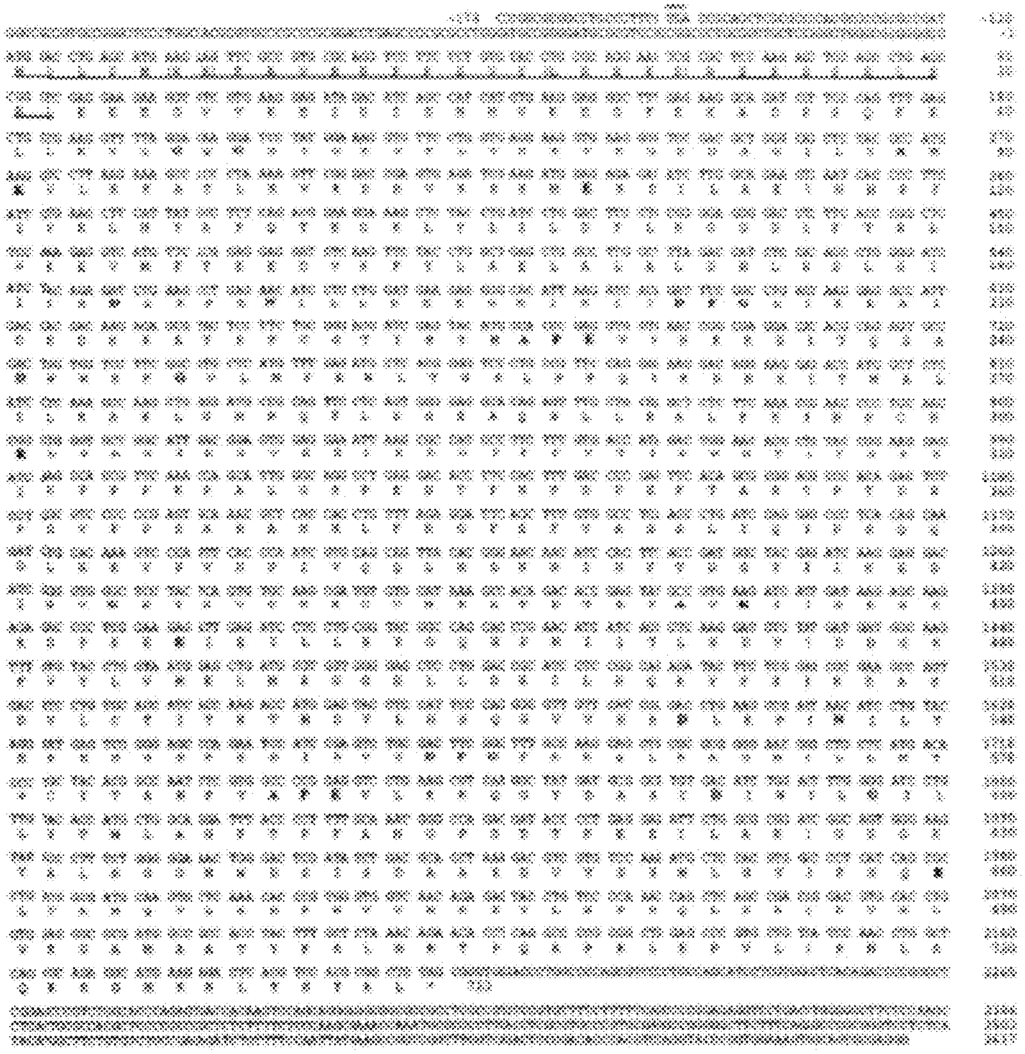
FIGS. 43A-43C shows cDNA cloning, in vitro translation, and detection of endogenous RSK3 by immunoblotting.
Figure 43:
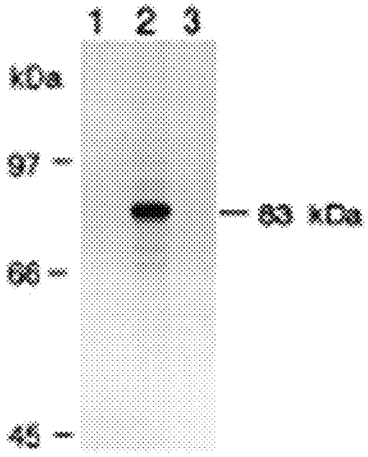
Figure 43:
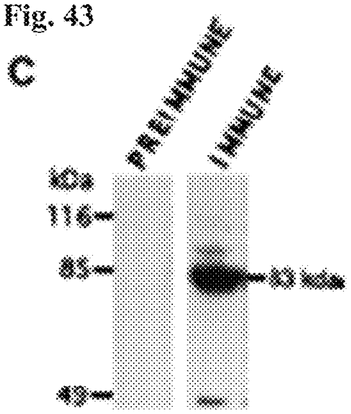
Figure 46:
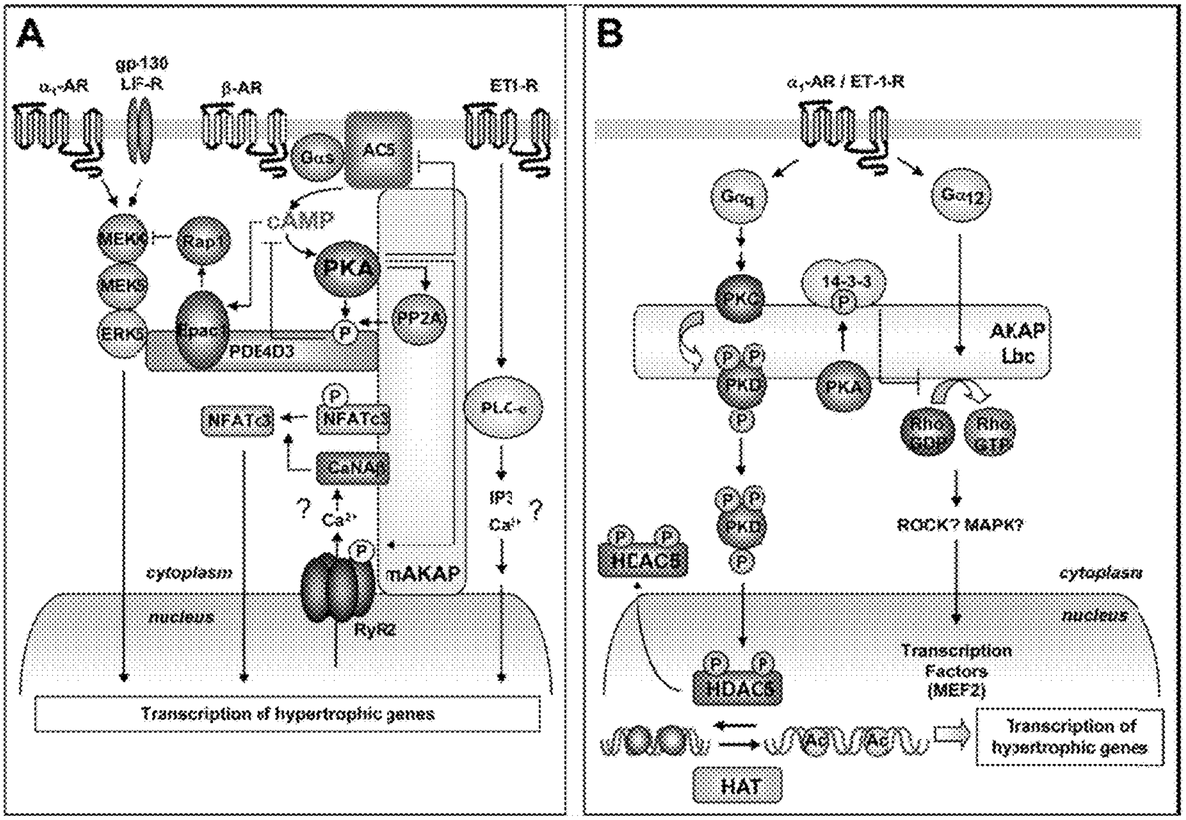
FIG. 46. Regulation of cardiac hypertrophy by AKAP complexes. A: mAKAP assembles a multienzyme signaling complex at the outer nuclear membrane containing AC5, PKA, PDE4D3, PP2A, RyR2, calcineurin AP (CaNAβ), nuclear factor of activated T cells 3 (NFATc3), exchange protein activated by cAMP 1 (Epac1), and ERK5. Activation of AC5 by β-adrenergic stimulation generates cAMP, which in turn activates anchored PKA at submicromolar concentrations. In a negative feedback loop, activated PKA phosphorylates PDE4D3, leading to its activation and increased cAMP degradation, and AC5, leading to its inactivation and decreased cAMP synthesis. Anchored PKA also regulates the activity of PP2A, which promotes PDE4D3 dephosphorylation, and RyR2, which enhances $Ca^{2+}$ mobilization from intracellular stores. This is proposed to induce the activation of CaNAβ, which, in turn, dephosphorylates and activates NFATc3 to promote hypertrophic gene transcription. Very high concentrations of cAMP (in μM) also stimulate Epac1. This in turn activates the GTPase Ras-related protein 1 (Rap1), which exerts an inhibitory effect on the MEK5-ERK5 pathway. In the absence of very high local cAMP, Epac1 is inactivated and the hypertrophic ERK5 pathway de-repressed. Stimulation of endothelin-1 receptors (ET1Rs) activates mAKAPβ-bound PLCε, which, in turn, promotes cardiomyocyte hypertrophy via a signaling pathway that remains to be elucidated. B: activated $\alpha_1$-ARs and $ET_1Rs$ stimulate the Rho-guanine nucleotide exchange factor (GEF) activity of AKAP-lymphoid blast crisis (AKAP-Lbc) through $G\alpha_{12}$. GTP-bound RhoA is released from the AKAP-Lbc complex and promotes cardiomyocyte hypertrophy via a signaling pathway that remains to be elucidated. Activation of AKAP-Lbc-anchored PKA promotes the phosphorylation of the anchoring protein on serine-1565. This induces the recruitment of 14-3-3, which inhibits the RhoGEF activity of AKAP-Lbc. AKAP-Lbc also recruits PKC0 and PKD. Upon stimulation by the $G\alpha_q$-phospholipase C pathway by $\alpha_1$-ARs and $ET_1Rs$, PKCη becomes activated and phosphorylates PKD. Active PKD phosphorylates histone deacetylase 5 (HDAC5), causing its export from the nucleus. This favors myocyte-specific enhancer-binding factor 2 (MEF2)-dependent hypertrophic gene transcription. LIF-R, leukemia inhibitor factor receptor; IP3, inositol trisphosphate 1,4,5-trisphosphate.
Figure 47:
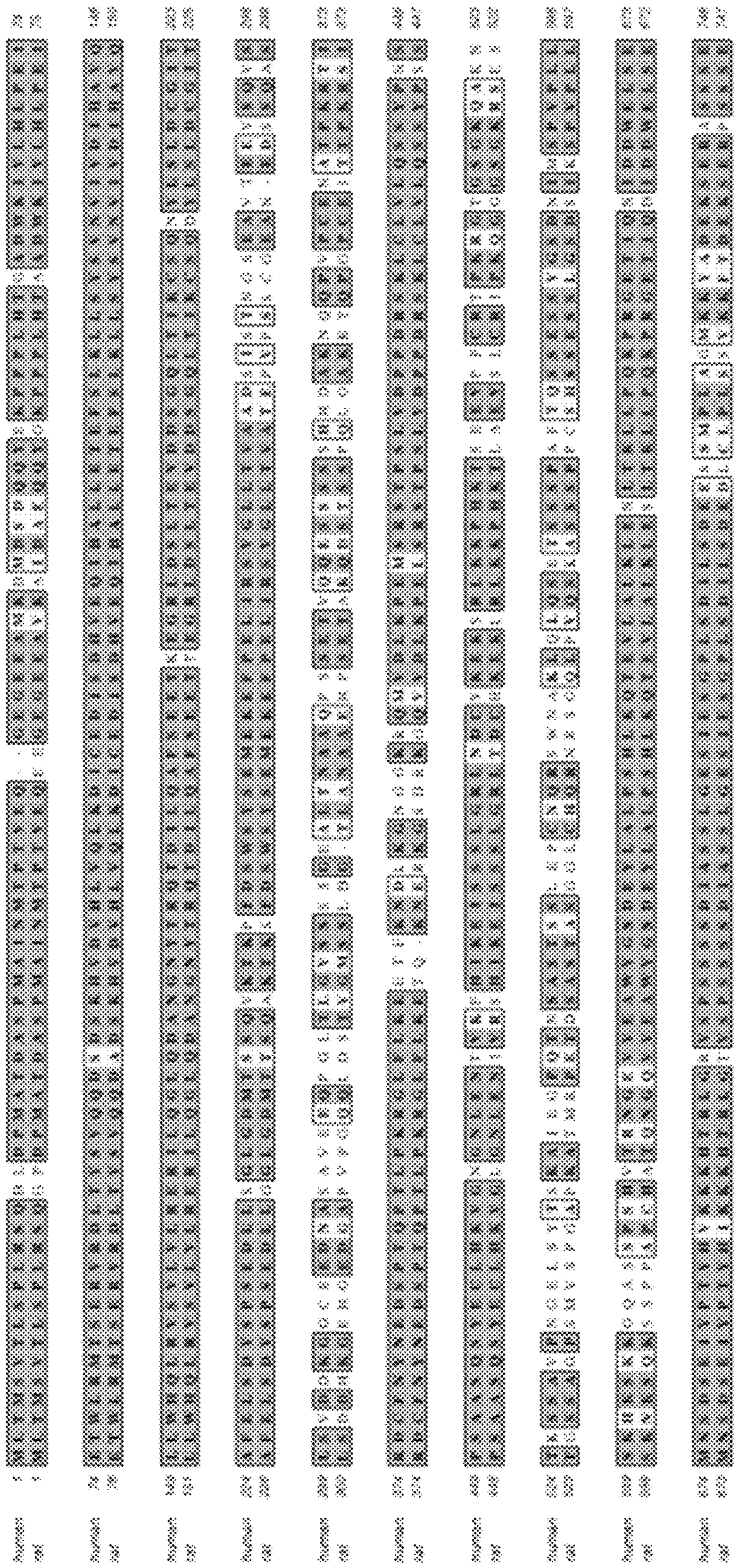
FIG. 47 shows the primary structure of human [SEQ ID NO:25] and rat [SEQ ID NO:2] mAKAP. Human and rat amino acid sequences are aligned using the MacVector gene analysis program. Identical residues are in gray and conservative substitutions are in light gray. The putative RII-α-binding site in rat mAKAP is outlined with brackets.
Figure 47:
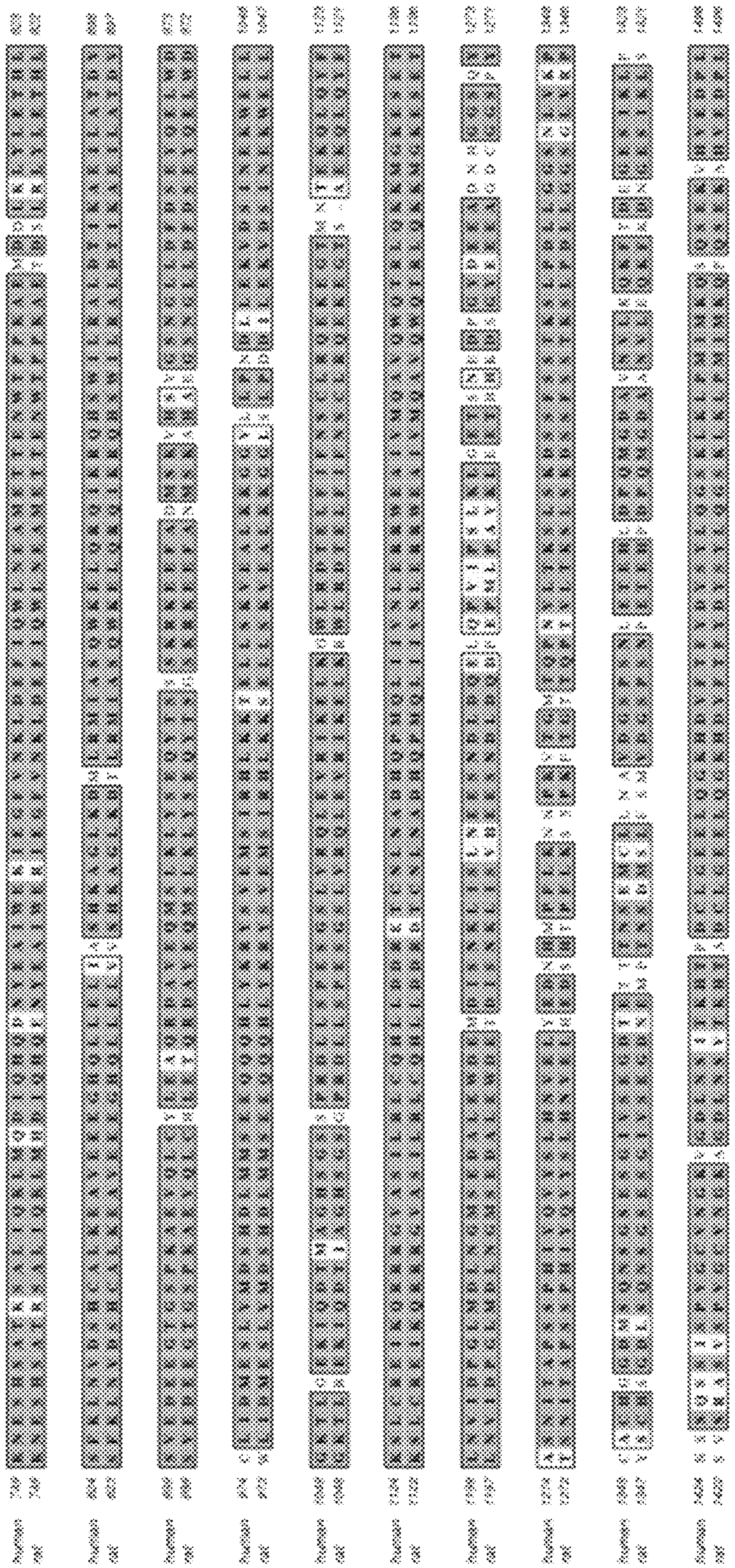
Figure 47:
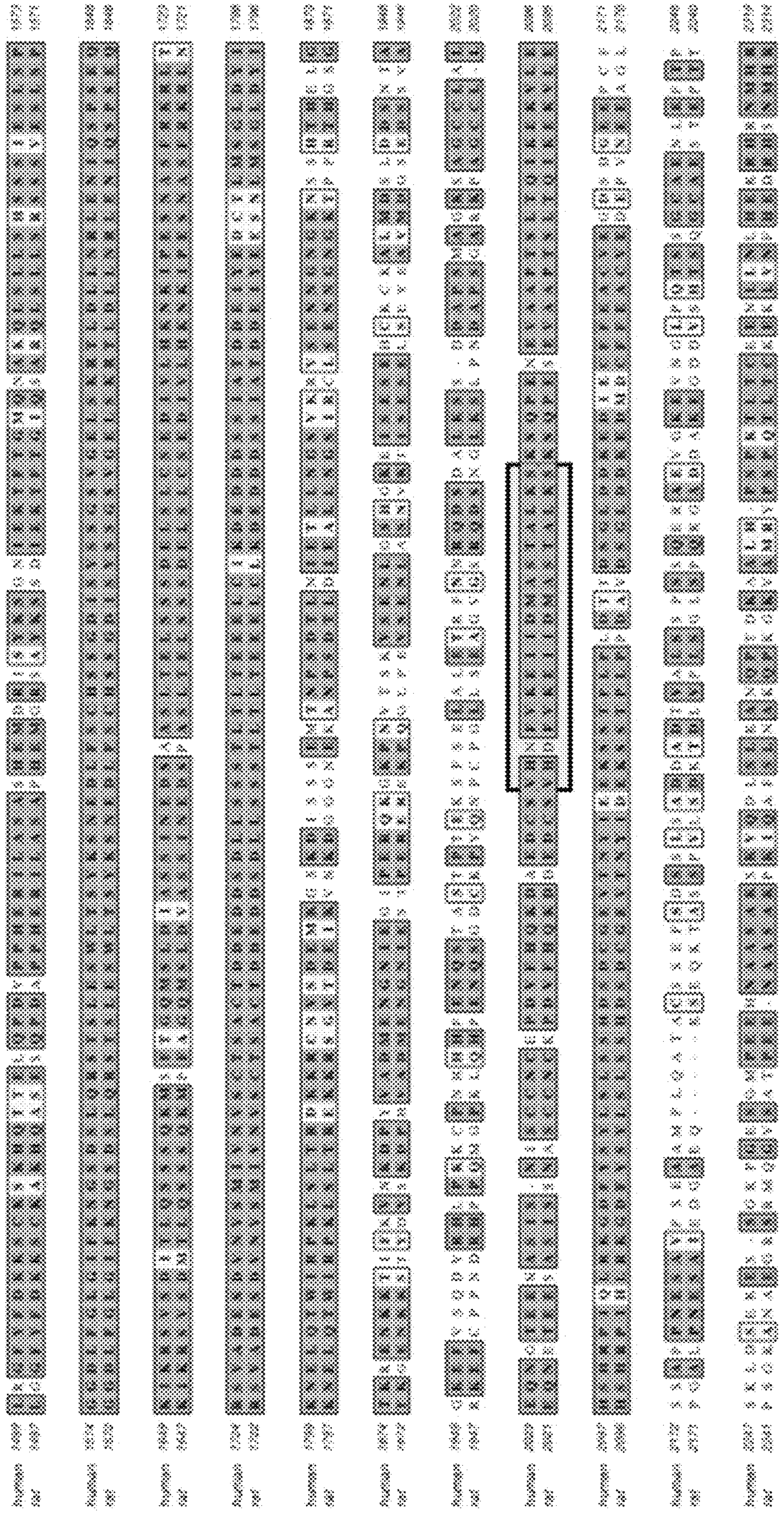

AAV9 containing the indicated CIS plasmid encoding myc-GFP-mAKAP 1694-1833 were injected into neonatal wildtype mice. 2 week TAC was performed and analyzed as above at 8 weeks of age. (FIGS. 41-42).

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

REFERENCES

Abrenica B, AlShaaban M, Czubryt M P. The A-kinase anchor protein AKAP121 is a negative regulator of cardiomyocyte hypertrophy. J Mol Cell Cardiol 46: 674-681, 2009.

Anjum R, Blenis J. The RSK family of kinases: emerging roles in cellular signalling. Nat Rev Mol Cell Biol. 2008; 9(10):747-758.

Abrenica B, AlShaaban M, Czubryt M P. The A-kinase anchor protein AKAP121 is a negative regulator of cardiomyocyte hypertrophy. J Mol Cell Cardiol 46: 674-681, 2009.

Anjum R, Blenis J. The RSK family of kinases: emerging roles in cellular signalling. Nat Rev Mol Cell Biol. 2008; 9(10):747-758.

Appert-Collin A, Cotecchia S, Nenniger-Tosato M, Pedrazzini T, Diviani D. The A-kinase anchoring protein (AKAP)-Lbc-signaling complex mediates alpha1 adrenergic receptor-induced cardiomyocyte hypertrophy. Proc Natl Acad Sci USA 104: 10140-10145, 2007.

Avkiran M, Cook A R, Cuello F. Targeting Na+/H+ exchanger regula-tion for cardiac protection: a RSKy approach? Curr Opin Pharmacol. 2008; 8:133-140.

Bain J, Plater L, Elliott M, Shpiro N, Hastie C J, McLauchlan H, Klevernic I, Arthur J S, Alessi D R, Cohen P. The selectivity of protein kinase inhibitors: a further update. Biochem J. 2007; 408:297-315

Bauman A L, Michel J J, Henson E, Dodge-Kafka K L, Kapiloff M S, "The mAKAP signalosome and cardiac myocyte hypertrophy," IUBMB Life. 2007 March; 59(3): 163-9. Review.

Beene D L, Scott J D. A-kinase anchoring proteins take shape. Curr Opin Cell Biol 19: 192-198, 2007.

Bers D M. Calcium cycling and signaling in cardiac myocytes. Annu Rev Physiol 70: 23-49, 2008.

Brown J H, Del Re D P, Sussman M A. The Rac and Rho hall of fame: a decade of hypertrophic signaling hits. Circ Res 98: 730-742, 2006. 6. Burns-Hamuro L L, Ma Y, Kammerer S, Reineke U, Self C, Cook C, Buck M, Chojkier M. C/EBPbeta-Thr217 phosphorylation signaling contributes to the development of lung injury and fibrosis in mice. PLoS One. 2011; 6(10):e25497.

Cappola T P. Molecular remodeling in human heart failure. J Am Coil Cardiol 51: 137-138, 2008.

Cariolato L, Cavin S, Diviani D. A-kinase anchoring protein (AKAP)-Lbc anchors a PKN-based signaling complex involved in alpha1-adrenergic receptor-induced p38 activation. J Biol Chem 286: 7925-7937, 2011.

Carlucci A, Lignitto L, Feliciello A. Control of mitochondria dynamics and oxidative metabolism by cAMP, AKAPs and the proteasome. Trends Cell Biol 18: 604-613, 2008.

Carnegie G K, Smith F D, McConnachie G, Langeberg L K, Scott J D. AKAP-Lbc nucleates a protein kinase D activation scaffold. Mol Cell 15: 889-899, 2004.

Carnegie G K, Soughayer J, Smith F D, Pedroja B S, Zhang F, Diviani D, Bristow M R, Kunkel M T, Newton A C, Langeberg L K, Scott J D. AKAP-Lbc mobilizes a cardiac hypertrophy signaling pathway. Mol Cell 32: 169-179, 2008.

Chaturvedi D, Poppleton H M, Stringfield T, Barbier A, Patel T B. Subcellular localization and biological actions of activated RSK1 are determined by its interactions with subunits of cyclic AMP-dependent protein kinase. Mol Cell Biol. 2006; 26:4586-4600.

Chen L, Kurokawa J, Kass R S. Phosphorylation of the A-kinase anchoring protein Yotiao contributes to protein kinase A regulation of a heart potassium channel. J Biol Chem 280: 31347-31352, 2005.

Chen L, Kurokawa J, Kass R S. Phosphorylation of the A-kinase-anchoring protein Yotiao contributes to protein kinase A regulation of a heart potassium channel. J Biol Chem 280: 31347-31352, 2005.

Chen L, Marquardt M L, Tester D J, Sampson K J, Ackerman M J, Kass R S. Mutation of an A-kinase-anchoring protein causes long-QT syndrome. Proc Natl Acad Sci USA 104: 20990-20995, 2007.

Chen P P, Patel J R, Rybakova I N, Walker J W, Moss R L. Protein kinase A-induced myofilament desensitization to Ca2+ as a result of phosphorylation of cardiac myosin-binding protein C. J Gen Physiol 136: 615-627, 2010.

Christian F, Szaszak M, Friedl S, Drewianka S, Lorenz D, Goncalves A, Furkert J, Vargas C, Schmieder P, Gotz F, Zuhlke K, Moutty M, Gottert H, Joshi M, Reif B, Haase H, Morano I, Grossmann S, Klukovits A, Verli J, Gaspar R, Noack C, Bergmann M, Kass R, Hampel K, Kashin D, Genieser H G, Herberg F W, Willoughby D, Cooper D M, Baillie G S, Houslay M D, von Kries J P, Zimmermann B, Rosenthal W, Klussmann E. Small molecule AKAP-protein kinase A (PKA) interaction disruptors that activate PKA interfere with compartmentalized cAMP signaling in cardiac myocytes. J Biol Chem 286: 9079-9096, 2011.

Cuello F, Snabaitis A K, Cohen M S, Taunton J, Avkiran M. Evidence for direct regulation of myocardial Na+/H+ exchanger isoform 1 phosphorylation and activity by 90-kDa ribosomal S6 kinase (RSK): effects of the novel and specific RSK inhibitor fmk on responses to alpha1-adrenergic stimulation. Mol Pharmacol. 2007; 71:799-806.

Diviani D, Abuin L, Cotecchia S, Pansier L. Anchoring of both PKA and 14-3-3 inhibits the Rho-GEF activity of the AKAP-Lbc signaling complex. EMBO J 23: 2811-2820, 2004.

Diviani D, Dodge-Kafka K L, Li J, Kapiloff M S. A-kinase anchoring proteins: scaffolding proteins in the heart," Am J Physiol Heart Circ Physiol. 2011 November; 301(5): H1742-53.

Diviani D, Soderling J, Scott J D. AKAP-Lbc anchors protein kinase A and nucleates Galpha 12-selective Rho-mediated stress fiber formation. J Biol Chem 276: 44247-44257, 2001.

Dodge K L, Khouangsathiene S, Kapiloff M S, Mouton R, Hill E V, Houslay M D, Langeberg L K, Scott J D. mAKAP assembles a protein kinase A/PDE4 phosphodiesterase cAMP signaling module. EMBO J 20: 1921-1930, 2001.

Dodge-Kafka K L, Bauman A, Kapiloff M S, A-kinase anchoring proteins as the basis for cAMP signaling," Handb Exp Pharmacol. 2008; (186):3-14.

Dodge-Kafka K L, Bauman A, Mayer N, Henson E, Heredia L, Ahn J, McAvoy T, Nairn A C, Kapiloff M S. cAMP-stimulated protein phosphatase 2A activity associated with muscle A kinase-anchoring protein (mAKAP) signaling complexes inhibits the phosphorylation and activity of the cAMP-specific phosphodiesterase PDE4D3. J Biol Chem. 2010; 285:11078-11086.

Dodge-Kafka K L, Bauman A, Mayer N, Henson E, Heredia L, Ahn J, McAvoy T, Nairn AC, Kapiloff M S. cAMP-stimulated protein phosphatase 2A activity associated with muscle A kinase-anchoring protein (mAKAP) signaling complexes inhibits the phosphorylation and activity of the cAMP-specific phosphodiesterase PDE4D3. J Biol Chem 285: 11078-11086, 2010.

Dodge-Kafka K L, Kapiloff M S, "The mAKAP signaling complex: integration of cAMP, calcium, and MAP kinase signaling pathways," Eur J Cell Biol. 2006 July; 85(7): 593-602. Epub 2006 Feb. 7. Review.

Dodge-Kafka K L, Soughayer J, Pare G C, Carlisle Michel J J, Langeberg L K, Kapiloff M S, Scott J D, "The protein kinase A anchoring protein mAKAP coordinates two integrated cAMP effector pathways," Nature. 2005 Sep. 22; 437(7058):574-8.

Dummler B A, Hauge C, Silber J, Yntema H G, Kruse L S, Kofoed B, Hemmings B A, Alessi D R, Frodin M. Functional characterization of human RSK4, a new 90-kDa ribosomal S6 kinase, reveals constitutive activation in most cell types. J Biol Chem. 2005; 280:13304-13314

Edgley A J, Krum H, Kelly D J. Targeting fibrosis for the treatment of heart failure: a role for transforming growth factor-beta. Cardiovasc Ther. 2012; 30(1):e30-40.

Eide T, Coghlan V, Orstavik S, Holsve C, Solberg R, Skalhegg B S, Lamb N J, Langeberg L, Fernandez A, Scott J D, Jahnsen T, Tasken K. Molecular cloning, chromosomal localization, and cell cycle-dependent subcellular distribution of the A-kinase anchoring protein, AKAP95. Exp Cell Res 238: 305-316, 1998.

Escobar M, Cardenas C, Colavita K, Petrenko N B, Franzini-Armstrong C. Structural evidence for perinuclear calcium microdo-mains in cardiac myocytes. J Mol Cell Cardiol 50: 451-459, 2011.

Fabiato A. Calcium-induced release of calcium from the cardiac sarco-plasmic reticulum. Am J Physiol Cell Physiol 245: C1-C14, 1983.

Farah C S, Reinach F C. The troponin complex and regulation of muscle contraction. FASEB J 9: 755-767, 1995.

Faul C, Dhume A, Schecter A D, Mundel P. Protein kinase A, Ca2+/calmodulin-dependent kinase II, and calcineurin regulate the intracellular trafficking of myopodin between the Z-disc and the nucleus of cardiac myocytes. Mol Cell Biol 27: 8215-8227, 2007.

Fink M A, Zakhary D R, Mackey J A, Desnoyer R W, Apperson-Hansen C, Damron D S, Bond M. AKAP-mediated targeting of protein kinase a regulates contractility in cardiac myocytes. Circ Res 88: 291-297, 2001.

Fodstad H, Swan H, Laitinen P, Piippo K, Paavonen K, Viitasalo M, Toivonen L, Kontula K. Four potassium channel mutations account for 73% of the genetic spectrum underlying long-QT syndrome (LQTS) and provide evidence for a strong founder effect in Finland. Ann Med 36, Suppl 1: 53-63, 2004.

Francis S H, Corbin J D. Structure and function of cyclic nuleotide-dependent protein kinases. Annu Rev Physiol 56: 237-272, 1994.

Fraser I D, Tavalin S J, Lester L B, Langeberg L K, Westphal A M, Dean R A, Marrion N V, Scott J D. A novel lipid-anchored A-kinase anchoring protein facilitates cAMP-responsive membrane events. EMBO J 17: 2261-2272, 1998.

Frey N, Katus H A, Olson E N, Hill J A. Hypertrophy of the heart: a new therapeutic target? Circulation 109: 1580-1589, 2004.

Fuller M D, Emrick M A, Sadilek M, Scheuer T, Catterall W A. Molecular mechanism of calcium channel regulation in the fight-or-flight response. Sci Signal 3: ra70, 2010.

Gaffin R D, Pena J R, Alves M S, Dias F A, Chowdhury S A, Heinrich L S, Goldspink P H, Kranias E G, Wieczorek D F, Wolska B M. Long-term rescue of a familial hypertrophic cardiomyopathy caused by a mutation in the thin filament protein, tropomyosin, via modulation of a calcium cycling protein. J. Mol. Cell. Cardiol. 2011 November; 51(5):812-20.

Gao T, Yatani A, Dell'Acqua M L, Sako H, Green S A, Dascal N, Scott J D, Hosey M M. cAMP-dependent regulation of cardiac L-type Ca2+ channels requires membrane targeting of PKA and phosphorylation of channel subunits. Neuron 19: 185-196, 1997.

Gao Y, Dickerson J B, Guo F, Zheng J, Zheng Y. Rational design and characterization of a Rac GTPase-specific small molecule inhibitor. Proc Natl Acad Sci USA 101: 7618-7623, 2004.

Gelb B D, Tartaglia M. RAS signaling pathway mutations and hypertro-phic cardiomyopathy: getting into and out of the thick of it. J Clin Invest. 2011; 121:844-847.

Gentilucci L, Tolomelli A, Squassabia F. Peptides and peptidomimetics in medicine, surgery and biotechnology. Curr Med Chem 13: 2449-2466, 2006.

Gold M G, Lygren B, Dokurno P, Hoshi N, McConnachie G, Tasken K, Carlson C R, Scott J D, Barford D. Molecular basis of AKAP specificity for PKA regulatory subunits. Mol Cell 24: 383-395, 2006.

Goldschmidt-Clermont P J, Seo D M, Wang L, Beecham G W, Liu Z J, Vazquez-Padron R I, Dong C, Hare J M, Kapiloff M S, Bishopric N H, Pericak-Vance M, Vance J M, Velazquez O C, "Inflammation, stem cells and atherosclerosis genetics," Curr Opin Mol Ther. 2010 December; 12(6):712-23. Review.

Good M C, Zalatan J G, Lim W A. Scaffold proteins: hubs for controlling the flow of cellular information. Science. 2011; 332:680-686.

Gould K L, Bretscher A, Esch F S, Hunter T. cDNA cloning and sequencing of the protein-tyrosine kinase substrate, ezrin, reveals homol-ogy to band 4.1. EMBO J 8: 4133-4142, 1989. Gray P C, Scott J D, Catterall W A. Regulation of ion channels by cAMP-dependent protein kinase and A-kinase anchoring proteins. Curr Opin Neurobiol 8: 330-334, 1998.

Guo T, Cornea R L, Huke S, Camors E, Yang Y, Picht E, Fruen B R, Bers D M. Kinetics of FKBP12.6 binding to ryanodine receptors in permeabilized cardiac myocytes and effects on Ca sparks. Circ Res 106: 1743-1752, 2010.

Hagemann D, Xiao R P. Dual site phospholamban phosphorylation and its physiological relevance in the heart. Trends Cardiovasc Med 12: 51-56, 2002.

Hanks S K, Quinn A M, Hunter T. The protein kinase family: conserved features and deduced phylogeny of the catalytic domains. Science. 1988; 241:42-52.

Harada H, Becknell B, Wilm M, Mann M, Huang U, Taylor S S, Scott J D, Korsmeyer S J. Phosphorylation and inactivation of BAD by mitochondria-anchored protein kinase A. Mol Cell 3: 413-422, 1999.

Hell J W. Beta-adrenergic regulation of the L-type Ca2+ channel CaV1.2 by PKA rekindles excitement. Sci Signal 3: pe33, 2010.

Henn V, Edemir B, Stefan E, Wiesner B, Lorenz D, Theilig F, Schmitt R, Vossebein L, Tamma G, Beyermann M, Krause E, Herberg F W, Valenti G, Bachmann S, Rosenthal W, Klussmann E. Identification of a novel A-kinase anchoring protein 18 isoform and evidence for its role in the vasopressin-induced aquaporin-2 shuttle in renal principal cells. J Biol Chem 279: 26654-26665, 2004.

Hill J A, Olson E N. Cardiac plasticity. N Engl J Med 358: 1370-1380, 2008.

Huang U, Durick K, Weiner J A, Chun J, Taylor S S. D-AKAP2, a novel protein kinase A anchoring protein with a putative RGS domain. Proc Natl Acad Sci USA 94: 11184-11189, 1997.

Huang U, Durick K, Weiner J A, Chun J, Taylor S S. Identification of a novel dual specificity protein kinase A anchoring protein, D-AKAP1. J Biol Chem 272: 8057-8064, 1997.

Huang U, Durick K, Weiner J A, Chun J, Taylor S S. Identification of a novel protein kinase A anchoring protein that binds both type I and type II regulatory subunits. J Biol Chem. 1997; 272:8057-8064.

Hulme J T, Ahn M, Hauschka S D, Scheuer T, Catterall W A. A novel leucine zipper targets AKAP15 and cyclic AMP-dependent protein ki-nase to the C terminus of the skeletal muscle Ca2+ channel and modu-lates its function. J Biol Chem 277: 4079-4087, 2002.

Hulme J T, Lin T W, Westenbroek R E, Scheuer T, Catterall W A. Beta-adrenergic regulation requires direct anchoring of PKA to cardiac CaV1.2 channels via a leucine zipper interaction with A kinase-anchor-ing protein 15. Proc Natl Acad Sci USA 100: 13093-13098, 2003.

Hulme J T, Westenbroek R E, Scheuer T, Catterall W A. Phosphory-lation of serine 1928 in the distal C-terminal domain of cardiac CaV1.2 channels during beta1-adrenergic regulation. Proc Natl Acad Sci USA 103: 16574-16579, 2006.

Hundsrucker C, Klussmann E. Direct AKAP-mediated protein-protein interactions as potential drug targets. Hand Exp Pharmacol 186: 483-503, 2008.

Hundsrucker C, Krause G, Beyermann M, Prinz A, Zimmermann B, Diekmann O, Lorenz D, Stefan E, Nedvetsky P, Dathe M, Christian F, McSorley T, Krause E, McConnachie G, Herberg F W, Scott J D, Rosenthal W, Klussmann E. High-affinity AKAP7delta-protein kinase A interaction yields novel protein kinase A-anchoring disruptor peptides. Biochem J 396: 297-306, 2006.

Jaakkola P, Mole D R, Tian Y M, Wilson M I, Gielbert J, Gaskell S J, Kriegsheim A, Hebestreit H F, Mukherji M, Schofield C J, Maxwell P H, Pugh C W, Ratcliffe P J. Targeting of HIF-alpha to the von Hippel-Lindau ubiquitylation complex by 02-regulated prolyl hydroxylation. Science 292: 468-472, 2001.

Kamisago M, Sharma S D, DePalma S R, Solomon S, Sharma P, McDonough B, Smoot L, Mullen M P, Woolf P K, Wigle E D, Seidman J G, Seidman C E. Mutations in sarcomere protein genes as a cause of dilated cardiomyopathy. N Engl J Med 343: 1688-1696, 2000.

Kammerer S, Burns-Hamuro L L, Ma Y, Hamon S C, Canaves J M, Shi M M, Nelson M R, Sing C F, Cantor C R, Taylor S S, Braun A. Amino acid variant in the kinase binding domain of dual-specific A kinase-anchoring protein 2: a disease susceptibility polymorphism. Proc Natl Acad Sci USA 100: 4066-4071, 2003.

Kapiloff M S, Chandrasekhar K D, "A-kinase anchoring proteins: temporal and spatial regulation of intracellular signal transduction in the cardiovascular system," Journal Cardiovasc Pharmacol. 2011 October; 58(4):337-8.

Kapiloff M S, Jackson N, Airhart N. mAKAP and the ryanodine receptor are part of a multi-component signaling complex on the cardiomyocyte nuclear envelope. J Cell Sci 114: 3167-3176, 2001.

Kapiloff M S, Piggott L A, Sadana R, Li J, Heredia L A, Henson E, Efendiev R, Dessauer C W, "An adenylyl cyclase-mAKAPbeta signaling complex regulates cAMP levels in cardiac myocytes," J Biol Chem. 2009 Aug. 28; 284(35):23540-6.

Kapiloff M S, Schillace R V, Westphal A M, Scott J D. mAKAP: an A-kinase anchoring protein targeted to the nuclear membrane of differentiated myocytes. J Cell Sci 112: 2725-2736, 1999.

Kehat I, Davis J, Tiburcy M, Accornero F, Saba-El-Leil M K, Maillet M, York A J, Lorenz J N, Zimmermann W H, Meloche S, Molkentin J D. Extracellular signal-regulated kinases 1 and 2 regulate the balance between eccentric and concentric cardiac growth. Circ Res. 2011; 108:176-183.

Kehat I, Molkentin J D. Molecular pathways underlying cardiac re-modeling during pathophysiological stimulation. Circulation. 2010; 122:2727-2735.

Kentish J C, McCloskey D T, Layland J, Palmer S, Leiden J M, Martin A F, Solaro R J. Phosphorylation of troponin I by protein kinase A accelerates relaxation and cross-bridge cycle kinetics in mouse ventric-ular muscle. Circ Res 88: 1059-1065, 2001.

Kido M, Du L, Sullivan C C, Li X, Deutsch R, Jamieson S W, Thistlethwaite P A. Hypoxia-inducible factor 1-alpha reduces infarction and attenuates progression of cardiac dysfunction after myocardial in-farction in the mouse. J Am Coll Cardiol 46: 2116-2124, 2005.

Kimura T E, Jin J, Zi M, Prehar S, Liu W, Oceandy D, Abe J, Neyses L, Weston A H, Cartwright E J, Wang X. Targeted deletion of the extracel-lular signal-regulated protein kinase 5 attenuates hypertrophic response and promotes pressure overload-induced apoptosis in the heart. Circ Res. 2010; 106:961-970.

Kinderman F S, Kim C, von Daake S, Ma Y, Pham B Q, Spraggon G, Xuong N H, Jennings P A, Taylor S S. A dynamic mechanism for AKAP binding to RII isoforms of cAMP-dependent protein kinase. Mol Cell 24: 397-408, 2006.

Klussmann E, Edemir B, Pepperle B, Tamma G, Henn V, Klauschenz E, Hundsrucker C, Maric K, Rosenthal W. Ht31: the first protein kinase A anchoring protein to integrate protein kinase A and Rho signaling. FEBS Lett 507: 264-268, 2001.

Kodama H, Fukuda K, Pan J, Sano M, Takahashi T, Kato T, Makino S, Manabe T, Murata M, Ogawa S. Significance of ERK cascade compared with JAK/STAT and PI3-K pathway in gp130-mediated cardiac hypertrophy. Am J Physiol Heart Circ Physiol. 2000; 279(4):H1635-1644.

Kontaridis M I, Yang W, Bence K K, Cullen D, Wang B, Bodyak N, Ke Q, Hinek A, Kang P M, Liao R, Neel B G. Deletion of Ptpn11 (Shp2) in cardiomyocytes causes dilated cardiomyopathy via effects on the extracellular signal-regulated kinase/mitogen-activated protein kinase and RhoA signaling pathways. Circulation. 2008; 117: 1423-1435.

Kritzer M D, Li J, Dodge-Kafka K, Kapiloff M S, "AKAPs: the architectural underpinnings of local cAMP signaling," J Mol Cell Cardiol. 2012 February; 52(2):351-8.

Lacana E, Maceyka M, Milstien S, Spiegel S. Cloning and character-ization of a protein kinase A anchoring protein (AKAP)-related protein that interacts with and regulates sphingosine kinase 1 activity. J Biol Chem 277: 32947-32953, 2002.

Layland J, Solaro R J, Shah A M. Regulation of cardiac contractile function by troponin I phosphorylation. Cardiovasc Res 66: 12-21, 2005.

Lester L B, Langeberg L K, Scott J D. Anchoring of protein kinase A facilitates hormone-mediated insulin secretion. Proc Natl Acad Sci USA 94: 14942-14947, 1997.

Li H, Adamik R, Pacheco-Rodriguez G, Moss J, Vaughan M. Protein kinase A-anchoring (AKAP) domains in brefeldin A-inhibited guanine nucleotide-exchange protein 2 (BIG2). Proc Natl Acad Sci USA 100: 1627-1632, 2003.

Li J, Kritzer M D, Michel J J, Le A, Thakur H, Gayanilo M, Passariello C L, Negro A, Danial J B, Oskouei B, Sanders M, Hare J M, Hanauer A, Dodge-Kafka K, Kapiloff M S, "Anchored p90 ribosomal S6 kinase 3 is required for cardiac myocyte hypertrophy," Circ Res. 2013 Jan. 4; 112(1):128-39.

Li J, Negro A, Lopez J, Bauman A L, Henson E, Dodge-Kafka K, Kapiloff M S. The mAKAPbeta scaffold regulates cardiac myocyte hypertrophy via recruitment of activated calcineurin. J Mol Cell Cardiol 48: 387-394, 2010.

Li J, Negro A, Lopez J, Bauman A L, Henson E, Dodge-Kafka K, Kapiloff M S, "The mAKAPbeta scaffold regulates cardiac myocyte hypertrophy via recruitment of activated calcineurin," J Mol Cell Cardiol. 2010 February; 48(2):387-94.

Li J, Vargas M A, Kapiloff M S, Dodge-Kafka K L, Regulation of MEF2 transcriptional activity by calcineurin/mAKAP complexes," Exp Cell Res. 2013 Feb. 15; 319(4):447-54.

Lohse M J, Engelhardt S, Eschenhagen T. What is the role of beta-adrenergic signaling in heart failure? Circ Res 93: 896-906, 2003.

Lu J T, Kass R S. Recent progress in congenital long QT syndrome. Curr Opin Cardiol 25: 216-221, 2010.

Lygren B, Carlson C R, Santamaria K, Lissandron V, McSorley T, Lorenz D, Wiesner B, Rosenthal W, Zaccolo M, Tasken K, Klussmann E. AKAP-complex regulates the Ca2+ reuptake into heart sarcoplasmic reticulum. EMBO Rep 8: 1061-1067, 2007.

Lygren B, Tasken K. The potential use of AKAP18delta as a drug target in heart failure patients. Expert Opin Biol Ther 8: 1099-1108, 2008.

Maloney D J, Hecht S M. Synthesis of a potent and selective inhibitor of p90 Rsk. Org Lett. 2005; 7:1097-1099.

Maron B J, Maron M S. Hypertrophic cardiomyopathy. Lancet. 2013; 381(9862):242-255.

Maruyama Y, Nishida M, Sugimoto Y, Tanabe S, Turner J H, Kozasa T, Wada T, Nagao T, Kurose H. Galpha(12/13) mediates alpha(1)-adrenergic receptor-induced cardiac hypertrophy. Circ Res 91: 961-969, 2002.

Marx S O, Kurokawa J, Reiken S, Motoike H, D'Armiento J, Marks A R, Kass R S. Requirement of a macromolecular signaling complex for beta adrenergic receptor modulation of the KCNQ1-KCNE1 potassium channel. Science 295: 496-499, 2002.

Marx S O, Reiken S, Hisamatsu Y, Gaburjakova M, Gaburjakova J, Yang Y M, Rosemblit N, Marks A R. Phosphorylation-dependent regulation of ryanodine receptors: a novel role for leucine/isoleucine zippers. J Cell Biol. 2001; 153:699-708.

Marx S O, Reiken S, Hisamatsu Y, Jayaraman T, Burkhoff D, Rosemblit N, Marks A R. PKA phosphorylation dissociates FKBP12.6 from the calcium release channel (ryanodine receptor): defective regula tion in failing hearts. Cell 101: 365-376, 2000.

Maxwell P H, Wiesener M S, Chang G W, Clifford S C, Vaux E C, Cockman M E, Wykoff C C, Pugh C W, Maher E R, Ratcliffe P J. The tumour suppressor protein VHL targets hypoxia-inducible factors for oxygen-dependent proteolysis. Nature 399: 271-275, 1999.

Mayers C M, Wadell J, McLean K, Venere M, Malik M, Shibata T, Driggers P H, Kino T, Guo X C, Koide H, Gorivodsky M, Grinberg A, Mukhopadhyay M, Abu-Asab M, Westphal H, Segars J H. The Rho guanine nucleotide exchange factor AKAP13 (BRX) is essential for cardiac development in mice. J Biol Chem 285: 12344-12354, 2010.

McConnell B K, Popovic Z, Mal N, Lee K, Bautista J, Forudi F, Schwartzman R, Jin J P, Penn M, Bond M. Disruption of protein kinase A interaction with A-kinase-anchoring proteins in the heart in vivo: effects on cardiac contractility, protein kinase A phosphorylation, and troponin I proteolysis. J Biol Chem 284: 1583-1592, 2009.

McKinsey T A, Kass D A. Small-molecule therapies for cardiac hypertrophy: moving beneath the cell surface. Nat Rev Drug Discov. 2007; 6:617-635.

Michel J J, Townley I K, Dodge-Kafka K L, Zhang F, Kapiloff M S, Scott J D, "Spatial restriction of PDK1 activation cascades by anchoring to mAKAPalpha," Mol Cell. 2005 Dec. 9; 20(5):661-72.

Michele D E, Gomez C A, Hong K E, Westfall M V, Metzger J M. Cardiac dysfunction in hypertrophic cardiomyopathy mutant tropomyosin mice is transgene-dependent, hypertrophy-independent, and improved by beta-blockade. Circ. Res. 2002; 91(3):255-262.

Morissette M R, Sah V P, Glembotski C C, Brown J H. The Rho effector, PKN, regulates ANF gene transcription in cardiomyocytes through a serum response element. Am J Physiol Heart Circ Physiol 278: H1769-H1774, 2000.

Naga Prasad S V, Barak L S, Rapacciuolo A, Caron M G, Rockman H A. Agonist-dependent recruitment of phosphoinositide 3-kinase to the membrane by beta-adrenergic receptor kinase 1. A role in receptor sequestration. J Biol Chem 276: 18953-18959, 2001.

Naga Prasad S V, Laporte S A, Chamberlain D, Caron M G, Barak L, Rockman H A. Phosphoinositide 3-kinase regulates $beta_2$-adrenergic receptor endocytosis by AP-2 recruitment to the receptor/beta-arrestin complex. J Cell Biol 158: 563-575, 2002.

Nakagami H, Kikuchi Y, Katsuya T, Morishita R, Akasaka H, Saitoh S, Rakugi H, Kaneda Y, Shimamoto K, Ogihara T. Gene polymor-phism of myospryn (cardiomyopathy-associated 5) is associated with left ventricular wall thickness in patients with hypertension. Hypertens Res 30: 1239-1246, 2007.

Nakamura A, Rokosh D G, Paccanaro M, Yee R R, Simpson P C, Grossman W, Foster E. LV systolic performance improves with development of hypertrophy after transverse aortic constriction in mice. Am J Physiol Heart Circ Physiol. 2001; 281:H1104-1112

Nakayama K, Frew U, Hagensen M, Skals M, Habelhah H, Bhoumik A, Kadoya T, Erdjument-Bromage H, Tempst P, Frappell P B, Bowtell D D, Ronai Z. Siah2 regulates stability of prolyl-hydroxylases, controls HIFlalpha abundance, and modulates physiological responses to hypoxia. Cell 117: 941-952, 2004.

Nauert J B, Klauck T M, Langeberg L K, Scott J D. Gravin, an autoan-tigen recognized by serum from myasthenia gravis patients, is a kinase scaffold protein. Curr Biol 7: 52-62, 1997.

Nerbonne J M, Kass R S. Molecular physiology of cardiac repolariza-tion. Physiol Rev 85: 1205-1253, 2005.

Negro A, Dodge-Kafka K, Kapiloff M S, "Signalosomes as Therapeutic Targets," Prog Pediatr Cardiol. 2008 April; 25(1):51-56.

Nichols C B, Rossow C F, Navedo M F, Westenbroek R E, Catterall W A, Santana L F, McKnight G S. Sympathetic stimulation of adult cardiomyocytes requires association of AKAP5 with a subpopulation of L-type calcium channels. Circ Res 107: 747-756, 2010.

Nicol R L, Frey N, Pearson G, Cobb M, Richardson J, Olson E N. Activated MEK5 induces serial assembly of sarcomeres and eccentric cardiac hypertrophy. EMBO J. 2001; 20:2757-2767.

Niggli E, Lederer W J. Voltage-independent calcium release in heart muscle. Science 250: 565-568, 1990.

Papa S, Sardanelli A M, Scacco S, Petruzzella V, Technikova-Dobrova Z, Vergari R, Signorile A. The NADH: ubiquinone oxidoreductase (complex I) of the mammalian respiratory chain and the cAMP cascade. J Bioenerg Biomembr 34: 1-10, 2002.

Oka T, Xu J, Kaiser R A, Melendez J, Hambleton M, Sargent M A, Lorts A, Brunskill E W, Dom G W, 2nd, Conway S J, Aronow B J, Robbins J, Molkentin J D. Genetic manipulation of periostin expression reveals a role in cardiac hypertrophy and ventricular remodeling. Circ. Res. 2007; 101(3):313-321.

Olson G L, Cantor C R, Braun A, Taylor S S. Designing isoform-specific peptide disruptors of protein kinase A localization. Proc Natl Acad Sci USA 100: 4072-4077, 2003.

Pare G C, Bauman A L, McHenry M, Michel J J, Dodge-Kafka K L, Kapiloff M S. The mAKAP complex participates in the induction of cardiac myocyte hypertrophy by adrenergic receptor signaling. J Cell Sci 118: 5637-5646, 2005.

Pare G C, Easlick J L, Mislow J M, McNally E M, Kapiloff M S. Nesprin-1alpha contributes to the targeting of mAKAP to the cardiac myocyte nuclear envelope. Exp Cell Res 303: 388-399, 2005.

Patel H H, Hamuro L L, Chun B J, Kawaraguchi Y, Quick A, Re-bolledo B, Pennypacker J, Thurston J, Rodriguez-Pinto N, Self C, Olson G, Insel P A, Giles W R, Taylor S S, Roth D M. Disruption of protein kinase A localization using a trans-activator of transcription (TAT)-conjugated A-kinase-anchoring peptide reduces cardiac function. J Biol Chem 285: 27632-27640, 2010.

Pawson C T, Scott J D. Signal integration through blending, bolstering and bifurcating of intracellular information. Nat Struct Mol Biol 17: 653-658, 2010.

Perino A, Ghigo A, Ferrero E, Morello F, Santulli G, Baillie G S, Damilano F, Dunlop A J, Pawson C, Walser R, Levi R, Altruda F, Silengo L, Langeberg L K, Neubauer G, SH, Lembo G, Wymann M P, Wetzker R, Houslay M D, Iaccarino G, Scott J D, Hirsch E. Integrating cardiac PIP3 and cAMP signaling through a PKA anchoring function of p110gamma. Mol Cell 42: 84-95, 2011.

Perrino C, Feliciello A, Schiattarella G G, Esposito G, Guerriero R, Zaccaro L, Del Gatto A, Saviano M, Garbi C, Carangi R, Di Lorenzo E, Donato G, Indolfi C, Avvedimento V E, Chiariello M. AKAP121 downregulation impairs protective cAMP signals, promotes mitochon-drial dysfunction, and increases oxidative stress. Cardiovasc Res 88: 101-110, 2010.

Perrino C, Naga Prasad S V, Mao L, Noma T, Yan Z, Kim H S, Smithies O, Rockman H A. Intermittent pressure overload triggers hypertrophy-independent cardiac dysfunction and vascular rarefaction. J Clin Invest. 2006; 116:1547-1560.

Prabhakar R, Boivin G P, Grupp I L, Hoit B, Arteaga G, Solaro J R, Wieczorek D F. A familial hypertrophic cardiomyopathy alpha-tropomyosin mutation causes severe cardiac hypertrophy and death in mice. J. Mol. Cell. Cardiol. 2001; 33(10):1815-1828.

Reynolds J G, McCalmon S A, Tomczyk T, Naya F J. Identification and mapping of protein kinase A binding sites in the costameric protein myospryn. Biochim Biophys Acta 1773: 891-902, 2007.

Richards S A, Dreisbach V C, Murphy L O, Blenis J. Characterization of regulatory events associated with membrane targeting of p90 ribosomal S6 kinase 1. Mol Cell Biol. 2001; 21:7470-7480

Rockman H A, Koch W J, Lefkowitz R J. Seven-transmembrane-span-ning receptors and heart function. Nature 415: 206-212, 2002.

Rockman H A, Ross R S, Harris A N, Knowlton K U, Steinhelper M E, Field L J, Ross J Jr, Chien K R. Segregation of atrial-specific and in-ducible expression of an atrial natriuretic factor transgene in an in vivo murine model of cardiac hypertrophy. Proc Natl Acad Sci USA. 1991; 88:8277-8281.

Roger V L, Go A S, Lloyd-Jones D M, Adams R J, Berry J D, Brown T M, Camethon M R, Dai S, de Simone G, Ford E S, Fox C S, Fullerton H J, Gillespie C, Greenlund K J, Hailpern S M, Heit J A, Ho P M, Howard V J, Kissela B M, Kittner S J, Lackland D T, Lichtman J H, Lisabeth L D, Makuc D M, Marcus G M, Marelli A, Matchar D B, McDermott M M, Meigs J B, Moy C S, Mozaffarian D, Mussolino M E, Nichol G, Paynter N P, Rosamond W D, Sorlie P D, Stafford R S, Turan T N, Turner M B, Wong N D, Wylie-Rosett J; American Heart Association Statistics Committee and Stroke Statistics Subcommittee. Heart disease and stroke statistics-2011 update: a report from the American Heart Association. Circulation 123: e18-e209, 2011.

Rose B A, Force T, Wang Y. Mitogen-activated protein kinase signaling in the heart: angels versus demons in a heart-breaking tale. Physiol Rev. 2010; 90:1507-1546.

Russell M A, Lund L M, Haber R, McKeegan K, Cianciola N, Bond M. The intermediate filament protein, synemin, is an AKAP in the heart. Arch Biochem Biophys 456: 204-215, 2006.

Sadoshima J, Qiu Z, Morgan J P, Izumo S. Angiotensin II and other hypertrophic stimuli mediated by G protein-coupled receptors activate tyrosine kinase, mitogen-activated protein kinase, and 90-kD S6 kinase in cardiac myocytes. The critical role of Ca(2+)-dependent signaling. Circ. Res. 1995; 76(1):1-15.

Sapkota G P, Cummings L, Newell F S, Armstrong C, Bain J, Frodin M, Grauert M, Hoffmann M, Schnapp G, Steegmaier M, Cohen P, Alessi D R. BI-D1870 is a specific inhibitor of the p90 RSK (ribosomal S6 kinase) isoforms in vitro and in vivo. Biochem J. 2007; 401:29-38.

Scholten A, Poh M K, van Veen T A, van Breukelen B, Vos M A, Heck A J. Analysis of the cGMP/cAMP interactome using a chemical proteom-ics approach in mammalian heart tissue validates sphingosine kinase type 1-interacting protein as a genuine and highly abundant AKAP. J Proteome Res 5: 1435-1447, 2006.

Scholten A, van Veen T A, Vos M A, Heck A J. Diversity of cAMP-dependent protein kinase isoforms and their anchoring proteins in mouse ventricular tissue. J Proteome Res 6: 1705-1717, 2007.

Schulze D H, Mughal M, Lederer W J, Ruknudin A M. Sodium/cal-cium exchanger (NCX1) macromolecular complex. J Biol Chem 278: 28849-28855, 2003.

Semenza G L. Hypoxia-inducible factor 1 (HIF-1) pathway. Sci STKE 2007: cm8, 2007.

Semenza G L. Regulation of oxygen homeostasis by hypoxia-inducible factor 1. Physiology 24: 97-106, 2009.

Sfichi-Duke L, Garcia-Cazarin M L, Sumandea C A, Sievert G A, Balke C W, Zhan D Y, Morimoto S, Sumandea M P. Cardiomyopathy-causing deletion K210 in cardiac troponin T alters phosphorylation propensity of sarcomeric proteins. J Mol Cell Cardiol 48: 934-942, 2010.

Shan J, Betzenhauser M J, Kushnir A, Reiken S, Meli A C, Wronska A, Dura M, Chen B X, Marks A R. Role of chronic ryanodine receptor phosphorylation in heart failure and beta-adrenergic receptor blockade in mice. J Clin Invest 120: 4375-4387, 2010.

Shan J, Kushnir A, Betzenhauser M J, Reiken S, Li J, Lehnart S E, Lindegger N, Mongillo M, Mohler P J, Marks A R. Phosphorylation of the ryanodine receptor mediates the cardiac fight or flight response in mice. J Clin Invest 120: 4388-4398, 2010.

Shyu K G, Wang M T, Wang B W, Chang C C, Leu J G, Kuan P, Chang H. Intramyocardial injection of naked DNA encoding HIF-1alpha/VP16 hybrid to enhance angiogenesis in an acute myocardial infarction model in the rat. Cardiovasc Res 54: 576-583, 2002.

Singh A, Redden J M, Kapiloff M S, Dodge-Kafka K L, "The large isoforms of A-kinase anchoring protein 18 mediate the phosphorylation of inhibitor-1 by protein kinase A and the inhibition of protein phosphatase 1 activity," Mol Pharmacol. 2011 March; 79(3):533-40.

Skroblin P, Grossmann S, Schafer G, Rosenthal W, Klussmann E. Mechanisms of protein kinase A anchoring. Int Rev Cell Mol Biol 283: 235-330, 2010.

Smith F D, Langeberg L K, Cellurale C, Pawson T, Morrison D K, Davis R J, Scott J D. AKAP-Lbc enhances cyclic AMP control of the ERK1/2 cascade. Nat Cell Biol 12: 1242-1249, 2010.

Smith J A, Poteet-Smith C E, Xu Y, Errington T M, Hecht S M, Lannigan D A. Identification of the first specific inhibitor of p90 ribosomal S6 ki-nase (RSK) reveals an unexpected role for RSK in cancer cell prolifera-tion. Cancer Res. 2005; 65:1027-1034.

Spinale F G, Janicki J S, Zile M R. Membrane-associated matrix proteolysis and heart failure. Circ. Res. 2013; 112(1):195-208.

Stelzer J E, Patel J R, Walker J W, Moss R L. Differential roles of cardiac myosin-binding protein C and cardiac troponin I in the myofi-brillar force responses to protein kinase A phosphorylation. Circ Res 101: 503-511, 2007.

Sumandea C A, Garcia-Cazarin M L, Bozio C H, Sievert G A, Balke C W, Sumandea M P. Cardiac troponin T, a sarcomeric AKAP, tethers protein kinase A at the myofilaments. J Biol Chem 286: 530-541, 2011

Takeishi Y, Huang Q, Abe J, Che W, Lee J D, Kawakatsu H, Hoit B D, Berk B C, Walsh R A. Activation of mitogen-activated protein kinases and p90 ribosomal S6 kinase in failing human hearts with dilated cardiomy-opathy. Cardiovasc Res. 2002; 53:131-137.

Terrenoire C, Houslay M D, Baillie G S, Kass R S. The cardiac IKs potassium channel macromolecular complex includes the phosphodiesterase PDE4D3. J Biol Chem 284: 9140-9146, 2009.

Thomas G M, Rumbaugh G R, Harrar D B, Huganir R L. Ribosomal S6 kinase 2 interacts with and phosphorylates PDZ domain-containing proteins and regulates AMPA receptor transmission. Proc Natl Acad Sci USA. 2005; 102:15006-15011.

Tingley W G, Pawlikowska L, Zaroff J G, Kim T, Nguyen T, Young S G, Vranizan K, Kwok P Y, Whooley M A, Conklin B R. Gene-trapped mouse embryonic stem cell-derived cardiac myocytes and human genet-ics implicate AKAP10 in heart rhythm regulation. Proc Natl Acad Sci USA 104: 8461-8466, 2007.

Uys G M, Ramburan A, Loos B, Kinnear C J, Korkie L J, Mouton J, Riedemann J, Moolman-Smook J. Myomegalin is a novel A-kinase anchoring protein involved in the phosphorylation of cardiac myosin binding protein C. BMC Cell Biol 12: 18, 2011.

Vargas M A, Tirnauer J S, Glidden N, Kapiloff M S, Dodge-Kafka K L, "Myocyte enhancer factor 2 (MEF2) tethering to muscle selective A-kinase anchoring protein (mAKAP) is necessary for myogenic differentiation," Cell Signal. 2012 August; 24(8):1496-503.

Wong W, Goehring A S, Kapiloff M S, Langeberg L K, Scott J D, "mAKAP compartmentalizes oxygen-dependent control of HIF-1alpha," Sci Signal. 2008 Dec. 23; 1(51).

Welch E J, Jones B W, Scott J D. Networking with AKAPs: context-dependent regulation of anchored enzymes. Mol Interv 10: 86-97, 2010. 114. Wu X, Simpson J, Hong J H, Kim K H, Thavarajah N K, Backx P H, Neel B G, Araki T. MEK-ERK pathway modulation ameliorates disease phe-notypes in a mouse model of Noonan syndrome associated with the Raf1(L613V) mutation. J Clin Invest. 2011; 121:1009-1025.

Wollert K C, Taga T, Saito M, Narazaki M, Kishimoto T, Glembotski C C, Vernallis A B, Heath J K, Pennica D, Wood W I, Chien K R. Cardiotrophin-1 activates a distinct form of cardiac muscle cell hypertrophy. Assembly of sarcomeric units in series VIA gp130/leukemia inhibitory factor receptor-dependent pathways. J Biol Chem. 1996; 271:9535-9545.

Xu J, Ismat F A, Wang T, Lu M M, Antonucci N, Epstein J A. Cardiomyocyte-specific loss of neurofibromin promotes cardiac hypertrophy and dysfunction. Circ Res. 2009; 105:304-311.

Yang K C, Jay P Y, McMullen J R, Nerbonne J M. Enhanced car-diac PI3Ka signalling mitigates arrhythmogenic electrical remodel-ling in pathological hypertrophy and heart failure. Cardiovasc Res. 2012; 93:252-262.

Zhang L, Malik S, Kelley G G, Kapiloff M S, Smrcka A V, "Phospholipase C epsilon scaffolds to muscle-specific A kinase anchoring protein (mAKAPbeta) and integrates multiple hypertrophic stimuli in cardiac myocytes," J Biol Chem. 2011 Jul. 1; 286(26):23012-21.

Zhao Y, Bjorbaek C, Moller D E. Regulation and interaction of pp90(rsk) isoforms with mitogen-activated protein kinases. J Biol Chem. 1996; 271:29773-29779.

The invention claimed is:

1. A viral-based gene therapy vector encoding a fragment of a muscle A-kinase anchoring protein β (mAKAPβ) amino acid sequence, wherein said fragment consists of a p90 ribosomal S6 kinase type 3 (RSK3) binding domain that is at least 80% homologous to amino acids 1696-1835 of SEQ ID NO: 25.

2. The viral-based gene therapy vector of claim 1, wherein the viral vector is adeno-associated virus (AAV).

3. The viral-based gene therapy vector of claim 2, wherein the viral vector is AAV9.

4. The viral-based gene therapy vector of claim 1, wherein the viral vector is AAV2.

5. The viral-based gene therapy vector of claim 1, wherein said fragment is at least 85% homologous to amino acids 1696-1835 of SEQ ID NO: 25.

6. The viral-based gene therapy vector of claim 1, wherein said fragment is at least 90% homologous to amino acids 1696-1835 of SEQ ID NO: 25.

7. The viral-based gene therapy vector of claim 1, wherein said fragment is at least 95% homologous to amino acids 1696-1835 of SEQ ID NO: 25.

8. The viral-based gene therapy vector of claim 1, wherein said fragment is at least 90% identical to amino acids 1696-1835 of SEQ ID NO: 25.

9. The viral-based gene therapy vector of claim 1, wherein said fragment is at least 95% identical to amino acids 1696-1835 of SEQ ID NO: 25.

10. A pharmaceutical composition comprising the viral-based gene therapy vector of claim 1 and a pharmaceutically acceptable carrier.

11. A method of treating a disease or condition, comprising administering to a patient in need thereof the pharmaceutical composition of claim 10.

12. The method of claim 11, wherein said disease or condition affects the heart.

13. The method of claim 12, wherein said disease or condition is ventricular myocyte hypertrophy.

14. The method of claim 11, wherein said disease or condition is caused by hypertension, coronary artery disease, myocardial infarction, valvular disease, primary cardiomyopathy, congenital heart disease, arrhythmia, pulmonary disease, diabetes, anemia, or hyperthyroidism.

15. The method of claim 11, wherein said disease or condition is caused by neurohumoral activation.

16. The method of claim 11, wherein said disease or condition is associated with the nervous system.

17. The method of claim 11, wherein said disease or condition is associated with immunity.

18. The method of claim 11, wherein said disease or condition affects muscles.

19. The method of claim 11, wherein said disease or condition is associated with cancer.

20. The method of claim 11, wherein said disease or condition is heart disease.

* * * * *

SEQUENCE LISTING

```
Sequence total quantity: 26
SEQ ID NO: 1            moltype = AA  length = 733
FEATURE                 Location/Qualifiers
source                  1..733
                        mol_type = protein
                        organism = Homo sapiens
SEQUENCE: 1
MDLSMKKFAV RRFFSVYLRR KSRSKSSSLS RLEEEGVVKE IDISHHVKEG FEKADPSQFE  60
LLKVLGQGSY GKVFLVRKVK GSDAGQLYAM KVLKKATLKV RDRVRSKMER DILAEVNHPF  120
IVKLHYAFQT EGKLYLILDF LRGGDLFTRL SKEVMFTEED VKFYLAELAL ALDHLHSLGI  180
IYRDLKPENI LLDEEGHIKI TDFGLSKEAI DHDKRAYSFC GTIEYMAPEV VNRRGHTQSA  240
DWWSFGVLMF EMLTGSLPFQ GKDRKETMAL ILKAKLGMPQ FLSGEAQSLL RALFKRNPCN  300
RLGAGIDGVE EIKRHPFFVT IDWNTLYRKE IKPPFKPAVG RPEDTFHFDP EFTARTPTDS  360
PGVPPSANAH HLFRGFSFVA SSLIQEPSQQ DLHKVPVHPI VQQLHGNNIH FTDGYEIKED  420
IGVGSYSVCK RCVHKATDTE YAVKIIDKSK RDPSEEIEIL LRYGQHPNII TLKDVYDDGK  480
FVYLVMELMR GGELLDRILR QRYFSEREAS DVLCTITKTM DYLHSQGVVH RDLKPSNILY  540
RDESGSPESI RVCDFGFAKQ LRAGNGLLMT PCYTANFVAP EVLKRQGYDA ACDIWSLGIL  600
LYTMLAGFTP FANGPDDTPE EILARIGSGK YALSGGNWDS ISDAAKDVVS KMLHVDPHQR  660
LTAMQVLKHP WVVNREYLSP NQLSRQDVHL VKGAMAATYF ALNRTPQAPR LEPVLSSNLA  720
QRRGMKRLTS TRL                                                    733

SEQ ID NO: 2            moltype = AA  length = 2314
FEATURE                 Location/Qualifiers
source                  1..2314
                        mol_type = protein
                        organism = Rattus norvegicus
SEQUENCE: 2
MLTMSVTLSP LRSQGPDPMA TDASPMAINM TPTVEQEEGE GEEAVKAIDA EQQYGKPPPL  60
HTAADWKIVL HLPEIETWLR MTSERVRDLT YSVQQDADSK HVDVHLVQLK DICEDISDHV  120
EQIHALLETE FSLKLLSYSV NVIVDIHAVQ LLWHQLRVSV LVLRERILQG LQDANGNYTR  180
QTDILQAFSE ETTEGRLDSL TEVDDSGQLT IKCSQDYLSL DCGITAFELS DYSPSEDLLG  240
GLGDMTTSQA KTKSFDSWSY SEMEKEFPEL IRSVGLLTVA TEPVPSSCGE ANEDSSQASL  300
SDDHKGEHGE DGAPVPGQQL DSTVGMSSLD GTLANAAEHP SETAKQDSTS SPQLGAKKTQ  360
PGPCEITTPK RSIRDCFNYN EDSPTQPTLP KRGLFLKETQ KNERKGSDRK GQVVDLKPEL  420
SRSTPSLVDP PDRSKLCLVL QSSYPSSPSA ASQSYECLHK VGLGNLENIV RSHIKEISSS  480
LGRLTDCHKE KLRLKKPHKT LAEVSLCRIP KQGGGSGKRS ESTGSSAGPS MVSPGAPKAT  540
MRPETDSAST ASGGLCHQRN RSGQLPVQSK ASSSPPCSHS SESSLGSDSI KSPVPLLSKN  600
KSQKSSPPAP CHATQNGQVV EAWYGSDEYL ALPSHLKQTE VLALKLESLT KLLPQKPRGE  660
TIQDIDDWEL SEMNSDSEIY PTYHIKKKHT RLGTVSPSSS SDIASSLGES IESGPLSDIL  720
SDEDLCLPLS SVKKFTDEKS ERPSSSEKNE SHSATRSALI QKLMHDIQHQ ENYEAIWERI  780
EGFVNKLDEF IQWLNEAMET TENWTPPKAE TDSLRLYLET HLSFKLNVDS HCALKEAVEE  840
EGHQLLELVV SHKAGLKDTL RMIASQWKEL QRQIKRQHSW ILRALDTIKA EILATDVSVE  900
DEEGTGSPKA EVQLCHLETQ RDAVEQMSLK LYSEQYTSGS KRKEEFANMS KAHAEGSNGL  960
LDFDSEYQEL WDWLIDMESL VMDSHDLMMS EEQQQHLYKR YSVEMSIRHL KKSELLSKVE  1020
ALKKGGLSLP DDILEKVDSI NEKWELLGKT LREKIQDTIA GHSGSGPRDL LSPESGSLVR  1080
QLEVRIKELK RWLRDTELFI FNSCLRQEKE GTSAEKQLQY FKSLCREIKQ RRRGVASILR  1140
LCQHLLDDRD TCNLNADHQP MQLIIVNLER RWEAIVMQAV QWQTRLQKKM GKESETLNVI  1200
DPGLMDLNGM SEDALEWDET DISNKLISVH EESNDLDQDP EPMLPAVKLE ETHHKDSGYE  1260
EEAGDCGGSP YTSNITAPSS PHIYQVYSLH NVELHEDSHT PFLKSSPKFT GTTQPTVLTK  1320
SLSKDSSFSS TKSLPDLLGG SGLVRPYSCH SGDLSQNSGS ESGIVSEGDN EMPTNSDMSL  1380
FSMVDGSPSN PETEHPDPQM GDAANVLEQK FKDNGESIKL SSVSRASVSP VGCVNGKAGD  1440
LNSVTKHTAD CLGEELQGKH DVFTFYDYSY LQGSKLKLPM IMKQPQSEKA HVEDPLLGGF  1500
YFDKKSCKAK HQASESQPDA PPHERILASA PHEMGRSAYK SSDIEKTFTG IQSARQLSLL  1560
SRSSSVESLS PGGDLFGLGI FKNGSDSLQR STSLESWLTS YKSNEDLFSC HSSGDISVSS  1620
GSVGELSKRT LDLLNRLENI QSPSEQKIKR SVSDMTLQSS SQKMPFAGQM SLDVASSINE  1680
DSPASLTELS SSDELSLCSE DIVLHKNKIP ESNASFRKRL NRSVADESDV NVSMIVNVSC  1740
TSACTDDEDD SDLLSSSTLT LTEEELCLKD EDDDSSIATD DEIYEESNLM SGLDYIKNEL  1800
QTWIRPKLSL TREKKRSGVT DEIKVNKDGG GNEKANPSDT LDIEALLNGS IRCLSENNGN  1860
GKTPPRTHGS GTKGENKKST YDVSKDPHVA DMENGNIEST PEREREKPQG LPEVSENLAS  1920
NVKTISESEL SEYEAVMDGS EDSSVARKEF CPPNDRHPPQ MGPKLQHPEN QSGDCKPVQN  1980
PCPGLLSEAG VGSRQDSNGL KSLPNDAPSG ARKPAGCCLL EQNETEESAS ISSNASCCNC  2040
KPDVFHQKDD EDCSVHDFVK EIIDMASTAL KSKSQPESEV AAPTSLTQIK EKVLEHSHRP  2100
IHLRKGDFYS YLSLSSHDSD CGEVTNYIDE KSSTPLPPDA VDSGLDDKED MDCFFEACVE  2160
DEPVNEEAGL PGALPNESAI EDGAEQKSEQ KTASSPVLSD KTDLVPLSGL SPQKGADDAK  2220
EGDDVSHTSQ GCAESTEPTT PSGKANAEGR SRMQGVSATP EENAASAKPK IQAFSLNAKQ  2280
PKGKVAMRYP SPQTLTCKEK LVNFHEDRHS NMHR                             2314

SEQ ID NO: 3            moltype = RNA  length = 19
FEATURE                 Location/Qualifiers
misc_feature            1..19
                        note = siRNA Rat RSK3 On Targetplus J-080945-10
source                  1..19
                        mol_type = other RNA
                        organism = synthetic construct
SEQUENCE: 3
cgcaagaagt cgcgctcca                                              19

SEQ ID NO: 4            moltype = RNA  length = 19
```

-continued

```
FEATURE                Location/Qualifiers
misc_feature           1..19
                       note = siRNA Rat RSK3 On-Targetplus J-080945-11
source                 1..19
                       mol_type = other RNA
                       organism = synthetic construct
SEQUENCE: 4
ttgagatcct cctgcggta                                              19

SEQ ID NO: 5           moltype = DNA  length = 24
FEATURE                Location/Qualifiers
misc_feature           1..24
                       note = Oligonucleotide Rat RSK3 rRSK3+0.2
source                 1..24
                       mol_type = other DNA
                       organism = synthetic construct
SEQUENCE: 5
gaacatgaag aagttcacgg tgcg                                        24

SEQ ID NO: 6           moltype = DNA  length = 25
FEATURE                Location/Qualifiers
misc_feature           1..25
                       note = Oligonucleotide Rat RSK3 rRSK3-0.5
source                 1..25
                       mol_type = other DNA
                       organism = synthetic construct
SEQUENCE: 6
tctctctcca tcttagaccg gaccc                                       25

SEQ ID NO: 7           moltype = DNA  length = 28
FEATURE                Location/Qualifiers
misc_feature           1..28
                       note = Oligonucleotide Mouse RSK3 RSK3Ex2+5'
source                 1..28
                       mol_type = other DNA
                       organism = synthetic construct
SEQUENCE: 7
ccccagagca aacaactttc tcagattg                                    28

SEQ ID NO: 8           moltype = DNA  length = 31
FEATURE                Location/Qualifiers
misc_feature           1..31
                       note = oligonucleotide RSK3Ex2-3'
source                 1..31
                       mol_type = other DNA
                       organism = synthetic construct
SEQUENCE: 8
cgattctgac aatcacaggc tcaactaatg t                                31

SEQ ID NO: 9           moltype = AA  length = 28
FEATURE                Location/Qualifiers
source                 1..28
                       mol_type = protein
                       organism = Homo sapiens
SEQUENCE: 9
TDFGLSKEAI DHEKKAYSFC GTVEYMAP                                    28

SEQ ID NO: 10          moltype = AA  length = 23
FEATURE                Location/Qualifiers
source                 1..23
                       mol_type = protein
                       organism = Homo sapiens
SEQUENCE: 10
EFTSRTPKDS PGIPPSAGAH QLF                                         23

SEQ ID NO: 11          moltype = AA  length = 28
FEATURE                Location/Qualifiers
source                 1..28
                       mol_type = protein
                       organism = Homo sapiens
SEQUENCE: 11
TDFGLSKESI DHEKKAYSFC GTVEYMAP                                    28

SEQ ID NO: 12          moltype = AA  length = 23
FEATURE                Location/Qualifiers
source                 1..23
                       mol_type = protein
                       organism = Homo sapiens
SEQUENCE: 12
```

-continued

```
EFTAKTPKDS PGIPPSANAH QLF                                          23

SEQ ID NO: 13          moltype = AA  length = 28
FEATURE                Location/Qualifiers
source                 1..28
                       mol_type = protein
                       organism = Homo sapiens
SEQUENCE: 13
TDFGLSKEAI DHDKRAYSFC GTIEYMAP                                     28

SEQ ID NO: 14          moltype = AA  length = 23
FEATURE                Location/Qualifiers
source                 1..23
                       mol_type = protein
                       organism = Homo sapiens
SEQUENCE: 14
EFTARTPTDS PGVPPSANAH HLF                                          23

SEQ ID NO: 15          moltype = AA  length = 28
FEATURE                Location/Qualifiers
source                 1..28
                       mol_type = protein
                       organism = Homo sapiens
SEQUENCE: 15
TDFGLSKESV DQEKKAYSFC GTVEYMAP                                     28

SEQ ID NO: 16          moltype = AA  length = 23
FEATURE                Location/Qualifiers
source                 1..23
                       mol_type = protein
                       organism = Homo sapiens
SEQUENCE: 16
EFTAKTPKDS PGLPASANAH QLF                                          23

SEQ ID NO: 17          moltype = AA  length = 29
FEATURE                Location/Qualifiers
source                 1..29
                       mol_type = protein
                       organism = Homo sapiens
SEQUENCE: 17
TDFGLSKEFV ADETERAYSF CGTIEYMAP                                    29

SEQ ID NO: 18          moltype = AA  length = 22
FEATURE                Location/Qualifiers
source                 1..22
                       mol_type = protein
                       organism = Homo sapiens
SEQUENCE: 18
EFTEMDPTYS PAALPQSSEK LF                                           22

SEQ ID NO: 19          moltype = AA  length = 29
FEATURE                Location/Qualifiers
source                 1..29
                       mol_type = protein
                       organism = Homo sapiens
SEQUENCE: 19
TDFGLSKEFL TEEKERTFSF CGTIEYMAP                                    29

SEQ ID NO: 20          moltype = AA  length = 23
FEATURE                Location/Qualifiers
source                 1..23
                       mol_type = protein
                       organism = Homo sapiens
SEQUENCE: 20
EFTRLEPVYS PPGSPPPGDP RIF                                          23

SEQ ID NO: 21          moltype = DNA  length = 2791
FEATURE                Location/Qualifiers
source                 1..2791
                       mol_type = unassigned DNA
                       organism = Homo sapiens
SEQUENCE: 21
cccggcgcgg cctgcccttt gtgaccgcag ctcgcgcccc acgccccgcg cccatggccg  60
ccgtgccggg ctccctggcc acgcgtgccc gcccgcggac ctgagccccg cgcctgggat  120
gccggggatg cgcgtccccc ggccctgcgg ctgctccggg ctgggcgcgg ggcgatggac  180
ctgagcatga agaagttcgc cgtgcgcagg ttcttctctg tgtacctgcg caggaagtcg  240
cgctccaaga gctccagcct gagccggctc gaggaagaag gtgtcgtgaa ggagatagac  300
atcagccatc atgtgaagga gggctttgag aaggcagatc cttcccagtt tgagctgctg  360
aaggttttag gacaaggatc ctatggaaag gtgttcctgg tgaggaaggt gaaggggtcc  420
```

```
gacgctgggc agctctacgc catgaaggtc cttaagaaag ccaccctaaa agttcgggac  480
cgagtgagat cgaagatgga gagagacatc ttggcagaag tgaatcaccc cttcattgtg  540
aagcttcatt atgcctttca gacggaagga aagctctacc tgatcctgga cttcctgcgg  600
ggaggggacc tcttcacccg gctctccaaa gaggtcatgt tcacggagga ggatgtcaag  660
ttctacctgg ctgagctggc cttggcttta gaccatctcc acagcctggg gatcatctac  720
agagatctga agcctgagaa catcctcctg gatgaagagg ggcacattaa gatcacagat  780
ttcggcctga gtaaggaggc cattgaccac gacaagagag cgtactcctt ctgcgggacg  840
atcgagtaca tggcaccccga ggtggtgaac cggcgaggac acacgcagag tgccgactgg  900
tggtccttcg gcgtgctcat gtttgagatg ctcacggggt ccctgccgtt ccaggggaag  960
gacaggaagg agaccatggc tctcatcctc aaagccaagc tggggatgcc gcagttcctc  1020
agtggggagg cacagagttt gctgcgagct ctcttcaaac ggaacccctg caaccggctg  1080
ggtgctggca ttgacggagt ggaggaaatt aagcgccatc ccttctttgt gaccatagac  1140
tggaacacgc tgtaccggaa ggagatcaag ccaccgttca aaccagcatt gggcaggcct  1200
gaggacacct tccactttga ccccgagttc acagcgcgga cgcccacaga ctctcctggc  1260
gtccccccga gtgcaaacgc tcatcacctg tttagaggat tcagctttgt ggcctcaagc  1320
ctgatccagg agccctcaca gcaagatctg cacaaagtcc cagttcaccc aatcgtgcag  1380
cagttacacg ggaacaacat ccacttcacc gatggctacg agatcaagga ggacatcggg  1440
gtgggctcct actcagtgtg caagcgatgt gtgcataaag ccacagacac cgagtatgcc  1500
gtgaagatca ttgataagag caagagagac ccctcggaag agattgagat cctcctgcgg  1560
tacggccagc acccgaacat catcaccctc aaggatgtct atgatgatgg caagtttgtg  1620
tacctggtaa tggagctgat gcgtggtggg gagctcctgg accgcatcct ccggcagaga  1680
tacttctcgg agcgcgaagc cagtgacgtc ctgtgcacca tcaccaagac catggactac  1740
ctccattccc aggggggttgt tcatcgagac ctgaagccga gtaacatcct gtacagggat  1800
gagtcgggga gcccagaatc catccgagtc tgcgacttcg gctttgccaa gcagctgcgc  1860
gcggggaacg ggctgctcat gacaccctgc tacacggcca atttcgtggc cccggaggtc  1920
ctgaagcgtc aaggctatga tgcggcgtgt gacatctgga gtttggggat cctgttgtac  1980
accatgctgg caggatttac cccttttgca aatgggccag acgatacccc tgaggagatt  2040
ctggcgcgga tcggcagtgg gaagtatgcc ctttctgggg gaaactggga ctcgatatct  2100
gacgcagcta aagacgtcgt gtccaagatg ctccacgtgg accctcatca gcgcctgacg  2160
gcgatgcaag tgctcaaaca cccgtgggtg gtcaacagag agtacctgtc cccaaaccag  2220
ctcagccgac aggacgtgca cctggtgaag ggcgcgatgg ccgccaccta ctttgctcta  2280
aacagaacac ctcaggcccc gcggctggag cccgtgctgt catccaacct ggctcagcgc  2340
agaggcatga agagactcac gtccacgcgg ctgtagcggg tgggaccctg gccccagcgt  2400
cccctgccag catcctcgtg ggctcacaga ccccggcctc ggagcccgtc tggcacccag  2460
agtgaccaca agtccagcag ggaggcggcg ccgcctcgcc gtgtccgtgt ttcttttttc  2520
agcccccggag aggtcctgac ctgggggctt ctccaagcct cactgcgcca cgctccccgc  2580
ccgctctctt ttctcccaag cgaaaccaaa tgcgcccctt cacctcgcgt gcccgtgcga  2640
ggccgggggc ttctttcaga gcccgcgggt cctctcatac atggcttctg tgtctgccga  2700
gagatctgtt ttccaattat gaagccggtc ggtttggtca gactcccgac acccacgtcc  2760
aggtacccgg tggaaagtgg cagtgcgagg g                                 2791

SEQ ID NO: 22          moltype = AA  length = 733
FEATURE                Location/Qualifiers
source                 1..733
                       mol_type = protein
                       organism = Homo sapiens
SEQUENCE: 22
MDLSMKKFAV RRFFSVYLRR KSRSKSSSLS RLEEEGVVKE IDISHHVKEG FEKADPSQFE  60
LLKVLGQGSY GKVFLVRKVK GSDAGQLYAM KVLKKATLKV RDRVRSKMER DILAEVNHPF  120
IVKLHYAFQT EGKLYLILDF LRGGDLFTRL SKEVMFTEED VKFYLAELAL ALDHLHSLGI  180
IYRDLKPENI LLDEEGHIKI TDFGLSKEAI DHDKRAYSFC GTIEYMAPEV VNRRGHTQSA  240
DWWSFGVLMF EMLTGSLPFQ GKDRKETMAL ILKAKLGMPQ FLSGEAQSLL RALFKRNPCN  300
RLGAGIDGVE EIKRHPFFVT IDWNTLYRKE IKPPFKPALG RPEDTFHFDP EFTARTPTDS  360
PGVPPSANAH HLFRGFSFVA SSLIQEPSQQ DLHKVPVHPI VQQLHGNNIH FTDGYEIKED  420
IGVGSYSVCK RCVHKATDTE YAVKIIDKSK RDPSEEIEIL LRYGQHPNII TLKDVYDDGK  480
FVYLVMELMR GGELLDRILR QRYFSEREAS DVLCTITKTM DYLHSQGVVH RDLKPSNILY  540
RDESGSPESI RVCDFGFAKQ LRAGNGLLMT PCYTANFVAP EVLKRQGYDA ACDIWSLGIL  600
LYTMLAGFTP FANGPDDTPE EILARIGSGK YALSGGNWDS ISDAAKDVVS KMLHVDPHQR  660
LTAMQVLKHP WVVNREYLSP NQLSRQDVHL VKGAMAATYF ALNRTPQAPR LEPVLSSNLA  720
QRRGMKRLTS TRL                                                     733

SEQ ID NO: 23          moltype = DNA  length = 5817
FEATURE                Location/Qualifiers
source                 1..5817
                       mol_type = unassigned DNA
                       organism = Homo sapiens
SEQUENCE: 23
gcggagaagg aggcggaggg agcgattgtg gccccggccg cggtggccgg cgcggcctgc  60
cctttgtgac cgcagctcgc gccccacgcc ccgcgcccat ggccgccgtg ccgggctccc  120
tggccacgcg tgcccgcccg cggacctgag ccccgcgcct gggatgccgg ggatgcgcgt  180
cccccggccc tgcggctgct ccgggctggg cgcggggcga tggacctgag catgaagaag  240
ttcgccgtgc gcaggttctt ctctgtgtac ctgcgcagga agtcgcgctc caagagctcc  300
agcctgagcc ggctcgagga agaaggcgtc gtgaaggaga tagacatcag ccatcatgtg  360
aaggagggct ttgagaaggc agatccttcc cagtttgagc tgctgaaggt tttaggacaa  420
ggatcctatg gaaaggtgtt cctggtgagg aaggtgaagg ggtccgacgc tgggcagctc  480
tacgccatga aggtccttaa gaaagccacc ctaaaagttc gggaccgagt gagatcgaag  540
atggagagag acatcttggc agaagtgaat caccccttca ttgtgaagct tcattatgcc  600
tttcagacgg aaggaaagct ctacctgatc ctggacttcc tgcggggagg ggacctcttc  660
acccggctct ccaaagaggt catgttcacg gaggaggatg tcaagttcta cctggctgag  720
```

-continued

```
ctggccttgg ctttagacca tctccacagc ctggggatca tctacagaga tctgaagcct  780
gagaacatcc tcctggatga agaggggcac attaagatca cagatttcgg cctgagtaag  840
gaggccattg accacgacaa gagagcgtac tccttctgcg ggacgatcga gtacatggcg  900
cccgaggtgg tgaaccggcg aggacacacg cagagtgccg actggtggtc cttcggcgtg  960
ctcatgtttg agatgctcac ggggtccctg ccgttccagg ggaaggacag gaaggagacc  1020
atggctctca tcctcaaagc caagctgggg atgccgcagt tcctcagtgg ggaggcacag  1080
agtttgctgc gagctctctt caaacggaac ccctgcaacc ggctgggtgc tggcattgac  1140
ggagtggagg aaattaagcg ccatcccttc tttgtgacca tagactggaa cacgctgtac  1200
cggaaggaga tcaagccacc gttcaaacca gcagtgggca ggcctgagga caccttccac  1260
tttgaccccg agttcacagc gcggacgccc acagactctc ctggcgtccc cccgagtgca  1320
aacgctcatc acctgtttag aggattcagc tttgtggcct caagcctgat ccaggagccc  1380
tcacagcaag atctgcacaa agtcccagtt cacccaatcg tgcagcagtt acacgggaac  1440
aacatccact tcaccgatgg ctacgagatc aaggaggaca tcggggtggg ctcctactca  1500
gtgtgcaagc gatgtgtgca taaagccaca gacaccgagt atgccgtgaa gatcattgat  1560
aagagcaaga gagacccctc ggaagagatt gagatcctcc tgcggtacgg ccagcacccg  1620
aacatcatca ccctcaagga tgtctatgat gatggcaagt ttgtgtacct ggtaatggag  1680
ctgatgcgtg gtggggagct cctggaccgc atcctccggc agagatactt ctcggagcgc  1740
gaagccagtg acgtcctgtg caccatcacc aagaccatgg actacctcca ttcccagggg  1800
gttgttcatc gagacctgaa gccgagtaac atcctgtaca gggatgagtc ggggagccca  1860
gaatccatcc gagtctgcga cttcggcttt gccaagcagc tgcgcgcggg gaacgggctg  1920
ctcatgacac cctgctacac ggccaatttc gtggccccgg aggtcctgaa gcgtcaaggc  1980
tatgatgcgg cgtgtgacat ctggagtttg ggatcctgt tgtacaccat gctggcagga  2040
tttacccctt ttgcaaatgg gccagacgat accctgagg agattctggc gcggatcggc  2100
agtgggaagt atgccctttc tgggggaaac tgggactcga tatctgacgc agctaaagac  2160
gtcgtgtcca agatgctcca cgtggaccct catcagcgcc tgacggcgat gcaagtgctc  2220
aaacacccgt gggtggtcaa cagagagtac ctgtccccaa accagctcag ccgacaggac  2280
gtgcacctgg tgaagggcgc gatggccgcc acctactttg ctctaaacag aacacctcag  2340
gccccgcggc tggagcccgt gctgtcatcc aacctggctc agcgcagagg catgaagaga  2400
ctcacgtcca cgcggctgta gcgggtggga ccctggcccc agcgtcccct gccagcatcc  2460
tcgtgggctc acagaccccg gcctcggagc ccgtctggca cccagagtga ccacaagtcc  2520
agcagggagg cggcgcccgc cctcgccgtg tccgtgtttt ctttttcagc cccggagagg  2580
gtcctgacct gggggcttct ccaagcctca ctgcgccagc ctccccgccc gctctctttt  2640
ctcccaagcg aaaccaaatg cgccccttca cctcgcgtgc ccgtgcgagg ccgggggctt  2700
ctttcagagc ccgcgggtcc tctcatacat ggcttctgtt tctgccgaga gatctgtttt  2760
ccaattatga agccggtcgg tttggtcaga ctcccgacac ccacgtccca ggtacccggt  2820
gggaaagtgg cagtgcgagg gcgcagccat tggtggttgc agggccccag agggctgggg  2880
tgacctggca tcccggggct ccccacgggc tggatgacgg ggttggcact gtggcgtcca  2940
ggaggagatg cctggttctg cccaaaataa tccaaagagc cgtttcctcc tcgcccttca  3000
gtttttgcct gaggtgctgg gtagcccatc ctttcctctg tcccagattc aaatgaggag  3060
taagagccca gacgagagga aggcaggctg gatctttgcc ttgagagctc cgtgtcacca  3120
ggatggaagg gggtgcctct cggaggagcc tgtgtccacc tccagtctcg gctttccccg  3180
gggggccaag cgcactgggc tgccgtctgt ccccagctcc cgtggccaca cagctatctg  3240
gaggctttgc agggagtcgt gggttctcgc acctgctcag ccctgtgtcg gcttcctgtg  3300
tgctcaccta aagctgtggt tttgctgtgt tcacttcgat ttttctggtc tgtggagaaa  3360
ctgtgaattg gagaaatgga gctctgtggc ttcccaccca aaccttctca gtccagctgg  3420
aggctggagg gagacacagg ccccacccag cagactgagg ggcagaggca caggtgggag  3480
ggcagcggag atcagcgtgg acaggagcga tgcactttgt agatgctgtg gctttgtgtt  3540
gcgttttgtg tctctgttgc acagatctgt tttttcacac tgatccgtat tcccctgggt  3600
gtgcacacag ggcgggtgtg gggcatttag gccatgctgt gctctacttc attgagtaaa  3660
atcgagtgag aggttccggg cagcaggatc gacgcccagt ccagccggca gagggaacac  3720
acgggtcctt cattgtcctg taagggtgtt gaagatgctc cctggcggcc cccaagcaga  3780
ctagatggga ggaggcgccg ctcagcccct caccctgcat cactgaagag cggcgcctct  3840
gcagcaagca gggcttcagg aggtgcccgc tggccacagc caggttttcc ctaagaagat  3900
gttattttgt tgggttttgt tccccctcca tctcgattct cgtacccaac taaaaaaaaa  3960
aaaataaaga aaaaatgtgc tgcgttctga aaaataactc cttagcttgg tctgattgtt  4020
ttcagacctt aaaatataaa cttgtttcac aagctttaat ccatgtggat tttttttttc  4080
ttagagaacc acaaaacata aaaggagcaa gtcggactga atacctgttt ccatagtgcc  4140
cacagggtat tcctcacatt ttctccatag aagatgcttt ttcccaaggc tagaacgact  4200
tccaccatga tgaatttgct ttttaggtct taattatttc acttcttttt agaaacttag  4260
gaagaagtgg ataatcctga ggtcacacaa tctgtcctcc cagaaatgaa caaaagtcat  4320
caccttttct gcttgctaca caggcaacga ttcccccatc agctgcccgg accctttggc  4380
ctggcttggt gtgcaggcct gtctgtttgc ttaaagtcag tgggttctgg tgcagggagt  4440
gagaagtggg ggaagtgaaa gggaaagcat ccgtgagaaa gcggccacgg ttttccctcc  4500
ttgtgtgccc atggggcacc agctcatggt ctttttcagt catcccagtt tgtacagact  4560
tagcttctga actctaagaa tgccaaaggg accgacgaga ctccccatca cagcgagctc  4620
tgtccttaca tgtatttgat gtgcatcagc ggaggagaac actggcttgg ccctgctccg  4680
ctgagtgtct gtgaaatacc tctactttcc ctcccatatc cagaacaaaa tgatacttga  4740
catccttcca caaaagtcag cctaaagaag ttatggtatc atatgttaaa ctaagctttc  4800
aaaaacctta gtgaaatagc aagtgactgc tttcaagcag cagtcgacat gtaaatgaag  4860
gtgttcttag aattcgcatt ttgccagctc agcgcacctc cacaacgaat gaaatgctcc  4920
gtatgatttg cacaaatgac atagacctcc ccaaaagtta actggctctc cttcctcaca  4980
cagttcatca taacccaacc ccccaccccc gggtcatgaa aatcacagaa cttataaaca  5040
cattgaaccc tagatctcag gcttcctgac ctaccgccag tggccccttg ctggccaccc  5100
tatagggtcc tccttccctg gcagcccccc atgtgggaga aatacctgat tctcccaatc  5160
tgcagtggga gagctttgct gaattccatc ccaaagtcaa acatgggcaa gaggtgagga  5220
tttcactttt accctcaagt ccgatttgtc tgtgatttta aactaactgt gtatgtattg  5280
atgtttggaa gattgtttga attttaaagt gataatagta cttaatgtta tccagtattg  5340
ttcattaaat ggtgttatcc taaagctgca cttgggattt ttacctaacg ctttactgat  5400
tctctcaagc acatggcaaa gtttgatttg cactccgttc atttctgaca cgttttgctg  5460
```

-continued

```
cctcctacct ttctaagcgt catgcaaatt cgagaatgga gaaggacgct gccggtccct  5520
gagcggtgtg gagagggcgg aaggtggact ccagcgcagc ttgaggggct gaggacggag  5580
gctgcagcat ctgtgtcgtt ctactgagca cgcttctctg cctcgctcct gactcagcac  5640
tttgttcact ggctcagcag ttatgtttac acatcatttt tatgttcctg ctttgtaatt  5700
catgtttgag atgggtggcc actgtacaga tatttattac gctttccaga ctttctgaat  5760
agattttttt gaataaacat ggttttatga agtgtaatct ttttctagcc taacaat     5817

SEQ ID NO: 24          moltype = DNA  length = 8841
FEATURE                Location/Qualifiers
source                 1..8841
                       mol_type = unassigned DNA
                       organism = Rattus norvegicus
SEQUENCE: 24
gcatcatgca gcaggtcaaa caaggcatct cctagtattg catcctccag atgtgctgta  60
aacatcaaaa ggagacgctg ggagcaggag atgctgtttt ggaaagaagt aaggcttaga  120
tttctccatg ttaaccatga gcgtgacact ttccccactg aggtcacagg gcccagatcc  180
catggcgacg gatgcttcac ccatggccat caacatgaca cccactgtgg agcaggagga  240
aggagaggga gaggaagccg tgaaggccat agacgctgag cagcagtatg gaaagccacc  300
tccgctccac acagcagccg actggaagat tgtcctgcac ttacctgaga ttgagacctg  360
gctccggatg acctcagaga gggtccgtga cctgacctac tcagtccagc aggatgcaga  420
cagcaagcat gtggatgtgc atctagttca gctgaaggac atttgtgagg atatttctga  480
ccatgtggag cagatccatg ccctccttga gacggagttt tccctaaagc tgctgtccta  540
ctcggtcaac gtcatcgtag acatccacgc agtacagctg ctctggcacc agctccgcgt  600
atccgtgctg gtcctccggg agcgcatcct acaaggtctg caggacgcca atggcaacta  660
caccaggcag actgacattc tgcaagcgtt ctctgaagaa acaacggagg gccggcttga  720
ttcccttaca gaagtggacg actcagggca gttaactatc aaatgttcac aggattactt  780
gtctctggat tgtggcatta ccgcatttga actctccgac tacagtccaa gtgaggatct  840
gcttggtggc ctgggcgaca tgaccaccag ccaggccaaa actaaatctt ttgactcttg  900
gagctacagt gagatggaga aagagttccc tgagcttatc cgaagcgttg ggctgcttac  960
agtggccacc gagcctgtcc cttccagctg tggagaagcc aatgaggatt catctcaagc  1020
gtccctttca gatgatcaca aaggtgaaca cggggaagac ggtgctcccg tacctggaca  1080
gcagctggac tcaacggtgg gaatgtcttc cttagacggc acgctggcaa atgctgccga  1140
acacccttcg gagacagcaa aacaagactc tacttcctcc ccacagcttg gtgcgaagaa  1200
aacccagcct ggtccttgtg aaattacgac tcccaagaga tccatccgcg attgctttaa  1260
ttataacgag gactccccca cacagcccac attacccaaa agagggcttt ttctaaaaga  1320
aactcaaaag aatgagcgca aaggcagtga caggaagggg caggtggttg atttaaagcc  1380
tgaactgagc agaagcaccc cttccctggt ggacccccct gacagatcga agctctgcct  1440
agtgttgcag tcctcctacc ccagcagccc ttctgctgcc agccagtcct atgaatgttt  1500
gcacaaggtg gggctcggca atcttgaaaa catagtcaga agtcacatta aagaaatttc  1560
ttccagtctg ggaaggctta ctgactgcca taaagagaaa ttgcgactga aaaagccaca  1620
caagaccttg gccgaagtgt ctctgtgcag aatccctaaa cagggaggcg gttcaggaaa  1680
gcgatctgag agcaccggga gctcagcagg gcccagcatg gtatcacctg gagctcccaa  1740
agccacgatg agaccagaaa cagattctgc gtctacagcc tcaggtggcc tgtgccacca  1800
gagaaatcgc agtggacaat tgccagtgca gtcgaaggcc tccagttcac cccccttgcag  1860
tcacagcagt gaatcttctc ttggctcaga tagcatcaaa tccccggttc ctcttctttc  1920
aaaaaacaaa agccaaaaaa gctccccacc tgctccatgt cacgccacac agaacggtca  1980
ggtggtggag gcctggtacg gctctgatga gtacctagcg ctgccctctc acctgaagca  2040
gacggaggtg ttagctctca agctggagag cctaaccaag ctcctacccc agaaacccag  2100
aggagagacc atccaggata ttgatgactg ggaactgtct gaaatgaatt cagattccga  2160
aatctatcca acataccaca tcaagaaaaa acacacgaga ctgggcacag tgtctccaag  2220
ctcatccagc gacatagcct catctctcgg ggagagcatt gaatccgggc ccctgagtga  2280
cattctttct gacgaggact tatgtctgcc cctctccagc gtgaaaaagt tcactgacga  2340
gaaatcagag agaccttcat cctccgagaa gaacgagagc cattctgcaa caagatcagc  2400
tttgattcag aaactaatgc acgatattca gcaccaagag aactatgaag ccatctggga  2460
aagaattgag gggtttgtga acaagctgga tgaattcatt cagtggctaa acgaagccat  2520
ggagaccacc gagaactgga ctcctcctaa agccgagacc gacagcctcc ggctgtacct  2580
ggagacacac ttgagtttta agttgaacgt agacagccac tgtgccctca aggaagccgt  2640
ggaggaagaa ggacaccaac ttcttgagct cgttgtatct cacaaagcag gactgaagga  2700
cacgctgagg atgattgcga gtcaatggaa ggagctgcag aggcaaatca aacggcaaca  2760
cagctggatt ctcagagccc tggacaccat caaagccgag atactggcta ctgatgtgtc  2820
tgtggaggac gaggaggga cggg aagccc caaggccgag gttcagctct gccacctgga  2880
aacacagaga gacgccgtgg aacagatgtc cctgaagctg tacagcgagc agtacaccag  2940
cgggagcaag aggaaggaag agtttgccaa catgtcgaaa gcgcacgcgg agggaagcaa  3000
tgggcttctg gactttgatt cagaatatca ggagctctgg gattggctga ttgacatgga  3060
gtccctcgtg atggacagcc acgacctgat gatgtcagag gagcagcagc agcatcttta  3120
caagaggtac agtgtggaaa tgtccatcag gcatctgaaa aagtcagagc tactcagcaa  3180
ggttgaagct ttgaagaaag gtggcctttc actaccagac gatatcctgg aaaaagtgga  3240
ttcaattaat gaaaaatggg agctgcttgg gaaaacccta agagagaaga tacaggacac  3300
aatagcgggg cacagtgggt cgggcccacg tgacctgcta tctcctgaaa gcggaagcct  3360
ggtaaggcag ctggaggtca ggatcaaaga gctgaaaagg tggctaagag atacagagct  3420
tttcatcttc aattcctgtc tgagacaaga gaaggaagga acaagcgccg agaaacagct  3480
ccaatacttt aagtcgctct gtcgtgagat caagcagcgg cgtcgaggag tggcctccat  3540
tctgaggttg tgccagcacc ttctggatga ccgggacacg tgcaacctga acgcagatca  3600
ccagcccatg cagctgatca ttgtaaacct cgagaggcgg tgggaggcca tcgtcatgca  3660
agctgtccag tggcaaacac ggttacaaaa gaagatgggg aaggaatccg agactttgaa  3720
tgtgattgat cctggcttga tggacctgaa tggaatgagt gaggatgccc tggaatggga  3780
tgaaacagac ataagtaaca aactcattag tgtgcatgaa gaatcaaacg accttgatca  3840
agacccagag cctatgctac ccgcagtgaa gcttgaagag acacaccaca aggactctgg  3900
ttatgaagag gaggcaggtg actgtggagg gtctccgtat acctcaaata tcactgcacc  3960
```

-continued ttccagccca cacatttacc aagtgtacag tcttcacaat gtggagctcc acgaggacag 4020
ccacactcca tttctgaaaa gcagccctaa gttcacaggc acaacacagc ctactgtttt 4080
aactaagagc ctcagcaagg actcttcctt ttcatctaca aaatcgttac cagaccttct 4140
agggggttcc ggtttggtga ggccttactc gtgtcacagt ggagacttga gccagaattc 4200
aggcagtgag agtggaattg tcagcgaagg agacaacgag atgccgacca actctgacat 4260
gagcttgttc agtatggtag acgggtcccc aagtaaccct gaaacggagc atccggaccc 4320
acaaatggga gatgcagcca atgtgctaga gcaaaagttt aaagacaacg gggaaagcat 4380
taagctttca agtgtctctc gggcatccgt ctcaccagtg ggttgtgtaa atggaaaagc 4440
aggggattta aacagtgtta ccaaacacac tgctgattgt ttgggagaag aactacaagg 4500
aaaacatgac gtgtttacat tttatgatta ctcgtacctc caaggctcaa aactcaaatt 4560
accaatgata atgaaacagc cacagagtga aaaggcacac gtggaggatc cccttcttgg 4620
tggtttttat tttgataaaa agtcctgcaa agctaaacat caggcttcag agtcacaacc 4680
agatgcgcct ccccacgaaa ggattctggc aagcgcgccc cacgagatgg gacgcagcgc 4740
atacaaaagt agcgacatag agaagacatt cacgggcatt cagagtgcca gacagctctc 4800
ccttctatct cgtagctcat ctgtagagtc cctttctcca gggggtgatt tgtttggatt 4860
gggaatcttt aaaaatggca gtgacagcct ccagcggagc acttctttag aaagttggtt 4920
gacatcctat aagagcaatg aggatctctt tagctgtcac agctctgggg acataagtgt 4980
gagcagtggc tcagttggtg agctgagtaa gaggacgtta gaccttctga atcgcctgga 5040
gaatatacag agcccctcgg agcaaaagat caagcggagt gtttctgaca tgactctaca 5100
aagcagttcc caaaagatgc ccttcgctgg ccagatgtca ctggatgtcg catcctccat 5160
caatgaagac tctccggcat ctcttacaga actgagtagt agcgatgagc tctctctttg 5220
ctcggaggac attgtgttac acaaaaacaa gatcccagaa tccaacgcat cattcaggaa 5280
gcgcctgaat cgctcagtgg ctgatgagag cgacgtcaat gttagcatga ttgtcaatgt 5340
gtcctgcacc tctgcttgca ctgatgatga agatgacagc gacctcctct ccagctccac 5400
tctcacctta actgaagaag agctgtgcct caaagatgag gatgacgact ccagtattgc 5460
aacagatgat gaaatttatg aagagagcaa cctgatgtct gggctggact acataaagaa 5520
tgaactgcag acttggataa gaccaaaact ttccttgacg agagaaaaga aacggtccgg 5580
tgtcactgat gaaataaagg tcaataaaga tgggggaggc aatgagaagg ccaatccctc 5640
ggacaccctg gacatcgagg cccttctcaa tggctccata agatgtcttt ccgaaaacaa 5700
cgggaatggt aagactccgc ccagaactca tggctcagga accaaaggtg aaaataagaa 5760
aagtacgtat gacgttagta aggatccgca cgtggctgac atggaaaatg gcaatattga 5820
aagtacccca gaaagagaaa gggagaagcc acaagggctt ccagaggtgt cagagaacct 5880
tgcttcaaat gtgaaaacga tttctgaatc tgagctcagc gagtatgaag cagtaatgga 5940
tggttctgag gattcaagtg ttgccagaaa ggaattttgt cccccaaatg acagacatcc 6000
tccacagatg ggtcccaaac tccagcatcc cgaaaatcaa agtggcgact gcaagccagt 6060
ccagaaccct tgcccggggc tactgtcgga agctggcgtt ggaagcaggc aagacagcaa 6120
tggactaaaa tctttgccta acgatgcacc aagtggggct agaaaacctg ccggttgctg 6180
cctgctggag cagaatgaga cagaggaaag tgcttctatc agcagcaacg cttcctgttg 6240
caactgcaag ccagatgttt tccatcaaaa agatgatgaa gattgttcag tacatgactt 6300
tgttaaggaa atcattgaca tggcatcaac agccctaaaa agtaagtcac agcctgaaag 6360
tgaggtggcc gcacccacat cactaaccca aattaaggag aaggtgttag agcattcgca 6420
ccggcccata cacctgagaa agggggactt ttactcctac ttatcacttt cgtcccacga 6480
cagtgactgt ggggaggtca ccaattacat agatgagaag agcagtactc cattgccacc 6540
ggacgctgtg gactctggct tagatgacaa ggaagacatg gactgcttct ttgaagcttg 6600
tgttgaggat gagcctgtca atgaggaagc tggtctcccc ggtgcccttc ccaatgaatc 6660
agccatcgag gatggagcag agcaaaagtc agaacaaaag acagccagct ctcctgtgct 6720
cagtgacaag acagacctgg tgcctctttc aggactttcc cctcagaagg gagctgatga 6780
tgcaaaggaa ggagatgatg tgtctcacac ttcccagggc tgtgcagaga gcacagagcc 6840
taccaccccc tcaggaaagg ccaatgcaga ggggaggtca agaatgcaag gtgtatcagc 6900
aacgccagaa gaaaacgctg cttcggccaa accgaaaatt caagctttct ctttgaatgc 6960
aaaacagcca aaaggcaagg ttgccatgag gtatcccagc cccaaactc taacctgtaa 7020
agagaagctc gtaaactttc atgaagatcg acacagtaac atgcataggt agagtgtaat 7080
gcccccacgc atggaaatca tctcattgaa agatagcctg gctgaagctc agggctagcc 7140
caatccaccc tgggccggtc ttgggctcca tcctgttatc actgccgcct gtcacattga 7200
ctttctgaag acgaaccttc cttccgaatg cagtctgtcc acgtgggcct ctcgacctgg 7260
atgtgtgcat tgcttctctt aggtgatcat cctagttcca caaagctgct tgttctcccg 7320
tggattcctg tcccaagcta cctctggcaa ccctgtctct ccagcaagac ttcggttttc 7380
cctccccctc ctcccccccc ttaaagttcc gcggctcacc aaattgatgg tccatcaaac 7440
ccactgtctg gaatgatacc cctcccatca gtacttgacc aatgttatgt tttgctctga 7500
aaactttcgc tgtattagac caatgtttat tgaaagagat ttacctaaaa agcccgccct 7560
tgatttggtt gcagtataga ggagacacat tgatccttct aacaaaatta agtgatgtct 7620
gaaagcgcca ttttaattat ttctttttaa ataatgatct atgcagcact tcaagaaaca 7680
actataacag tgttgtatct tataaactgg tacattctac tattaagttt gtttttggtt 7740
tctatgcttc ttgaggtggt gatgagaaaa atggtttttt ttttaaaacg gtgtgccttg 7800
ctgtattact tatagcattt attaaaaagc tgctttcatg gtaagattac actggtttga 7860
aaggaggaaa tagcaaggtt aagatgcgtg cataatttct gtatatatgt ataagctagt 7920
gcaaacactg atgtatgaca gtataaaatg ctttcatgtt tgtgatgtcc agtggtgtgg 7980
aatataagcc ttaaacccgt tcgattgcat ggtaattaaa attggcataa taaaaatagc 8040
ttattggggg aaaggaaaat taatgatctc ttctacctgt gtttaccaat ttctttcatg 8100
tggttctggg aaagaaaaag aaacaaaccc catatattag cttccaaaat atccatattg 8160
cacagaaggc ttaagttgct tagactacag actgggcctg aagacttcat gattttccaa 8220
atttttctgt ttcactataa acatccgaaa tagcaaagat ttctttcccc tccatcaaca 8280
gcattttatt ctgaatgttt ttatttctac ttgttaatgg tttaaagttg tatttggaga 8340
tctcttacat gccctaattt attttaaata tttgaatggg tttggtggat ggtatagaaa 8400
atttaattat tattttattt aaactacaga tttcaggtgt atttattttg ttaaatattc 8460
catttggtct tttggtcttt ttatgacttg aaagtttcag cttttaattt atatcataac 8520
tcctactaaa gtgcctgaca cacagtaggt atttcataga gtttcctgaa ttagagtatt 8580
gggtggttta tatatatata tatatatatg agattcctgc attaaaacta gaaaaagatg 8640
tgcaaagtga accagacaca gcatattatc agatttcaaa aaggaaagag aacatagcca 8700

-continued

```
cagaaatgac aatcattcat tcagtagatt agcatctttt gcctgcaagt caccattcta  8760
gattcaggga gagcagctat gaccgatgca ctgcctttgg aggcttctgt gttagagaca  8820
gagtgacctc gtgccgaatt c                                            8841

SEQ ID NO: 25           moltype = AA  length = 2319
FEATURE                 Location/Qualifiers
source                  1..2319
                        mol_type = protein
                        organism = Homo sapiens
SEQUENCE: 25
MLTMSVTLSP LRSQDLDPMA TDASPMAINM TPTVEQGEGE EAMKDMDSDQ QYEKPPPLHT  60
GADWKIVLHL PEIETWLRMT SERVRDLTYS VQQDSDSKHV DVHLVQLKDI CEDISDHVEQ  120
IHALLETEFS LKLLSYSVNV IVDIHAVQLL WHQLRVSVLV LRERILQGLQ DANGNYTRQT  180
DILQAFSEET KEGRLDSLTE VDDSGQLTIK CSQNYLSLDC GITAFELSDY SPSEDLLSGL  240
GDMTSSQVKT KPFDSWSYSE MEKEFPELIR SVGLLTVAAD SISTNGSEAV TEEVSQVSLS  300
VDDKGGCEED NASAVEEQPG LTLGVSSSSG EALTNAAQPS SETVQQESSS SSHHDAKNQQ  360
PVPCENATPK RTIRDCFNYN EDSPTQPTLP KRGLFLKEET FKNDLKGNGG KRQMVDLKPE  420
MSRSTPSLVD PPDRSKLCLV LQSSYPNSPS AASQSYECLH KVGNGNLENT VKFHIKEISS  480
SLGRLNDCYK EKSRLKKPHK TSEEVPPCRT PKRGTGSGKQ AKNTKSSAVP NGELSYTSKA  540
IEGPQTNSAS TSSLEPCNQR SWNAKLQLQS ETSSSPAFTQ SSESSVGSDN IMSPVPLLSK  600
HKSKKGQASS PSHVTRNGEV VEAWYGSDEY LALPSHLKQT EVLALKLENL TKLLPQKPRG  660
ETIQNIDDWE LSEMNSDSEI YPTYHVKKKH TRLGRVSPSS SSDIASSLGE SIESGPLSDI  720
LSDEESSMPL AGMKKYADEK SERASSSEKN ESHSATKSAL IQKLMQDIQH QDNYEAIWEK  780
IEGFVNKLDE FIQWLNEAME TTENWTPPKA EMDDLKLYLE THLSFKLNVD SHCALKEAVE  840
EEGHQLLELI ASHKAGLKDM LRMIASQWKE LQRQIKRQHS WILRALDTIK AEILATDVSV  900
EDEEGTGSPK AEVQLCYLEA QRDAVEQMSL KLYSEQYTSS SKRKEEFADM SKVHSVGSNG  960
LLDFDSEYQE LWDCLIDMES LVMDSHDLMM SEEQQHLYK RYSVEMSIRH LKKTELLSKV  1020
EALKKGGVLL PNDLLEKVDS INEKWELLGK TLGEKIQDTM AGHSGSSPRD LLSPESGSLV  1080
RQLEVRIKEL KGWLRDTELF IFNSCLRQEK EGTMNTEKQL QYFKSLCREI KQRRRGVASI  1140
LRLCQHLLDD RETCNLNADH QPMQLIIVNL ERRWEAIVMQ AVQWQTRLQK KMGKESETLN  1200
VIDPGLMDLN GMSEDALEWD EMDISNKLIS LNEESNDLDQ ELQPVIPSLK LGETSNEDPG  1260
YDEEADNHGG SQYASNITAP SSPHIYQVYS LHNVELYEDN HMPFLKNNPK VTGMTQPNVL  1320
TKSLSKDSSF SSTKSLPDLL GGSNLVKPCA CHGGDMSQNS GSESGIVSEG DTETTTNSEM  1380
CLLNAVDGSP SNLETEHLDP QMGDAVNVLK QKFTDEGESI KLPNSSQSSI SPVGCVNGKV  1440
GDLNSITKHT PDCLGEELQG KHDVFTFYDY SYLQGSKLKL PMIMKQSQSE KVHVEDPLLR  1500
GFYFDKKSCK SKHQTTELQP DVPPHERILA SASHEMDRIS YKSGNIEKTF TGMQNAKQLS  1560
LLSHSSSIES LSPGGDLFGL GIFKNGSDSL QRSTSLESWL TSYKSNEDLF SCHSSGDISV  1620
SSGSVGELSK RTLDLLNRLE NIQSPSEQKI KRSVSDITLQ SSSQKMSFTG QMSLDIASSI  1680
NEDSAASLTE LSSSDELSLC SEDIVLHKNK IPESNASFRK RLTRSVADES DVNVSMIVNV  1740
SCTSACTDDE DDSDLLSSST LTLTEEELCI KDEDDDSSIA TDDEIYEDCT LMSGLDYIKN  1800
ELQTWIRPKL SLTRDKKRCN VSDEMKGSKD ISSSEMTNPS DTLNIETLLN GSVKRVSENN  1860
GNGKNSSHTH ELGTKRENKK TIFKVNKDPY VADMENGNIE GIPERQKGKP NVTSKVSENL  1920
GSHGKEISES EHCKCKALMD SLDDSNTAGK EFVSQDVRHL PKKCPNHHHF ENQSTASTPT  1980
EKSFSELALE TRFNNRQDSD ALKSSDDAPS MAGKSAGCCL ALEQNGTEEN ASISNISCCN  2040
CEPDVFHQKD AEDCSVHNFV KEIIDMASTA LKSKSQPENE VAAPTSLTQI KEKVLEHSHR  2100
PIQLRKGDFY SYLSLSSHDS DCGEVTNYIE EKSSTPLPLD TTDSGLDDKE DIECFFEACV  2160
EGDSDGEEPC FSSAPPNESA VPSEAAMPLQ ATACSSEFSD SSLSADDADT VALSSPSSQE  2220
RAEVGKEVNG LPQTSSGCAE NLEFTPSKLD SEKESSGKPG ESGMPEEHNA ASAKSKVQDL  2280
SLKANQPTDK AALHPSPKTL TCEENLLNLH EKRHRNMHR                          2319

SEQ ID NO: 26           moltype = AA  length = 14
FEATURE                 Location/Qualifiers
REGION                  1..14
                        note = Peptide
source                  1..14
                        mol_type = protein
                        organism = synthetic construct
SEQUENCE: 26
KFAVRRFFSV YLRR                                                    14
```